(12) United States Patent
Hook et al.

(10) Patent No.: US 7,615,616 B2
(45) Date of Patent: Nov. 10, 2009

(54) BIOINFORMATIC METHOD FOR IDENTIFYING SURFACE-ANCHORED PROTEINS FROM GRAM-POSITIVE BACTERIA AND PROTEINS OBTAINED THEREBY

(75) Inventors: Magnus Hook, Houston, TX (US); Yi Xu, Houston, TX (US); Jouko V. Sillanpaa, Houston, TX (US); Narayana Sthanam, Birmingham, AL (US); Karthe Ponnuraj, Birmingham, AL (US); Joseph M. Patti, Cumming, GA (US); Jeff T. Hutchins, Cumming, GA (US); Andrea Hall, Acworth, GA (US); Maria G. Bowden, Sugarland, TX (US)

(73) Assignees: The Texas A&M University System, College Station, TX (US); Inhibitex, Inc., Alpharetta, GA (US); The UAB Research Foundation, Birmingham, AL (US)

( * ) Notice: Subject to any disclaimer, the term of this patent is extended or adjusted under 35 U.S.C. 154(b) by 283 days.

(21) Appl. No.: 10/661,809

(22) Filed: Sep. 15, 2003

(65) Prior Publication Data

US 2004/0101919 A1 May 27, 2004

Related U.S. Application Data

(60) Provisional application No. 60/410,303, filed on Sep. 13, 2002.

(51) Int. Cl.
*C07K 16/00* (2006.01)

(52) U.S. Cl. ............... 530/387.1; 530/388.1; 424/130.1; 424/133.1; 424/139.1; 424/141.1; 424/150.1; 424/164.1; 435/243; 435/975

(58) Field of Classification Search .............. 530/387.1, 530/388.1; 435/243, 975; 424/130.1, 133.1, 424/139.1, 141.1, 150.1, 164.1
See application file for complete search history.

(56) References Cited

U.S. PATENT DOCUMENTS

| 6,008,341 | A | 12/1999 | Foster et al. |
| 6,426,074 | B1 | 7/2002 | Michel et al. |
| 6,448,043 | B1 * | 9/2002 | Choi et al. ................. 435/69.3 |
| 6,617,156 | B1 * | 9/2003 | Doucette-Stamm et al. ........................ 435/320.1 |
| 2002/0045737 | A1 | 4/2002 | Choi et al. |
| 2002/0061545 | A1 | 5/2002 | Choi et al. |

FOREIGN PATENT DOCUMENTS

| WO | 98/50554 A2 * | 11/1998 |
| WO | WO-98/50554 | 11/1998 |
| WO | WO-00/68242 | 11/2000 |

OTHER PUBLICATIONS

Perkins, et al, "Structural organization of the fibrinogen-binding region of the clumping factor B MSCRAMM of *Staphylococcus aureus*", Nov. 30, 2001, pp. 44721-44728, vol. 276, No. 48, Journal of Biological Chemistry.
Rich, et al, "Ace is a collagen-binding MSCRAMM from *Enterococcus faecalis*" Sep. 17, 1999, pp. 26939-26945, vol. 274, No. 38, Journal of Biological Chemistry.
Champion et al, "Novel fold and assembly of the repetitive B region of the *Staphylococcus aureus* collagen-binding surface protein", 2000, pp. 67-78, vol. 8, Structure.
Database UniProt Entry Q836M0_ENTFA Jun. 1, 2003, Paulsen, I.T. et al.: "Von Willebrand factor type A domain protein" XP002426339 acession No. Q836M0 *abstract* & I.T. Paulsen et al.: "Role of mobile DNA in the evolution of vancomycin-resistant *Enterococcus faecalis*" Science, vol. 299, Mar. 28, 2003, pp. 2071-2074, XP002268057.
Database UniProt Entry Q836L9_ENTFA Jun. 1, 2003, Paulsen, I.T. et al.: "cell wall surface anchor family protein" XP002426340 accession No. Q836L9 *the whole document* & I.T. Paulsen et al.: "Role of mobile DNA in the evolution of vancomycin-resistant *Enterococcus faecalis*" Science, vol. 299, Mar. 28, 2003, pp. 2071-2074, XP002268057.

* cited by examiner

*Primary Examiner*—Jennifer E Graser
(74) *Attorney, Agent, or Firm*—B. Aaron Schulman; Terry L. Wright; Stites & Harbison PLLC

(57) ABSTRACT

A bioinformatic method is provided for identifying and isolating proteins with MSCRAMM®—like characteristics from Gram positive bacteria, such as *Enterococcus, Staphylococcus, Streptococcus* and *Bacillus* bacteria, which can then be utilized in methods to prevent and treat infections caused by Gram-positive bacteria. The method involves identifying from sequence information those proteins with a putative C-terminal LPXTG (SEQ ID NO:1) cell wall sorting signal and other structural similarities to MSCRAMM® proteins having the LPXTG-anchored cell wall proteins. The MSCRAMM® proteins and immunogenic regions therein that are identified and isolated using the present invention may be used to generate antibodies useful in the diagnosis, treatment or prevention of Gram positive bacterial infections.

10 Claims, 2 Drawing Sheets

Figure 1:
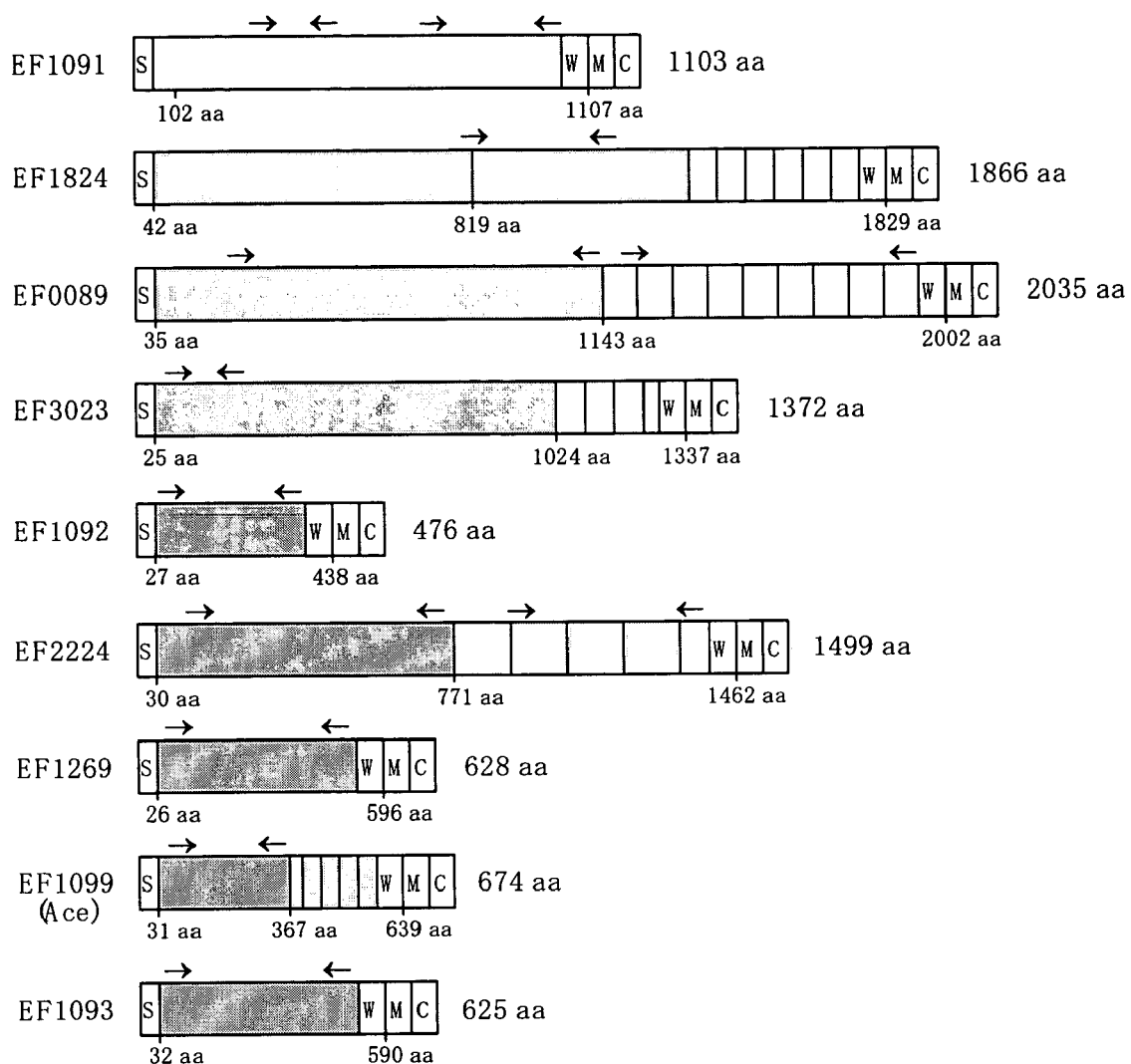

Coomassie-stained SDS-PAGE of the *E. coli*-expressed and purified A domains of *E. faecalis* LPxTG proteins. a, EF1091; b, EF1824; c, EF0089; d, EF3023; e, EF1092; f, EF2224; g, EF1269; h, Ace; I, EF1093.

SEQUENCE LISTING

<160> NUMBER OF SEQ ID NOS: 24

<210> SEQ ID NO 1
<211> LENGTH: 5
<212> TYPE: PRT
<213> ORGANISM: Staphylococcus epidermidis
<220> FEATURE:
<221> NAME/KEY: MISC_FEATURE
<222> LOCATION: (3)..(3)
<223> OTHER INFORMATION: X = any amino acid

<400> SEQUENCE: 1

Leu Pro Xaa Thr Gly
1               5

<210> SEQ ID NO 2
<211> LENGTH: 777
<212> TYPE: PRT
<213> ORGANISM: Staphylococcus epidermidis

<400> SEQUENCE: 2

Gln Glu Gln Thr Ala Lys Glu Asp Val Ala Asp Ser Ala Thr Ser Val
1               5                   10                  15

Gly Ala Ile Val Ser Ile Glu Lys Ala Glu Lys Asn Phe Val Ile Thr
            20                  25                  30

Tyr Ala Ser Gly Lys Lys Ala Gln Ile Ser Ile Leu Asn Asp His Leu
        35                  40                  45

Phe Arg Tyr His Leu Asp Pro Thr Gly Lys Phe Glu Glu Tyr Pro Thr
    50                  55                  60

Pro Asn Asp Pro Lys His Val Ala Lys Ile Thr Ala Lys Thr Met Ala
65                  70                  75                  80

Asp Tyr Gly Thr Gln Ala Phe Glu Gln Thr Asn Val Thr Asp Ser Gly
                85                  90                  95

Asn Gln Phe Ile Leu Glu Asn Asn Gly Leu Lys Ile Met Phe Glu Lys
            100                 105                 110

Glu Ser Ala Leu Met Lys Val Leu Asp Lys Lys Asn Gln Val Ile
        115                 120                 125

Leu Glu Glu Thr Ala Pro Leu Ser Phe Lys Asn Asp Lys Ala Thr Gln
130                 135                 140

Thr Leu Lys Gln Ser Ser Gln Glu Asn Tyr Phe Gly Gly Thr Gln
145                 150                 155                 160

Asn Gly Arg Phe Thr His Lys Gly Thr Ala Ile Gln Ile Val Asn Thr
                165                 170                 175

Asn Asn Trp Val Asp Gly Val Ala Ser Pro Asn Pro Phe Tyr Trp
            180                 185                 190

Ser Thr Ala Gly Tyr Gly Val Val Arg Asn Thr Trp Lys Pro Gly Asn
        195                 200                 205

Tyr Asp Phe Gly Ser His Asp Pro Gln Lys Thr Thr Thr His Glu
    210                 215                 220

Gly Thr Asp Phe Asp Ala Phe Tyr Phe Asn Asp Ser Ser Ala Gly
225                 230                 235                 240

Ile Leu Lys Asp Tyr Tyr Glu Leu Thr Gly Lys Pro Ala Leu Met Pro
                245                 250                 255

Glu Tyr Gly Phe Tyr Glu Ala His Leu Asn Ala Tyr Asn Arg Asp Tyr
            260                 265                 270

Trp Val Lys Val Ala Glu Gly Thr Ala Gly Ala Val Lys Phe Glu Asp

-continued

```
                275                 280                 285
Gly Asn Phe Tyr Lys Glu Tyr Gln Pro Gly Asp Leu Gly Asn Leu Asn
    290                 295                 300
Gly Thr Leu Glu Ser Leu Asn Gly Glu Lys Glu Asn Tyr Gln Phe Ser
305                 310                 315                 320
Ala Arg Ala Val Ile Asp Arg Tyr Lys Lys Asn Asp Met Pro Leu Gly
                325                 330                 335
Trp Phe Leu Pro Asn Asp Gly Tyr Gly Ala Gly Tyr Gly Gln Thr Asp
                340                 345                 350
Ser Leu Asp Gly Asp Val Gln Asn Leu Lys Glu Phe Thr Glu Tyr Ala
            355                 360                 365
Gln Ala Asn Gly Val Glu Val Gly Leu Trp Thr Gln Ser Asn Leu His
        370                 375                 380
Pro Ala Asp Pro Lys Asn Pro Lys Lys Gly Glu Arg Asp Ile Ala Lys
385                 390                 395                 400
Glu Val Ser Val Ala Gly Val Lys Ala Leu Lys Thr Asp Val Ala Trp
                405                 410                 415
Val Gly Tyr Gly Tyr Ser Phe Gly Leu Asn Gly Val Glu Asp Ala Ala
            420                 425                 430
Asn Val Phe Val Lys Glu Thr Asp Gly Ala Val Arg Pro Met Ile Val
        435                 440                 445
Ser Leu Asp Gly Trp Ala Gly Thr Gln Arg His Ala Gly Ile Trp Thr
    450                 455                 460
Gly Asp Gln Thr Gly Gly Gln Trp Glu Tyr Ile Arg Phe His Ile Pro
465                 470                 475                 480
Thr Tyr Ile Gly Thr Ser Leu Ser Gly Gln Pro Asn Val Gly Ser Asp
                485                 490                 495
Met Asp Gly Ile Phe Gly Gly Lys Asn Lys Glu Ile Asn Ile Arg Asp
            500                 505                 510
Phe Gln Trp Lys Thr Phe Thr Pro Val Gln Leu Asn Met Asp Gly Trp
        515                 520                 525
Gly Ser Asn Pro Lys Thr Pro Phe Ala Phe Asp Gln Glu Ala Thr Asp
    530                 535                 540
Leu Asn Arg Ala Tyr Leu Lys Leu Lys Ser Met Met Met Pro Tyr Asn
545                 550                 555                 560
Tyr Ser Ile Ala Lys Glu Ser Val Asp Gly Leu Pro Met Val Arg Ala
                565                 570                 575
Met Ala Leu Glu Phe Pro Asn Glu Gly Thr Ala Tyr Thr Lys Asp Ser
            580                 585                 590
Gln Tyr Gln Tyr Met Trp Gly Pro Asn Leu Leu Val Ala Pro Ile Tyr
        595                 600                 605
Asn Gly Asn Gln Asp Glu Ala Gly Asn Ser Ile Arg Asp Gly Ile Tyr
    610                 615                 620
Leu Pro Asp Glu Lys Gln Val Trp Val Asp Leu Phe Thr Gly Glu Lys
625                 630                 635                 640
Tyr Gln Gly Gly Arg Val Leu Asn Gly Val Lys Thr Pro Leu Trp Lys
                645                 650                 655
Val Pro Val Phe Val Lys Asp Gly Ser Ile Ile Pro Met Thr Asn Pro
            660                 665                 670
Asn Asn Asn Pro Lys Glu Ile Gln Arg Asp Gln Arg Ser Phe Leu Ile
        675                 680                 685
Tyr Pro Asn Gly Thr Thr Ser Phe Asn Met Tyr Glu Asp Asp Gly Ile
    690                 695                 700
```

```
Ser Thr Ser Tyr Glu Ala Gly Gln Ser Ala Thr Thr Lys Ile Asn Ser
705                 710                 715                 720

Gln Gly Pro Lys Ser Asn Glu Lys Gly Asp Leu Thr Val Thr Ile Glu
            725                 730                 735

Pro Thr Lys Gly Ser Tyr Lys Asp Phe Val Asp Glu Arg Ser Thr Thr
            740                 745                 750

Leu Asp Leu Leu Ala Ser Glu Ala Pro Glu Ser Val Thr Ala Met Val
            755                 760                 765

Gly Gly Thr Glu Val Thr Leu Lys Gln
770                 775

<210> SEQ ID NO 3
<211> LENGTH: 1010
<212> TYPE: PRT
<213> ORGANISM: Staphylococcus epidermidis

<400> SEQUENCE: 3

Ala Ala Asn Lys Glu Glu Phe Leu Ala Gly Thr Asn Leu Tyr Tyr Phe
1               5                   10                  15

Asp Lys Glu Phe Gln Val Asn Gln Tyr Leu Ser Glu Ala Ser Gly Glu
            20                  25                  30

Lys Leu Asn Gln Ser Ala Leu Ser Val Lys Leu Ala Lys Gln Ser Val
        35                  40                  45

Thr Ala Lys Asp Val Gln Ile Thr Val Lys Gly Phe Ile Asn Lys Gly
    50                  55                  60

Thr Val Asp Gly Gly Asn Thr Thr Val Asp Asp Gln Leu Thr Ile Pro
65                  70                  75                  80

Ala Asn Val Ala Ile Asn Glu Glu Lys Thr Thr Pro Ser Ser Leu Thr
                85                  90                  95

Leu Gln Trp Asp Gln Val Thr Glu Ala Thr Ser Tyr Glu Val Glu Arg
            100                 105                 110

Asp Gly Thr Val Phe Gly Asn Ile Gln Thr Asn Thr Ala Thr Phe Asp
        115                 120                 125

Gly Phe Ser Phe Leu Ser Glu His Thr Phe Arg Val Arg Ala Val Gly
    130                 135                 140

Lys Asn Gly Val Ser Glu Trp Ser Glu Pro Ile Lys Gly Lys Thr Gln
145                 150                 155                 160

Asp Asp Pro Tyr Lys Glu Thr Ile Asn Gln Val Lys Ala Thr Ser Asn
                165                 170                 175

Leu Pro Glu Gln Pro Gly Ala Glu Leu Lys Lys Leu Thr Asp Lys Asp
            180                 185                 190

Leu Ser Thr Gly Trp His Thr Asn Trp Ser Thr Gly Ile Ala Asn Pro
        195                 200                 205

Ser Asp Gly Asn Phe Leu Ser Leu Lys Phe Asp Leu Gly Ala Glu Tyr
    210                 215                 220

Gln Met Asp Lys Ile Glu Tyr Leu Pro Arg Asp Asn Ala Gly Asn Gly
225                 230                 235                 240

Asn Ile Leu Gln Leu Gln Tyr Arg Thr Ser Lys Asp Gly Ala Asn Trp
                245                 250                 255

Thr Glu Phe Ser Glu Pro Ile Asn Trp Lys Gln Asp Ala Leu Thr Lys
            260                 265                 270

Thr Ile Glu Thr Lys Asp Gln Ala Tyr Arg Phe Val Glu Met Lys Val
        275                 280                 285

Leu Lys Ser Val Gly Asn Phe Gly Ser Gly Arg Glu Met Leu Phe Tyr
```

```
                290                 295                 300
Lys Gln Pro Gly Thr Glu Gly Ile Leu His Gly Asp Ile Thr Asn Asp
305                 310                 315                 320

Gly Thr Ile Asp Glu Asn Asp Ala Met Ser Tyr Arg Asn Tyr Thr Gly
                325                 330                 335

Leu Glu Ser Val Asp Ser Asp Phe Asn Gly Tyr Val Glu Lys Gly Asp
                340                 345                 350

Leu Asn Lys Asn Gly Val Ile Asp Ala Tyr Asp Ile Ser Tyr Val Leu
                355                 360                 365

Arg Gln Leu Asp Gly Gly Ile Glu Ile Pro Asp Val Glu Glu Ile Ala
370                 375                 380

Gly Gly Leu Ser Leu Ala Val Val Asn Glu Asn Gly Lys Asp Thr Tyr
385                 390                 395                 400

Leu Pro Gly Asp Thr Leu Thr Phe Ile Leu Lys Gly Gln Asp Leu Lys
                405                 410                 415

Asn Ile Asn Ala Leu Ser Thr Lys Met Ser Phe Asp Ser Ser Lys Phe
                420                 425                 430

Glu Leu Val Gly Gln Pro Ala Thr Thr Asn Asn Thr Gln Gln Met Glu
                435                 440                 445

Asn Tyr Ser Lys Tyr Arg Lys His Ser Asn Asp Val Glu Asn Leu Tyr
                450                 455                 460

Leu Val Leu Ser Asn Gln Gly Asn Lys Gln Leu Leu Asn Gly Ser Met
465                 470                 475                 480

Asp Leu Val Thr Phe Lys Val Lys Val Lys Glu Thr Thr Arg Val Lys
                485                 490                 495

Arg Ala Thr Thr Val Glu Gln Pro Leu Gln Phe Asp Met Ser Gln Gly
                500                 505                 510

Leu Leu Val Gly Gln Gly Phe Gln Gln Ala Thr Leu Ser Asp Phe Ser
                515                 520                 525

Val Thr Val Lys Pro Thr Glu Leu Val Asp Lys Glu Leu Leu Gln Ala
                530                 535                 540

Leu Ile Thr Leu Asn Gln Ala Arg Val Glu Lys Glu Tyr Thr Pro Glu
545                 550                 555                 560

Thr Trp Ala Ile Phe Lys Pro Ile Leu Asp Glu Ala Val Ala Val Leu
                565                 570                 575

Ala Asn Glu Gln Ala Thr Gln Thr Asp Val Ser Ala Ala Glu Asn
                580                 585                 590

Leu Glu Lys Ala Ala Ser Gln Leu Glu Lys Met Pro Asp Val Ala Asn
                595                 600                 605

Lys Ala Asp Leu Glu Lys Ala Ile Gln Glu Gly Leu Ala Lys Lys Pro
                610                 615                 620

Ser Asp Gly Gln Glu Phe Thr Glu Thr Lys Lys Val Leu Glu Glu
625                 630                 635                 640

Ser Leu Ala Ala Ala Gln Lys Val Phe Ala Gln Lys Val Thr Gln
                645                 650                 655

Glu Glu Ile Asp Gln Ala Thr Lys Thr Leu Arg Glu Ala Ile Ala Gln
                660                 665                 670

Leu Lys Glu Gln Pro Val Ala Val Asp Lys Glu Thr Leu Lys Glu Gln
                675                 680                 685

Ile Ala Gln Ala Arg Gly Arg Lys Pro Glu Glu Gly Tyr Gln Phe Thr
                690                 695                 700

Lys Glu Thr Glu Lys Gln Leu Gln Glu Ala Ile Gln Ala Ala Glu Ala
705                 710                 715                 720
```

-continued

```
Ile Val Ala Lys Glu Thr Ala Thr Lys Glu Val Ser Glu Ala Leu
                725                 730                 735

Asn Ala Leu Glu Thr Ala Met Ala Gln Leu Lys Glu Val Pro Leu Val
            740                 745                 750

Asn Lys Asp Gln Leu Gln Glu Val Val Lys Arg Ala Gln Gln Val Thr
        755                 760                 765

Pro Ser Glu Gly His Gln Phe Thr Ala Ser Ser Leu Gln Glu Leu Gln
    770                 775                 780

Lys Ala Leu Leu Ala Ala Lys Asn Thr Leu Lys Asn Pro Ala Ala Asn
785                 790                 795                 800

Gln Lys Met Ile Asp Glu Ala Val Ala Glu Leu Thr Ser Ala Ile Asp
                805                 810                 815

Gly Leu Gln Glu Glu Val Leu Val Thr Asp Lys Lys Ala Leu Glu Ala
            820                 825                 830

Met Ile Ala Lys Ala Lys Ala Ile Lys Pro Ser Ala Gly Lys Glu Phe
        835                 840                 845

Thr Ser Glu Ser Lys Ala Arg Leu Thr Glu Ala Ile Asp Gln Ala Glu
    850                 855                 860

Gly Ile Leu Ala Asp Lys Asn Ala Arg Gln Glu Gln Ile Asp Ile Ala
865                 870                 875                 880

Glu Lys Asn Val Lys Thr Ala Leu Asp Ser Leu Glu Glu Gln Val Leu
                885                 890                 895

Gln Thr Asp Lys Thr Lys Leu Lys Glu Leu Leu Gln Lys Ala Glu Thr
            900                 905                 910

Leu Lys Pro Lys Ala Gly Lys Gln Phe Thr Lys Ala Ser Gln Glu Ala
        915                 920                 925

Leu Ala Glu Ala Ile Lys Gln Ala Lys Ala Leu Val Glu Asp Pro Asn
    930                 935                 940

Ala Thr Gln Glu Ala Val Asp Lys Cys Leu Ser Ile Leu Ser Gln Ala
945                 950                 955                 960

Ile Glu Ala Met Ala Glu Glu Pro Ile Ser Ser Asn Ser Thr Gly Asn
                965                 970                 975

Asn Gly Asn His Ser Thr Val Ser Gly Thr Gly Gly Val Thr Ser Gln
            980                 985                 990

Gly Lys Gly Thr Ala Thr Gly Gly Thr Thr Thr Lys Thr  Thr Thr Ser
        995                 1000                1005

Gly Thr
    1010
```

<210> SEQ ID NO 4
<211> LENGTH: 1108
<212> TYPE: PRT
<213> ORGANISM: Staphylococcus epidermidis

<400> SEQUENCE: 4

```
Glu Glu Val Asn Ser Asp Gly Gln Leu Thr Leu Gly Glu Val Lys Gln
1               5                   10                  15

Thr Ser Gln Gln Glu Met Thr Leu Ala Leu Gln Gly Lys Ala Gln Pro
            20                  25                  30

Val Thr Gln Glu Val Val His Tyr Ser Ala Asn Val Ser Ile Lys
        35                  40                  45

Ala Ala His Trp Ala Ala Pro Asn Asn Thr Arg Lys Ile Gln Val Asp
    50                  55                  60

Asp Gln Lys Lys Gln Ile Gln Ile Glu Leu Asn Gln Gln Ala Leu Ala
```

```
                65                  70                  75                  80
Asp Thr Leu Val Leu Thr Leu Asn Pro Thr Ala Thr Glu Asp Val Thr
                        85                  90                  95

Phe Ser Tyr Gly Gln Gln Gln Arg Ala Leu Thr Leu Lys Thr Gly Thr
                100                 105                 110

Asp Pro Thr Glu Ser Thr Ala Ile Thr Ser Pro Ala Ala Ser Ala
                115                 120                 125

Asn Glu Gly Ser Thr Glu Ala Ser Thr Asn Ser Ser Val Pro Arg
        130                 135                 140

Ser Ser Glu Glu Thr Val Ala Ser Thr Thr Lys Ala Ile Glu Ser Lys
145                 150                 155                 160

Thr Thr Glu Ser Thr Thr Val Lys Pro Arg Val Ala Gly Pro Thr Asp
                    165                 170                 175

Ile Ser Asp Tyr Phe Thr Gly Asp Glu Thr Thr Ile Ile Asp Asn Phe
                180                 185                 190

Glu Asp Pro Ile Tyr Leu Asn Pro Asp Gly Thr Pro Ala Thr Pro Pro
            195                 200                 205

Tyr Lys Glu Asp Val Thr Ile His Trp Asn Phe Asn Trp Ser Ile Pro
210                 215                 220

Glu Asp Val Arg Glu Gln Met Lys Ala Gly Asp Tyr Phe Glu Phe Gln
225                 230                 235                 240

Leu Pro Gly Asn Leu Lys Pro Asn Lys Pro Gly Ser Gly Asp Leu Val
                245                 250                 255

Asp Ala Glu Gly Asn Val Tyr Gly Thr Tyr Thr Ile Ser Glu Asp Gly
            260                 265                 270

Thr Val Arg Phe Thr Phe Asn Glu Arg Ile Thr Ser Glu Ser Asp Ile
        275                 280                 285

His Gly Asp Phe Ser Leu Asp Thr His Leu Asn Asp Ser Asp Gly Arg
        290                 295                 300

Gly Pro Gly Asp Trp Val Ile Asp Ile Pro Thr Gln Glu Asp Leu Pro
305                 310                 315                 320

Pro Val Val Ile Pro Ile Val Pro Asp Thr Glu Gln Gln Ile Asp Lys
                325                 330                 335

Gln Gly His Phe Asp Arg Thr Pro Asn Pro Ser Ala Ile Thr Trp Thr
                340                 345                 350

Val Asp Ile Asn Gln Ala Met Lys Asp Gln Thr Asn Pro Thr Val Thr
            355                 360                 365

Glu Thr Trp Pro Thr Gly Asn Thr Phe Lys Ser Val Lys Val Tyr Glu
        370                 375                 380

Leu Val Met Asn Leu Asp Gly Thr Ile Lys Glu Val Gly Arg Glu Leu
385                 390                 395                 400

Ser Pro Asp Glu Tyr Thr Val Asp Lys Asn Gly Asn Val Thr Ile Lys
                405                 410                 415

Gly Asp Thr Asn Lys Ala Tyr Arg Leu Glu Tyr Gln Thr Thr Ile Asp
                420                 425                 430

Glu Ala Val Ile Pro Asp Gly Gly Asp Val Pro Phe Lys Asn His
            435                 440                 445

Ala Thr Leu Thr Ser Asp Asn Pro Asn Gly Leu Asp Ala Glu Ala
        450                 455                 460

Thr Val Thr Ala Thr Tyr Gly Lys Met Leu Asp Lys Arg Asn Ile Asp
465                 470                 475                 480

Tyr Asp Glu Ala Asn Gln Glu Phe Thr Trp Glu Ile Asn Tyr Asn Tyr
                485                 490                 495
```

```
Gly Glu Gln Thr Ile Pro Lys Asp Gln Ala Val Ile Thr Asp Thr Met
            500                 505                 510

Gly Asp Asn Leu Thr Phe Glu Pro Asp Ser Leu His Leu Tyr Ser Val
        515                 520                 525

Thr Phe Asp Asp Lys Gly Asn Glu Val Val Gly Ala Glu Leu Val Glu
    530                 535                 540

Gly Lys Asp Tyr Lys Val Val Ile Asn Gly Asp Gly Ser Phe Ala Ile
545                 550                 555                 560

Asp Phe Leu His Asp Val Thr Gly Ala Val Lys Ile Asp Tyr Lys Thr
            565                 570                 575

Lys Val Asp Gly Ile Val Glu Gly Asp Val Ala Val Asn Asn Arg Val
        580                 585                 590

Asp Val Gly Thr Gly Gln His Ser Glu Asp Asp Gly Thr Ala Ser Gln
    595                 600                 605

Gln Asn Ile Ile Lys Asn Thr Gly Ala Val Asp Tyr Gln Asn Ser Thr
610                 615                 620

Ile Gly Trp Thr Leu Ala Val Asn Gln Asn Asn Tyr Leu Met Glu Asn
625                 630                 635                 640

Ala Val Ile Thr Asp Thr Tyr Glu Pro Val Pro Gly Leu Thr Met Val
            645                 650                 655

Pro Asn Ser Leu Val Val Lys Asp Thr Thr Gly Ala Gln Leu Thr
        660                 665                 670

Leu Gly Lys Asp Phe Met Val Glu Ile Thr Arg Asn Ala Asp Gly Glu
    675                 680                 685

Thr Gly Phe Lys Val Ser Phe Ile Gly Ala Tyr Ala Lys Thr Ser Asp
690                 695                 700

Ala Phe His Ile Thr Tyr Thr Thr Phe Phe Asp Val Thr Glu Leu Asp
705                 710                 715                 720

Ala Asn Asn Pro Ala Leu Asp His Tyr Arg Asn Thr Ala Ala Ile Asp
            725                 730                 735

Trp Thr Asp Glu Ala Gly Asn His His Ser Glu Asp Ser Lys Pro
        740                 745                 750

Phe Lys Pro Leu Pro Ala Phe Asp Leu Asn Ala Gln Lys Ser Gly Val
    755                 760                 765

Tyr Asn Ala Val Thr Lys Glu Ile Thr Trp Thr Ile Ala Val Asn Leu
770                 775                 780

Ser Asn Asn Arg Leu Val Asp Ala Phe Leu Thr Asp Pro Ile Leu Thr
785                 790                 795                 800

Asn Gln Thr Tyr Leu Ala Gly Ser Leu Lys Val Tyr Glu Gly Asn Thr
            805                 810                 815

Lys Pro Asp Gly Ser Val Glu Lys Val Lys Pro Thr Gln Pro Leu Thr
        820                 825                 830

Asp Ile Thr Met Glu Glu Pro Ser Glu Lys Asn Gln Asn Thr Trp Arg
    835                 840                 845

Val Asp Phe Pro Asn Asp Ser Arg Thr Tyr Val Ile Glu Phe Lys Thr
850                 855                 860

Ser Val Asp Glu Lys Val Ile Glu Gly Ser Ala Ser Tyr Asp Asn Thr
865                 870                 875                 880

Ala Ser Tyr Thr Asn Gln Gly Ser Ser Arg Asp Val Thr Gly Lys Val
            885                 890                 895

Ser Ile Gln His Gly Gly Glu Ser Val Lys Lys Gly Gly Glu Tyr His
        900                 905                 910
```

-continued

```
Lys Asp Asp Pro Asp His Val Tyr Trp His Val Met Ile Asn Gly Ala
            915                 920                 925

Gln Ser Val Leu Asp Asp Val Ile Thr Asp Thr Pro Ser Pro Asn
    930                 935                 940

Gln Val Leu Asp Pro Glu Ser Leu Val Ile Tyr Gly Thr Asn Val Thr
945                 950                 955                 960

Glu Asp Gly Thr Ile Thr Pro Asp Lys Ser Val Ile Leu Glu Gly
            965                 970                 975

Lys Asp Tyr Thr Leu Glu Val Thr Thr Asp Asn Glu Thr Gly Gln Gln
            980                 985                 990

Lys Ile Val Val Lys Met Ala His  Ile Glu Ala Pro Tyr  Tyr Met Glu
            995                 1000                1005

Tyr Arg Ser Leu Val Thr Ser  Ser Ala Ala Gly Ser  Thr Asp Thr
        1010                1015                1020

Val Ser Asn Gln Val Ser Ile  Thr Gly Asn Gly Ser  Glu Val Val
    1025                1030                1035

His Gly Asp Asp Asn Gly Asp  Val Val Asp Ile  Asp His Ser
    1040                1045                1050

Gly Gly His Ala Thr Gly Thr  Lys Gly Lys Ile Gln  Leu Lys Lys
    1055                1060                1065

Thr Ala Met Asp Glu Thr Thr  Ile Leu Ala Gly Ala  His Phe Gln
    1070                1075                1080

Ile Trp Asp Gln Ala Lys Thr  Gln Val Leu Arg Glu  Gly Thr Val
    1085                1090                1095

Asp Ala Thr Gly Val Ile Thr  Phe Gly Gly
    1100                1105

<210> SEQ ID NO 5
<211> LENGTH: 999
<212> TYPE: PRT
<213> ORGANISM: Staphylococcus epidermidis

<400> SEQUENCE: 5

Glu Glu Ile Thr Asp Leu Phe Leu Gln Lys Glu Val Thr Tyr Ser Gly
1               5                   10                  15

Val Glu Gly Gly Lys Ile Gly Glu Asn Trp Lys Tyr Pro Gln Phe Val
            20                  25                  30

Gly Glu Lys Ala Val Asp Gly Asp Glu Thr Thr Arg Trp Ser Ala Asp
        35                  40                  45

Lys Gln Asp Glu Gln Trp Leu Ile Val Asp Leu Gly Glu Val Lys Asn
    50                  55                  60

Ile Gly Glu Leu Val Leu Gln Leu His Ala Glu Ser Pro Val Tyr Glu
65                  70                  75                  80

Ile Leu Val Ser Thr Asp Gly Glu Ser Tyr Gln Ser Ile Phe Lys Glu
                85                  90                  95

Glu Asn Gly Lys Gly Gly Gln Pro Thr Lys Lys Tyr Ile Asp Gly Asn
            100                 105                 110

Asn Val Gln Ala Arg Phe Val Lys Tyr Gln Gln Met Lys Met Trp Gln
        115                 120                 125

His Thr Asn Lys Gln Phe Tyr Ser Ser Ile Ile Ser Phe Glu Ala
    130                 135                 140

Tyr Glu Lys Lys Arg Leu Pro Glu Ala Ile Lys Leu Leu Thr Glu Asn
145                 150                 155                 160

Leu Thr Ile Ser Glu Lys Arg Lys Gln Gln Leu Ala Phe Glu Val Ser
                165                 170                 175
```

-continued

Pro Ala Gly Val Asp Ile Thr Glu Asp Gln Ile Glu Trp Ser Ser Ser
          180                 185                 190

Asp Pro Thr Ile Val Thr Val Asp Gln Thr Gly Asn Leu Thr Ala Val
          195                 200                 205

Lys Ser Gly Glu Ala Lys Val Thr Val Lys Ile Lys Gly Thr Glu Ile
210                 215                 220

Ser Asp Thr Ile Pro Val Thr Val Ala Glu Asn Lys Gln Tyr Ala
225                 230                 235                 240

Glu Met Arg Ala Lys Trp Lys Met Arg Leu Leu Gly Thr Thr Gln Tyr
                245                 250                 255

Asp Asn Asp Ala Asp Val Gln Gln Tyr Arg Ala Gln Ile Ala Thr Glu
              260                 265                 270

Ser Leu Ala Leu Trp Gln Thr Leu Asn Gln Ala Ala Asp Arg Glu Tyr
              275                 280                 285

Leu Trp Glu Arg Lys Pro Ser Asp Thr Val Ser Ala Asp Tyr Thr Thr
          290                 295                 300

Gln Phe Thr Asn Ile Lys Lys Leu Ala Leu Gly Tyr Tyr Glu Pro Ser
305                 310                 315                 320

Ser Glu Leu Phe Glu Lys Pro Glu Val Tyr Asp Ala Ile Val Lys Gly
                325                 330                 335

Ile Glu Phe Met Ile Asp Thr Lys Lys Tyr Asn Gly Tyr Tyr Thr
              340                 345                 350

Gly Asn Trp Trp Asp Trp Gln Ile Gly Ser Ala Gln Pro Leu Thr Asp
          355                 360                 365

Thr Leu Ile Leu His Asp Asp Leu Leu Asn Thr Asp Ala Glu Lys
          370                 375                 380

Leu Asn Lys Phe Thr Ala Pro Leu Met Leu Tyr Ala Lys Asp Pro Asn
385                 390                 395                 400

Ile Gln Trp Pro Ile Tyr Arg Ala Thr Gly Ala Asn Leu Thr Asp Ile
              405                 410                 415

Ser Ile Thr Val Leu Gly Thr Gly Leu Leu Leu Glu Asp Asn Gln Arg
          420                 425                 430

Leu Val Gln Val Gln Glu Ala Val Pro Ser Val Leu Lys Ser Val Ser
          435                 440                 445

Ser Gly Asp Gly Leu Tyr Pro Asp Gly Ser Leu Ile Gln His Gly Tyr
450                 455                 460

Phe Pro Tyr Asn Gly Ser Tyr Gly Asn Glu Leu Leu Lys Gly Phe Gly
465                 470                 475                 480

Arg Ile Gln Thr Ile Leu Gln Gly Ser Asp Trp Glu Met Asn Asp Pro
              485                 490                 495

Asn Ile Ser Asn Leu Phe Asn Val Val Asp Lys Gly Tyr Leu Gln Leu
              500                 505                 510

Met Val Asn Gly Lys Met Pro Ser Met Val Ser Gly Arg Ser Ile Ser
          515                 520                 525

Arg Ala Pro Glu Thr Asn Pro Phe Thr Thr Glu Phe Glu Ser Gly Lys
          530                 535                 540

Glu Thr Ile Ala Asn Leu Thr Leu Ile Ala Lys Phe Ala Pro Glu Asn
545                 550                 555                 560

Leu Arg Asn Asp Ile Tyr Thr Ser Ile Gln Thr Trp Leu Gln Gln Ser
                565                 570                 575

Gly Ser Tyr Tyr His Phe Phe Lys Lys Pro Arg Asp Phe Glu Ala Leu
          580                 585                 590

```
Ile Asp Leu Lys Asn Val Val Asn Ser Ala Ser Pro Ala Gln Ala Thr
        595                 600                 605
Pro Met Gln Ser Leu Asn Val Tyr Gly Ser Met Asp Arg Val Leu Gln
        610                 615                 620
Lys Asn Asn Glu Tyr Ala Val Gly Ile Ser Met Tyr Ser Gln Arg Val
625                 630                 635                 640
Gly Asn Tyr Glu Phe Gly Asn Thr Glu Asn Lys Lys Gly Trp His Thr
                645                 650                 655
Ala Asp Gly Met Leu Tyr Leu Tyr Asn Gln Asp Phe Ala Gln Phe Asp
                660                 665                 670
Glu Gly Tyr Trp Ala Thr Ile Asp Pro Tyr Arg Leu Pro Gly Thr Thr
                675                 680                 685
Val Asp Thr Arg Glu Leu Ala Asn Gly Ala Tyr Thr Gly Lys Arg Ser
        690                 695                 700
Pro Gln Ser Trp Val Gly Gly Ser Asn Gly Gln Val Ala Ser Ile
705                 710                 715                 720
Gly Met Phe Leu Asp Lys Ser Asn Glu Gly Met Asn Leu Val Ala Lys
                725                 730                 735
Lys Ser Trp Phe Leu Leu Asp Gly Gln Ile Ile Asn Leu Gly Ser Gly
                740                 745                 750
Ile Thr Gly Thr Thr Asp Ala Ser Ile Glu Thr Ile Leu Asp Asn Arg
        755                 760                 765
Met Ile His Pro Gln Glu Val Lys Leu Asn Gln Gly Ser Asp Lys Asp
        770                 775                 780
Asn Ser Trp Ile Ser Leu Ser Ala Ala Asn Pro Leu Asn Asn Ile Gly
785                 790                 795                 800
Tyr Val Phe Pro Asn Ser Met Asn Thr Leu Asp Val Gln Ile Glu Glu
                805                 810                 815
Arg Ser Gly Arg Tyr Gly Asp Ile Asn Glu Tyr Phe Val Asn Asp Lys
                820                 825                 830
Thr Tyr Thr Asn Thr Phe Ala Lys Ile Ser Lys Asn Tyr Gly Lys Thr
        835                 840                 845
Val Glu Asn Gly Thr Tyr Glu Tyr Leu Thr Val Val Gly Lys Thr Asn
        850                 855                 860
Glu Glu Ile Ala Ala Leu Ser Lys Asn Lys Gly Tyr Thr Val Leu Glu
865                 870                 875                 880
Asn Thr Ala Asn Leu Gln Ala Ile Glu Ala Gly Asn Tyr Val Met Met
                885                 890                 895
Asn Thr Trp Asn Asn Asp Gln Glu Ile Ala Gly Leu Tyr Ala Tyr Asp
                900                 905                 910
Pro Met Ser Val Ile Ser Glu Lys Ile Asp Asn Gly Val Tyr Arg Leu
                915                 920                 925
Thr Leu Ala Asn Pro Leu Gln Asn Asn Ala Ser Val Ser Ile Glu Phe
        930                 935                 940
Asp Lys Gly Ile Leu Glu Val Ala Ala Asp Pro Glu Ile Ser Val
945                 950                 955                 960
Asp Gln Asn Ile Ile Thr Leu Asn Ser Ala Gly Leu Asn Gly Ser Ser
                965                 970                 975
Arg Ser Ile Ile Val Lys Thr Thr Pro Glu Val Thr Lys Glu Ala Leu
                980                 985                 990
Glu Lys Leu Ile Gln Glu Gln
        995
```

<210> SEQ ID NO 6
<211> LENGTH: 741
<212> TYPE: PRT
<213> ORGANISM: Staphylococcus epidermidis

<400> SEQUENCE: 6

Gln Glu Val Thr Ser Asp Ala Glu Lys Thr Val Glu Lys Asp Gly Leu
1               5                   10                  15

Lys Val Ile Gly Lys Ile Glu Asp Thr Ser Ser Gln Glu Asp Ile Lys
            20                  25                  30

Thr Val Thr Tyr Glu Val Thr Asn Thr Arg Asp Val Pro Ile Lys Asp
        35                  40                  45

Leu Ile Leu Lys Gln Lys Asn Thr Asn Asp Ser Pro Ile Lys Phe Val
    50                  55                  60

Leu Asp Thr Leu Ser Glu Arg Gly Pro Thr Ser Leu Glu Glu Gln
65                  70                  75                  80

Ala Lys Val Glu Thr Asn Glu Lys Asp Gln Thr Thr Asp Ile Lys Leu
                85                  90                  95

Leu Asn Leu Gln Pro Asn Ser Thr Arg Lys Ile Thr Ile Asn Gly Gln
            100                 105                 110

Ile Thr Thr Lys Ala Ser Asn Lys Leu Leu Val Ser Val Leu Ile Glu
        115                 120                 125

Asp Asn Glu Lys Gly Thr Leu Val Ile Asp Leu Pro Ser Lys Asp Ile
    130                 135                 140

Leu Ala Asp Lys Glu Ser Val Ser Lys Glu Lys Gln Glu Thr Ser Glu
145                 150                 155                 160

Thr Lys Val Glu Asn Gln Ala Asn Glu Thr Ala Ser Ser Thr Asn Glu
                165                 170                 175

Met Thr Ala Thr Thr Ser Asn Glu Thr Lys Pro Glu Ala Gly Lys Ala
            180                 185                 190

Ile Glu Ser Ile Gln Glu Thr Ala Leu Thr Gln Ala Thr Glu Ser Pro
        195                 200                 205

Glu Gln Pro Pro Leu Lys Ala Gln Pro Thr Gly Pro Leu Val Pro Pro
    210                 215                 220

Thr Pro Gly Arg Gly Phe Asn Thr Pro Ile Tyr Gln Ser Val His Lys
225                 230                 235                 240

Gly Glu Leu Phe Ser Thr Gly Asn Thr Asn Leu Lys Ile Ala Asn Glu
                245                 250                 255

Asn Thr Ala Ala Ala Gln Thr Phe Leu Asn Thr Arg Gly Ala Ser Ser
            260                 265                 270

Gly Tyr Ala Ile Asn Asn Phe Pro Leu Glu Phe Ala Asp Val Asp Asn
        275                 280                 285

Asp Pro Asn Thr Tyr Asn Ser Ser Arg Ala Tyr Ile Asp Leu Asn Gly
    290                 295                 300

Ala Lys Glu Ile Ala Trp Ala Gly Leu Phe Trp Ser Ala Ser Arg Tyr
305                 310                 315                 320

Lys Gly Pro Ala Tyr Gly Thr Asn Leu Ser Asp Glu Glu Ile Ser Ala
                325                 330                 335

Pro Val Gln Phe Thr Thr Pro Asn Gly Thr Val Gln Arg Val Ser Pro
            340                 345                 350

Gln Arg Tyr His Arg Ile Asp Gln Asp Ala Thr Asn Pro Gly Gln Arg
        355                 360                 365

Phe Gly Tyr Asn Asn Thr Gly Phe Ser Asn Tyr Ala Asp Val Thr Ser
    370                 375                 380

```
Ile Leu Gln Gly Asp Lys Ser Ala Thr Gly Ser Tyr Thr Leu Ala Asp
385                 390                 395                 400

Ile Pro Met Thr Ser Ser Leu Asn Gly Gln Tyr Gln Tyr Tyr Asn Phe
            405                 410                 415

Ser Gly Trp Ser Leu Phe Val Val Thr Lys Asp Gln Ala Ser Lys Ser
            420                 425                 430

Arg Ala Phe Ser Ile Tyr Tyr Gly Ala Arg Gly Asn Ala Ala Gly Thr
            435                 440                 445

Asn Asn Glu Phe Thr Met Ser Asn Phe Leu Thr Ala Lys Gln Gly Asn
450                 455                 460

Leu Asp Pro Ile Val Thr Trp Phe Thr Val Gln Gly Asp Lys Tyr Trp
465                 470                 475                 480

Thr Gly Asp Asn Ala Gln Ile Lys Asn Ser Ala Gly Thr Trp Val Asn
            485                 490                 495

Ile Ser Asn Thr Leu Asn Pro Val Asn Asn Ala Met Asn Ala Thr Val
            500                 505                 510

Thr Asp Asn Asp Glu His Met Val Asp Lys Tyr Pro Gly Lys Phe Ala
            515                 520                 525

Pro Asp His Pro Asn Phe Leu Asp Ile Asp Ile Asp Arg Met Ala Ile
530                 535                 540

Pro Glu Gly Val Leu Asn Ala Gly Gln Asn Gln Ile Asn Phe Arg Thr
545                 550                 555                 560

Thr Ser Ser Gly Asp Asp Tyr Ser Thr Asn Ala Ile Gly Phe Ala Val
            565                 570                 575

Asn Ala Glu Thr Pro Glu Phe Glu Ile Lys Lys Glu Ile Val Glu Pro
            580                 585                 590

Lys Glu Thr Tyr Lys Val Gly Glu Thr Ile Thr Tyr Arg Val Ser Leu
            595                 600                 605

Lys Asn Thr Lys Ala Asp Ser Glu Ala Ile Asn Ser Val Ser Lys Asp
            610                 615                 620

Ala Leu Asp Gly Arg Leu Asn Tyr Leu Pro Gly Ser Leu Lys Ile Ile
625                 630                 635                 640

Ser Gly Pro Asn Ser Gly Glu Lys Thr Asp Ala Ser Gly Asp Asp Gln
            645                 650                 655

Ala Glu Tyr Asp Glu Thr Asn Lys Gln Ile Ile Val Arg Val Gly Asn
            660                 665                 670

Gly Ala Thr Ala Thr Gln Gly Gly Ser Tyr Lys Ala Asp Thr Ala Glu
            675                 680                 685

Thr Ile Tyr Glu Phe Lys Ala Arg Ile Asn Glu Arg Ala Lys Ala Asn
            690                 695                 700

Glu Leu Val Pro Asn Ser Ala Thr Val Glu Ala Val Asp Ile Leu Thr
705                 710                 715                 720

Ser Ala Lys Val Asn Glu Thr Ser Asn Ile Val Glu Ala Lys Ile Ala
            725                 730                 735

Asp Glu Gln Val Thr
            740

<210> SEQ ID NO 7
<211> LENGTH: 570
<212> TYPE: PRT
<213> ORGANISM: Staphylococcus epidermidis

<400> SEQUENCE: 7

Glu Thr Gly Tyr Ala Gln Thr Glu Pro Thr Ser Thr Ser Glu Thr Asn
1               5                   10                  15
```

-continued

```
Gln Ile Ser Ala Thr Pro Asn Val Val Pro Arg Lys Gln Val Gly Asn
             20                  25                  30

Ile Val Thr Ala Ile Gln Leu Thr Asp Lys Glu Gly Asn Pro Leu Gly
         35                  40                  45

Thr Ile Asn Gln Tyr Thr Asp Ile Tyr Leu Arg Ile Glu Phe Asn Leu
     50                  55                  60

Pro Asp Asn Thr Val Asn Ser Gly Asp Thr Ser Val Ile Thr Leu Pro
 65                  70                  75                  80

Glu Glu Leu Arg Leu Glu Lys Asn Met Thr Phe Asn Val Val Asp Asp
                 85                  90                  95

Thr Gly Thr Val Val Ala Ile Ala Gln Thr Asp Val Ala Asn Lys Thr
            100                 105                 110

Val Thr Leu Thr Tyr Thr Asp Tyr Val Glu Asn His Ala Asn Ile Ser
        115                 120                 125

Gly Ser Leu Tyr Phe Thr Ser Leu Ile Asp Phe Glu Asn Val Glu Asn
    130                 135                 140

Glu Ser Lys Ile Pro Ile Tyr Val Thr Val Glu Gly Glu Lys Ile Phe
145                 150                 155                 160

Ala Gly Asp Leu Asp Tyr Gln Gly Glu Gly Asp Val Asn Glu Lys
                165                 170                 175

Phe Ser Lys Tyr Ser Trp Phe Ile Glu Asp Pro Thr Glu Ile Tyr
            180                 185                 190

Asn Val Leu Arg Ile Asn Pro Thr Gly Gln Thr Tyr Thr Asp Leu Glu
        195                 200                 205

Val Glu Asp Val Leu Lys Thr Glu Ser Leu Ser Tyr Met Lys Asp Thr
    210                 215                 220

Met Lys Ile Glu Arg Gly Gln Trp Thr Leu Asp Gly Asn Ala Ile Trp
225                 230                 235                 240

Gln Phe Thr Pro Glu Glu Asp Ile Thr Asp Gln Leu Ala Val Gln Tyr
                245                 250                 255

Gly Pro Asp Asp Arg Asn Phe Ser Val His Phe Gly Asn Ile Gly Thr
            260                 265                 270

Asn Glu Tyr Arg Ile Thr Tyr Lys Thr Lys Ile Asp His Leu Pro Glu
        275                 280                 285

Lys Gly Glu Thr Phe Thr Asn Tyr Ala Lys Leu Thr Glu Asn Gln Thr
    290                 295                 300

Val Val Glu Glu Val Glu Val Ser Arg Val Ser Gln Thr Gly Gly Gly
305                 310                 315                 320

Glu Ala Asn Gly Glu Gln Tyr Val Val Glu Ile His Lys Glu Asp Glu
                325                 330                 335

Ala Gly Gln Arg Leu Ala Gly Ala Glu Phe Glu Leu Ile Arg Asn Ser
            340                 345                 350

Thr Asn Gln Thr Val Ala Lys Ile Thr Asp Gln Asn Gly Thr Ala
        355                 360                 365

Ile Val Lys Gly Leu Leu Lys Asp Asn Tyr Thr Leu Val Glu Thr Lys
    370                 375                 380

Ala Pro Thr Gly Tyr Gln Leu Ser Gln Asn Lys Ile Pro Ile Thr Pro
385                 390                 395                 400

Glu Asp Phe Gly Lys Asn Leu Val Ala Leu Lys Thr Val Val Asn His
                405                 410                 415

Lys Ile Ser Tyr Gln Pro Val Ala Ala Ser Phe Leu Ala Gly Lys Val
            420                 425                 430
```

```
Leu Leu Gly Lys Pro Leu Lys Asp Ala Glu Phe Gln Phe Glu Leu Leu
            435                 440                 445

Asp Glu Lys Gly Thr Val Leu Glu Thr Val Ser Asn Asp Thr Leu Gly
        450                 455                 460

Lys Ile Gln Phe Ser Pro Leu Thr Phe Glu Thr Pro Gly Asn Tyr Gln
465                 470                 475                 480

Tyr Thr Ile Arg Glu Val Asn Thr Gln Gln Thr Gly Val Ser Tyr Asp
                485                 490                 495

Thr His Asn Leu Gln Val Gln Val Thr Val Glu Ala Leu Leu Gly Asn
            500                 505                 510

Leu Val Ala Thr Thr Gln Tyr Asp Gly Gly Gln Val Phe Thr Asn His
        515                 520                 525

Tyr Thr Pro Glu Lys Pro Ile Glu Ser Thr Thr Pro Pro Thr Ser Gly
530                 535                 540

Thr Thr Asp Thr Thr Thr Asn Ser Thr Thr Glu Thr Thr Ser Ile Thr
545                 550                 555                 560

Ile Glu Lys Gln Ala Ile Arg Asn Lys Glu
            565                 570

<210> SEQ ID NO 8
<211> LENGTH: 3309
<212> TYPE: DNA
<213> ORGANISM: Staphylococcus epidermidis

<400> SEQUENCE: 8
atgataacag atgagaatga taaaacgaat attaatatcg agttaaatct tctcaaccaa      60
acagagcagc cattacaacg agaaattcaa ttgaaaaatg cacagttcat ggatactgct     120
gtaattgaaa agacggata ttcttaccaa gtgactaatg gtacgcttta tctgactttg     180
gacgcacaag taaaaaagcc ggtacagctt cgttagctg ttgagcaaag ttcgcttcaa     240
acagctcagc cacctaagtt attgtatgaa acaacgaat atgatgtttc agttacttct     300
gaaaaaataa cagtagagga ttctgctaaa gaatcaactg aaccagaaaa aataactgta     360
ccagaaaata cgaaagaaac taacaaaaat gattcggctc agaaaaaac agaacagccg     420 accgcaacag aagaggtaac caatccattt gcagaagcaa gaatggcgcc agctactttg     480
agagcgaatc tggcactgcc tttaattgca ccacaataca cgacggataa ttctgggact     540
tatccgacag ctaattggca gcccacaggc aatcaaaatg tgttaaacca tcaagggaat     600
aaagacggta gtgcacaatg ggacggccaa acgagttgga atggggaccc tactaatcgc     660
acaaattctt atattgagta tggcggtaca ggagaccaag ccgattatgc catccgaaaa     720
tatgctagag aaacaacaac accagggctt tttgatgtat atcttaatgt gcgtgggaat     780
gttcagaaag aaatcacgcc attggatttg gtcttagtcg ttgactggtc cggtagtatg     840
aatgaaaaca tcggattgg tgaagttcaa aaaggagtga accgttttgt tgatacattg     900
gcagatagcg gtattaccaa taacatcaac atgggctatg ttggctactc aagtgacggt     960
tataataaca acgccattca atggggccg tttgatacag tcaaaaatcc aattaaaaat    1020
attacgccaa gtagcactag aggaggaact ttcactcaaa aagcattaag agatgctggt    1080
gatatgttag caacgccaaa tggacataag aaagtcattg tacttttaac ggatggcgtc    1140
ccaaccttct cttataaagt gagtcgagtt caaacagagg cggatggtcg cttttacggg    1200
acacaattta cgaatcgaca agatcaacca ggtagcactt cttatatctc tggtagctat    1260
aatgcgccag atcaaaacaa tatcaataaa cggattaaca gtacgtttat cgccacgata    1320
```

```
ggtgaggcaa tggtcttaaa acaacgtggg attgaaatac atggattggg cattcaattg    1380
caaagcgatc cacgagctaa tttatctaaa caacaagttg aagataaaat gcgtgagatg    1440
gtgtcagccg atgaaaatgg agacctttat tatgaatccg cggattatgc accagacatt    1500
tctgattatt tagcgaaaaa agccgttcag atttcaggaa cggttgtaaa cggaaaagta    1560
gttgatccaa ttgctgaacc ttttaaatac gagccaaata cattatcaat gaaaagtgtg    1620
ggtcctgttc aggttcaaac attaccagaa gtgtcgctaa caggcgctac aattaatagt    1680
aatgagattt atttgggtaa agggcaagaa attcaaattc attatcaagt acgtattcaa    1740
acagagtcag aaaacttcaa acctgatttt tggtatcaaa tgaatggtcg acaacgtttt    1800
cagccattag ccacggcccc tgaaaaagtt gattttgggg ttccttcggg aaaagcacct    1860
ggcgtgaagt taaacgtgaa aaaaatctgg aagagtatg atcaagaccc gacaagtcgg    1920
ccagataatg tgatttatga attagtaga aagcaagtaa ctgacacagc caactggcaa    1980
actgggtata ttaaattatc aaaaccagaa aatgatacca gcaatagttg ggagcgcaaa    2040
aatgtaaccc aactttccaa aaccgcggat gaaagctatc aagaagttct tgggcttccc    2100
caatacaaca atcaaggaca agcttttcaat tatcaaacaa cccgtgaatt agcagttcct    2160
ggttacagtc aagaaaaaat cgacgatact acttggaaaa acacgaagca gttcaagcca    2220
ttagatttaa aagtaatcaa aaattcttcc tcaggtgaga aaaacttagt gggagccgtc    2280
tttgaattga gtggtaaaaa tgttcaaaca acattagtgg acaataaaga tggtagctat    2340
tccttgccaa aagatgtgcg cctacaaaaa ggggaacgct atacattaac tgaagtaaaa    2400
gcacctgcag acatgagtt aggcaagaaa acgacttggc aaattgaggt gagtgagcaa    2460
ggcaaagtaa gcatcgatgg acaagaagtg accaccacaa atcaagttat tccattggaa    2520
attgaaaata aattttcttc tttgccaatc agaattagaa aatacaccat gcaaaatggc    2580
aaacaagtga acttagcaga ggcgactttt gcgttgcaaa gaaaaaatgc tcaaggaagt    2640
taccaaactg tggcaactca aaaaacagat actacaggat tgagctattt taaaattagt    2700
gaacctggtg agtatcgaat ggtggaacaa tcaggaccat taggctacga cactcttgct    2760
ggaaattatg aatttactgt tgataaatat gggaaaattc actatgcagg caaaaatatt    2820
gaagaaaatg cgccagaatg gacactgaca catcaaaata atttgaaacc ttttgactta    2880
acagttaata aaaaagccga taatcagacg ccacttaaag gagcgaaatt ccgtttaaca    2940
ggaccagata cggatattga attaccaaaa gatggcaaag aaacggatac ttttgttttt    3000
gaaaacttaa aaccagggaa atatgttcta acagaaacct ttacgccaga aggatatcag    3060
gggttaaaag aaccaatcga attaataatt cgtgaagatg gttcagtcac gatagatggg    3120
gaaaaagtag cagatgtttt aatttctgga gagaagaata atcaaattac tttagacgtt    3180
acgaaccaag caaaggttcc tttacctgaa actggtggca taggacgctt gtggttttac    3240
ttgatagcga ttagtacatt cgtgatagcg ggtgtttatc tctttattag acgaccagaa    3300
gggagtgtg                                                            3309
```

<210> SEQ ID NO 9
<211> LENGTH: 1103
<212> TYPE: PRT
<213> ORGANISM: Staphylococcus epidermidis

<400> SEQUENCE: 9

```
Met Ile Thr Asp Glu Asn Asp Lys Thr Asn Ile Asn Ile Glu Leu Asn
1               5                   10                  15
```

-continued

```
Leu Leu Asn Gln Thr Glu Gln Pro Leu Gln Arg Glu Ile Gln Leu Lys
         20                  25                  30

Asn Ala Gln Phe Met Asp Thr Ala Val Ile Glu Lys Asp Gly Tyr Ser
         35                  40                  45

Tyr Gln Val Thr Asn Gly Thr Leu Tyr Leu Thr Leu Asp Ala Gln Val
 50                  55                  60

Lys Lys Pro Val Gln Leu Ser Leu Ala Val Glu Gln Ser Ser Leu Gln
 65                  70                  75                  80

Thr Ala Gln Pro Pro Lys Leu Leu Tyr Glu Asn Asn Glu Tyr Asp Val
                 85                  90                  95

Ser Val Thr Ser Glu Lys Ile Thr Val Glu Asp Ser Ala Lys Glu Ser
                100                 105                 110

Thr Glu Pro Glu Lys Ile Thr Val Pro Glu Asn Thr Lys Glu Thr Asn
                115                 120                 125

Lys Asn Asp Ser Ala Pro Glu Lys Thr Glu Gln Pro Thr Ala Thr Glu
130                 135                 140

Glu Val Thr Asn Pro Phe Ala Glu Ala Arg Met Ala Pro Ala Thr Leu
145                 150                 155                 160

Arg Ala Asn Leu Ala Leu Pro Leu Ile Ala Pro Gln Tyr Thr Thr Asp
                165                 170                 175

Asn Ser Gly Thr Tyr Pro Thr Ala Asn Trp Gln Pro Thr Gly Asn Gln
                180                 185                 190

Asn Val Leu Asn His Gln Gly Asn Lys Asp Gly Ser Ala Gln Trp Asp
                195                 200                 205

Gly Gln Thr Ser Trp Asn Gly Asp Pro Thr Asn Arg Thr Asn Ser Tyr
                210                 215                 220

Ile Glu Tyr Gly Gly Thr Gly Asp Gln Ala Asp Tyr Ala Ile Arg Lys
225                 230                 235                 240

Tyr Ala Arg Glu Thr Thr Thr Pro Gly Leu Phe Asp Val Tyr Leu Asn
                245                 250                 255

Val Arg Gly Asn Val Gln Lys Glu Ile Thr Pro Leu Asp Leu Val Leu
                260                 265                 270

Val Val Asp Trp Ser Gly Ser Met Asn Glu Asn Asn Arg Ile Gly Glu
                275                 280                 285

Val Gln Lys Gly Val Asn Arg Phe Val Asp Thr Leu Ala Asp Ser Gly
                290                 295                 300

Ile Thr Asn Asn Ile Asn Met Gly Tyr Val Gly Tyr Ser Ser Asp Gly
305                 310                 315                 320

Tyr Asn Asn Asn Ala Ile Gln Met Gly Pro Phe Asp Thr Val Lys Asn
                325                 330                 335

Pro Ile Lys Asn Ile Thr Pro Ser Ser Thr Arg Gly Gly Thr Phe Thr
                340                 345                 350

Gln Lys Ala Leu Arg Asp Ala Gly Asp Met Leu Ala Thr Pro Asn Gly
                355                 360                 365

His Lys Lys Val Ile Val Leu Leu Thr Asp Gly Val Pro Thr Phe Ser
                370                 375                 380

Tyr Lys Val Ser Arg Val Gln Thr Glu Ala Asp Gly Arg Phe Tyr Gly
385                 390                 395                 400

Thr Gln Phe Thr Asn Arg Gln Asp Gln Pro Gly Ser Thr Ser Tyr Ile
                405                 410                 415

Ser Gly Ser Tyr Asn Ala Pro Asp Gln Asn Asn Ile Asn Lys Arg Ile
                420                 425                 430

Asn Ser Thr Phe Ile Ala Thr Ile Gly Glu Ala Met Val Leu Lys Gln
```

-continued

```
            435                 440                 445
Arg Gly Ile Glu Ile His Gly Leu Gly Ile Gln Leu Gln Ser Asp Pro
450                 455                 460
Arg Ala Asn Leu Ser Lys Gln Gln Val Glu Asp Lys Met Arg Glu Met
465                 470                 475                 480
Val Ser Ala Asp Glu Asn Gly Asp Leu Tyr Tyr Glu Ser Ala Asp Tyr
                485                 490                 495
Ala Pro Asp Ile Ser Asp Tyr Leu Ala Lys Lys Ala Val Gln Ile Ser
                500                 505                 510
Gly Thr Val Val Asn Gly Lys Val Val Asp Pro Ile Ala Glu Pro Phe
                515                 520                 525
Lys Tyr Glu Pro Asn Thr Leu Ser Met Lys Ser Val Gly Pro Val Gln
                530                 535                 540
Val Gln Thr Leu Pro Glu Val Ser Leu Thr Gly Ala Thr Ile Asn Ser
545                 550                 555                 560
Asn Glu Ile Tyr Leu Gly Lys Gly Gln Glu Ile Gln Ile His Tyr Gln
                565                 570                 575
Val Arg Ile Gln Thr Glu Ser Glu Asn Phe Lys Pro Asp Phe Trp Tyr
                580                 585                 590
Gln Met Asn Gly Arg Thr Thr Phe Gln Pro Leu Ala Thr Ala Pro Glu
                595                 600                 605
Lys Val Asp Phe Gly Val Pro Ser Gly Lys Ala Pro Gly Val Lys Leu
                610                 615                 620
Asn Val Lys Lys Ile Trp Glu Glu Tyr Asp Gln Asp Pro Thr Ser Arg
625                 630                 635                 640
Pro Asp Asn Val Ile Tyr Glu Ile Ser Arg Lys Gln Val Thr Asp Thr
                645                 650                 655
Ala Asn Trp Gln Thr Gly Tyr Ile Lys Leu Ser Lys Pro Glu Asn Asp
                660                 665                 670
Thr Ser Asn Ser Trp Glu Arg Lys Asn Val Thr Gln Leu Ser Lys Thr
                675                 680                 685
Ala Asp Glu Ser Tyr Gln Glu Val Leu Gly Leu Pro Gln Tyr Asn Asn
                690                 695                 700
Gln Gly Gln Ala Phe Asn Tyr Gln Thr Thr Arg Glu Leu Ala Val Pro
705                 710                 715                 720
Gly Tyr Ser Gln Glu Lys Ile Asp Asp Thr Thr Trp Lys Asn Thr Lys
                725                 730                 735
Gln Phe Lys Pro Leu Asp Leu Lys Val Ile Lys Asn Ser Ser Ser Gly
                740                 745                 750
Glu Lys Asn Leu Val Gly Ala Val Phe Glu Leu Ser Gly Lys Asn Val
                755                 760                 765
Gln Thr Thr Leu Val Asp Asn Lys Asp Gly Ser Tyr Ser Leu Pro Lys
                770                 775                 780
Asp Val Arg Leu Gln Lys Gly Glu Arg Tyr Thr Leu Thr Glu Val Lys
785                 790                 795                 800
Ala Pro Ala Gly His Glu Leu Gly Lys Lys Thr Thr Trp Gln Ile Glu
                805                 810                 815
Val Ser Glu Gln Gly Lys Val Ser Ile Asp Gly Gln Glu Val Thr Thr
                820                 825                 830
Thr Asn Gln Val Ile Pro Leu Glu Ile Glu Asn Lys Phe Ser Ser Leu
                835                 840                 845
Pro Ile Arg Ile Arg Lys Tyr Thr Met Gln Asn Gly Lys Gln Val Asn
850                 855                 860
```

Leu Ala Glu Ala Thr Phe Ala Leu Gln Arg Lys Asn Ala Gln Gly Ser
865                 870                 875                 880

Tyr Gln Thr Val Ala Thr Gln Lys Thr Asp Thr Thr Gly Leu Ser Tyr
            885                 890                 895

Phe Lys Ile Ser Glu Pro Gly Glu Tyr Arg Met Val Glu Gln Ser Gly
            900                 905                 910

Pro Leu Gly Tyr Asp Thr Leu Ala Gly Asn Tyr Glu Phe Thr Val Asp
            915                 920                 925

Lys Tyr Gly Lys Ile His Tyr Ala Gly Lys Asn Ile Glu Glu Asn Ala
930                 935                 940

Pro Glu Trp Thr Leu Thr His Gln Asn Asn Leu Lys Pro Phe Asp Leu
945                 950                 955                 960

Thr Val Asn Lys Lys Ala Asp Asn Gln Thr Pro Leu Lys Gly Ala Lys
                965                 970                 975

Phe Arg Leu Thr Gly Pro Asp Thr Asp Ile Glu Leu Pro Lys Asp Gly
            980                 985                 990

Lys Glu Thr Asp Thr Phe Val Phe Glu Asn Leu Lys Pro Gly Lys Tyr
            995                 1000                1005

Val Leu Thr Glu Thr Phe Thr Pro Glu Gly Tyr Gln Gly Leu Lys
    1010                1015                1020

Glu Pro Ile Glu Leu Ile Ile Arg Glu Asp Gly Ser Val Thr Ile
    1025                1030                1035

Asp Gly Glu Lys Val Ala Asp Val Leu Ile Ser Gly Glu Lys Asn
    1040                1045                1050

Asn Gln Ile Thr Leu Asp Val Thr Asn Gln Ala Lys Val Pro Leu
    1055                1060                1065

Pro Glu Thr Gly Gly Ile Gly Arg Leu Trp Phe Tyr Leu Ile Ala
    1070                1075                1080

Ile Ser Thr Phe Val Ile Ala Gly Val Tyr Leu Phe Ile Arg Arg
    1085                1090                1095

Pro Glu Gly Ser Val
    1100

<210> SEQ ID NO 10
<211> LENGTH: 1428
<212> TYPE: DNA
<213> ORGANISM: Staphylococcus epidermidis

<400> SEQUENCE: 10
atgaaaaacg cacgttggtt aagtatttgc gtcatgctac tcgctctttt cgggttttca      60
cagcaagcat tagcagaggc atcgcaagca agcgttcaag ttacgttgca caaattattg     120
ttccctgatg gtcaattacc agaacagcag caaaacacag gggaagaggg aacgctgctt     180
caaaattatc ggggcttaaa tgacgtcact tatcaagtct atgatgtgac ggatccgttt     240
tatcagcttc gttctgaagg aaaaacggtc caagaggcac agcgtcaatt agcagaaacc     300
ggtgcaacaa atagaaaacc gatcgcagaa gataaaacac agacaataaa tggagaagat     360
ggagtggttt cttttttcatt agctagcaaa gattcgcagc aacgagataa agcctattta     420
tttgttgaag cggaagcacc agaagtggta aaggaaaaag ctagcaaccct agtagtgatt     480 ttgcctgttc aagatccaca agggcaatcg ttaacgcata ttcatttata tccaaaaaat     540
gaagaaaatg cctatgactt accaccactt gaaaaaacgg tactcgataa gcaacaaggc     600
tttaatcaag gagagcacat taactatcag ttaacgactc agattccagc gaatatttta     660

-continued

```
ggatatcagg aattccgttt gtcagataag gcggatacaa cgttgacact tttaccagaa      720
tcaattgagg taaaagtggc tggaaaaaca gttactacag gttacacact gacgacgcaa      780
aagcatggat ttacgcttga tttttcaatt aaagacttac aaaactttgc aaatcaaaca      840
atgactgtgt cgtatcaaat gcgtttagaa aagaccgctg aacctgacac tgcgattaac      900
aacgaaggac aattagtcac ggacaaacat accttgacta aaagagccac agttcgtaca      960
ggcggcaagt cttttgtcaa agttgatagt gaaaatgcga aaatcacctt gccagaggct     1020
gtttttatcg tcaaaaatca agcggggaaa tacctcaatg aaacagcaaa cgggtatcgt     1080
tggcaaaaag aaaaagcatt agctaaaaaa ttcacgtcta atcaagccgg tgaattttca     1140
gttaaaggct taaagatgg ccagtacttc ttggaagaaa tctctgcacc aaaaggttat      1200
cttctgaatc aaacagaaat tccttttacg gtgggaaaaa attcttatgc aacgaacgga     1260
caacgaacag caccgttaca tgtaatcaat aaaaaagtaa aagagtcagg cttcttacca     1320
aaaacaaatg aagaacgttc tatttggttg acgattgcag gcctgctaat cattgggatg     1380
gtagtcattt ggctatttta tcaaaaacaa aaagaggag agagaaaa                   1428
```

<210> SEQ ID NO 11
<211> LENGTH: 476
<212> TYPE: PRT
<213> ORGANISM: Staphylococcus epidermidis

<400> SEQUENCE: 11

```
Met Lys Asn Ala Arg Trp Leu Ser Ile Cys Val Met Leu Leu Ala Leu
1               5                   10                  15

Phe Gly Phe Ser Gln Gln Ala Leu Ala Glu Ala Ser Gln Ala Ser Val
            20                  25                  30

Gln Val Thr Leu His Lys Leu Leu Phe Pro Asp Gly Gln Leu Pro Glu
        35                  40                  45

Gln Gln Gln Asn Thr Gly Glu Glu Gly Thr Leu Leu Gln Asn Tyr Arg
    50                  55                  60

Gly Leu Asn Asp Val Thr Tyr Gln Val Tyr Asp Val Thr Asp Pro Phe
65                  70                  75                  80

Tyr Gln Leu Arg Ser Glu Gly Lys Thr Val Gln Glu Ala Gln Arg Gln
                85                  90                  95

Leu Ala Glu Thr Gly Ala Thr Asn Arg Lys Pro Ile Ala Glu Asp Lys
            100                 105                 110

Thr Gln Thr Ile Asn Gly Glu Asp Gly Val Val Ser Phe Ser Leu Ala
        115                 120                 125

Ser Lys Asp Ser Gln Gln Arg Asp Lys Ala Tyr Leu Phe Val Glu Ala
    130                 135                 140

Glu Ala Pro Glu Val Val Lys Glu Lys Ala Ser Asn Leu Val Val Ile
145                 150                 155                 160

Leu Pro Val Gln Asp Pro Gln Gly Gln Ser Leu Thr His Ile His Leu
                165                 170                 175

Tyr Pro Lys Asn Glu Glu Asn Ala Tyr Asp Leu Pro Pro Leu Glu Lys
            180                 185                 190

Thr Val Leu Asp Lys Gln Gln Gly Phe Asn Gln Gly Glu His Ile Asn
        195                 200                 205

Tyr Gln Leu Thr Thr Gln Ile Pro Ala Asn Ile Leu Gly Tyr Gln Glu
    210                 215                 220

Phe Arg Leu Ser Asp Lys Ala Asp Thr Leu Thr Leu Leu Pro Glu
225                 230                 235                 240
```

Ser Ile Glu Val Lys Val Ala Gly Lys Thr Val Thr Gly Tyr Thr
            245                 250                 255

Leu Thr Thr Gln Lys His Gly Phe Thr Leu Asp Phe Ser Ile Lys Asp
            260                 265                 270

Leu Gln Asn Phe Ala Asn Gln Thr Met Thr Val Ser Tyr Gln Met Arg
            275                 280                 285

Leu Glu Lys Thr Ala Glu Pro Asp Thr Ala Ile Asn Asn Glu Gly Gln
            290                 295                 300

Leu Val Thr Asp Lys His Thr Leu Thr Lys Arg Ala Thr Val Arg Thr
305                 310                 315                 320

Gly Gly Lys Ser Phe Val Lys Val Asp Ser Glu Asn Ala Lys Ile Thr
                325                 330                 335

Leu Pro Glu Ala Val Phe Ile Val Lys Asn Gln Ala Gly Glu Tyr Leu
            340                 345                 350

Asn Glu Thr Ala Asn Gly Tyr Arg Trp Gln Lys Glu Lys Ala Leu Ala
            355                 360                 365

Lys Lys Phe Thr Ser Asn Gln Ala Gly Glu Phe Ser Val Lys Gly Leu
            370                 375                 380

Lys Asp Gly Gln Tyr Phe Leu Glu Glu Ile Ser Ala Pro Lys Gly Tyr
385                 390                 395                 400

Leu Leu Asn Gln Thr Glu Ile Pro Phe Thr Val Gly Lys Asn Ser Tyr
                405                 410                 415

Ala Thr Asn Gly Gln Arg Thr Ala Pro Leu His Val Ile Asn Lys Lys
            420                 425                 430

Val Lys Glu Ser Gly Phe Leu Pro Lys Thr Asn Glu Glu Arg Ser Ile
            435                 440                 445

Trp Leu Thr Ile Ala Gly Leu Leu Ile Ile Gly Met Val Val Ile Trp
            450                 455                 460

Leu Phe Tyr Gln Lys Gln Lys Arg Gly Glu Arg Lys
465                 470                 475

<210> SEQ ID NO 12
<211> LENGTH: 1881
<212> TYPE: DNA
<213> ORGANISM: Staphylococcus epidermidis

<400> SEQUENCE: 12
atgaagcaat taaaaaagt tggtacacc gttagtacct tgttactaat tttgccactt      60
ttcacaagtg tattagggac aacaactgca tttgcagaag aaaatgggga gagcgcacag    120
ctcgtgattc acaaaaagaa aatgacggat ttaccagatc cgcttattca aaatagcggg    180
aaagaaatga gcgagtttga taaatatcaa ggactggcag atgtgacgtt tagtattat     240 aacgtgacga acgaatttta cgagcaacga gcggcaggcg caagcgttga tgcagctaaa    300
caagctgtcc aaagtttaac tcctgggaaa cctgttgctc aaggaaccac cgatgcaaat    360
gggaatgtca ctgttcagtt acctaaaaaa caaaatggta agatgcagt gtataccatt    420 aaagaagaac aaagagggg tgtagttgct gctacgaata tggtggtggc gttcccagtt    480
tacgaaatga tcaagcaaac agatggttcc tataaatatg aacagaaga attagcggtt    540 gttcatattt atcctaaaaa tgtggtagcc aatgatggta gtttacatgt gaaaaaagta    600
ggaactgctg aaaatgaagg attaaatggc gcagaatttg ttatttctaa aagcgaaggc    660
tcaccaggca cagtaaaata tatccaagga gtcaaagatg gattatatac atggacaacg    720
gataaagaac aagcaaaacg ctttattact gggaaaagtt atgaaattgg cgaaaatgat    780

```
ttcacagaag cagagaatgg aacgggagaa ttaacagtta aaaatcttga ggttggttcg      840
tatattttag aagaagtaaa agctccaaat aatgcagaat taattgaaaa tcaaacaaaa      900
acaccattta caattgaagc aaacaatcaa acacctgttg aaaaaacagt caaaaatgat      960
acctctaaag ttgataaaac aacaccaagc ttagatggta agatgtggc aattggcgaa     1020 aaaattaaat atcaaatttc tgtaaatatt ccattgggga ttgcagacaa agaaggcgac     1080
gctaataaat acgtcaaatt caatttagtt gataaacatg atgcagcctt aacttttgat     1140
aacgtgactt ctggagagta tgcttatgcg ttatatgatg gggatacagt gattgctcct     1200
gaaaattatc aagtgactga acaagcaaat ggcttcactg tcgccgttaa tccagcgtat     1260
attcctacgc taacaccagg cggcacacta aaattcgttt actttatgca tttaaatgaa     1320
aaagcagatc tacgaaagg ctttaaaaat gaggcgaatg ttgataacgg tcataccgac     1380
gaccaaacac caccaactgt tgaagttgtg acaggtggga acgtttcat taaagtcgat     1440 ggcgatgtga cagcgacaca agccttggcg ggagcttcct ttgtcgtccg tgatcaaaac     1500
agcgacacag caaattattt gaaaatcgat gaaacaacga agcagcaac ttgggtgaaa     1560 acaaaagctg aagcaactac ttttacaaca acggctgatg gattagttga tatcacaggg     1620
cttaaatacg gtacctatta tttagaagaa actgtagctc ctgatgatta tgtcttgtta     1680
acaaatcgga ttgaatttgt ggtcaatgaa caatcatatg cacaacaga aaacctagtt     1740 tcaccagaaa aagtaccaaa caaacacaaa ggtaccttac cttcaacagg tggcaaagga     1800
atctacgttt acttaggaag tggcgcagtc ttgctactta ttgcaggagt ctactttgct     1860
agacgtagaa aagaaaatgc t                                              1881

<210> SEQ ID NO 13
<211> LENGTH: 627
<212> TYPE: PRT
<213> ORGANISM: Staphylococcus epidermidis

<400> SEQUENCE: 13

Met Lys Gln Leu Lys Lys Val Trp Tyr Thr Val Ser Thr Leu Leu Leu
1               5                   10                  15

Ile Leu Pro Leu Phe Thr Ser Val Leu Gly Thr Thr Ala Phe Ala
                20                  25                  30

Glu Glu Asn Gly Glu Ser Ala Gln Leu Val Ile His Lys Lys Lys Met
            35                  40                  45

Thr Asp Leu Pro Asp Pro Leu Ile Gln Asn Ser Gly Lys Glu Met Ser
        50                  55                  60

Glu Phe Asp Lys Tyr Gln Gly Leu Ala Asp Val Thr Phe Ser Ile Tyr
65                  70                  75                  80

Asn Val Thr Asn Glu Phe Tyr Glu Gln Arg Ala Ala Gly Ala Ser Val
                85                  90                  95

Asp Ala Ala Lys Gln Ala Val Gln Ser Leu Thr Pro Gly Lys Pro Val
            100                 105                 110

Ala Gln Gly Thr Thr Asp Ala Asn Gly Asn Val Thr Val Gln Leu Pro
        115                 120                 125

Lys Lys Gln Asn Gly Lys Asp Ala Val Tyr Thr Ile Lys Glu Glu Pro
    130                 135                 140

Lys Glu Gly Val Val Ala Ala Thr Asn Met Val Val Ala Phe Pro Val
145                 150                 155                 160

Tyr Glu Met Ile Lys Gln Thr Asp Gly Ser Tyr Lys Tyr Gly Thr Glu
                165                 170                 175
```

```
Glu Leu Ala Val Val His Ile Tyr Pro Lys Asn Val Val Ala Asn Asp
            180                 185                 190
Gly Ser Leu His Val Lys Lys Val Gly Thr Ala Glu Asn Glu Gly Leu
            195                 200             205
Asn Gly Ala Glu Phe Val Ile Ser Lys Ser Gly Ser Pro Gly Thr
        210                 215                 220
Val Lys Tyr Ile Gln Gly Val Lys Asp Gly Leu Tyr Thr Trp Thr Thr
225                 230                 235                 240
Asp Lys Glu Gln Ala Lys Arg Phe Ile Thr Gly Lys Ser Tyr Glu Ile
                245                 250                 255
Gly Glu Asn Asp Phe Thr Glu Ala Glu Asn Gly Thr Gly Glu Leu Thr
                260                 265                 270
Val Lys Asn Leu Glu Val Gly Ser Tyr Ile Leu Glu Glu Val Lys Ala
            275                 280                 285
Pro Asn Asn Ala Glu Leu Ile Glu Asn Gln Thr Lys Thr Pro Phe Thr
        290                 295                 300
Ile Glu Ala Asn Asn Gln Thr Pro Val Glu Lys Thr Val Lys Asn Asp
305                 310                 315                 320
Thr Ser Lys Val Asp Lys Thr Thr Pro Ser Leu Asp Gly Lys Asp Val
                325                 330                 335
Ala Ile Gly Glu Lys Ile Lys Tyr Gln Ile Ser Val Asn Ile Pro Leu
                340                 345                 350
Gly Ile Ala Asp Lys Glu Gly Asp Ala Asn Lys Tyr Val Lys Phe Asn
            355                 360                 365
Leu Val Asp Lys His Asp Ala Ala Leu Thr Phe Asp Asn Val Thr Ser
        370                 375                 380
Gly Glu Tyr Ala Tyr Ala Leu Tyr Asp Gly Asp Thr Val Ile Ala Pro
385                 390                 395                 400
Glu Asn Tyr Gln Val Thr Glu Gln Ala Asn Gly Phe Thr Val Ala Val
                405                 410                 415
Asn Pro Ala Tyr Ile Pro Thr Leu Thr Pro Gly Gly Thr Leu Lys Phe
                420                 425                 430
Val Tyr Phe Met His Leu Asn Glu Lys Ala Asp Pro Thr Lys Gly Phe
            435                 440                 445
Lys Asn Glu Ala Asn Val Asp Asn Gly His Thr Asp Asp Gln Thr Pro
        450                 455                 460
Pro Thr Val Glu Val Thr Gly Gly Lys Arg Phe Ile Lys Val Asp
465                 470                 475                 480
Gly Asp Val Thr Ala Thr Gln Ala Leu Ala Gly Ala Ser Phe Val Val
                485                 490                 495
Arg Asp Gln Asn Ser Asp Thr Ala Asn Tyr Leu Lys Ile Asp Glu Thr
                500                 505                 510
Thr Lys Ala Ala Thr Trp Val Lys Thr Lys Ala Glu Ala Thr Thr Phe
            515                 520                 525
Thr Thr Thr Ala Asp Gly Leu Val Asp Ile Thr Gly Leu Lys Tyr Gly
        530                 535                 540
Thr Tyr Tyr Leu Glu Glu Thr Val Ala Pro Asp Asp Tyr Val Leu Leu
545                 550                 555                 560
Thr Asn Arg Ile Glu Phe Val Val Asn Glu Gln Ser Tyr Gly Thr Thr
                565                 570                 575
Glu Asn Leu Val Ser Pro Glu Lys Val Pro Asn Lys His Lys Gly Thr
            580                 585                 590
Leu Pro Ser Thr Gly Gly Lys Gly Ile Tyr Val Tyr Leu Gly Ser Gly
```

```
                595                 600                 605
Ala Val Leu Leu Leu Ile Ala Gly Val Tyr Phe Ala Arg Arg Arg Lys
    610                 615                 620

Glu Asn Ala
625

<210> SEQ ID NO 14
<211> LENGTH: 3387
<212> TYPE: DNA
<213> ORGANISM: Staphylococcus epidermidis

<400> SEQUENCE: 14
atgacgacca cagggaagaa actgaaagtt attttcatgc tgataatatt gagtttatca      60
aactttgtgc cattatctgc aatagcagac actacagatg atccaacagt tttagaaaca     120
atttcagctg aagtcatttc ggatcagtct ggaaaaaaag cactgaacat caagctaaat     180
gcgaataaca ccagtgctga aaagatagaa aagaaattg gtctagtcga aaattactta     240
agtgatgtgg aagaaaaga aggagatggc tatgcttatc aggtaaatag cgggaaaatt     300
acgttggaaa tctcatcaaa cactaaacaa actatcgatc tgagttttcc aatcgatcca     360
gcactttacc acagccaggc aaacaagctg atcgtcgata taaagaata tgacattatt     420 gatgagacag aaaataagaa agatacagat gtgtcagtac aaagccaga cgaaatagaa     480 gaagaatcat caaaagaaaa cgaaaattct gtcagcccat ttacattgcc tacattatcc     540
ttgccagctg tgagtgtgcc atctaatcaa acgattccta cagaatatac aacagatgat     600
cagggcactt atcctaaagc cagttggcaa cctacaggaa atacaaatgt tcttgatcat     660
caaggcaata aaaacggaac aaatcaatgg gatggtataa attcttggaa tggagatcct     720
aatgatcgga cccattcgta tatcgaatat ggaggaaccg gtaatcaagc agactatgcg     780
atacgaaagt atgcaaagga aacaagtaca cccggattgt ttgatgttta tttgaatgct     840
cgtggaaatg tacaaaaaga tatcacgcct cttgatctcg tattggtcgt agactggtca     900
ggaagtatga cgacaataa tcggatcggt gaagtaaaga ttggtgtcga tcgttttgtc     960
gatactttag cagatagcgg tatcacagac aaaatcaata tgggatatgt cggctactca    1020
agcgaaggat atagctacag taacggtgca gtacagatgg gttcatttga ttcagtgaaa    1080
aatcaagtaa aatccattac accttcacgg acaaatggtg gtacttttac acaaaaagca    1140
ctaagagatg caggaagcat gctatccgtt ccaaatggac ataaaaagt gatcgttttg    1200 ctgacggatg gtgtaccaac atttttcctat aaagtacagc gggtacacgc acaatcaagc    1260
agcaattatt acggaactca gttttctaat acgcaagatc ggccgggaaa tacttctcta    1320
atctcaagaa tctatgatgc acctgaccaa acaatctat ccagaagaat cgacagtacg    1380
tttatcgcaa ccatcggaga agcgatggca ctcaaagaac gaggaatcga aatacatggt    1440
cttggcatcc aacttcaaag cgatccggca gctggtctct caaaagcaga gtagagtct    1500 cgtatgcgac aaatggtttc atcagatgaa aaaggcgatc tttactatga atcagctgat    1560
catgcaacag atatctctga ataccctagcc aaaaaagctg tacagatctc agcaactgta    1620
agcaatggac aaataaatga tccaatcgca gaaccattca tttatcagcc tggtacactt    1680
tcagtcaaga gtgtggggac aagtcctaca acggtcactc catctatttc catagaagga    1740 ataccatca agagcaatca gatctatttta ggaaaagacc aagaaatcca aatccattac    1800
caagtgagaa tccaaacaga aaatgaggac ttccatccaa atttctgta tcaaatgaac    1860 ggcaggacaa cttttccagcc aaacattgat accaatgaat tagctgaatt cggtataccca    1920
```

```
tctgctaaag ctcccggagt cagtcttcac atcaaaaagt tatgggaaga atttgacaac    1980
aatctagctg atcgtccaga tcaagttact tttgagattc aacgggaaca tacgacaaat    2040
gctgcagctt ggaaaaacgg atatattcga atcattaaac cagctaaaga tacaacaaat    2100
acgtgggaac gtgcagacat tgacaaatta tctgcaaata gcggagaaag ttatcaagag    2160
atattatcac tacctcaata caataatcaa ggtcaagcat tcagttacca acaatcaaa    2220 gaattacctg taccaggata cgattctcaa caaatagatg caatgacatg gaaaaatact    2280
aaacaattca caccgttaaa cttgaaaata cgaaaaatt cctctacagg tgaaaaggat    2340
cttattggcg ctgttttcaa attaacagga gattctattg atactttact aacagatcat    2400
ggcgacggaa cctattctct tccagaaaat gtcaaattgc aaaagaaat gacctatacg    2460 ctgacagaaa caaaagctcc agaagggcat ggattaagca aaaagactac ttgggaaatc    2520
aagatcgctt ctgatggtac ggtaaccatt gatggaaaaa cagtcactac ttccgatgat    2580
acgatccagt tgactattga aaatcctttt gttgaagttc ctgtagcagt acgtaagtat    2640
gcgatgcaag ggacggacaa agagataaat cttaaaggag cagcattttc cctacagaaa    2700
aaagaagcaa atggtactta tcagccaatt gacagccaaa caacgaatga aaaaggtctt    2760
gccagttttg attcactcac acctggtaaa tatcgagtcg ttgaaacagc tggtcctgcc    2820
ggatatgata cttcgccggg aaattatgaa ttccaaatcg ataaatatgg aaaaatcatt    2880
tacacgggaa aaaataccga atgacaaat aatgtatgga cgctcactca tcaaaatcga    2940
ctaaaagcgt tgatctaac ggtacacaaa aaagaagaca acggacagac attaaaagga    3000
gcaaaattca gactgcaggg accagaaatg gacttagaat cgccaaaaga tggacaagaa    3060
acagatacct ttctattcga aatttaaaa cctggaactt atacgctgac cgaaactttt    3120
acaccagaag gataccaagg tctaaaagag ccagttacta tagttataca cgaagatggg    3180
tcaattcaag tggatggaca agatcatgaa tctgttctgt caccaggagc caaaacaac    3240 cagatttctt tagacatcac gaatcaggca aaagtaccat tacctgaaac gggaggaatt    3300
ggccgtttag gaatctatct agtagggatg attggttgtg cgttttctat ttggtatctt    3360
tttttgaaaa aagaaagagg gggcagc                                        3387
```

<210> SEQ ID NO 15
<211> LENGTH: 1129
<212> TYPE: PRT
<213> ORGANISM: Staphylococcus epidermidis

<400> SEQUENCE: 15

```
Met Thr Thr Thr Gly Lys Lys Leu Lys Val Ile Phe Met Leu Ile Ile
1               5                   10                  15

Leu Ser Leu Ser Asn Phe Val Pro Leu Ser Ala Ile Ala Asp Thr Thr
                20                  25                  30

Asp Asp Pro Thr Val Leu Glu Thr Ile Ser Ala Glu Val Ile Ser Asp
            35                  40                  45

Gln Ser Gly Lys Lys Ala Leu Asn Ile Lys Leu Asn Ala Asn Asn Thr
        50                  55                  60

Ser Ala Glu Lys Ile Glu Lys Glu Ile Gly Leu Val Glu Asn Tyr Leu
65                  70                  75                  80

Ser Asp Val Glu Arg Lys Glu Gly Asp Gly Tyr Ala Tyr Gln Val Asn
                85                  90                  95

Ser Gly Lys Ile Thr Leu Glu Ile Ser Ser Asn Thr Lys Gln Thr Ile
                100                 105                 110
```

-continued

Asp Leu Ser Phe Pro Ile Asp Pro Ala Leu Tyr His Ser Gln Ala Asn
            115                 120                 125

Lys Leu Ile Val Asp Asn Lys Glu Tyr Asp Ile Ile Asp Glu Thr Glu
        130                 135                 140

Asn Lys Lys Asp Thr Asp Val Ser Val Pro Lys Pro Asp Glu Ile Glu
145                 150                 155                 160

Glu Glu Ser Ser Lys Glu Asn Glu Asn Ser Val Ser Pro Phe Thr Leu
                165                 170                 175

Pro Thr Leu Ser Leu Pro Ala Val Ser Val Pro Ser Asn Gln Thr Ile
            180                 185                 190

Pro Thr Glu Tyr Thr Thr Asp Gln Gly Thr Tyr Pro Lys Ala Ser
            195                 200                 205

Trp Gln Pro Thr Gly Asn Thr Asn Val Leu Asp His Gln Gly Asn Lys
        210                 215                 220

Asn Gly Thr Asn Gln Trp Asp Gly Ile Asn Ser Trp Asn Gly Asp Pro
225                 230                 235                 240

Asn Asp Arg Thr His Ser Tyr Ile Glu Tyr Gly Gly Thr Gly Asn Gln
                245                 250                 255

Ala Asp Tyr Ala Ile Arg Lys Tyr Ala Lys Glu Thr Ser Thr Pro Gly
            260                 265                 270

Leu Phe Asp Val Tyr Leu Asn Ala Arg Gly Asn Val Gln Lys Asp Ile
        275                 280                 285

Thr Pro Leu Asp Leu Val Leu Val Val Asp Trp Ser Gly Ser Met Asn
        290                 295                 300

Asp Asn Asn Arg Ile Gly Glu Val Lys Ile Gly Val Asp Arg Phe Val
305                 310                 315                 320

Asp Thr Leu Ala Asp Ser Gly Ile Thr Asp Lys Ile Asn Met Gly Tyr
            325                 330                 335

Val Gly Tyr Ser Ser Glu Gly Tyr Ser Tyr Ser Asn Gly Ala Val Gln
            340                 345                 350

Met Gly Ser Phe Asp Ser Val Lys Asn Gln Val Lys Ser Ile Thr Pro
        355                 360                 365

Ser Arg Thr Asn Gly Gly Thr Phe Thr Gln Lys Ala Leu Arg Asp Ala
370                 375                 380

Gly Ser Met Leu Ser Val Pro Asn Gly His Lys Lys Val Ile Val Leu
385                 390                 395                 400

Leu Thr Asp Gly Val Pro Thr Phe Ser Tyr Lys Val Gln Arg Val His
            405                 410                 415

Ala Gln Ser Ser Ser Asn Tyr Tyr Gly Thr Gln Phe Ser Asn Thr Gln
            420                 425                 430

Asp Arg Pro Gly Asn Thr Ser Leu Ile Ser Arg Ile Tyr Asp Ala Pro
        435                 440                 445

Asp Gln Asn Asn Leu Ser Arg Arg Ile Asp Ser Thr Phe Ile Ala Thr
        450                 455                 460

Ile Gly Glu Ala Met Ala Leu Lys Glu Arg Gly Ile Glu Ile His Gly
465                 470                 475                 480

Leu Gly Ile Gln Leu Gln Ser Asp Pro Ala Ala Gly Leu Ser Lys Ala
                485                 490                 495

Glu Val Glu Ser Arg Met Arg Gln Met Val Ser Ser Asp Glu Lys Gly
            500                 505                 510

Asp Leu Tyr Tyr Glu Ser Ala Asp His Ala Thr Asp Ile Ser Glu Tyr
            515                 520                 525

```
Leu Ala Lys Lys Ala Val Gln Ile Ser Ala Thr Val Ser Asn Gly Gln
    530                 535                 540

Ile Asn Asp Pro Ile Ala Glu Pro Phe Ile Tyr Gln Pro Gly Thr Leu
545                 550                 555                 560

Ser Val Lys Ser Val Gly Thr Ser Pro Thr Thr Val Thr Pro Ser Ile
                565                 570                 575

Ser Ile Glu Gly Asn Thr Ile Lys Ser Asn Gln Ile Tyr Leu Gly Lys
            580                 585                 590

Asp Gln Glu Ile Gln Ile His Tyr Gln Val Arg Ile Gln Thr Glu Asn
        595                 600                 605

Glu Asp Phe His Pro Asn Phe Trp Tyr Gln Met Asn Gly Arg Thr Thr
    610                 615                 620

Phe Gln Pro Asn Ile Asp Thr Asn Glu Leu Ala Glu Phe Gly Ile Pro
625                 630                 635                 640

Ser Ala Lys Ala Pro Gly Val Ser Leu His Ile Lys Lys Leu Trp Glu
                645                 650                 655

Glu Phe Asp Asn Asn Leu Ala Asp Arg Pro Asp Gln Val Thr Phe Glu
            660                 665                 670

Ile Gln Arg Glu His Thr Thr Asn Ala Ala Ala Trp Lys Asn Gly Tyr
        675                 680                 685

Ile Arg Ile Ile Lys Pro Ala Lys Asp Thr Thr Asn Thr Trp Glu Arg
    690                 695                 700

Ala Asp Ile Asp Lys Leu Ser Ala Asn Ser Gly Glu Ser Tyr Gln Glu
705                 710                 715                 720

Ile Leu Ser Leu Pro Gln Tyr Asn Asn Gln Gly Gln Ala Phe Ser Tyr
                725                 730                 735

Gln Thr Ile Lys Glu Leu Pro Val Pro Gly Tyr Asp Ser Gln Gln Ile
            740                 745                 750

Asp Ala Met Thr Trp Lys Asn Thr Lys Gln Phe Thr Pro Leu Asn Leu
        755                 760                 765

Lys Ile Thr Lys Asn Ser Ser Thr Gly Glu Lys Asp Leu Ile Gly Ala
    770                 775                 780

Val Phe Lys Leu Thr Gly Asp Ser Ile Asp Thr Leu Leu Thr Asp His
785                 790                 795                 800

Gly Asp Gly Thr Tyr Ser Leu Pro Glu Asn Val Lys Leu Gln Lys Glu
                805                 810                 815

Met Thr Tyr Thr Leu Thr Glu Thr Lys Ala Pro Glu Gly His Gly Leu
            820                 825                 830

Ser Lys Lys Thr Thr Trp Glu Ile Lys Ile Ala Ser Asp Gly Thr Val
        835                 840                 845

Thr Ile Asp Gly Lys Thr Val Thr Thr Ser Asp Thr Ile Gln Leu
    850                 855                 860

Thr Ile Glu Asn Pro Phe Val Glu Val Pro Val Ala Val Arg Lys Tyr
865                 870                 875                 880

Ala Met Gln Gly Thr Asp Lys Glu Ile Asn Leu Lys Gly Ala Ala Phe
                885                 890                 895

Ser Leu Gln Lys Lys Glu Ala Asn Gly Thr Tyr Gln Pro Ile Asp Ser
            900                 905                 910

Gln Thr Thr Asn Glu Lys Gly Leu Ala Ser Phe Asp Ser Leu Thr Pro
        915                 920                 925

Gly Lys Tyr Arg Val Val Glu Thr Ala Gly Pro Ala Gly Tyr Asp Thr
    930                 935                 940

Ser Pro Gly Asn Tyr Glu Phe Gln Ile Asp Lys Tyr Gly Lys Ile Ile
```

```
                945            950           955            960
        Tyr Thr Gly Lys Asn Thr Glu Met Thr Asn Asn Val Trp Thr Leu Thr
                        965              970              975
        His Gln Asn Arg Leu Lys Ala Phe Asp Leu Thr Val His Lys Lys Glu
                    980              985              990
        Asp Asn Gly Gln Thr Leu Lys Gly Ala Lys Phe Arg Leu Gln Gly Pro
                    995             1000             1005
        Glu Met Asp Leu Glu Ser Pro Lys Asp Gly Gln Glu Thr Asp Thr
                   1010             1015              1020
        Phe Leu Phe Glu Asn Leu Lys Pro Gly Thr Tyr Thr Leu Thr Glu
                   1025             1030             1035
        Thr Phe Thr Pro Glu Gly Tyr Gln Gly Leu Lys Glu Pro Val Thr
                   1040             1045             1050
        Ile Val Ile His Glu Asp Gly Ser Ile Gln Val Asp Gly Gln Asp
                   1055             1060             1065
        His Glu Ser Val Leu Ser Pro Gly Ala Lys Asn Asn Gln Ile Ser
                   1070             1075             1080
        Leu Asp Ile Thr Asn Gln Ala Lys Val Pro Leu Pro Glu Thr Gly
                   1085             1090             1095
        Gly Ile Gly Arg Leu Gly Ile Tyr Leu Val Gly Met Ile Gly Cys
                   1100             1105             1110
        Ala Phe Ser Ile Trp Tyr Leu Phe Leu Lys Lys Glu Arg Gly Gly
                   1115             1120             1125
        Ser

<210> SEQ ID NO 16
<211> LENGTH: 1422
<212> TYPE: DNA
<213> ORGANISM: Staphylococcus epidermidis

<400> SEQUENCE: 16
atgaaaaaac ttggttggct tagtatgtgt ctcttcttgt tactatttaa accagctttt      60
actcaggtag caacagaaac agaaacagaa atggttcaga ttactttaca caaattgctt     120
ttcccaaacg ggcaactgcc gaaaaatcat ccaaatgacg acaagaaaa agctttatta      180
caaacgtatc gaggattaaa tggtgtcaca ttccaagttt atgatgtcac agattctttt     240
taccatctac gggaaaaggg caaaacggta gaagaagcac aagcagagat cgcaaaaaac     300
ggtgcgtctt ccggtatgtt taccgcagaa gcaacaacta caactcttaa caacgaagat     360
ggtatcgctt cttttttctct ggccgctaaa gatcaagaaa aagagataa agcgtatctt     420
ttcattgaat ccaaagtacc agaagtcgtc aaagaaaagg cagagaatat ggtagttgtt     480
cttcctgtac atggacaaaa caatcaaaaa ctttcaacta tccatttgta tcctaaaaat     540
gaagaaaacg actaccctga tccaccttt gagaaggtat tagaagagcc tagaaatgat     600
tttacgattg gtgaaaaaat cacttattcc ttgcatacga caattcctgt aaatatcctt     660
gactatcaaa agttcgaatt gtcagatagt gcggatgaag cattaacgtt tttacctaat     720
agtttaacga tttcatcgaa tggagaaaag ctgacagaag gctttgtcat acacaagaaa     780
cctcacggat tgatgttttt attttcgatc ccttcgttgg aaaaatatgc tggaaaaaaa     840
ctgaccattt cttatcagat gcagctaagc agtacagcac aggcgaacaa ggaaatcaac     900
aacaacggaa cactggattt tggttttggt gtcagtacaa agaagtctc tgtatataca     960
gggagtaagc aatttgtcaa aatcgagaca ataaaccag ataaacgatt agctggcgca    1020
```

```
gtattcctta ttaaaaacaa agcaggaaat tacctccagc aaacagccaa cggatacaag    1080
tggacaaaga acgaatcaga tgcgcttcac ctgatttccg ataaaaatgg cgcttttca     1140 atttccgggt tgaaaacagg aagttatcga ttaaaagaga tcgaagcacc ttctggttat    1200
attttaagtg aaacagaaat tccgtttacc atttcaactt ttctttctga ggataaagag    1260
gcggacagta tattgaaagt agtcaataaa aaagaaaata gccgtccatt tcttccaaaa    1320
acaaacgaaa cgaaaaatac acttttaggc gttgttggta tggtattcgc aagctttgca    1380
atctggttgt ttatcaaaaa aagaacagga gtgaaaaaat ga                      1422
```

<210> SEQ ID NO 17
<211> LENGTH: 473
<212> TYPE: PRT
<213> ORGANISM: Staphylococcus epidermidis

<400> SEQUENCE: 17

```
Met Lys Lys Leu Gly Trp Leu Ser Met Cys Leu Phe Leu Leu Leu Phe
 1               5                  10                  15

Lys Pro Ala Phe Thr Gln Val Ala Thr Glu Thr Glu Thr Glu Met Val
            20                  25                  30

Gln Ile Thr Leu His Lys Leu Leu Phe Pro Asn Gly Gln Leu Pro Lys
        35                  40                  45

Asn His Pro Asn Asp Gly Gln Glu Lys Ala Leu Leu Gln Thr Tyr Arg
    50                  55                  60

Gly Leu Asn Gly Val Thr Phe Gln Val Tyr Asp Val Thr Asp Ser Phe
65                  70                  75                  80

Tyr His Leu Arg Glu Lys Gly Lys Thr Val Glu Glu Ala Gln Ala Glu
                85                  90                  95

Ile Ala Lys Asn Gly Ala Ser Ser Gly Met Phe Thr Ala Glu Ala Thr
            100                 105                 110

Thr Thr Thr Leu Asn Asn Glu Asp Gly Ile Ala Ser Phe Ser Leu Ala
        115                 120                 125

Ala Lys Asp Gln Glu Lys Arg Asp Lys Ala Tyr Leu Phe Ile Glu Ser
    130                 135                 140

Lys Val Pro Glu Val Val Lys Glu Lys Ala Glu Asn Met Val Val Val
145                 150                 155                 160

Leu Pro Val His Gly Gln Asn Asn Gln Lys Leu Ser Thr Ile His Leu
                165                 170                 175

Tyr Pro Lys Asn Glu Glu Asn Asp Tyr Pro Asp Pro Phe Glu Lys
            180                 185                 190

Val Leu Glu Glu Pro Arg Asn Asp Phe Thr Ile Gly Glu Lys Ile Thr
        195                 200                 205

Tyr Ser Leu His Thr Thr Ile Pro Val Asn Ile Leu Asp Tyr Gln Lys
    210                 215                 220

Phe Glu Leu Ser Asp Ser Ala Asp Glu Ala Leu Thr Phe Leu Pro Asn
225                 230                 235                 240

Ser Leu Thr Ile Ser Ser Asn Gly Glu Lys Leu Thr Glu Gly Phe Val
                245                 250                 255

Ile His Lys Lys Pro His Gly Phe Asp Val Leu Phe Ser Ile Pro Ser
            260                 265                 270

Leu Glu Lys Tyr Ala Gly Lys Lys Leu Thr Ile Ser Tyr Gln Met Gln
        275                 280                 285

Leu Ser Ser Thr Ala Gln Ala Asn Lys Glu Ile Asn Asn Gly Thr
    290                 295                 300
```

```
Leu Asp Phe Gly Phe Gly Val Ser Thr Lys Lys Val Ser Val Tyr Thr
305                 310                 315                 320

Gly Ser Lys Gln Phe Val Lys Ile Glu Thr Asn Lys Pro Asp Lys Arg
            325                 330                 335

Leu Ala Gly Ala Val Phe Leu Ile Lys Asn Lys Ala Gly Asn Tyr Leu
            340                 345                 350

Gln Gln Thr Ala Asn Gly Tyr Lys Trp Thr Lys Asn Glu Ser Asp Ala
        355                 360                 365

Leu His Leu Ile Ser Asp Lys Asn Gly Ala Phe Ser Ile Ser Gly Leu
    370                 375                 380

Lys Thr Gly Ser Tyr Arg Leu Lys Glu Ile Glu Ala Pro Ser Gly Tyr
385                 390                 395                 400

Ile Leu Ser Glu Thr Glu Ile Pro Phe Thr Ile Ser Thr Phe Leu Ser
                405                 410                 415

Glu Asp Lys Glu Ala Asp Ser Ile Leu Lys Val Val Asn Lys Lys Glu
            420                 425                 430

Asn Ser Arg Pro Phe Leu Pro Lys Thr Asn Glu Thr Lys Asn Thr Leu
        435                 440                 445

Leu Gly Val Val Gly Met Val Phe Ala Ser Phe Ala Ile Trp Leu Phe
    450                 455                 460

Ile Lys Lys Arg Thr Gly Val Lys Lys
465                 470

<210> SEQ ID NO 18
<211> LENGTH: 1878
<212> TYPE: DNA
<213> ORGANISM: Staphylococcus epidermidis

<400> SEQUENCE: 18
atgaaaaatc ataaaaaaat aaacgttatg ttaggagtcc ttttccttat tttaccatta        60
ctcacaaaca gcttcggcgc aaaaaaagtg tttgcagagg agacagcagc tcaagtcatc       120
cttcataaaa agaaaatgac tgatttaccc gatcctttaa tccaaaacag cgggaaagaa       180
atgagcgaat cgatcaata ccaaggatta gccgatattt cattttcagt ttataacgtc        240
actcaagaat tttatgcgca acgagataaa ggagcgtccg tggatgcagc aaaacaagca       300
gtccagtctt tgactcctgg taccccagtt gcttcaggaa cgacagatgc tgatggaaat       360
gtcactttat ctttacctaa aaaacaaaat gggaaagatg cagtctacac gatcaaagaa       420
gaaccaaaag acggagtgtc agctgccgca acatggtttt agctttccc tgtatatgag        480 atgatcaaac aagcagatgg ctcttataaa tacgggacag aagaactaga tactatccat       540
ctctacccta aaaatacagt cggtaatgat ggaacgttga agttacaaa aatcggtact        600 gccgaaaacg aagcactaaa tggagcagaa tttattattt ctaaagaaga aggaacacca       660
agcgtcaaaa aatacatcca aagtgtcaca gatggattgt acacttggac aactgatcaa       720
accaaagcca acatttcat tactggtcat tcttatgaca tcggcaacaa tgactttgcc        780
gaggcatcta ttgaaaaagg ccagttgatc gttaatcatt tagaagttgg aaaatataat       840
ttagaagaag taaaagctcc tgataatgcg gaaatgattg aaaagcaaac aatcacgcct       900
tttgagatcc tggcaaatag ccaaacacca gtagaaaaga ccatcaaaaa tgatacgtct       960
aaagttgata aaacaacacc tcaattgaat ggaaaagatg tcgcaatcgg tgaaaaaatt      1020
caatatgaga tttctgtcaa tatcccatta ggtatcgctg ataaagaagg aacgcaaaac      1080
aagtacacaa cattccaaact tatcgatact catgacgctg ctttaacatt tgataatgat      1140
```

-continued

```
tcttcaggaa cgtatgctta tgccttatat gatggaaata aagaaatcga cccagtaaat    1200
tattctgtca ctgagcaaac agacggattc acggtttcag ttgatccgaa ttatattcct    1260
tcattaactc ctggcggtac attgaaattc gtttactata tgcatttgaa cgaaaaagca    1320
gatccaacca aaggattttc taaccaagca aatgtcgata cgggcatac aaatgatcaa     1380 acaccaccgt cagtcgatgt cgttactggg ggcaaacgat ttgttaaagt agatggtgac    1440
gttacatcag accaaacact tgctggagca gaattcgtcg ttcgtgatca agatagtgac    1500
acagcgaaat atttatcgat cgacccatcc acaaaagccg tcagctgggt atcggcgaaa    1560
gaatcagcaa cggttttac aaccacaagt aacggtttaa tcgatgtgac aggtctaaaa     1620
tatggcacgt actatctgga agaaacgaaa gcgccagaaa aatatgttcc attaacaaac    1680
cgtgtagcat ttactatcga tgaacaatct tatgtaacag caggacagtt gatttctcct    1740
gaaaaaatac caaataaaca caaaggtaca cttccttcaa caggcggtaa gggaatctat    1800
gtgtatatcg gtgcaggagt agtccttcta ctgattgctg gactgtactt tgctagacgc    1860
aagcacagtc agatttag                                                 1878
```

<210> SEQ ID NO 19
<211> LENGTH: 625
<212> TYPE: PRT
<213> ORGANISM: Staphylococcus epidermidis

<400> SEQUENCE: 19

```
Met Lys Asn His Lys Lys Ile Asn Val Met Leu Gly Val Leu Phe Leu
1               5                   10                  15

Ile Leu Pro Leu Leu Thr Asn Ser Phe Gly Ala Lys Lys Val Phe Ala
                20                  25                  30

Glu Glu Thr Ala Ala Gln Val Ile Leu His Lys Lys Met Thr Asp
            35                  40                  45

Leu Pro Asp Pro Leu Ile Gln Asn Ser Gly Lys Glu Met Ser Glu Phe
        50                  55                  60

Asp Gln Tyr Gln Gly Leu Ala Asp Ile Ser Phe Ser Val Tyr Asn Val
65                  70                  75                  80

Thr Gln Glu Phe Tyr Ala Gln Arg Asp Lys Gly Ala Ser Val Asp Ala
                85                  90                  95

Ala Lys Gln Ala Val Gln Ser Leu Thr Pro Gly Thr Pro Val Ala Ser
            100                 105                 110

Gly Thr Thr Asp Ala Asp Gly Asn Val Thr Leu Ser Leu Pro Lys Lys
        115                 120                 125

Gln Asn Gly Lys Asp Ala Val Tyr Thr Ile Lys Glu Pro Lys Asp
    130                 135                 140

Gly Val Ser Ala Ala Ala Asn Met Val Leu Ala Phe Pro Val Tyr Glu
145                 150                 155                 160

Met Ile Lys Gln Ala Asp Gly Ser Tyr Lys Tyr Gly Thr Glu Glu Leu
                165                 170                 175

Asp Thr Ile His Leu Tyr Pro Lys Asn Thr Val Gly Asn Asp Gly Thr
            180                 185                 190

Leu Lys Val Thr Lys Ile Gly Thr Ala Glu Asn Glu Ala Leu Asn Gly
        195                 200                 205

Ala Glu Phe Ile Ile Ser Lys Glu Glu Gly Thr Pro Ser Val Lys Lys
    210                 215                 220

Tyr Ile Gln Ser Val Thr Asp Gly Leu Tyr Thr Trp Thr Thr Asp Gln
225                 230                 235                 240
```

-continued

```
Thr Lys Ala Lys His Phe Ile Thr Gly His Ser Tyr Asp Ile Gly Asn
                245                 250                 255

Asn Asp Phe Ala Glu Ala Ser Ile Glu Lys Gly Gln Leu Ile Val Asn
            260                 265                 270

His Leu Glu Val Gly Lys Tyr Asn Leu Glu Val Lys Ala Pro Asp
        275                 280                 285

Asn Ala Glu Met Ile Glu Lys Gln Thr Ile Thr Pro Phe Glu Ile Leu
    290                 295                 300

Ala Asn Ser Gln Thr Pro Val Glu Lys Thr Ile Lys Asn Asp Thr Ser
305                 310                 315                 320

Lys Val Asp Lys Thr Thr Pro Gln Leu Asn Gly Lys Asp Val Ala Ile
                325                 330                 335

Gly Glu Lys Ile Gln Tyr Glu Ile Ser Val Asn Ile Pro Leu Gly Ile
            340                 345                 350

Ala Asp Lys Glu Gly Thr Gln Asn Lys Tyr Thr Thr Phe Lys Leu Ile
        355                 360                 365

Asp Thr His Asp Ala Ala Leu Thr Phe Asp Asn Asp Ser Ser Gly Thr
    370                 375                 380

Tyr Ala Tyr Ala Leu Tyr Asp Gly Asn Lys Glu Ile Asp Pro Val Asn
385                 390                 395                 400

Tyr Ser Val Thr Glu Gln Thr Asp Gly Phe Thr Val Ser Val Asp Pro
                405                 410                 415

Asn Tyr Ile Pro Ser Leu Thr Pro Gly Gly Thr Leu Lys Phe Val Tyr
            420                 425                 430

Tyr Met His Leu Asn Glu Lys Ala Asp Pro Thr Lys Gly Phe Ser Asn
        435                 440                 445

Gln Ala Asn Val Asp Asn Gly His Thr Asn Asp Gln Thr Pro Pro Ser
    450                 455                 460

Val Asp Val Val Thr Gly Gly Lys Arg Phe Lys Val Asp Gly Asp
465                 470                 475                 480

Val Thr Ser Asp Gln Thr Leu Ala Gly Ala Glu Phe Val Val Arg Asp
                485                 490                 495

Gln Asp Ser Asp Thr Ala Lys Tyr Leu Ser Ile Asp Pro Ser Thr Lys
            500                 505                 510

Ala Val Ser Trp Val Ser Ala Lys Glu Ser Ala Thr Val Phe Thr Thr
        515                 520                 525

Thr Ser Asn Gly Leu Ile Asp Val Thr Gly Leu Lys Tyr Gly Thr Tyr
    530                 535                 540

Tyr Leu Glu Glu Thr Lys Ala Pro Glu Lys Tyr Val Pro Leu Thr Asn
545                 550                 555                 560

Arg Val Ala Phe Thr Ile Asp Glu Gln Ser Tyr Val Thr Ala Gly Gln
                565                 570                 575

Leu Ile Ser Pro Glu Lys Ile Pro Asn Lys His Lys Gly Thr Leu Pro
            580                 585                 590

Ser Thr Gly Gly Lys Gly Ile Tyr Val Tyr Ile Gly Ala Gly Val Val
        595                 600                 605

Leu Leu Leu Ile Ala Gly Leu Tyr Phe Ala Arg Arg Lys His Ser Gln
    610                 615                 620

Ile
625

<210> SEQ ID NO 20
<211> LENGTH: 2402
<212> TYPE: PRT
```

<213> ORGANISM: Staphylococcus epidermidis

<400> SEQUENCE: 20

```
Met Lys Asn Lys Gln Gly Phe Leu Pro Asn Leu Leu Asn Lys Tyr Gly
1               5                   10                  15
Ile Arg Lys Leu Ser Ala Gly Thr Ala Ser Leu Leu Ile Gly Ala Thr
            20                  25                  30
Leu Val Phe Gly Ile Asn Gly Gln Val Lys Ala Ala Glu Thr Asp Asn
        35                  40                  45
Ile Val Ser Gln Asn Gly Asp Asn Lys Thr Asn Asp Ser Glu Ser Ser
    50                  55                  60
Asp Lys Glu Leu Val Lys Ser Glu Asp Lys Thr Ser Ser Thr Ser
65                  70                  75                  80
Thr Asp Thr Asn Leu Glu Ser Glu Phe Asp Gln Asn Asn Asn Pro Ser
                85                  90                  95
Ser Ile Glu Glu Ser Thr Asn Arg Asn Asp Glu Asp Thr Leu Asn Gln
            100                 105                 110
Arg Thr Ser Thr Glu Thr Glu Lys Asp Thr His Val Lys Ser Ala Asp
        115                 120                 125
Thr Gln Thr Thr Asn Glu Thr Thr Asn Lys Asn Asp Asp Asn Ala Thr
    130                 135                 140
Thr Asn His Thr Glu Ser Ile Ser Asp Glu Ser Thr Tyr Gln Ser Asp
145                 150                 155                 160
Asp Ser Lys Thr Thr Gln His Asp Asn Ser Asn Thr Asn Gln Asp Thr
                165                 170                 175
Gln Ser Thr Leu Asn Pro Thr Ser Lys Glu Ser Ser Asn Lys Asp Glu
            180                 185                 190
Ala Thr Ser Pro Thr Pro Lys Glu Ser Thr Ser Ile Glu Lys Thr Asn
        195                 200                 205
Leu Ser Asn Asp Ala Asn His Gln Thr Thr Asp Glu Val Asn His Ser
    210                 215                 220
Asp Ser Asp Asn Met Thr Asn Ser Thr Pro Asn Asp Thr Glu Asn Glu
225                 230                 235                 240
Leu Asp Thr Thr Gln Leu Thr Ser His Asp Glu Ser Pro Ser Pro Gln
                245                 250                 255
Ser Asp Asn Phe Thr Gly Phe Thr Asn Leu Met Ala Thr Pro Leu Asn
            260                 265                 270
Leu Arg Asn Asp Asn Pro Arg Ile Asn Leu Leu Ala Ala Thr Glu Asp
        275                 280                 285
Thr Lys Pro Lys Thr Tyr Lys Lys Pro Asn Asn Ser Glu Tyr Ser Tyr
    290                 295                 300
Leu Leu Asn Asp Leu Gly Tyr Asp Ala Thr Thr Val Lys Glu Asn Ser
305                 310                 315                 320
Asp Leu Arg His Ala Gly Ile Ser Gln Ser Gln Asp Asn Thr Gly Ser
                325                 330                 335
Val Ile Lys Leu Asn Leu Thr Lys Trp Leu Ser Leu Gln Ser Asp Phe
            340                 345                 350
Val Asn Gly Gly Lys Val Asn Leu Ser Phe Ala Gln Ser Asp Phe Tyr
        355                 360                 365
Thr Gln Ile Glu Ser Ile Thr Leu Asn Asp Val Lys Met Asp Thr Thr
    370                 375                 380
Asn Asn Gly Gln Asn Trp Ser Ala Pro Ile Asn Gly Ser Thr Val Arg
385                 390                 395                 400
```

-continued

```
Ser Gly Leu Ile Gly Ser Val Thr Asn His Asp Ile Val Ile Thr Leu
            405                 410                 415
Lys Asn Ser Gln Thr Leu Ser Ser Leu Gly Tyr Ser Asn Asn Lys Pro
        420                 425                 430
Val Tyr Leu Thr His Thr Trp Thr Thr Asn Asp Gly Ala Ile Ala Glu
            435                 440                 445
Glu Ser Ile Gln Val Ala Ser Ile Thr Pro Thr Leu Asp Ser Lys Ala
    450                 455                 460
Pro Asn Thr Ile Gln Lys Ser Asp Phe Thr Ala Gly Arg Met Thr Asn
465                 470                 475                 480
Lys Ile Lys Tyr Asp Ser Ser Gln Asn Ser Ile Lys Ser Val His Thr
            485                 490                 495
Phe Lys Pro Asn Glu Asn Phe Leu Gln Thr Asp Tyr Arg Ala Val Leu
        500                 505                 510
Tyr Ile Lys Glu Gln Val Asn Lys Glu Leu Ile Pro Tyr Ile Asp Pro
    515                 520                 525
Asn Ser Val Lys Leu Tyr Val Ser Asp Pro Asp Gly Asn Pro Ile Ser
    530                 535                 540
Gln Asp Arg Tyr Val Asn Gly Ser Ile Asp Asn Asp Gly Leu Phe Asp
545                 550                 555                 560
Ser Ser Lys Ile Asn Glu Ile Ser Ile Lys Asn Asn Asn Thr Ser Gly
            565                 570                 575
Gln Leu Ser Asn Ala Arg Thr Ser Leu Asp Arg Asn Val Phe Phe Gly
        580                 585                 590
Thr Leu Gly Gln Ser Arg Ser Tyr Thr Ile Ser Tyr Lys Leu Lys Asp
    595                 600                 605
Gly Tyr Thr Leu Glu Ser Val Ala Ser Lys Val Ser Ala Arg Glu Thr
    610                 615                 620
Phe Asp Ser Trp Met Glu Val Asp Tyr Leu Asp Ser Tyr Asp Ser Gly
625                 630                 635                 640
Ala Pro Asn Lys Arg Leu Leu Gly Ser Tyr Ala Ser Ser Tyr Ile Asp
            645                 650                 655
Met Ile Asp Arg Ile Pro Pro Val Ala Pro Lys Ala Asn Ser Ile Thr
        660                 665                 670
Thr Glu Asp Thr Ser Ile Lys Gly Thr Ala Glu Val Asp Thr Asn Ile
    675                 680                 685
Asn Leu Thr Phe Asn Asp Gly Arg Thr Leu Asn Gly Lys Val Asp Ser
    690                 695                 700
Asn Gly Asn Phe Ser Ile Ala Ile Pro Ser Tyr Tyr Val Leu Thr Gly
705                 710                 715                 720
Lys Glu Thr Ile Lys Ile Thr Ser Ile Asp Lys Gly Asp Asn Val Ser
            725                 730                 735
Pro Ala Ile Thr Ile Ser Val Ile Asp Lys Thr Pro Pro Ala Val Lys
        740                 745                 750
Ala Ile Ser Asn Lys Thr Gln Lys Val Asn Thr Glu Ile Glu Pro Ile
    755                 760                 765
Lys Ile Glu Ala Thr Asp Asn Ser Gly Gln Ala Val Thr Asn Lys Val
    770                 775                 780
Glu Gly Leu Pro Ala Gly Met Thr Phe Asp Glu Ala Thr Asn Thr Ile
785                 790                 795                 800
Ser Gly Thr Pro Ser Glu Val Gly Ser Tyr Asp Ile Thr Val Thr Thr
            805                 810                 815
Thr Asp Glu Asn Gly Asn Ser Glu Thr Thr Thr Phe Thr Ile Asp Val
```

```
                          820                 825                 830
Glu Asp Thr Thr Lys Pro Thr Val Glu Ser Val Ala Asp Gln Thr Gln
            835                 840                 845
Glu Val Asn Thr Glu Ile Glu Pro Ile Lys Ile Glu Ala Thr Asp Asn
        850                 855                 860
Ser Gly Arg Ala Val Thr Asn Lys Val Asp Gly Leu Pro Asp Gly Val
865                 870                 875                 880
Thr Phe Asp Glu Ala Thr Asn Thr Ile Ser Gly Thr Pro Ser Glu Val
                885                 890                 895
Gly Ser Tyr Asp Ile Thr Val Thr Thr Asp Glu Ser Gly Asn Val
            900                 905                 910
Thr Glu Thr Ile Phe Thr Ile Asp Val Glu Asp Thr Thr Lys Pro Thr
        915                 920                 925
Val Glu Ser Ile Ala Gly Gln Thr Gln Glu Val Asn Thr Glu Ile Glu
930                 935                 940
Pro Ile Lys Ile Glu Ala Lys Asp Asn Ser Gly Gln Thr Val Thr Asn
945                 950                 955                 960
Lys Val Asp Gly Leu Pro Asp Gly Val Thr Phe Asp Glu Ala Thr Asn
                965                 970                 975
Thr Ile Ser Gly Thr Pro Ser Glu Val Gly Ser Tyr Asp Val Thr Val
            980                 985                 990
Thr Thr Thr Asp Glu Ser Gly Asn Ser Glu Thr Thr Thr Phe Thr Ile
        995                 1000                1005
Glu Val Lys Asp Thr Thr Lys Pro Thr Val Glu Ser Val Ala Asp
    1010                1015                1020
Gln Thr Gln Glu Val Asn Thr Glu Ile Glu Pro Ile Lys Ile Glu
    1025                1030                1035
Ala Arg Asp Asn Ser Gly Gln Ala Val Thr Asn Lys Val Asp Gly
    1040                1045                1050
Leu Pro Asp Gly Val Thr Phe Asp Glu Ala Thr Asn Thr Ile Ser
    1055                1060                1065
Gly Thr Pro Ser Glu Val Gly Ser Tyr Asp Ile Thr Val Thr Thr
    1070                1075                1080
Thr Asp Glu Ser Gly Asn Val Thr Glu Thr Thr Phe Thr Ile Glu
    1085                1090                1095
Val Glu Asp Thr Thr Lys Pro Thr Val Glu Asn Val Ala Asp Gln
    1100                1105                1110
Thr Gln Glu Val Asn Thr Glu Ile Thr Pro Ile Thr Ile Glu Ser
    1115                1120                1125
Glu Asp Asn Ser Gly Gln Thr Val Thr Asn Lys Val Asp Gly Leu
    1130                1135                1140
Pro Asp Gly Val Thr Phe Asp Glu Thr Thr Asn Thr Ile Ser Gly
    1145                1150                1155
Thr Pro Ser Lys Val Gly Ser Tyr Asp Ile Thr Val Thr Thr Thr
    1160                1165                1170
Asp Glu Ser Gly Asn Ala Thr Glu Thr Thr Phe Thr Ile Glu Val
    1175                1180                1185
Glu Asp Thr Thr Lys Pro Val Glu Asn Val Ala Gly Gln Thr
    1190                1195                1200
Gln Glu Ile Asn Thr Glu Ile Glu Pro Ile Lys Ile Glu Ala Thr
    1205                1210                1215
Asp Asn Ser Gly Gln Ala Val Thr Asn Lys Val Glu Gly Leu Pro
    1220                1225                1230
```

-continued

```
Ala Gly Val Thr Phe Asp Glu Ala Thr Asn Thr Ile Ser Gly Thr
    1235                1240                1245

Pro Ser Glu Val Gly Ser Tyr Thr Val Thr Val Thr Thr Met Asp
    1250                1255                1260

Glu Ser Gly Asn Ala Thr Glu Thr Thr Phe Thr Ile Asp Val Glu
    1265                1270                1275

Asp Thr Thr Lys Pro Thr Val Glu Ser Val Ala Asp Gln Thr Gln
    1280                1285                1290

Glu Val Asn Thr Glu Ile Thr Pro Ile Thr Ile Glu Ser Glu Asp
    1295                1300                1305

Asn Ser Asp Gln Ala Val Thr Asn Lys Val Asp Gly Leu Pro Asp
    1310                1315                1320

Gly Val Thr Phe Asp Glu Ala Thr Asn Thr Ile Ser Gly Thr Pro
    1325                1330                1335

Ser Glu Val Gly Ser Tyr Thr Val Thr Val Thr Thr Asp Glu
    1340                1345                1350

Ser Gly Asn Ala Thr Glu Thr Thr Phe Thr Ile Asp Val Glu Asp
    1355                1360                1365

Thr Thr Lys Pro Thr Val Lys Ser Val Ser Asp Gln Thr Gln Glu
    1370                1375                1380

Val Asn Thr Glu Ile Thr Pro Ile Lys Ile Glu Ala Thr Asp Asn
    1385                1390                1395

Ser Gly Gln Thr Val Thr Asn Lys Val Asp Gly Leu Pro Asp Gly
    1400                1405                1410

Ile Thr Phe Asp Glu Ala Thr Asn Thr Ile Ser Gly Thr Pro Ser
    1415                1420                1425

Glu Val Gly Ser Tyr Asp Ile Thr Val Thr Thr Asp Glu Ser
    1430                1435                1440

Gly Asn Ala Thr Glu Thr Thr Phe Thr Ile Asn Val Glu Asp Thr
    1445                1450                1455

Thr Lys Pro Thr Val Glu Asp Ile Ala Asp Gln Thr Gln Glu Val
    1460                1465                1470

Asn Thr Glu Ile Glu Pro Ile Lys Ile Glu Ala Thr Asp Asn Gly
    1475                1480                1485

Gly Gln Ala Val Thr Asn Lys Val Asp Gly Leu Pro Asp Gly Val
    1490                1495                1500

Thr Phe Asp Glu Ala Thr Asn Thr Ile Ser Gly Thr Pro Ser Glu
    1505                1510                1515

Val Gly Ser Tyr Asp Ile Ile Val Thr Thr Asp Glu Asn Gly
    1520                1525                1530

Asn Ser Glu Thr Thr Thr Phe Thr Ile Asp Val Glu Asp Thr Thr
    1535                1540                1545

Lys Pro Thr Val Glu Ser Val Val Asp Gln Thr Gln Glu Val Asn
    1550                1555                1560

Thr Glu Ile Thr Pro Ile Lys Ile Glu Ala Thr Asp Asn Ser Gly
    1565                1570                1575

Gln Ala Val Ala Asn Lys Val Asp Gly Leu Pro Asn Gly Val Thr
    1580                1585                1590

Phe Asp Glu Thr Thr Asn Thr Ile Ser Gly Thr Pro Ser Glu Val
    1595                1600                1605

Gly Ser Tyr Asp Ile Ile Val Thr Thr Thr Asp Glu Ser Gly Asn
    1610                1615                1620
```

```
Val Thr Glu Thr Ile Phe Thr Ile Asp Val Glu Asp Thr Thr Lys
1625                1630                1635

Pro Thr Val Glu Ser Ile Ala Gly Gln Thr Gln Glu Val Asn Thr
1640                1645                1650

Glu Ile Glu Pro Ile Lys Ile Glu Ala Thr Asp Asn Ser Gly Gln
1655                1660                1665

Ala Val Thr Asn Lys Val Asp Gly Leu Pro Asn Gly Val Thr Phe
1670                1675                1680

Asp Glu Ala Thr Asn Thr Ile Ser Gly Thr Pro Ser Glu Val Gly
1685                1690                1695

Ile Tyr Thr Val Thr Val Thr Thr Thr Asp Glu Ser Gly Asn Ala
1700                1705                1710

Thr Glu Thr Thr Phe Thr Ile Asp Val Glu Asp Thr Thr Lys Pro
1715                1720                1725

Thr Val Glu Ser Val Ala Asp Gln Thr Gln Glu Val Asn Thr Glu
1730                1735                1740

Ile Thr Pro Ile Thr Ile Glu Ser Glu Asp Asn Ser Gly Gln Ala
1745                1750                1755

Val Thr Asn Lys Val Glu Gly Leu Pro Ala Gly Met Thr Phe Asp
1760                1765                1770

Glu Thr Thr Asn Thr Ile Ser Gly Thr Pro Ser Glu Val Gly Ser
1775                1780                1785

Tyr Thr Val Thr Val Thr Thr Asp Glu Ser Gly Asn Glu Thr
1790                1795                1800

Glu Thr Thr Phe Thr Ile Asp Val Glu Asp Thr Thr Lys Pro Thr
1805                1810                1815

Val Glu Ser Ile Ala Asn Gln Thr Gln Glu Val Asn Thr Glu Ile
1820                1825                1830

Thr Pro Ile Lys Ile Glu Ala Thr Asp Asn Ser Gly Gln Ala Val
1835                1840                1845

Thr Asn Lys Val Asp Gly Leu Pro Asn Gly Val Thr Phe Asp Glu
1850                1855                1860

Thr Thr Asn Thr Ile Ser Gly Thr Pro Ser Glu Val Gly Ser Tyr
1865                1870                1875

Asp Ile Lys Val Thr Thr Thr Asp Glu Ser Gly Asn Ala Thr Glu
1880                1885                1890

Thr Thr Phe Thr Ile Asn Val Glu Asp Thr Thr Lys Pro Thr Val
1895                1900                1905

Glu Ser Val Ala Asp Gln Thr Gln Glu Ile Asn Thr Glu Ile Glu
1910                1915                1920

Pro Ile Lys Ile Glu Ala Arg Asp Asn Ser Gly Gln Ala Val Thr
1925                1930                1935

Asn Lys Val Asp Gly Leu Pro Asp Gly Val Thr Phe Asp Glu Ala
1940                1945                1950

Thr Asn Thr Ile Ser Gly Thr Pro Ser Glu Val Gly Ser Tyr Asp
1955                1960                1965

Ile Thr Val Thr Thr Thr Asp Glu Ser Gly Asn Ala Thr Glu Thr
1970                1975                1980

Thr Phe Thr Ile Asp Val Glu Asp Thr Thr Lys Pro Thr Val Glu
1985                1990                1995

Asp Ile Thr Asp Gln Thr Gln Glu Ile Asn Thr Glu Met Thr Pro
2000                2005                2010

Ile Lys Ile Glu Ala Thr Asp Asn Ser Gly Gln Ala Val Thr Asn
```

-continued

```
          2015                2020                2025
Lys Val Glu Gly Leu Pro Asp Gly Val Thr Phe Asp Glu Ala Thr
     2030                2035                2040
Asn Thr Ile Ser Gly Thr Pro Ser Glu Val Gly Lys Tyr Leu Ile
     2045                2050                2055
Thr Ile Thr Thr Ile Asp Lys Asp Gly Asn Thr Ala Thr Thr Thr
     2060                2065                2070
Leu Thr Ile Asn Val Ile Asp Thr Thr Thr Pro Glu Gln Pro Thr
     2075                2080                2085
Ile Asn Lys Val Thr Glu Asn Ser Thr Glu Val Asn Gly Arg Gly
     2090                2095                2100
Glu Pro Gly Thr Val Val Glu Val Thr Phe Pro Asp Gly Asn Lys
     2105                2110                2115
Val Glu Gly Lys Val Asp Ser Asp Gly Asn Tyr His Ile Gln Ile
     2120                2125                2130
Pro Ser Glu Thr Thr Leu Lys Gly Gly Gln Pro Leu Gln Val Ile
     2135                2140                2145
Ala Ile Asp Lys Ala Gly Asn Lys Ser Glu Ala Thr Thr Thr Asn
     2150                2155                2160
Val Ile Asp Thr Thr Ala Pro Glu Gln Pro Thr Ile Asn Lys Val
     2165                2170                2175
Thr Glu Asn Ser Thr Glu Val Ser Gly Arg Gly Glu Pro Gly Thr
     2180                2185                2190
Val Val Glu Val Thr Phe Pro Asp Gly Asn Lys Val Glu Gly Lys
     2195                2200                2205
Val Asp Ser Asp Gly Asn Tyr His Ile Gln Ile Pro Ser Asp Glu
     2210                2215                2220
Arg Phe Lys Val Gly Gln Gln Leu Ile Val Lys Val Val Asp Glu
     2225                2230                2235
Glu Gly Asn Val Ser Glu Pro Ser Ile Thr Met Val Gln Lys Glu
     2240                2245                2250
Asp Lys Asn Ser Glu Lys Leu Ser Thr Val Thr Gly Thr Val Thr
     2255                2260                2265
Lys Asn Asn Ser Lys Ser Leu Lys His Lys Ala Ser Glu Gln Gln
     2270                2275                2280
Ser Tyr His Asn Lys Ser Glu Lys Ile Lys Asn Val Asn Lys Pro
     2285                2290                2295
Thr Lys Ile Val Glu Lys Asp Met Ser Thr Tyr Asp Tyr Ser Arg
     2300                2305                2310
Tyr Ser Lys Asp Ile Ser Asn Lys Asn Asn Lys Ser Ala Thr Phe
     2315                2320                2325
Glu Gln Gln Asn Val Ser Asp Ile Asn Asn Gln Tyr Ser Arg
     2330                2335                2340
Asn Lys Val Asn Gln Pro Val Lys Lys Ser Arg Lys Asn Glu Ile
     2345                2350                2355
Asn Lys Asp Leu Pro Gln Thr Gly Glu Glu Asn Phe Asn Lys Ser
     2360                2365                2370
Thr Leu Phe Gly Thr Leu Val Ala Ser Leu Gly Ala Leu Leu Leu
     2375                2380                2385
Phe Phe Lys Arg Arg Lys Lys Asp Glu Asn Asp Glu Lys Glu
     2390                2395                2400
```

<210> SEQ ID NO 21

```
<211> LENGTH: 892
<212> TYPE: PRT
<213> ORGANISM: Staphylococcus epidermidis

<400> SEQUENCE: 21

Leu Phe Gly Leu Gly His Asn Glu Ala Lys Ala Glu Glu Asn Thr Val
1               5                   10                  15

Gln Asp Val Lys Asp Ser Asn Met Asp Asp Glu Leu Ser Asp Ser Asn
            20                  25                  30

Asp Gln Ser Ser Asn Glu Glu Lys Asn Asp Val Ile Asn Asn Ser Gln
        35                  40                  45

Ser Ile Asn Thr Asp Asp Asn Gln Ile Lys Lys Glu Glu Thr Asn
50                  55                  60

Ser Asn Asp Ala Ile Glu Asn Arg Ser Lys Asp Ile Thr Gln Ser Thr
65                  70                  75                  80

Thr Asn Val Asp Glu Asn Glu Ala Thr Phe Leu Gln Lys Thr Pro Gln
                85                  90                  95

Asp Asn Thr Gln Leu Lys Glu Glu Val Val Lys Glu Pro Ser Ser Val
            100                 105                 110

Glu Ser Ser Asn Ser Ser Met Asp Thr Ala Gln Gln Pro Ser His Thr
        115                 120                 125

Thr Ile Asn Ser Glu Ala Ser Ile Gln Thr Ser Asp Asn Glu Glu Asn
130                 135                 140

Ser Arg Val Ser Asp Phe Ala Asn Ser Lys Ile Ile Glu Ser Asn Thr
145                 150                 155                 160

Glu Ser Asn Lys Glu Glu Asn Thr Ile Glu Gln Pro Asn Lys Val Arg
                165                 170                 175

Glu Asp Ser Ile Thr Ser Gln Pro Ser Ser Tyr Lys Asn Ile Asp Glu
            180                 185                 190

Lys Ile Ser Asn Gln Asp Glu Leu Leu Asn Leu Pro Ile Asn Glu Tyr
        195                 200                 205

Glu Asn Lys Val Arg Pro Leu Ser Thr Thr Ser Ala Gln Pro Ser Ser
210                 215                 220

Lys Arg Val Thr Val Asn Gln Leu Ala Ala Glu Gln Gly Ser Asn Val
225                 230                 235                 240

Asn His Leu Ile Lys Val Thr Asp Gln Ser Ile Thr Glu Gly Tyr Asp
                245                 250                 255

Asp Ser Asp Gly Ile Ile Lys Ala His Asp Ala Glu Asn Leu Ile Tyr
            260                 265                 270

Asp Val Thr Phe Glu Val Asp Lys Val Lys Ser Gly Asp Thr Met
        275                 280                 285

Thr Val Asn Ile Asp Lys Asn Thr Val Pro Ser Asp Leu Thr Asp Ser
290                 295                 300

Phe Ala Ile Pro Lys Ile Lys Asp Asn Ser Gly Glu Ile Ile Ala Thr
305                 310                 315                 320

Gly Thr Tyr Asp Asn Thr Asn Lys Gln Ile Thr Tyr Thr Phe Thr Asp
                325                 330                 335

Tyr Val Asp Lys Tyr Glu Asn Ile Ala His Leu Lys Leu Thr Ser
            340                 345                 350

Tyr Ile Asp Lys Ser Lys Val Pro Asn Asn Thr Lys Leu Asp Val
        355                 360                 365

Glu Tyr Lys Thr Ala Leu Ser Ser Val Asn Lys Thr Ile Thr Val Glu
370                 375                 380

Tyr Gln Lys Pro Asn Glu Asn Arg Thr Ala Asn Leu Gln Ser Met Phe
```

```
                        -continued
385                 390                 395                 400
Thr Asn Ile Asp Thr Lys Asn His Thr Val Glu Gln Thr Ile Tyr Ile
                405                 410                 415
Asn Pro Leu Arg Tyr Ser Ala Lys Glu Thr Asn Val Asn Ile Ser Gly
                420                 425                 430
Asn Gly Asp Glu Gly Ser Thr Ile Ile Asp Asp Ser Thr Ile Ile Lys
                435                 440                 445
Val Tyr Lys Val Gly Asp Asn Gln Asn Leu Pro Asp Ser Asn Arg Ile
                450                 455                 460
Tyr Asp Tyr Ser Glu Tyr Glu Asp Val Thr Asn Asp Tyr Ala Gln
465                 470                 475                 480
Leu Gly Asn Asn Asn Asp Val Asn Ile Asn Phe Gly Asn Ile Asp Ser
                485                 490                 495
Pro Tyr Ile Ile Lys Val Ile Ser Lys Tyr Asp Pro Asn Lys Asp Asp
                500                 505                 510
Tyr Thr Thr Ile Gln Gln Thr Val Thr Met Gln Thr Thr Ile Asn Glu
                515                 520                 525
Tyr Thr Gly Glu Phe Arg Thr Ala Ser Tyr Asp Asn Thr Ile Ala Phe
                530                 535                 540
Ser Thr Ser Ser Gly Gln Gly Gln Gly Asp Leu Pro Pro Glu Lys Thr
545                 550                 555                 560
Tyr Lys Ile Gly Asp Tyr Val Trp Glu Asp Val Asp Lys Asp Gly Ile
                565                 570                 575
Gln Asn Thr Asn Asp Asn Glu Lys Pro Leu Ser Asn Val Leu Val Thr
                580                 585                 590
Leu Thr Tyr Pro Asp Gly Thr Ser Lys Ser Val Arg Thr Asp Glu Glu
                595                 600                 605
Gly Lys Tyr Gln Phe Asp Gly Leu Lys Asn Gly Leu Thr Tyr Lys Ile
                610                 615                 620
Thr Phe Glu Thr Pro Glu Gly Tyr Thr Pro Thr Leu Lys His Ser Gly
625                 630                 635                 640
Thr Asn Pro Ala Leu Asp Ser Glu Gly Asn Ser Val Trp Val Thr Ile
                645                 650                 655
Asn Gly Gln Asp Asp Met Thr Ile Asp Ser Gly Phe Tyr Gln Thr Pro
                660                 665                 670
Lys Tyr Ser Leu Gly Asn Tyr Val Trp Tyr Asp Thr Asn Lys Asp Gly
                675                 680                 685
Ile Gln Gly Asp Asp Glu Lys Gly Ile Ser Gly Val Lys Val Thr Leu
                690                 695                 700
Lys Asp Glu Asn Gly Asn Ile Ile Ser Thr Thr Thr Thr Asp Glu Asn
705                 710                 715                 720
Gly Lys Tyr Gln Phe Asp Asn Leu Asn Ser Gly Asn Tyr Ile Val His
                725                 730                 735
Phe Asp Lys Pro Ser Gly Met Thr Gln Thr Thr Thr Asp Ser Gly Asp
                740                 745                 750
Asp Asp Glu Gln Asp Ala Asp Gly Glu Glu Val His Val Thr Ile Thr
                755                 760                 765
Asp His Asp Asp Phe Ser Ile Asp Asn Gly Tyr Tyr Asp Asp Asp Ser
                770                 775                 780
Asp Ser Asp Ser Asp Ser Asp Ser Asp Ser Asp Ser Asp Ser Asp Ser
785                 790                 795                 800
Ser Asp Ser Asp Ser Asp Ser Asp Ser Asp Ser Asp Ser Asp Ser Asp
                805                 810                 815
```

Ser Asp Ser Asp Ser Asp Ser Asp Ser Asp Ser Asp Ser Asp
            820                 825                 830

Ser Asp Ser Asp Ser Asp Ser Gly Leu Asp Asn Ser Ser Asp Lys Asn
            835                 840                 845

Thr Lys Asp Lys Leu Pro Asp Thr Gly Ala Asn Glu Asp His Asp Ser
            850                 855                 860

Lys Gly Thr Leu Leu Gly Ala Leu Phe Ala Gly Leu Gly Ala Leu Leu
865                 870                 875                 880

Leu Gly Lys Arg Arg Lys Asn Arg Lys Asn Lys Asn
                885                 890

<210> SEQ ID NO 22
<211> LENGTH: 1973
<212> TYPE: PRT
<213> ORGANISM: Staphylococcus epidermidis

<400> SEQUENCE: 22

Met Lys Glu Asn Lys Arg Lys Asn Asn Leu Asp Lys Asn Asn Thr Arg
1               5                   10                  15

Phe Ser Ile Arg Lys Tyr Gln Gly Tyr Gly Ala Thr Ser Val Ala Ile
            20                  25                  30

Ile Gly Phe Ile Ile Ile Ser Cys Phe Ser Glu Ala Lys Ala Asp Ser
        35                  40                  45

Asp Lys His Glu Ile Lys Ser His Gln Gln Ser Met Thr Asn His Leu
    50                  55                  60

Thr Thr Leu Pro Ser Asp Asn Gln Glu Asn Thr Ser Asn Asn Glu Phe
65                  70                  75                  80

Asn Asn Arg Asn His Asp Ile Ser His Leu Ser Leu Asn Lys Ser Ile
                85                  90                  95

Gln Met Asp Glu Leu Lys Lys Leu Ile Lys Gln Tyr Lys Ala Ile Asn
            100                 105                 110

Leu Asn Asp Lys Thr Glu Glu Ser Ile Lys Leu Phe Gln Ser Asp Leu
        115                 120                 125

Val Gln Ala Glu Ser Leu Ile Asn Asn Pro Gln Ser Gln Gln His Val
    130                 135                 140

Asp Ala Phe Tyr His Lys Phe Leu Asn Ser Ala Gly Lys Leu Arg Lys
145                 150                 155                 160

Lys Glu Thr Val Ser Ile Lys His Glu Arg Ser Glu Ser Asn Thr Tyr
                165                 170                 175

Arg Leu Gly Asp Glu Val Arg Ser Gln Thr Phe Ser His Ile Arg His
            180                 185                 190

Lys Arg Asn Ala Val Ser Phe Arg Asn Ala Asp Gln Ser Asn Leu Ser
        195                 200                 205

Thr Asp Pro Leu Lys Ala Asn Glu Ile Asn Pro Glu Ile Gln Asn Gly
    210                 215                 220

Asn Phe Ser Gln Val Ser Gly Gly Pro Leu Pro Thr Ser Ser Lys Arg
225                 230                 235                 240

Leu Thr Val Val Thr Asn Val Asp Asn Trp His Ser Tyr Ser Thr Asp
                245                 250                 255

Pro Asn Pro Glu Tyr Pro Met Phe Tyr Thr Thr Thr Ala Val Asn Tyr
            260                 265                 270

Pro Asn Phe Met Ser Asn Gly Asn Ala Pro Tyr Gly Val Ile Leu Gly
        275                 280                 285

Arg Thr Thr Asp Gly Trp Asn Arg Asn Val Ile Asp Ser Lys Val Ala

-continued

```
            290                 295                 300
Gly Ile Tyr Gln Asp Ile Asp Val Val Pro Gly Ser Glu Leu Asn Val
305                 310                 315                 320

Asn Phe Ile Ser Thr Ser Pro Val Phe Ser Asp Gly Ala Ala Gly Ala
                325                 330                 335

Lys Leu Lys Ile Ser Asn Val Glu Gln Asn Arg Val Leu Phe Asp Ser
                340                 345                 350

Arg Leu Asn Gly Met Gly Pro Tyr Pro Thr Gly Lys Leu Ser Ala Met
                355                 360                 365

Val Asn Ile Pro Asn Asp Ile Asn Arg Val Arg Ile Ser Phe Leu Pro
370                 375                 380

Val Ser Ser Thr Gly Arg Val Ser Val Gln Arg Ser Ser Arg Glu His
385                 390                 395                 400

Gly Phe Gly Asp Asn Ser Ser Tyr Tyr His Gly Ser Val Ser Asp
                405                 410                 415

Val Arg Ile Asn Ser Gly Ser Tyr Val Val Ser Lys Val Thr Gln Arg
                420                 425                 430

Glu Tyr Thr Thr Arg Pro Asn Ser Ser Asn Asp Thr Phe Ala Arg Ala
                435                 440                 445

Thr Ile Asn Leu Ser Val Glu Asn Lys Gly His Asn Gln Ser Lys Asp
                450                 455                 460

Thr Tyr Tyr Glu Val Ile Leu Pro Gln Asn Ser Arg Leu Ile Ser Thr
465                 470                 475                 480

Arg Gly Gly Ser Gly Asn Tyr Asn Asn Ala Thr Asn Lys Leu Ser Ile
                485                 490                 495

Arg Leu Asp Asn Leu Asn Pro Gly Asp Arg Arg Asp Ile Ser Tyr Thr
                500                 505                 510

Val Asp Phe Glu Ser Ser Ser Pro Lys Leu Ile Asn Leu Asn Ala His
                515                 520                 525

Leu Leu Tyr Lys Thr Asn Ala Thr Phe Arg Gly Asn Asp Gly Gln Arg
                530                 535                 540

Thr Gly Asp Asn Ile Val Asp Leu Gln Ser Ile Ala Leu Leu Met Asn
545                 550                 555                 560

Lys Asp Val Leu Glu Thr Glu Leu Asn Glu Ile Asp Lys Phe Ile Arg
                565                 570                 575

Asp Leu Asn Glu Ala Asp Phe Thr Ile Asp Ser Trp Ser Ala Leu Gln
                580                 585                 590

Glu Lys Met Thr Glu Gly Gly Asn Ile Leu Asn Glu Gln Asn Gln
                595                 600                 605

Val Ala Leu Glu Asn Gln Ala Ser Gln Glu Thr Ile Asn Asn Val Thr
610                 615                 620

Gln Ser Leu Glu Ile Leu Lys Asn Asn Leu Lys Tyr Lys Thr Pro Ser
625                 630                 635                 640

Gln Pro Ile Ile Lys Ser Asn Asn Gln Ile Pro Asn Ile Thr Ile Ser
                645                 650                 655

Pro Ala Asp Lys Ala Asp Lys Leu Thr Ile Thr Tyr Gln Asn Thr Asp
                660                 665                 670

Asn Glu Ser Ala Ser Ile Ile Gly Asn Lys Leu Asn Asn Gln Trp Ser
                675                 680                 685

Leu Asn Asn Asn Ile Pro Gly Ile Glu Ile Asp Met Gln Thr Gly Leu
                690                 695                 700

Val Thr Ile Asp Tyr Lys Ala Val Tyr Pro Glu Ser Val Val Gly Ala
705                 710                 715                 720
```

-continued

Asn Asp Lys Thr Gly Asn Ser Asp Ala Ser Ala Glu Ser Arg Ile Thr
            725                 730                 735

Met Pro Arg Lys Glu Ala Thr Pro Leu Ser Pro Ile Val Glu Ala Asn
            740                 745                 750

Glu Glu Arg Val Asn Val Val Ile Ala Pro Asn Gly Glu Ala Thr Gln
            755                 760                 765

Ile Ala Ile Lys Tyr Arg Thr Pro Asp Gly Gln Glu Ala Thr Leu Val
770                 775                 780

Ala Ser Lys Asn Gly Ser Ser Trp Thr Leu Asn Lys Gln Ile Asp Tyr
785                 790                 795                 800

Val Asn Ile Glu Glu Asn Ser Gly Lys Val Thr Ile Gly Tyr Gln Ala
            805                 810                 815

Val Gln Pro Glu Ser Glu Val Ile Ala Thr Glu Thr Lys Gly Asn Ser
            820                 825                 830

Asp Glu Ser Ala Glu Ser Arg Val Thr Met Pro Arg Lys Glu Ala Thr
            835                 840                 845

Pro His Ser Pro Ile Val Glu Ala Asn Glu Glu His Val Asn Val Thr
            850                 855                 860

Ile Ala Pro Asn Gly Glu Ala Thr Gln Ile Ala Ile Lys Tyr Arg Thr
865                 870                 875                 880

Pro Asp Gly Gln Glu Thr Thr Leu Ile Ala Ser Lys Asn Gly Ser Ser
            885                 890                 895

Trp Thr Leu Asn Lys Gln Ile Asp Tyr Val Asn Ile Glu Glu Asn Ser
            900                 905                 910

Gly Lys Val Thr Ile Gly Tyr Gln Ala Val Gln Leu Glu Ser Glu Val
            915                 920                 925

Ile Ala Thr Glu Thr Lys Gly Asn Ser Asp Ala Ser Ala Glu Ser Arg
            930                 935                 940

Ile Thr Met Leu Arg Lys Glu Ala Thr Pro His Ser Pro Ile Val Glu
945                 950                 955                 960

Ala Asn Glu Glu His Val Asn Val Thr Ile Ala Pro Asn Gly Glu Ala
            965                 970                 975

Thr Gln Ile Ala Ile Lys Tyr Arg Thr Pro Asp Gly Gln Glu Ala Thr
            980                 985                 990

Leu Val Ala Ser Lys Asn Glu Ser  Ser Trp Thr Leu Asn  Lys Gln Ile
            995                 1000                1005

Asp His Val Asn Ile Asp Glu  Asn Ser Gly Lys Val  Thr Ile Gly
            1010                1015                1020

Tyr Gln Ala Val Gln Pro Glu  Ser Glu Ile Ile Ala  Thr Glu Thr
            1025                1030                1035

Lys Gly Asn Ser Asp Ala Ser  Ala Glu Ser Arg Ile  Thr Met Pro
            1040                1045                1050

Arg Lys Glu Ala Thr Pro Ile  Pro Pro Thr Leu Glu  Ala Ser Val
            1055                1060                1065

Gln Glu Ala Ser Val Thr Val  Thr Pro Asn Glu Asn  Ala Thr Lys
            1070                1075                1080

Val Phe Ile Lys Tyr Leu Asp  Ile Asn Asp Glu Ile  Ser Thr Ile
            1085                1090                1095

Ile Ala Ser Lys Ile Asn Gln  Gln Trp Thr Leu Asn  Lys Asp Asn
            1100                1105                1110

Phe Gly Ile Lys Ile Asn Pro  Leu Thr Gly Lys Val  Ile Ile Ser
            1115                1120                1125

```
Tyr Val Ala Val Gln Pro Glu Ser Asp Val Ile Ala Ile Glu Ser
1130                1135                1140

Gln Gly Asn Ser Asp Leu Ser Glu Glu Ser Arg Ile Ile Met Pro
1145                1150                1155

Thr Lys Glu Glu Pro Pro Glu Pro Pro Ile Leu Glu Ser Asp Ser
1160                1165                1170

Ile Glu Ala Lys Val Asn Ile Phe Pro Asn Asp Glu Ala Thr Arg
1175                1180                1185

Ile Val Ile Met Tyr Thr Ser Leu Glu Gly Gln Glu Ala Thr Leu
1190                1195                1200

Val Ala Ser Lys Asn Glu Ser Ser Trp Thr Leu Asn Lys Gln Ile
1205                1210                1215

Asp His Val Asn Ile Asp Glu Asn Ser Gly Lys Val Thr Ile Gly
1220                1225                1230

Tyr Gln Ala Val Gln Pro Glu Ser Glu Val Ile Ala Thr Glu Thr
1235                1240                1245

Lys Gly Asn Ser Asp Ala Ser Ala Glu Ser Arg Val Thr Met Pro
1250                1255                1260

Arg Lys Glu Ala Thr Pro His Ser Pro Ile Val Glu Thr Asn Glu
1265                1270                1275

Glu Arg Val Asn Val Val Ile Ala Pro Asn Gly Glu Ala Thr Gln
1280                1285                1290

Ile Ala Ile Lys Tyr Arg Thr Pro Asp Gly Gln Glu Thr Thr Leu
1295                1300                1305

Ile Ala Ser Lys Asn Gly Ser Ser Trp Thr Leu Asn Lys Gln Ile
1310                1315                1320

Asp His Val Asn Ile Asp Glu Asn Ser Gly Lys Val Thr Ile Gly
1325                1330                1335

Tyr Gln Ala Val Gln Pro Glu Ser Glu Ile Ile Ala Thr Glu Thr
1340                1345                1350

Lys Gly Asn Ser Asp Ala Ser Ala Glu Ser Arg Ile Thr Met Pro
1355                1360                1365

Arg Lys Glu Ala Ile Pro His Ser Pro Ile Val Glu Ala Asn Glu
1370                1375                1380

Glu His Val Asn Val Thr Ile Ala Pro Asn Gly Glu Thr Thr Gln
1385                1390                1395

Ile Ala Val Lys Tyr Arg Thr Pro Asp Gly Gln Glu Ala Thr Leu
1400                1405                1410

Ile Ala Ser Lys Asn Glu Ser Ser Trp Thr Leu Asn Lys Gln Ile
1415                1420                1425

Asp His Val Asn Ile Asp Glu Asn Ser Gly Lys Val Thr Ile Gly
1430                1435                1440

Tyr Gln Ala Val Gln Pro Glu Ser Glu Val Ile Ala Thr Glu Thr
1445                1450                1455

Lys Gly Asn Ser Asp Ala Ser Ala Glu Ser Arg Ile Thr Met Pro
1460                1465                1470

Val Lys Glu Lys Thr Pro Ala Pro Pro Ile Ser Ile Ile Asn Glu
1475                1480                1485

Ser Asn Ala Ser Val Glu Ile Ile Pro Gln Val Asn Val Thr Gln
1490                1495                1500

Leu Ser Leu Gln Tyr Ile Asp Ala Lys Gly Gln Gln Gln Asn Leu
1505                1510                1515

Ile Ala Thr Leu Asn Gln Asn Gln Trp Thr Leu Asn Lys Asn Val
```

-continued

```
                1520                1525                1530

Ser His Ile Thr Val Asp Lys Asn Thr Gly Lys Val Leu Ile Asn
    1535                1540                1545

Tyr Gln Ala Val Tyr Pro Glu Ser Glu Val Ile Ala Arg Glu Ser
1550                1555                1560

Lys Gly Asn Ser Asp Ser Ser Asn Val Ser Met Val Ile Met Pro
1565                1570                1575

Arg Lys Thr Ala Thr Pro Lys Pro Pro Ile Ile Lys Val Asp Glu
1580                1585                1590

Met Asn Ala Ser Leu Ala Ile Ile Pro Tyr Lys Asn Asn Thr Ala
1595                1600                1605

Ile Asn Ile His Tyr Ile Asp Lys Lys Gly Ile Lys Ser Met Val
1610                1615                1620

Thr Ala Ile Lys Asn Asn Asp Gln Trp Gln Leu Asp Glu Lys Ile
1625                1630                1635

Lys Tyr Val Lys Ile Asp Ala Lys Thr Gly Thr Val Ile Ile Asn
1640                1645                1650

Tyr Gln Ile Val Gln Glu Asn Ser Glu Ile Ile Ala Thr Ala Ile
1655                1660                1665

Asn Gly Asn Ser Asp Lys Ser Glu Glu Val Lys Val Leu Met Pro
1670                1675                1680

Ile Lys Glu Phe Thr Pro Leu Ala Pro Leu Leu Glu Thr Asn Tyr
1685                1690                1695

Lys Lys Ala Thr Val Ser Ile Leu Pro Gln Ser Asn Ala Thr Lys
1700                1705                1710

Leu Asp Phe Lys Tyr Arg Asp Lys Lys Gly Asp Ser Lys Ile Ile
1715                1720                1725

Ile Val Lys Arg Phe Lys Asn Ile Trp Lys Ala Asn Glu Gln Ile
1730                1735                1740

Ser Gly Val Thr Ile Asn Pro Glu Phe Gly Gln Val Val Ile Asn
1745                1750                1755

Tyr Gln Ala Val Tyr Pro Glu Ser Asp Ile Leu Ala Ala Gln Tyr
1760                1765                1770

Val Gly Asn Ser Asp Ala Ser Glu Trp Ala Lys Val Lys Met Pro
1775                1780                1785

Lys Lys Glu Leu Ala Pro His Ser Pro Ser Leu Ile Tyr Asp Asn
1790                1795                1800

Arg Asn Asn Lys Ile Leu Ile Ala Pro Asn Ser Asn Ala Thr Glu
1805                1810                1815

Met Glu Leu Ser Tyr Val Asp Lys Asn Asn Gln Ser Leu Lys Val
1820                1825                1830

Lys Ala Leu Lys Ile Asn Asn Arg Trp Lys Phe Asp Ser Ser Val
1835                1840                1845

Ser Asn Ile Ser Ile Asn Pro Asn Thr Gly Lys Ile Val Leu Gln
1850                1855                1860

Pro Gln Phe Leu Leu Thr Asn Ser Lys Ile Ile Val Phe Ala Lys
1865                1870                1875

Lys Gly Asn Ser Asp Ala Ser Ile Ser Val Ser Leu Arg Val Pro
1880                1885                1890

Ala Val Lys Lys Ile Glu Leu Glu Pro Met Phe Asn Val Pro Val
1895                1900                1905

Leu Val Ser Leu Asn Lys Lys Arg Ile Gln Phe Asp Asp Cys Ser
1910                1915                1920
```

```
Gly Val Lys Asn Cys Leu Asn Lys Gln Ile Ser Lys Thr Gln Leu
    1925                1930                1935

Pro Asp Thr Gly Tyr Ser Asp Lys Ala Ser Lys Ser Asn Ile Leu
    1940                1945                1950

Ser Val Leu Leu Leu Gly Phe Gly Phe Leu Ser Tyr Ser Arg Lys
    1955                1960                1965

Arg Lys Glu Lys Gln
    1970

<210> SEQ ID NO 23
<211> LENGTH: 10203
<212> TYPE: PRT
<213> ORGANISM: Staphylococcus epidermidis

<400> SEQUENCE: 23

Met Lys Ser Lys Pro Lys Leu Asn Gly Arg Asn Ile Cys Ser Phe Leu
1               5                   10                  15

Leu Ser Lys Cys Met Ser Tyr Ser Leu Ser Lys Leu Ser Thr Leu Lys
                20                  25                  30

Thr Tyr Asn Phe Gln Ile Thr Ser Asn Asn Lys Glu Lys Thr Ser Arg
            35                  40                  45

Ile Gly Val Ala Ile Ala Leu Asn Asn Arg Asp Lys Leu Gln Lys Phe
        50                  55                  60

Ser Ile Arg Lys Tyr Ala Ile Gly Thr Phe Ser Thr Val Ile Ala Thr
65                  70                  75                  80

Leu Val Phe Met Gly Ile Asn Thr Asn His Ala Ser Ala Asp Glu Leu
                85                  90                  95

Asn Gln Asn Gln Lys Leu Ile Lys Gln Leu Asn Gln Thr Asp Asp Asp
            100                 105                 110

Asp Ser Asn Thr His Ser Gln Glu Ile Glu Asn Asn Lys Gln Asn Ser
        115                 120                 125

Ser Gly Lys Thr Glu Ser Leu Arg Ser Ser Thr Ser Gln Asn Gln Ala
    130                 135                 140

Asn Ala Arg Leu Ser Asp Gln Phe Lys Asp Thr Asn Glu Thr Ser Gln
145                 150                 155                 160

Gln Leu Pro Thr Asn Val Ser Asp Asp Ser Ile Asn Gln Ser His Ser
                165                 170                 175

Glu Ala Asn Met Asn Asn Glu Pro Leu Lys Val Asp Asn Ser Thr Met
            180                 185                 190

Gln Ala His Ser Lys Ile Val Ser Asp Ser Asp Gly Asn Ala Ser Glu
        195                 200                 205

Asn Lys His His Lys Leu Thr Glu Asn Val Leu Ala Glu Ser Arg Ala
    210                 215                 220

Ser Lys Asn Asp Lys Glu Lys Glu Asn Leu Gln Glu Lys Asp Lys Ser
225                 230                 235                 240

Gln Gln Val His Pro Pro Leu Asp Lys Asn Ala Leu Gln Ala Phe Phe
                245                 250                 255

Asp Ala Ser Tyr His Asn Tyr Arg Met Ile Asp Arg Asp Arg Ala Asp
            260                 265                 270

Ala Thr Glu Tyr Gln Lys Val Lys Ser Thr Phe Asp Tyr Val Asn Asp
        275                 280                 285

Leu Leu Gly Asn Asn Gln Asn Ile Pro Ser Glu Gln Leu Val Ser Ala
    290                 295                 300

Tyr Gln Gln Leu Glu Lys Ala Leu Glu Leu Ala Arg Thr Leu Pro Gln
```

-continued

```
            305                 310                 315                 320
        Gln Ser Thr Thr Glu Lys Arg Gly Arg Arg Ser Thr Arg Ser Val Val
                        325                 330                 335
        Glu Asn Arg Ser Ser Arg Ser Asp Tyr Leu Asp Ala Arg Thr Glu Tyr
                        340                 345                 350
        Tyr Val Ser Lys Asp Asp Asp Ser Gly Phe Pro Pro Gly Thr Phe
                        355                 360                 365
        Phe His Ala Ser Asn Arg Arg Trp Pro Tyr Asn Leu Pro Arg Ser Arg
                370                 375                 380
        Asn Ile Leu Arg Ala Ser Asp Val Gln Gly Asn Ala Tyr Ile Thr Thr
        385                 390                 395                 400
        Lys Arg Leu Lys Asp Gly Tyr Gln Trp Asp Ile Leu Phe Asn Ser Asn
                        405                 410                 415
        His Lys Gly His Glu Tyr Met Tyr Tyr Trp Phe Gly Leu Pro Ser Asp
                        420                 425                 430
        Gln Thr Pro Thr Gly Pro Val Thr Phe Thr Ile Ile Asn Arg Asp Gly
                        435                 440                 445
        Ser Ser Thr Ser Thr Gly Gly Val Gly Phe Gly Ser Gly Ala Pro Leu
                450                 455                 460
        Pro Gln Phe Trp Arg Ser Ala Gly Ala Ile Asn Ser Ser Val Ala Asn
        465                 470                 475                 480
        Asp Phe Lys His Gly Ser Ala Thr Asn Tyr Ala Phe Tyr Asp Gly Val
                        485                 490                 495
        Asn Asn Phe Ser Asp Phe Ala Arg Gly Gly Glu Leu Tyr Phe Asp Arg
                        500                 505                 510
        Glu Gly Ala Thr Gln Thr Asn Lys Tyr Tyr Gly Asp Glu Asn Phe Ala
                        515                 520                 525
        Leu Leu Asn Ser Glu Lys Pro Asp Gln Ile Arg Gly Leu Asp Thr Ile
                530                 535                 540
        Tyr Ser Phe Lys Gly Ser Gly Asp Val Ser Tyr Arg Ile Ser Phe Lys
        545                 550                 555                 560
        Thr Gln Gly Ala Pro Thr Ala Arg Leu Tyr Tyr Ala Ala Gly Ala Arg
                        565                 570                 575
        Ser Gly Glu Tyr Lys Gln Ala Thr Asn Tyr Asn Gln Leu Tyr Val Glu
                        580                 585                 590
        Pro Tyr Lys Asn Tyr Arg Asn Arg Val Gln Ser Asn Val Gln Val Lys
                        595                 600                 605
        Asn Arg Thr Leu His Leu Lys Arg Thr Ile Arg Gln Phe Asp Pro Thr
                610                 615                 620
        Leu Gln Arg Thr Thr Asp Val Pro Ile Leu Asp Ser Asp Gly Ser Gly
        625                 630                 635                 640
        Ser Ile Asp Ser Val Tyr Asp Pro Leu Ser Tyr Val Lys Asn Val Thr
                        645                 650                 655
        Gly Thr Val Leu Gly Ile Tyr Pro Ser Tyr Leu Pro Tyr Asn Gln Glu
                        660                 665                 670
        Arg Trp Gln Gly Ala Asn Ala Met Asn Ala Tyr Gln Ile Glu Glu Leu
                        675                 680                 685
        Phe Ser Gln Glu Asn Leu Gln Asn Ala Ala Arg Ser Gly Arg Pro Ile
                690                 695                 700
        Gln Phe Leu Val Gly Phe Asp Val Glu Asp Ser His His Asn Pro Glu
        705                 710                 715                 720
        Thr Leu Leu Pro Val Asn Leu Tyr Val Lys Pro Glu Leu Lys His Thr
                        725                 730                 735
```

-continued

```
Ile Glu Leu Tyr His Asp Asn Glu Lys Gln Asn Arg Lys Glu Phe Ser
            740                 745                 750

Val Ser Lys Arg Ala Gly His Gly Val Phe Gln Ile Met Ser Gly Thr
            755                 760             765

Leu His Asn Thr Val Gly Ser Gly Ile Leu Pro Tyr Gln Gln Glu Ile
            770             775                 780

Arg Ile Lys Leu Thr Ser Asn Glu Pro Ile Lys Asp Ser Glu Trp Ser
785                 790                 795                 800

Ile Thr Gly Tyr Pro Asn Thr Leu Thr Leu Gln Asn Ala Val Gly Arg
                805                 810                 815

Thr Asn Asn Ala Thr Glu Lys Asn Leu Ala Leu Val Gly His Ile Asp
            820                 825                 830

Pro Gly Asn Tyr Phe Ile Thr Val Lys Phe Gly Asp Lys Val Glu Gln
            835                 840                 845

Phe Glu Ile Arg Ser Lys Pro Thr Pro Arg Ile Ile Thr Thr Ala
            850                 855             860

Asn Glu Leu Arg Gly Asn Ser Asn His Lys Pro Glu Ile Arg Val Thr
865                 870                 875                 880

Asp Ile Pro Asn Asp Thr Thr Ala Lys Ile Lys Leu Val Met Gly Gly
                885                 890                 895

Thr Asp Gly Asp His Asp Pro Glu Ile Asn Pro Tyr Thr Val Pro Glu
            900                 905                 910

Asn Tyr Thr Val Val Ala Glu Ala Tyr His Asp Asn Asp Pro Ser Lys
            915                 920                 925

Asn Gly Val Leu Thr Phe Arg Ser Ser Asp Tyr Leu Lys Asp Leu Pro
930                 935                 940

Leu Ser Gly Glu Leu Lys Ala Ile Val Tyr Tyr Asn Gln Tyr Val Gln
945                 950                 955                 960

Ser Asn Phe Ser Asn Ser Val Pro Phe Ser Asp Thr Thr Pro Pro
                965                 970                 975

Thr Ile Asn Glu Pro Ala Gly Leu Val His Lys Tyr Tyr Arg Gly Asp
            980                 985                 990

His Val Glu Ile Thr Leu Pro Val  Thr Asp Asn Thr Gly  Gly Ser Gly
            995                 1000                1005

Leu Arg  Asp Val Asn Val Asn  Leu Pro Gln Gly Trp  Thr Lys Thr
    1010                1015                1020

Phe Thr  Ile Asn Pro Asn Asn  Asn Thr Glu Gly Thr  Leu Lys Leu
    1025                1030                1035

Ile Gly  Asn Ile Pro Ser Asn  Glu Ala Tyr Asn Thr  Thr Tyr His
    1040                1045                1050

Phe Asn  Ile Thr Ala Thr Asp  Asn Ser Gly Asn Thr  Thr Asn Pro
    1055                1060                1065

Ala Lys  Thr Phe Ile Leu Asn  Val Gly Lys Leu Ala  Asp Asp Leu
    1070                1075                1080

Asn Pro  Val Gly Leu Ser Arg  Asp Gln Leu Gln Leu  Val Thr Asp
    1085                1090                1095

Pro Ser  Ser Leu Ser Asn Ser  Glu Arg Glu Glu Val  Lys Arg Lys
    1100                1105                1110

Ile Ser  Glu Ala Asn Ala Asn  Ile Arg Ser Tyr Leu  Leu Gln Asn
    1115                1120                1125

Asn Pro  Ile Leu Ala Gly Val  Asn Gly Asp Val Thr  Phe Tyr Tyr
    1130                1135                1140
```

-continued

```
Arg Asp Gly Ser Val Asp Val Ile Asp Ala Glu Asn Val Ile Thr
1145                1150                1155

Tyr Glu Pro Glu Arg Lys Ser Ile Phe Ser Glu Asn Gly Asn Thr
1160                1165                1170

Asn Lys Lys Glu Ala Val Ile Thr Ile Ala Arg Gly Gln Asn Tyr
1175                1180                1185

Thr Ile Gly Pro Asn Leu Arg Lys Tyr Phe Ser Leu Ser Asn Gly
1190                1195                1200

Ser Asp Leu Pro Asn Arg Asp Phe Thr Ser Ile Ser Ala Ile Gly
1205                1210                1215

Ser Leu Pro Ser Ser Ser Glu Ile Ser Arg Leu Asn Val Gly Asn
1220                1225                1230

Tyr Asn Tyr Arg Val Asn Ala Lys Asn Ala Tyr His Lys Thr Gln
1235                1240                1245

Gln Glu Leu Asn Leu Lys Leu Lys Ile Val Glu Val Asn Ala Pro
1250                1255                1260

Thr Gly Asn Asn Arg Val Tyr Arg Val Ser Thr Tyr Asn Leu Thr
1265                1270                1275

Asn Asp Glu Ile Asn Lys Ile Lys Gln Ala Phe Lys Ala Ala Asn
1280                1285                1290

Ser Gly Leu Asn Leu Asn Asp Asn Asp Ile Thr Val Ser Asn Asn
1295                1300                1305

Phe Asp His Arg Asn Val Ser Ser Val Thr Val Thr Ile Arg Lys
1310                1315                1320

Gly Asp Leu Ile Lys Glu Phe Ser Ser Asn Leu Asn Asn Met Asn
1325                1330                1335

Phe Leu Arg Trp Val Asn Ile Arg Asp Asp Tyr Thr Ile Ser Trp
1340                1345                1350

Thr Ser Ser Lys Ile Gln Gly Arg Asn Thr Asp Gly Gly Leu Glu
1355                1360                1365

Trp Ser Pro Asp His Lys Ser Leu Ile Tyr Lys Tyr Asp Ala Thr
1370                1375                1380

Leu Gly Arg Gln Ile Asn Thr Asn Asp Val Leu Thr Leu Leu Gln
1385                1390                1395

Ala Thr Ala Lys Asn Ser Asn Leu Arg Ser Asn Ile Asn Ser Asn
1400                1405                1410

Glu Lys Gln Leu Ala Glu Arg Gly Ser Asn Gly Tyr Ser Lys Ser
1415                1420                1425

Ile Ile Arg Asp Asp Gly Glu Lys Ser Tyr Leu Leu Asn Ser Asn
1430                1435                1440

Pro Ile Gln Val Leu Asp Leu Val Glu Pro Asp Asn Gly Tyr Gly
1445                1450                1455

Gly Arg Gln Val Ser His Ser Asn Val Ile Tyr Asn Glu Lys Asn
1460                1465                1470

Ser Ser Ile Val Asn Gly Gln Val Pro Glu Ala Asn Gly Ala Ser
1475                1480                1485

Ala Phe Asn Ile Asp Lys Val Val Lys Ala Asn Ala Ala Asn Asn
1490                1495                1500

Gly Ile Met Gly Val Ile Tyr Lys Ala Gln Leu Tyr Leu Ala Pro
1505                1510                1515

Tyr Ser Pro Lys Gly Tyr Ile Glu Lys Leu Gly Gln Asn Leu Ser
1520                1525                1530

Asn Thr Asn Asn Val Ile Asn Val Tyr Phe Val Pro Ser Asp Lys
```

-continued

|       |       |       | 1535  |       |       |       | 1540  |       |       |       | 1545  |

Val Asn Pro Ser Ile Thr Val Gly Asn Tyr Asp His His Thr Val
1550                1555                1560

Tyr Ser Gly Glu Thr Phe Lys Asn Thr Ile Asn Val Asn Asp Asn
1565                1570                1575

Tyr Gly Leu Asn Thr Val Ala Ser Thr Ser Asp Ser Ala Ile Thr
1580                1585                1590

Met Thr Arg Asn Asn Asn Glu Leu Val Gly Gln Ala Pro Asn Val
1595                1600                1605

Thr Asn Ser Thr Asn Lys Ile Val Lys Val Lys Ala Thr Asp Lys
1610                1615                1620

Ser Gly Asn Glu Ser Ile Val Ser Phe Thr Val Asn Ile Lys Pro
1625                1630                1635

Leu Asn Glu Lys Tyr Arg Ile Thr Thr Ser Ser Ser Asn Gln Thr
1640                1645                1650

Pro Val Arg Ile Ser Asn Ile Gln Asn Asn Ala Asn Leu Ser Ile
1655                1660                1665

Glu Asp Gln Asn Arg Val Lys Ser Ser Leu Ser Met Thr Lys Ile
1670                1675                1680

Leu Gly Thr Arg Asn Tyr Val Asn Glu Ser Asn Asn Asp Val Arg
1685                1690                1695

Ser Gln Val Val Ser Lys Val Asn Arg Ser Gly Asn Asn Ala Thr
1700                1705                1710

Val Asn Val Thr Thr Thr Phe Ser Asp Gly Thr Thr Asn Thr Ile
1715                1720                1725

Thr Val Pro Val Lys His Val Leu Leu Glu Val Val Pro Thr Thr
1730                1735                1740

Arg Thr Thr Val Arg Gly Gln Gln Phe Pro Thr Gly Lys Gly Thr
1745                1750                1755

Ser Pro Asn Asp Phe Phe Ser Leu Arg Thr Gly Gly Pro Val Asp
1760                1765                1770

Ala Arg Ile Val Trp Val Asn Asn Gln Gly Pro Asp Ile Asn Ser
1775                1780                1785

Asn Gln Ile Gly Arg Asp Leu Thr Leu His Ala Glu Ile Phe Phe
1790                1795                1800

Asp Gly Glu Thr Thr Pro Ile Arg Lys Asp Thr Thr Tyr Lys Leu
1805                1810                1815

Ser Gln Ser Ile Pro Lys Gln Ile Tyr Glu Thr Thr Ile Asn Gly
1820                1825                1830

Arg Phe Asn Ser Ser Gly Asp Ala Tyr Pro Gly Asn Phe Val Gln
1835                1840                1845

Ala Val Asn Gln Tyr Trp Pro Glu His Met Asp Phe Arg Trp Ala
1850                1855                1860

Gln Gly Ser Gly Thr Pro Ser Ser Arg Asn Ala Gly Ser Phe Thr
1865                1870                1875

Lys Thr Val Thr Val Val Tyr Gln Asn Gly Gln Thr Glu Asn Val
1880                1885                1890

Asn Val Leu Phe Lys Val Lys Pro Asn Lys Pro Val Ile Asp Ser
1895                1900                1905

Asn Ser Val Ile Ser Lys Gly Gln Leu Asn Gly Gln Gln Ile Leu
1910                1915                1920

Val Arg Asn Val Pro Gln Asn Ala Gln Val Thr Leu Tyr Gln Ser
1925                1930                1935

-continued

```
Asn Gly Thr Val Ile Pro Asn Thr Asn Thr Thr Ile Asp Ser Asn
            1940                1945                1950

Gly Ile Ala Thr Val Thr Ile Gln Gly Thr Leu Pro Thr Gly Asn
            1955                1960                1965

Ile Thr Ala Lys Thr Ser Met Thr Asn Asn Val Thr Tyr Thr Lys
            1970                1975                1980

Gln Asn Ser Ser Gly Ile Ala Ser Asn Thr Thr Glu Asp Ile Ser
            1985                1990                1995

Val Phe Ser Glu Asn Ser Asp Gln Val Asn Val Thr Ala Gly Met
            2000                2005                2010

Gln Ala Lys Asn Asp Gly Ile Lys Ile Ile Lys Gly Thr Asn Tyr
            2015                2020                2025

Asn Phe Asn Asp Phe Asn Ser Phe Ile Ser Asn Ile Pro Ala His
            2030                2035                2040

Ser Thr Leu Thr Trp Asn Glu Glu Pro Asn Ser Trp Lys Asn Asn
            2045                2050                2055

Ile Gly Thr Thr Thr Lys Thr Val Thr Val Thr Leu Pro Asn His
            2060                2065                2070

Gln Gly Thr Arg Thr Val Asp Ile Pro Ile Thr Ile Tyr Pro Thr
            2075                2080                2085

Val Thr Ala Lys Asn Pro Val Arg Asp Gln Lys Gly Arg Asn Leu
            2090                2095                2100

Thr Asn Gly Thr Asp Val Tyr Asn Tyr Ile Ile Phe Glu Asn Asn
            2105                2110                2115

Asn Arg Leu Gly Gly Thr Ala Ser Trp Lys Asp Asn Arg Gln Pro
            2120                2125                2130

Asp Lys Asn Ile Ala Gly Val Gln Asn Leu Ile Ala Leu Val Asn
            2135                2140                2145

Tyr Pro Gly Ile Ser Thr Pro Leu Glu Val Pro Val Lys Val Trp
            2150                2155                2160

Val Tyr Asn Phe Asp Phe Thr Gln Pro Ile Tyr Lys Ile Gln Val
            2165                2170                2175

Gly Asp Thr Phe Pro Lys Gly Thr Trp Ala Gly Tyr Tyr Lys His
            2180                2185                2190

Leu Glu Asn Gly Glu Gly Leu Pro Ile Asp Gly Trp Lys Phe Tyr
            2195                2200                2205

Trp Asn Gln Gln Ser Thr Gly Thr Thr Ser Asp Gln Trp Gln Ser
            2210                2215                2220

Leu Ala Tyr Thr Arg Thr Pro Phe Val Lys Thr Gly Thr Tyr Asp
            2225                2230                2235

Val Val Asn Pro Ser Asn Trp Gly Val Trp Gln Thr Ser Gln Ser
            2240                2245                2250

Ala Lys Phe Ile Val Thr Asn Ala Lys Pro Asn Gln Pro Thr Ile
            2255                2260                2265

Thr Gln Ser Lys Thr Gly Asp Val Thr Val Thr Pro Gly Ala Val
            2270                2275                2280

Arg Asn Ile Leu Ile Ser Gly Thr Asn Asp Tyr Ile Gln Ala Ser
            2285                2290                2295

Ala Asp Lys Ile Val Ile Asn Lys Asn Gly Asn Lys Leu Thr Thr
            2300                2305                2310

Phe Val Lys Asn Asn Asp Gly Arg Trp Thr Val Glu Thr Gly Ser
            2315                2320                2325
```

```
Pro Asp Ile Asn Gly Ile Gly Pro Thr Asn Asn Gly Thr Ala Ile
2330                2335                2340

Ser Leu Ser Arg Leu Ala Val Arg Pro Gly Asp Ser Ile Glu Ala
2345                2350                2355

Ile Ala Thr Glu Gly Ser Gly Glu Thr Ile Ser Thr Ser Ala Thr
2360                2365                2370

Ser Glu Ile Tyr Ile Val Lys Ala Pro Gln Pro Glu Gln Val Ala
2375                2380                2385

Thr His Thr Tyr Asp Asn Gly Thr Phe Asp Ile Leu Pro Asp Asn
2390                2395                2400

Ser Arg Asn Ser Leu Asn Pro Thr Glu Arg Val Glu Ile Asn Tyr
2405                2410                2415

Thr Glu Lys Leu Asn Gly Asn Glu Thr Gln Lys Ser Phe Thr Ile
2420                2425                2430

Thr Lys Asn Asn Asn Gly Lys Trp Thr Ile Asn Asn Lys Pro Asn
2435                2440                2445

Tyr Val Glu Phe Asn Gln Asp Asn Gly Lys Val Val Phe Ser Ala
2450                2455                2460

Asn Thr Ile Lys Pro Asn Ser Gln Ile Thr Ile Thr Pro Lys Ala
2465                2470                2475

Gly Gln Gly Asn Thr Glu Asn Thr Asn Pro Thr Val Ile Gln Ala
2480                2485                2490

Pro Ala Gln His Thr Leu Thr Ile Asn Glu Ile Val Lys Glu Gln
2495                2500                2505

Gly Gln Asn Val Thr Asn Asp Asp Ile Asn Asn Ala Val Gln Val
2510                2515                2520

Pro Asn Lys Asn Arg Val Ala Ile Lys Gln Gly Asn Ala Leu Pro
2525                2530                2535

Thr Asn Leu Ala Gly Gly Ser Thr Ser His Ile Pro Val Val Ile
2540                2545                2550

Tyr Tyr Ser Asp Gly Ser Ser Glu Glu Ala Thr Glu Thr Val Arg
2555                2560                2565

Thr Lys Val Asn Lys Thr Glu Leu Ile Asn Ala Arg Arg Arg Leu
2570                2575                2580

Asp Glu Glu Ile Ser Lys Glu Asn Lys Thr Pro Ser Ser Ile Arg
2585                2590                2595

Asn Phe Asp Gln Ala Met Asn Arg Ala Gln Ser Gln Ile Asn Thr
2600                2605                2610

Ala Lys Ser Asp Ala Asp Gln Val Ile Gly Thr Glu Phe Ala Thr
2615                2620                2625

Pro Gln Gln Val Asn Ser Ala Leu Ser Lys Val Gln Ala Ala Gln
2630                2635                2640

Asn Lys Ile Asn Glu Ala Lys Ala Leu Leu Gln Asn Lys Ala Asp
2645                2650                2655

Asn Ser Gln Leu Val Arg Ala Lys Glu Gln Leu Gln Gln Ser Ile
2660                2665                2670

Gln Pro Ala Ala Ser Thr Asp Gly Met Thr Gln Asp Ser Thr Arg
2675                2680                2685

Asn Tyr Lys Asn Lys Arg Gln Ala Ala Glu Gln Ala Ile Gln His
2690                2695                2700

Ala Asn Ser Val Ile Asn Asn Gly Asp Ala Thr Ser Gln Gln Ile
2705                2710                2715

Asn Asp Ala Lys Asn Thr Val Glu Gln Ala Gln Arg Asp Tyr Val
```

```
                2720                2725                2730
Glu Ala Lys Ser Asn Leu Arg Ala Asp Lys Ser Gln Leu Gln Ser
                2735                2740                2745

Ala Tyr Asp Thr Leu Asn Arg Asp Val Leu Thr Asn Asp Lys Lys
                2750                2755                2760

Pro Ala Ser Val Arg Arg Tyr Asn Glu Ala Ile Ser Asn Ile Arg
                2765                2770                2775

Lys Glu Leu Asp Thr Ala Lys Ala Asp Ala Ser Ser Thr Leu Arg
                2780                2785                2790

Asn Thr Asn Pro Ser Val Glu Gln Val Arg Asp Ala Leu Asn Lys
                2795                2800                2805

Ile Asn Thr Val Gln Pro Lys Val Asn Gln Ala Ile Ala Leu Leu
                2810                2815                2820

Gln Pro Lys Glu Asn Asn Ser Glu Leu Val Gln Ala Lys Lys Arg
                2825                2830                2835

Leu Gln Asp Ala Val Asn Asp Ile Pro Gln Thr Gln Gly Met Thr
                2840                2845                2850

Gln Gln Thr Ile Asn Asn Tyr Asn Asp Lys Gln Arg Glu Ala Glu
                2855                2860                2865

Arg Ala Leu Thr Ser Ala Gln Arg Val Ile Asp Asn Gly Asp Ala
                2870                2875                2880

Thr Thr Gln Glu Ile Thr Ser Glu Lys Ser Lys Val Glu Gln Ala
                2885                2890                2895

Met Gln Ala Leu Thr Asn Ala Lys Ser Asn Leu Arg Ala Asp Lys
                2900                2905                2910

Asn Glu Leu Gln Thr Ala Tyr Asn Lys Leu Ile Glu Asn Val Ser
                2915                2920                2925

Thr Asn Gly Lys Lys Pro Ala Ser Ile Arg Gln Tyr Glu Thr Ala
                2930                2935                2940

Lys Ala Arg Ile Gln Asn Gln Ile Asn Asp Ala Lys Asn Glu Ala
                2945                2950                2955

Glu Arg Ile Leu Gly Asn Asp Asn Pro Gln Val Ser Gln Val Thr
                2960                2965                2970

Gln Ala Leu Asn Lys Ile Lys Ala Ile Gln Pro Lys Leu Thr Glu
                2975                2980                2985

Ala Ile Asn Met Leu Gln Asn Lys Glu Asn Asn Thr Glu Leu Val
                2990                2995                3000

Asn Ala Lys Asn Arg Leu Glu Asn Ala Val Asn Asp Thr Asp Pro
                3005                3010                3015

Thr His Gly Met Thr Gln Glu Thr Ile Asn Asn Tyr Asn Ala Lys
                3020                3025                3030

Lys Arg Glu Ala Gln Asn Glu Ile Gln Lys Ala Asn Met Ile Ile
                3035                3040                3045

Asn Asn Gly Asp Ala Thr Ala Gln Asp Ile Ser Ser Glu Lys Ser
                3050                3055                3060

Lys Val Glu Gln Val Leu Gln Ala Leu Gln Asn Ala Lys Asn Asp
                3065                3070                3075

Leu Arg Ala Asp Lys Arg Glu Leu Gln Thr Ala Tyr Asn Lys Leu
                3080                3085                3090

Ile Gln Asn Val Asn Thr Asn Gly Lys Lys Pro Ser Ser Ile Gln
                3095                3100                3105

Asn Tyr Lys Ser Ala Arg Arg Asn Ile Glu Asn Gln Tyr Asn Thr
                3110                3115                3120
```

-continued

```
Ala Lys Asn Glu Ala His Asn Val Leu Glu Asn Thr Asn Pro Thr
3125                3130                    3135

Val Asn Ala Val Glu Asp Ala Leu Arg Lys Ile Asn Ala Ile Gln
3140                3145                    3150

Pro Glu Val Thr Lys Ala Ile Asn Ile Leu Gln Asp Lys Glu Asp
3155                3160                    3165

Asn Ser Glu Leu Val Arg Ala Lys Glu Lys Leu Asp Gln Ala Ile
3170                3175                    3180

Asn Ser Gln Pro Ser Leu Asn Gly Met Thr Gln Glu Ser Ile Asn
3185                3190                    3195

Asn Tyr Thr Thr Lys Arg Arg Glu Ala Gln Asn Ile Ala Ser Ser
3200                3205                    3210

Ala Asp Thr Ile Ile Asn Asn Gly Asp Ala Ser Ile Glu Gln Ile
3215                3220                    3225

Thr Glu Asn Lys Ile Arg Val Glu Glu Ala Thr Asn Ala Leu Asn
3230                3235                    3240

Glu Ala Lys Gln His Leu Thr Ala Asp Thr Thr Ser Leu Lys Thr
3245                3250                    3255

Glu Val Arg Lys Leu Ser Arg Arg Gly Asp Thr Asn Asn Lys Lys
3260                3265                    3270

Pro Ser Ser Val Ser Ala Tyr Asn Asn Thr Ile His Ser Leu Gln
3275                3280                    3285

Ser Glu Ile Thr Gln Thr Glu Asn Arg Ala Asn Thr Ile Ile Asn
3290                3295                    3300

Lys Pro Ile Arg Ser Val Glu Glu Val Asn Asn Ala Leu His Glu
3305                3310                    3315

Val Asn Gln Leu Asn Gln Arg Leu Thr Asp Thr Ile Asn Leu Leu
3320                3325                    3330

Gln Pro Leu Ala Asn Lys Glu Ser Leu Lys Glu Ala Arg Asn Arg
3335                3340                    3345

Leu Glu Ser Lys Ile Asn Glu Thr Val Gln Thr Asp Gly Met Thr
3350                3355                    3360

Gln Gln Ser Val Glu Asn Tyr Lys Gln Ala Lys Ile Lys Ala Gln
3365                3370                    3375

Asn Glu Ser Ser Ile Ala Gln Thr Leu Ile Asn Asn Gly Asp Ala
3380                3385                    3390

Ser Asp Gln Glu Val Ser Thr Glu Ile Glu Lys Leu Asn Gln Lys
3395                3400                    3405

Leu Ser Glu Leu Thr Asn Ser Ile Asn His Leu Thr Val Asn Lys
3410                3415                    3420

Glu Pro Leu Glu Thr Ala Lys Asn Gln Leu Gln Ala Asn Ile Asp
3425                3430                    3435

Gln Lys Pro Ser Thr Asp Gly Met Thr Gln Gln Ser Val Gln Ser
3440                3445                    3450

Tyr Glu Arg Lys Leu Gln Glu Ala Lys Asp Lys Ile Asn Ser Ile
3455                3460                    3465

Asn Asn Val Leu Ala Asn Asn Pro Asp Val Asn Ala Ile Arg Thr
3470                3475                    3480

Asn Lys Val Glu Thr Glu Gln Ile Asn Asn Glu Leu Thr Gln Ala
3485                3490                    3495

Lys Gln Gly Leu Thr Val Asp Lys Gln Pro Leu Ile Asn Ala Lys
3500                3505                    3510
```

-continued

```
Thr Ala Leu Gln Gln Ser Leu Asp Asn Gln Pro Ser Thr Thr Gly
3515                3520                3525

Met Thr Glu Ala Thr Ile Gln Asn Tyr Asn Ala Lys Arg Gln Lys
3530                3535                3540

Ala Glu Gln Val Ile Gln Asn Ala Asn Lys Ile Ile Glu Asn Ala
3545                3550                3555

Gln Pro Ser Val Gln Val Ser Asp Glu Lys Ser Lys Val Glu
3560                3565                3570

Gln Ala Leu Ser Glu Leu Asn Asn Ala Lys Ser Ala Leu Arg Ala
3575                3580                3585

Asp Lys Gln Glu Leu Gln Gln Ala Tyr Asn Gln Leu Ile Gln Pro
3590                3595                3600

Thr Asp Leu Asn Asn Lys Lys Pro Ala Ser Ile Thr Ala Tyr Asn
3605                3610                3615

Gln Arg Tyr Gln Gln Phe Ser Asn Glu Leu Asn Ser Thr Lys Thr
3620                3625                3630

Asn Thr Asp Arg Ile Leu Lys Glu Gln Asn Pro Ser Val Ala Asp
3635                3640                3645

Val Asn Asn Ala Leu Asn Lys Val Arg Glu Val Gln Gln Lys Leu
3650                3655                3660

Asn Glu Ala Arg Ala Leu Leu Gln Asn Lys Glu Asp Asn Ser Ala
3665                3670                3675

Leu Val Arg Ala Lys Glu Gln Leu Gln Gln Ala Val Asp Gln Val
3680                3685                3690

Pro Ser Thr Glu Gly Met Thr Gln Gln Thr Lys Asp Asp Tyr Asn
3695                3700                3705

Ser Lys Gln Gln Ala Ala Gln Gln Glu Ile Ser Lys Ala Gln Gln
3710                3715                3720

Val Ile Asp Asn Gly Asp Ala Thr Thr Gln Gln Ile Ser Asn Ala
3725                3730                3735

Lys Thr Asn Val Glu Arg Ala Leu Glu Ala Leu Asn Asn Ala Lys
3740                3745                3750

Thr Gly Leu Arg Ala Asp Lys Glu Glu Leu Gln Asn Ala Tyr Asn
3755                3760                3765

Gln Leu Thr Gln Asn Ile Asp Thr Ser Gly Lys Thr Pro Ala Ser
3770                3775                3780

Ile Arg Lys Tyr Asn Glu Ala Lys Ser Arg Ile Gln Thr Gln Ile
3785                3790                3795

Asp Ser Ala Lys Asn Glu Ala Asn Ser Ile Leu Thr Asn Asp Asn
3800                3805                3810

Pro Gln Val Ser Gln Val Thr Ala Ala Leu Asn Lys Ile Lys Ala
3815                3820                3825

Val Gln Pro Glu Leu Asp Lys Ala Ile Ala Met Leu Lys Asn Lys
3830                3835                3840

Glu Asn Asn Asn Ala Leu Val Gln Ala Lys Gln Gln Leu Gln Gln
3845                3850                3855

Ile Val Asn Glu Val Asp Pro Thr Gln Gly Met Thr Thr Asp Thr
3860                3865                3870

Ala Asn Asn Tyr Lys Ser Lys Lys Arg Glu Ala Glu Asp Glu Ile
3875                3880                3885

Gln Lys Ala Gln Gln Ile Ile Asn Asn Gly Asp Ala Thr Glu Gln
3890                3895                3900

Gln Ile Thr Asn Glu Thr Asn Arg Val Asn Gln Ala Ile Asn Ala
```

-continued

```
               3905                     3910                    3915
    Ile  Asn  Lys  Ala  Lys  Asn  Asp  Leu  Arg  Ala  Asp  Lys  Ser  Gln  Leu
               3920                     3925                    3930
    Glu  Asn  Ala  Tyr  Asn  Gln  Leu  Ile  Gln  Asn  Val  Asp  Thr  Asn  Gly
               3935                     3940                    3945
    Lys  Lys  Pro  Ala  Ser  Ile  Gln  Gln  Tyr  Gln  Ala  Ala  Arg  Gln  Ala
               3950                     3955                    3960
    Ile  Glu  Thr  Gln  Tyr  Asn  Asn  Ala  Lys  Ser  Glu  Ala  His  Gln  Ile
               3965                     3970                    3975
    Leu  Glu  Asn  Ser  Asn  Pro  Ser  Val  Asn  Glu  Val  Ala  Gln  Ala  Leu
               3980                     3985                    3990
    Gln  Lys  Val  Glu  Ala  Val  Gln  Leu  Lys  Val  Asn  Asp  Ala  Ile  His
               3995                     4000                    4005
    Ile  Leu  Gln  Asn  Lys  Glu  Asn  Asn  Ser  Ala  Leu  Val  Thr  Ala  Lys
               4010                     4015                    4020
    Asn  Gln  Leu  Gln  Gln  Ser  Val  Asn  Asp  Gln  Pro  Leu  Thr  Thr  Gly
               4025                     4030                    4035
    Met  Thr  Gln  Asp  Ser  Ile  Asn  Asn  Tyr  Glu  Ala  Lys  Arg  Asn  Glu
               4040                     4045                    4050
    Ala  Gln  Ser  Ala  Ile  Arg  Asn  Ala  Glu  Ala  Val  Ile  Asn  Asn  Gly
               4055                     4060                    4065
    Asp  Ala  Thr  Ala  Lys  Gln  Ile  Ser  Asp  Glu  Lys  Ser  Lys  Val  Glu
               4070                     4075                    4080
    Gln  Ala  Leu  Ala  His  Leu  Asn  Asp  Ala  Lys  Gln  Gln  Leu  Thr  Ala
               4085                     4090                    4095
    Asp  Thr  Thr  Glu  Leu  Gln  Thr  Ala  Val  Gln  Gln  Leu  Asn  Arg  Arg
               4100                     4105                    4110
    Gly  Asp  Thr  Asn  Asn  Lys  Lys  Pro  Arg  Ser  Ile  Asn  Ala  Tyr  Asn
               4115                     4120                    4125
    Lys  Ala  Ile  Gln  Ser  Leu  Glu  Thr  Gln  Ile  Thr  Ser  Ala  Lys  Asp
               4130                     4135                    4140
    Asn  Ala  Asn  Ala  Val  Ile  Gln  Lys  Pro  Ile  Arg  Thr  Val  Gln  Glu
               4145                     4150                    4155
    Val  Asn  Asn  Ala  Leu  Gln  Gln  Val  Asn  Gln  Leu  Asn  Gln  Gln  Leu
               4160                     4165                    4170
    Thr  Glu  Ala  Ile  Asn  Gln  Leu  Gln  Pro  Leu  Ser  Asn  Asn  Asp  Ala
               4175                     4180                    4185
    Leu  Lys  Ala  Ala  Arg  Leu  Asn  Leu  Glu  Asn  Lys  Ile  Asn  Gln  Thr
               4190                     4195                    4200
    Val  Gln  Thr  Asp  Gly  Met  Thr  Gln  Gln  Ser  Ile  Glu  Ala  Tyr  Gln
               4205                     4210                    4215
    Asn  Ala  Lys  Arg  Val  Ala  Gln  Asn  Glu  Ser  Asn  Thr  Ala  Leu  Ala
               4220                     4225                    4230
    Leu  Ile  Asn  Asn  Gly  Asp  Ala  Asp  Glu  Gln  Gln  Ile  Thr  Thr  Glu
               4235                     4240                    4245
    Thr  Asp  Arg  Val  Asn  Gln  Gln  Thr  Thr  Asn  Leu  Thr  Gln  Ala  Ile
               4250                     4255                    4260
    Asn  Gly  Leu  Thr  Val  Asn  Lys  Glu  Pro  Leu  Glu  Thr  Ala  Lys  Thr
               4265                     4270                    4275
    Ala  Leu  Gln  Asn  Asn  Ile  Asp  Gln  Val  Pro  Ser  Thr  Asp  Gly  Met
               4280                     4285                    4290
    Thr  Gln  Gln  Ser  Val  Ala  Asn  Tyr  Asn  Gln  Lys  Leu  Gln  Ile  Ala
               4295                     4300                    4305
```

```
Lys Asn Glu Ile Asn Thr Ile Asn Asn Val Leu Ala Asn Asn Pro
4310            4315                4320

Asp Val Asn Ala Ile Lys Thr Asn Lys Ala Glu Ala Glu Arg Ile
    4325            4330                4335

Ser Asn Asp Leu Thr Gln Ala Lys Asn Asn Leu Gln Val Asp Thr
    4340            4345                4350

Gln Pro Leu Glu Lys Ile Lys Arg Gln Leu Gln Asp Glu Ile Asp
    4355            4360                4365

Gln Gly Thr Asn Thr Asp Gly Met Thr Gln Asp Ser Val Asp Asn
    4370            4375                4380

Tyr Asn Asp Ser Leu Ser Ala Ala Ile Ile Glu Lys Gly Lys Val
    4385            4390                4395

Asn Lys Leu Leu Lys Arg Asn Pro Thr Val Glu Gln Val Lys Glu
    4400            4405                4410

Ser Val Ala Asn Ala Gln Gln Val Ile Gln Asp Leu Gln Asn Ala
    4415            4420                4425

Arg Thr Ser Leu Val Pro Asp Lys Thr Gln Leu Gln Glu Ala Lys
    4430            4435                4440

Asn Arg Leu Glu Asn Ser Ile Asn Gln Gln Thr Asp Thr Asp Gly
    4445            4450                4455

Met Thr Gln Asp Ser Leu Asn Asn Tyr Asn Asp Lys Leu Ala Lys
    4460            4465                4470

Ala Arg Gln Asn Leu Glu Lys Ile Ser Lys Val Leu Gly Gly Gln
    4475            4480                4485

Pro Thr Val Ala Glu Ile Arg Gln Asn Thr Asp Glu Ala Asn Ala
    4490            4495                4500

His Lys Gln Ala Leu Asp Thr Ala Arg Ser Gln Leu Thr Leu Asn
    4505            4510                4515

Arg Glu Pro Tyr Ile Asn His Ile Asn Asn Glu Ser His Leu Asn
    4520            4525                4530

Asn Ala Gln Lys Asp Asn Phe Lys Ala Gln Val Asn Ser Ala Pro
    4535            4540                4545

Asn His Asn Thr Leu Glu Thr Ile Lys Asn Lys Ala Asp Thr Leu
    4550            4555                4560

Asn Gln Ser Met Thr Ala Leu Ser Glu Ser Ile Ala Asp Tyr Glu
    4565            4570                4575

Asn Gln Lys Gln Glu Asn Tyr Leu Asp Ala Ser Asn Asn Lys
    4580            4585                4590

Arg Gln Asp Tyr Asp Asn Ala Val Asn Ala Ala Lys Gly Ile Leu
    4595            4600                4605

Asn Gln Thr Gln Ser Pro Thr Met Ser Ala Asp Val Ile Asp Gln
    4610            4615                4620

Lys Ala Glu Asp Val Lys Arg Thr Lys Thr Ala Leu Asp Gly Asn
    4625            4630                4635

Gln Arg Leu Glu Val Ala Lys Gln Gln Ala Leu Asn His Leu Asn
    4640            4645                4650

Thr Leu Asn Asp Leu Asn Asp Ala Gln Arg Gln Thr Leu Thr Asp
    4655            4660                4665

Thr Ile Asn His Ser Pro Asn Ile Asn Ser Val Asn Gln Ala Lys
    4670            4675                4680

Glu Lys Ala Asn Thr Val Asn Thr Ala Met Thr Gln Leu Lys Gln
    4685            4690                4695
```

```
Thr Ile Ala Asn Tyr Asp Asp Glu Leu His Asp Gly Asn Tyr Ile
4700                4705                4710

Asn Ala Asp Lys Asp Lys Lys Asp Ala Tyr Asn Asn Ala Val Asn
4715                4720                4725

Asn Ala Lys Gln Leu Ile Asn Gln Ser Asp Ala Asn Gln Ala Gln
4730                4735                4740

Leu Asp Pro Ala Glu Ile Asn Lys Val Thr Gln Arg Val Asn Thr
4745                4750                4755

Thr Lys Asn Asp Leu Asn Gly Asn Asp Lys Leu Ala Glu Ala Lys
4760                4765                4770

Arg Asp Ala Asn Thr Thr Ile Asp Gly Leu Thr Tyr Leu Asn Glu
4775                4780                4785

Ala Gln Arg Asn Lys Ala Lys Glu Asn Val Gly Lys Ala Ser Thr
4790                4795                4800

Lys Thr Asn Ile Thr Ser Gln Leu Gln Asp Tyr Asn Gln Leu Asn
4805                4810                4815

Ile Ala Met Gln Ala Leu Arg Asn Ser Val Asn Asp Val Asn Asn
4820                4825                4830

Val Lys Ala Asn Ser Asn Tyr Ile Asn Glu Asp Asn Gly Pro Lys
4835                4840                4845

Glu Ala Tyr Asn Gln Ala Val Thr His Ala Gln Thr Leu Ile Asn
4850                4855                4860

Ala Gln Ser Asn Pro Glu Met Ser Arg Asp Val Val Asn Gln Lys
4865                4870                4875

Thr Gln Ala Val Asn Thr Ala His Gln Asn Leu His Gly Gln Gln
4880                4885                4890

Lys Leu Glu Gln Ala Gln Ser Ser Ala Asn Thr Glu Ile Gly Asn
4895                4900                4905

Leu Pro Asn Leu Thr Asn Thr Gln Lys Ala Lys Glu Lys Glu Leu
4910                4915                4920

Val Asn Ser Lys Gln Thr Arg Thr Glu Val Gln Glu Gln Leu Asn
4925                4930                4935

Gln Ala Lys Ser Leu Asp Ser Ser Met Gly Thr Leu Lys Ser Leu
4940                4945                4950

Val Ala Lys Gln Pro Thr Val Gln Lys Thr Ser Val Tyr Ile Asn
4955                4960                4965

Glu Asp Gln Pro Glu Gln Ser Ala Tyr Asn Asp Ser Ile Thr Met
4970                4975                4980

Gly Gln Thr Ile Ile Asn Lys Thr Ala Asp Pro Val Leu Asp Lys
4985                4990                4995

Thr Leu Val Asp Asn Ala Ile Ser Asn Ile Ser Thr Lys Glu Asn
5000                5005                5010

Ala Leu His Gly Glu Gln Lys Leu Thr Thr Ala Lys Thr Glu Ala
5015                5020                5025

Ile Asn Ala Leu Asn Thr Leu Ala Asp Leu Asn Thr Pro Gln Lys
5030                5035                5040

Glu Ala Ile Lys Thr Ala Ile Asn Thr Ala His Thr Arg Thr Asp
5045                5050                5055

Val Thr Ala Glu Gln Ser Lys Ala Asn Gln Ile Asn Ser Ala Met
5060                5065                5070

His Thr Leu Arg Gln Asn Ile Ser Asp Asn Glu Ser Val Thr Asn
5075                5080                5085

Glu Ser Asn Tyr Ile Asn Ala Glu Pro Glu Lys Gln His Ala Phe
```

-continued

```
         5090                5095                 5100

Thr Glu  Ala Leu Asn Asn Ala  Lys Glu Ile Val Asn  Glu Gln Gln
         5105                5110                 5115

Ala Thr  Leu Asp Ala Asn Ser  Ile Asn Gln Lys Ala  Gln Ala Ile
         5120                5125                 5130

Leu Thr  Thr Lys Asn Ala Leu  Asp Gly Glu Glu Gln  Leu Arg Arg
         5135                5140                 5145

Ala Lys  Glu Asn Ala Asp Gln  Glu Ile Asn Thr Leu  Asn Gln Leu
         5150                5155                 5160

Thr Asp  Ala Gln Arg Asn Ser  Glu Lys Gly Leu Val  Asn Ser Ser
         5165                5170                 5175

Gln Thr  Arg Thr Glu Val Ala  Ser Gln Leu Ala Lys  Ala Lys Glu
         5180                5185                 5190

Leu Asn  Lys Val Met Glu Gln  Leu Asn His Leu Ile  Asn Gly Lys
         5195                5200                 5205

Asn Gln  Met Ile Asn Ser Ser  Lys Phe Ile Asn Glu  Asp Ala Asn
         5210                5215                 5220

Gln Gln  Gln Ala Tyr Ser Asn  Ala Ile Ala Ser Ala  Glu Ala Leu
         5225                5230                 5235

Lys Asn  Lys Ser Gln Asn Pro  Glu Leu Asp Lys Val  Thr Ile Glu
         5240                5245                 5250

Gln Ala  Ile Asn Asn Ile Asn  Ser Ala Ile Asn Asn  Leu Asn Gly
         5255                5260                 5265

Glu Ala  Lys Leu Thr Lys Ala  Lys Glu Asp Ala Val  Ala Ser Ile
         5270                5275                 5280

Asn Asn  Leu Ser Gly Leu Thr  Asn Glu Gln Lys Pro  Lys Glu Asn
         5285                5290                 5295

Gln Ala  Val Asn Gly Ala Gln  Thr Arg Asp Gln Val  Ala Asn Lys
         5300                5305                 5310

Leu Arg  Asp Ala Glu Ala Leu  Asp Gln Ser Met Gln  Thr Leu Arg
         5315                5320                 5325

Asp Leu  Val Asn Asn Gln Asn  Ala Ile His Ser Thr  Ser Asn Tyr
         5330                5335                 5340

Phe Asn  Glu Asp Ser Thr Gln  Lys Asn Thr Tyr Asp  Asn Ala Ile
         5345                5350                 5355

Asp Asn  Gly Ser Thr Tyr Ile  Thr Gly Gln His Asn  Pro Glu Leu
         5360                5365                 5370

Asn Lys  Ser Thr Ile Asp Gln  Thr Ile Ser Arg Ile  Asn Thr Ala
         5375                5380                 5385

Lys Asn  Asp Leu His Gly Val  Glu Lys Leu Gln Arg  Asp Lys Gly
         5390                5395                 5400

Thr Ala  Asn Gln Glu Ile Gly  Gln Leu Gly Tyr Leu  Asn Asp Pro
         5405                5410                 5415

Gln Lys  Ser Gly Glu Glu Ser  Leu Val Asn Gly Ser  Asn Thr Arg
         5420                5425                 5430

Ser Glu  Val Glu Glu His Leu  Asn Glu Ala Lys Ser  Leu Asn Asn
         5435                5440                 5445

Ala Met  Lys Gln Leu Arg Asp  Lys Val Ala Glu Lys  Thr Asn Val
         5450                5455                 5460

Lys Gln  Ser Ser Asp Tyr Ile  Asn Asp Ser Thr Glu  His Gln Arg
         5465                5470                 5475

Gly Tyr  Asp Gln Ala Leu Gln  Glu Ala Glu Asn Ile  Ile Asn Glu
         5480                5485                 5490
```

-continued

```
Ile Gly Asn Pro Thr Leu Asn Lys Ser Glu Ile Glu Gln Lys Leu
        5495                5500                5505
Gln Gln Leu Thr Asp Ala Gln Asn Ala Leu Gln Gly Ser His Leu
        5510                5515                5520
Leu Glu Glu Ala Lys Asn Asn Ala Ile Thr Gly Ile Asn Lys Leu
        5525                5530                5535
Thr Ala Leu Asn Asp Ala Gln Arg Gln Lys Ala Ile Glu Asn Val
        5540                5545                5550
Gln Ala Gln Gln Thr Ile Pro Ala Val Asn Gln Gln Leu Thr Leu
        5555                5560                5565
Asp Arg Glu Ile Asn Thr Ala Met Gln Ala Leu Arg Asp Lys Val
        5570                5575                5580
Gly Gln Gln Asn Asn Val His Gln Gln Ser Asn Tyr Phe Asn Glu
        5585                5590                5595
Asp Glu Gln Pro Lys His Asn Tyr Asp Asn Ser Val Gln Ala Gly
        5600                5605                5610
Gln Thr Ile Ile Asp Lys Leu Gln Asp Pro Ile Met Asn Lys Asn
        5615                5620                5625
Glu Ile Glu Gln Ala Ile Asn Gln Ile Asn Thr Thr Gln Thr Ala
        5630                5635                5640
Leu Ser Gly Glu Asn Lys Leu His Thr Asp Gln Glu Ser Thr Asn
        5645                5650                5655
Arg Gln Ile Glu Gly Leu Ser Ser Leu Asn Thr Ala Gln Ile Asn
        5660                5665                5670
Ala Glu Lys Asp Leu Val Asn Gln Ala Lys Thr Arg Thr Asp Val
        5675                5680                5685
Ala Gln Lys Leu Ala Ala Ala Lys Glu Ile Asn Ser Ala Met Ser
        5690                5695                5700
Asn Leu Arg Asp Gly Ile Gln Asn Lys Glu Asp Ile Lys Arg Ser
        5705                5710                5715
Ser Ala Tyr Ile Asn Ala Asp Pro Thr Lys Val Thr Ala Tyr Asp
        5720                5725                5730
Gln Ala Leu Gln Asn Ala Glu Asn Ile Ile Asn Ala Thr Pro Asn
        5735                5740                5745
Val Glu Leu Asn Lys Ala Thr Ile Glu Gln Ala Leu Ser Arg Val
        5750                5755                5760
Gln Gln Ala Gln Gln Asp Leu Asp Gly Val Gln Gln Leu Ala Asn
        5765                5770                5775
Ala Lys Gln Gln Ala Thr Gln Thr Val Asn Gly Leu Asn Ser Leu
        5780                5785                5790
Asn Asp Gly Gln Lys Arg Glu Leu Asn Leu Leu Ile Asn Ser Ala
        5795                5800                5805
Asn Thr Arg Thr Lys Val Gln Glu Glu Leu Asn Lys Ala Thr Glu
        5810                5815                5820
Leu Asn His Ala Met Glu Ala Leu Arg Asn Ser Val Gln Asn Val
        5825                5830                5835
Asp Gln Val Lys Gln Ser Ser Asn Tyr Val Asn Glu Asp Gln Pro
        5840                5845                5850
Glu Gln His Asn Tyr Asp Asn Ala Val Asn Glu Ala Gln Ala Thr
        5855                5860                5865
Ile Asn Asn Asn Ala Gln Pro Val Leu Asp Lys Leu Ala Ile Glu
        5870                5875                5880
```

-continued

```
Arg Leu Thr Gln Thr Val Asn Thr Thr Lys Asp Ala Leu His Gly
    5885                5890                5895

Ala Gln Lys Leu Thr Gln Asp Gln Gln Ala Ala Glu Thr Gly Ile
    5900                5905                5910

Arg Gly Leu Thr Ser Leu Asn Glu Pro Gln Lys Asn Ala Glu Val
    5915                5920                5925

Ala Lys Val Thr Ala Ala Thr Thr Arg Asp Glu Val Arg Asn Ile
    5930                5935                5940

Arg Gln Glu Ala Thr Thr Leu Asp Thr Ala Met Leu Gly Leu Arg
    5945                5950                5955

Lys Ser Ile Lys Asp Lys Asn Asp Thr Lys Asn Ser Ser Lys Tyr
    5960                5965                5970

Ile Asn Glu Asp His Asp Gln Gln Ala Tyr Asp Asn Ala Val
    5975                5980                5985

Asn Asn Ala Gln Gln Val Ile Asp Glu Thr Gln Ala Thr Leu Ser
    5990                5995                6000

Ser Asp Thr Ile Asn Gln Leu Ala Asn Ala Val Thr Gln Ala Lys
    6005                6010                6015

Ser Asn Leu His Gly Asp Thr Lys Leu Gln His Asp Lys Asp Ser
    6020                6025                6030

Ala Lys Gln Thr Ile Ala Gln Leu Gln Asn Leu Asn Ser Ala Gln
    6035                6040                6045

Lys His Met Glu Asp Ser Leu Ile Asp Asn Glu Ser Thr Arg Thr
    6050                6055                6060

Gln Val Gln His Asp Leu Thr Glu Ala Gln Ala Leu Asp Gly Leu
    6065                6070                6075

Met Gly Ala Leu Lys Glu Ser Ile Lys Asp Tyr Thr Asn Ile Val
    6080                6085                6090

Ser Asn Gly Asn Tyr Ile Asn Ala Glu Pro Ser Lys Lys Gln Ala
    6095                6100                6105

Tyr Asp Ala Ala Val Gln Asn Ala Gln Asn Ile Ile Asn Gly Thr
    6110                6115                6120

Asn Gln Pro Thr Ile Asn Lys Gly Asn Val Thr Thr Ala Thr Gln
    6125                6130                6135

Thr Val Lys Asn Thr Lys Asp Ala Leu Asp Gly Asp His Arg Leu
    6140                6145                6150

Glu Glu Ala Lys Asn Asn Ala Asn Gln Thr Ile Arg Asn Leu Ser
    6155                6160                6165

Asn Leu Asn Asn Ala Gln Lys Asp Ala Glu Lys Asn Leu Val Asn
    6170                6175                6180

Ser Ala Ser Thr Leu Glu Gln Val Gln Gln Asn Leu Gln Thr Ala
    6185                6190                6195

Gln Gln Leu Asp Asn Ala Met Gly Glu Leu Arg Gln Ser Ile Ala
    6200                6205                6210

Lys Lys Asp Gln Val Lys Ala Asp Ser Lys Tyr Leu Asn Glu Asp
    6215                6220                6225

Pro Gln Ile Lys Gln Asn Tyr Asp Asp Ala Val Gln Arg Val Glu
    6230                6235                6240

Thr Ile Ile Asn Glu Thr Gln Asn Pro Glu Leu Leu Lys Ala Asn
    6245                6250                6255

Ile Asp Gln Ala Thr Gln Ser Val Gln Asn Ala Glu Gln Ala Leu
    6260                6265                6270

His Gly Ala Glu Lys Leu Asn Gln Asp Lys Gln Thr Ser Ser Thr
```

```
                   6275                6280                6285

Glu  Leu  Asp  Gly  Leu  Thr  Asp  Leu  Thr  Asp  Ala  Gln  Arg  Glu  Lys
                   6290                6295                6300

Leu  Arg  Glu  Gln  Ile  Asn  Thr  Ser  Asn  Ser  Arg  Asp  Asp  Ile  Lys
                   6305                6310                6315

Gln  Lys  Ile  Glu  Gln  Ala  Lys  Ala  Leu  Asn  Asp  Ala  Met  Lys  Lys
                   6320                6325                6330

Leu  Lys  Glu  Gln  Val  Ala  Gln  Lys  Asp  Gly  Val  His  Ala  Asn  Ser
                   6335                6340                6345

Asp  Tyr  Thr  Asn  Glu  Asp  Ser  Ala  Gln  Lys  Asp  Ala  Tyr  Asn  Asn
                   6350                6355                6360

Ala  Leu  Lys  Gln  Ala  Glu  Asp  Ile  Ile  Asn  Asn  Ser  Ser  Asn  Pro
                   6365                6370                6375

Asn  Leu  Asn  Ala  Gln  Asp  Ile  Thr  Asn  Ala  Leu  Asn  Asn  Ile  Lys
                   6380                6385                6390

Gln  Ala  Gln  Asp  Asn  Leu  His  Gly  Ala  Gln  Lys  Leu  Gln  Gln  Asp
                   6395                6400                6405

Lys  Asn  Thr  Thr  Asn  Gln  Ala  Ile  Gly  Asn  Leu  Asn  His  Leu  Asn
                   6410                6415                6420

Gln  Pro  Gln  Lys  Asp  Ala  Leu  Ile  Gln  Ala  Ile  Asn  Gly  Ala  Thr
                   6425                6430                6435

Ser  Arg  Asp  Gln  Val  Ala  Glu  Lys  Leu  Lys  Glu  Ala  Glu  Ala  Leu
                   6440                6445                6450

Asp  Glu  Ala  Met  Lys  Gln  Leu  Glu  Asp  Gln  Val  Asn  Gln  Asp  Asp
                   6455                6460                6465

Gln  Ile  Ser  Asn  Ser  Ser  Pro  Phe  Ile  Asn  Glu  Asp  Ser  Asp  Lys
                   6470                6475                6480

Gln  Lys  Thr  Tyr  Asn  Asp  Lys  Ile  Gln  Ala  Ala  Lys  Glu  Ile  Ile
                   6485                6490                6495

Asn  Gln  Thr  Ser  Asn  Pro  Thr  Leu  Asp  Lys  Gln  Lys  Ile  Ala  Asp
                   6500                6505                6510

Thr  Leu  Gln  Asn  Ile  Lys  Asp  Ala  Val  Asn  Asn  Leu  His  Gly  Asp
                   6515                6520                6525

Gln  Lys  Leu  Ala  Gln  Ser  Lys  Gln  Asp  Ala  Asn  Asn  Gln  Leu  Asn
                   6530                6535                6540

His  Leu  Asp  Asp  Leu  Thr  Glu  Glu  Gln  Lys  Asn  His  Phe  Lys  Pro
                   6545                6550                6555

Leu  Ile  Asn  Asn  Ala  Asp  Thr  Arg  Asp  Glu  Val  Asn  Lys  Gln  Leu
                   6560                6565                6570

Glu  Ile  Ala  Lys  Gln  Leu  Asn  Gly  Asp  Met  Ser  Thr  Leu  His  Lys
                   6575                6580                6585

Val  Ile  Asn  Asp  Lys  Asp  Gln  Ile  Gln  His  Leu  Ser  Asn  Tyr  Ile
                   6590                6595                6600

Asn  Ala  Asp  Asn  Asp  Lys  Lys  Gln  Asn  Tyr  Asp  Asn  Ala  Ile  Lys
                   6605                6610                6615

Glu  Ala  Glu  Asp  Leu  Ile  His  Asn  His  Pro  Asp  Thr  Leu  Asp  His
                   6620                6625                6630

Lys  Ala  Leu  Gln  Asp  Leu  Leu  Asn  Lys  Ile  Asp  Gln  Ala  His  Asn
                   6635                6640                6645

Glu  Leu  Asn  Gly  Glu  Ser  Arg  Phe  Lys  Gln  Ala  Leu  Asp  Asn  Ala
                   6650                6655                6660

Leu  Asn  Asp  Ile  Asp  Ser  Leu  Asn  Ser  Leu  Asn  Val  Pro  Gln  Arg
                   6665                6670                6675
```

-continued

```
Gln Thr Val Lys Asp Asn Ile Asn His Val Thr Thr Leu Glu Ser
    6680                6685                6690

Leu Ala Gln Glu Leu Gln Lys Ala Lys Glu Leu Asn Asp Ala Met
    6695                6700                6705

Lys Ala Met Arg Asp Ser Ile Met Asn Gln Glu Gln Ile Arg Lys
    6710                6715                6720

Asn Ser Asn Tyr Thr Asn Glu Asp Leu Ala Gln Gln Asn Ala Tyr
    6725                6730                6735

Asn His Ala Val Asp Lys Ile Asn Asn Ile Ile Gly Glu Asp Asn
    6740                6745                6750

Ala Thr Met Asp Pro Gln Ile Ile Lys Gln Ala Thr Gln Asp Ile
    6755                6760                6765

Asn Thr Ala Ile Asn Gly Leu Asn Gly Asp Gln Lys Leu Gln Asp
    6770                6775                6780

Ala Lys Thr Asp Ala Lys Gln Gln Ile Thr Asn Phe Thr Gly Leu
    6785                6790                6795

Thr Glu Pro Gln Lys Gln Ala Leu Glu Asn Ile Ile Asn Gln Gln
    6800                6805                6810

Thr Ser Arg Ala Asn Val Ala Lys Gln Leu Ser His Ala Lys Phe
    6815                6820                6825

Leu Asn Gly Lys Met Glu Glu Leu Lys Val Ala Val Ala Lys Ala
    6830                6835                6840

Ser Leu Val Arg Gln Asn Ser Asn Tyr Ile Asn Glu Asp Val Ser
    6845                6850                6855

Glu Lys Glu Ala Tyr Glu Gln Ala Ile Ala Lys Gly Gln Glu Ile
    6860                6865                6870

Ile Asn Ser Glu Asn Asn Pro Thr Ile Ser Ser Thr Asp Ile Asn
    6875                6880                6885

Arg Thr Ile Gln Glu Ile Asn Asp Ala Glu Gln Asn Leu His Gly
    6890                6895                6900

Asp Asn Lys Leu Arg Gln Ala Gln Glu Ile Ala Lys Asn Glu Ile
    6905                6910                6915

Gln Asn Leu Asp Gly Leu Asn Ser Ala Gln Ile Thr Lys Leu Ile
    6920                6925                6930

Gln Asp Ile Gly Arg Thr Thr Thr Lys Pro Ala Val Thr Gln Lys
    6935                6940                6945

Leu Glu Glu Ala Lys Ala Ile Asn Gln Ala Met Gln Gln Leu Lys
    6950                6955                6960

Gln Ser Ile Ala Asp Lys Asp Ala Thr Leu Asn Ser Ser Asn Tyr
    6965                6970                6975

Leu Asn Glu Asp Ser Glu Lys Lys Leu Ala Tyr Asp Asn Ala Val
    6980                6985                6990

Ser Gln Ala Glu Gln Leu Ile Asn Gln Leu Asn Asp Pro Thr Met
    6995                7000                7005

Asp Ile Ser Asn Ile Gln Ala Ile Thr Gln Lys Val Ile Gln Ala
    7010                7015                7020

Lys Asp Ser Leu His Gly Ala Asn Lys Leu Ala Gln Asn Gln Ala
    7025                7030                7035

Asp Ser Asn Leu Ile Ile Asn Gln Ser Thr Asn Leu Asn Asp Lys
    7040                7045                7050

Gln Lys Gln Ala Leu Asn Asp Leu Ile Asn His Ala Gln Thr Lys
    7055                7060                7065
```

-continued

```
Gln Gln Val Ala Glu Ile Ile Ala Gln Ala Asn Lys Leu Asn Asn
7070            7075            7080

Glu Met Gly Thr Leu Lys Thr Leu Val Glu Glu Gln Ser Asn Val
7085            7090            7095

His Gln Gln Ser Lys Tyr Ile Asn Glu Asp Pro Gln Val Gln Asn
7100            7105            7110

Ile Tyr Asn Asp Ser Ile Gln Lys Gly Arg Glu Ile Leu Asn Gly
7115            7120            7125

Thr Thr Asp Asp Val Leu Asn Asn Asn Lys Ile Ala Asp Ala Ile
7130            7135            7140

Gln Asn Ile His Leu Thr Lys Asn Asp Leu His Gly Asp Gln Lys
7145            7150            7155

Leu Gln Lys Ala Gln Gln Asp Ala Thr Asn Glu Leu Asn Tyr Leu
7160            7165            7170

Thr Asn Leu Asn Asn Ser Gln Arg Gln Ser Glu His Asp Glu Ile
7175            7180            7185

Asn Ser Ala Pro Ser Arg Thr Glu Val Ser Asn Asp Leu Asn His
7190            7195            7200

Ala Lys Ala Leu Asn Glu Ala Met Arg Gln Leu Glu Asn Glu Val
7205            7210            7215

Ala Leu Glu Asn Ser Val Lys Lys Leu Ser Asp Phe Ile Asn Glu
7220            7225            7230

Asp Glu Ala Ala Gln Asn Glu Tyr Ser Asn Ala Leu Gln Lys Ala
7235            7240            7245

Lys Asp Ile Ile Asn Gly Val Pro Ser Ser Thr Leu Asp Lys Ala
7250            7255            7260

Thr Ile Glu Asp Ala Leu Leu Glu Leu Gln Asn Ala Arg Glu Ser
7265            7270            7275

Leu His Gly Glu Gln Lys Leu Gln Glu Ala Lys Asn Gln Ala Val
7280            7285            7290

Ala Glu Ile Asp Asn Leu Gln Ala Leu Asn Pro Gly Gln Val Leu
7295            7300            7305

Ala Glu Lys Thr Leu Val Asn Gln Ala Ser Thr Lys Pro Glu Val
7310            7315            7320

Gln Glu Ala Leu Gln Lys Ala Lys Glu Leu Asn Glu Ala Met Lys
7325            7330            7335

Ala Leu Lys Thr Glu Ile Asn Lys Lys Glu Gln Ile Lys Ala Asp
7340            7345            7350

Ser Arg Tyr Val Asn Ala Asp Ser Gly Leu Gln Ala Asn Tyr Asn
7355            7360            7365

Ser Ala Leu Asn Tyr Gly Ser Gln Ile Ile Ala Thr Thr Gln Pro
7370            7375            7380

Pro Glu Leu Asn Lys Asp Val Ile Asn Arg Ala Thr Gln Thr Ile
7385            7390            7395

Lys Thr Ala Glu Asn Asn Leu Asn Gly Gln Ser Lys Leu Ala Glu
7400            7405            7410

Ala Lys Ser Asp Gly Asn Gln Ser Ile Glu His Leu Gln Gly Leu
7415            7420            7425

Thr Gln Ser Gln Lys Asp Lys Gln His Asp Leu Ile Asn Gln Ala
7430            7435            7440

Gln Thr Lys Gln Gln Val Asp Asp Ile Val Asn Asn Ser Lys Gln
7445            7450            7455

Leu Asp Asn Ser Met Asn Gln Leu Gln Gln Ile Val Asn Asn Asp
```

-continued

```
            7460              7465              7470
Asn Thr Val Lys Gln Asn Ser Asp Phe Ile Asn Glu Asp Ser Ser
            7475              7480              7485
Gln Gln Asp Ala Tyr Asn His Ala Ile Gln Ala Ala Lys Asp Leu
            7490              7495              7500
Ile Thr Ala His Pro Thr Ile Met Asp Lys Asn Gln Ile Asp Gln
            7505              7510              7515
Ala Ile Glu Asn Ile Lys Gln Ala Leu Asn Asp Leu His Gly Ser
            7520              7525              7530
Asn Lys Leu Ser Glu Asp Lys Lys Glu Ala Ser Glu Gln Leu Gln
            7535              7540              7545
Asn Leu Asn Ser Leu Thr Asn Gly Gln Lys Asp Thr Ile Leu Asn
            7550              7555              7560
His Ile Phe Ser Ala Pro Thr Arg Ser Gln Val Gly Glu Lys Ile
            7565              7570              7575
Ala Ser Ala Lys Gln Leu Asn Asn Thr Met Lys Ala Leu Arg Asp
            7580              7585              7590
Ser Ile Ala Asp Asn Asn Glu Ile Leu Gln Ser Ser Lys Tyr Phe
            7595              7600              7605
Asn Glu Asp Ser Glu Gln Gln Asn Ala Tyr Asn Gln Ala Val Asn
            7610              7615              7620
Lys Ala Lys Asn Ile Ile Asn Asp Gln Pro Thr Pro Val Met Ala
            7625              7630              7635
Asn Asp Glu Ile Gln Ser Val Leu Asn Glu Val Lys Gln Thr Lys
            7640              7645              7650
Asp Asn Leu His Gly Asp Gln Lys Leu Ala Asn Asp Lys Thr Asp
            7655              7660              7665
Ala Gln Ala Thr Leu Asn Ala Leu Asn Tyr Leu Asn Gln Ala Gln
            7670              7675              7680
Arg Gly Asn Leu Glu Thr Lys Val Gln Asn Ser Asn Ser Arg Pro
            7685              7690              7695
Glu Val Gln Lys Val Val Gln Leu Ala Asn Gln Leu Asn Asp Ala
            7700              7705              7710
Met Lys Lys Leu Asp Asp Ala Leu Thr Gly Asn Asp Ala Ile Lys
            7715              7720              7725
Gln Thr Ser Asn Tyr Ile Asn Glu Asp Thr Ser Gln Gln Val Asn
            7730              7735              7740
Phe Asp Glu Tyr Thr Asp Arg Gly Lys Asn Ile Val Ala Glu Gln
            7745              7750              7755
Thr Asn Pro Asn Met Ser Pro Thr Asn Ile Asn Thr Ile Ala Asp
            7760              7765              7770
Lys Ile Thr Glu Ala Lys Asn Asp Leu His Gly Val Gln Lys Leu
            7775              7780              7785
Lys Gln Ala Gln Gln Gln Ser Ile Asn Thr Ile Asn Gln Met Thr
            7790              7795              7800
Gly Leu Asn Gln Ala Gln Lys Glu Gln Leu Asn Gln Glu Ile Gln
            7805              7810              7815
Gln Thr Gln Thr Arg Ser Glu Val His Gln Val Ile Asn Lys Ala
            7820              7825              7830
Gln Ala Leu Asn Asp Ser Met Asn Thr Leu Arg Gln Ser Ile Thr
            7835              7840              7845
Asp Glu His Glu Val Lys Gln Thr Ser Asn Tyr Ile Asn Glu Thr
            7850              7855              7860
```

```
Val Gly Asn Gln Thr Ala Tyr Asn Asn Ala Val Asp Arg Val Lys
7865                7870                7875

Gln Ile Ile Asn Gln Thr Ser Asn Pro Thr Met Asn Pro Leu Glu
7880                7885                7890

Val Glu Arg Ala Thr Ser Asn Val Lys Ile Ser Lys Asp Ala Leu
7895                7900                7905

His Gly Glu Arg Glu Leu Asn Asp Asn Lys Asn Ser Lys Thr Phe
7910                7915                7920

Ala Val Asn His Leu Asp Asn Leu Asn Gln Ala Gln Lys Glu Ala
7925                7930                7935

Leu Thr His Glu Ile Glu Gln Ala Thr Ile Val Ser Gln Val Asn
7940                7945                7950

Asn Ile Tyr Asn Lys Ala Lys Ala Leu Asn Asn Asp Met Lys Lys
7955                7960                7965

Leu Lys Asp Ile Val Ala Gln Gln Asp Asn Val Arg Gln Ser Asn
7970                7975                7980

Asn Tyr Ile Asn Glu Asp Ser Thr Pro Gln Asn Met Tyr Asn Asp
7985                7990                7995

Thr Ile Asn His Ala Gln Ser Ile Ile Asp Gln Val Ala Asn Pro
8000                8005                8010

Thr Met Ser His Asp Glu Ile Glu Asn Ala Ile Asn Asn Ile Lys
8015                8020                8025

His Ala Ile Asn Ala Leu Asp Gly Glu His Lys Leu Gln Gln Ala
8030                8035                8040

Lys Glu Asn Ala Asn Leu Leu Ile Asn Ser Leu Asn Asp Leu Asn
8045                8050                8055

Ala Pro Gln Arg Asp Ala Ile Asn Arg Leu Val Asn Glu Ala Gln
8060                8065                8070

Thr Arg Glu Lys Val Ala Glu Gln Leu Gln Ser Ala Gln Ala Leu
8075                8080                8085

Asn Asp Ala Met Lys His Leu Arg Asn Ser Ile Gln Asn Gln Ser
8090                8095                8100

Ser Val Arg Gln Glu Ser Lys Tyr Ile Asn Ala Ser Asp Ala Lys
8105                8110                8115

Lys Glu Gln Tyr Asn His Ala Val Arg Glu Val Glu Asn Ile Ile
8120                8125                8130

Asn Glu Gln His Pro Thr Leu Asp Lys Glu Ile Ile Lys Gln Leu
8135                8140                8145

Thr Asp Gly Val Asn Gln Ala Asn Asn Asp Leu Asn Gly Val Glu
8150                8155                8160

Leu Leu Asp Ala Asp Lys Gln Asn Ala His Gln Ser Ile Pro Thr
8165                8170                8175

Leu Met His Leu Asn Gln Ala Gln Gln Asn Ala Leu Asn Glu Lys
8180                8185                8190

Ile Asn Asn Ala Val Thr Arg Thr Glu Val Ala Ala Ile Ile Gly
8195                8200                8205

Gln Ala Lys Leu Leu Asp His Ala Met Glu Asn Leu Glu Glu Ser
8210                8215                8220

Ile Lys Asp Lys Glu Gln Val Lys Gln Ser Ser Asn Tyr Ile Asn
8225                8230                8235

Glu Asp Ser Asp Val Gln Glu Thr Tyr Asp Asn Ala Val Asp His
8240                8245                8250
```

-continued

```
Val Thr Glu Ile Leu Asn Gln Thr Val Asn Pro Thr Leu Ser Ile
8255                8260                8265

Glu Asp Ile Glu His Ala Ile Asn Glu Val Asn Gln Ala Lys Lys
8270                8275                8280

Gln Leu Arg Gly Lys Gln Lys Leu Tyr Gln Thr Ile Asp Leu Ala
8285                8290                8295

Asp Lys Glu Leu Ser Lys Leu Asp Asp Leu Thr Ser Gln Gln Ser
8300                8305                8310

Ser Ser Ile Ser Asn Gln Ile Tyr Thr Ala Lys Thr Arg Thr Glu
8315                8320                8325

Val Ala Gln Ala Ile Glu Lys Ala Lys Ser Leu Asn His Ala Met
8330                8335                8340

Lys Ala Leu Asn Lys Val Tyr Lys Asn Ala Asp Lys Val Leu Asp
8345                8350                8355

Ser Ser Arg Phe Ile Asn Glu Asp Gln Pro Glu Lys Lys Ala Tyr
8360                8365                8370

Gln Gln Ala Ile Asn His Val Asp Ser Ile Ile His Arg Gln Thr
8375                8380                8385

Asn Pro Glu Met Asp Pro Thr Val Ile Asn Ser Ile Thr His Glu
8390                8395                8400

Leu Glu Thr Ala Gln Asn Asn Leu His Gly Asp Gln Lys Leu Ala
8405                8410                8415

His Ala Gln Gln Asp Ala Ala Asn Val Ile Asn Gly Leu Ile His
8420                8425                8430

Leu Asn Val Ala Gln Arg Glu Val Met Ile Asn Thr Asn Thr Asn
8435                8440                8445

Ala Thr Thr Arg Glu Lys Val Ala Lys Asn Leu Asp Asn Ala Gln
8450                8455                8460

Ala Leu Asp Lys Ala Met Glu Thr Leu Gln Gln Val Val Ala His
8465                8470                8475

Lys Asn Asn Ile Leu Asn Asp Ser Lys Tyr Leu Asn Glu Asp Ser
8480                8485                8490

Lys Tyr Gln Gln Gln Tyr Asp Arg Val Ile Ala Asp Ala Glu Gln
8495                8500                8505

Leu Leu Asn Gln Thr Thr Asn Pro Thr Leu Glu Pro Tyr Lys Val
8510                8515                8520

Asp Ile Val Lys Asp Asn Val Leu Ala Asn Glu Lys Ile Leu Phe
8525                8530                8535

Gly Ala Glu Lys Leu Ser Tyr Asp Lys Ser Asn Ala Asn Asp Glu
8540                8545                8550

Ile Lys His Met Asn Tyr Leu Asn Asn Ala Gln Lys Gln Ser Ile
8555                8560                8565

Lys Asp Met Ile Ser His Ala Ala Leu Arg Thr Glu Val Lys Gln
8570                8575                8580

Leu Leu Gln Gln Ala Lys Ile Leu Asp Glu Ala Met Lys Ser Leu
8585                8590                8595

Glu Asp Lys Thr Gln Val Val Ile Thr Asp Thr Thr Leu Pro Asn
8600                8605                8610

Tyr Thr Glu Ala Ser Glu Asp Lys Lys Glu Lys Val Asp Gln Thr
8615                8620                8625

Val Ser His Ala Gln Ala Ile Ile Asp Lys Ile Asn Gly Ser Asn
8630                8635                8640

Val Ser Leu Asp Gln Val Arg Gln Ala Leu Glu Gln Leu Thr Gln
```

-continued

```
              8645                  8650                  8655
Ala Ser  Glu Asn Leu Asp  Gly Asp Gln Arg  Val Glu Glu Ala Lys
         8660                  8665                  8670
Val His  Ala Asn Gln Thr  Ile Asp Gln Leu  Thr His Leu Asn Ser
         8675                  8680                  8685
Leu Gln  Gln Gln Thr Ala  Lys Glu Ser Val  Lys Asn Ala Thr Lys
         8690                  8695                  8700
Leu Glu  Glu Ile Ala Thr  Val Ser Asn Asn  Ala Gln Ala Leu Asn
         8705                  8710                  8715
Lys Val  Met Gly Lys Leu  Glu Gln Phe Ile  Asn His Ala Asp Ser
         8720                  8725                  8730
Val Glu  Asn Ser Asp Asn  Tyr Arg Gln Ala  Asp Asp Lys Ile
         8735                  8740                  8745
Ile Ala  Tyr Asp Glu Ala  Leu Glu His Gly  Gln Asp Ile Gln Lys
         8750                  8755                  8760
Thr Asn  Ala Thr Gln Asn  Glu Thr Lys Gln  Ala Leu Gln Gln Leu
         8765                  8770                  8775
Ile Tyr  Ala Glu Thr Ser  Leu Asn Gly Phe  Glu Arg Leu Asn His
         8780                  8785                  8790
Ala Arg  Pro Arg Ala Leu  Glu Tyr Ile Lys  Ser Leu Glu Lys Ile
         8795                  8800                  8805
Asn Asn  Ala Gln Lys Ser  Ala Leu Glu Asp  Lys Val Thr Gln Ser
         8810                  8815                  8820
His Asp  Leu Leu Glu Leu  Glu His Ile Val  Asn Glu Gly Thr Asn
         8825                  8830                  8835
Leu Asn  Asp Ile Met Gly  Glu Leu Ala Asn  Ala Ile Val Asn Asn
         8840                  8845                  8850
Tyr Ala  Pro Thr Lys Ala  Ser Ile Asn Tyr  Ile Asn Ala Asp Asn
         8855                  8860                  8865
Leu Arg  Lys Asp Asn Phe  Thr Gln Ala Ile  Asn Asn Ala Arg Asp
         8870                  8875                  8880
Ala Leu  Asn Lys Thr Gln  Gly Gln Asn Leu  Asp Phe Asn Ala Ile
         8885                  8890                  8895
Asp Thr  Phe Lys Asp Asp  Ile Phe Lys Thr  Lys Asp Ala Leu Asn
         8900                  8905                  8910
Gly Ile  Glu Arg Leu Thr  Ala Ala Lys Ser  Lys Ala Glu Lys Leu
         8915                  8920                  8925
Ile Asp  Ser Leu Lys Phe  Ile Asn Lys Ala  Gln Phe Thr His Ala
         8930                  8935                  8940
Asn Asp  Glu Ile Ile Asn  Thr Asn Ser Ile  Ala Gln Leu Ser Arg
         8945                  8950                  8955
Ile Val  Asn Gln Ala Phe  Asp Leu Asn Asp  Ala Met Lys Ser Leu
         8960                  8965                  8970
Arg Asp  Glu Leu Asn Asn  Gln Ala Phe Pro  Val Gln Ala Ser Ser
         8975                  8980                  8985
Asn Tyr  Ile Asn Ser Asp  Glu Asp Leu Lys  Gln Gln Phe Asp His
         8990                  8995                  9000
Ala Leu  Ser Asn Ala Arg  Lys Val Leu Ala  Lys Glu Asn Gly Lys
         9005                  9010                  9015
Asn Leu  Asp Glu Lys Gln  Ile Gln Gly Leu  Lys Gln Val Ile Glu
         9020                  9025                  9030
Asp Thr  Lys Asp Ala Leu  Asn Gly Ile Gln  Arg Leu Ser Lys Ala
         9035                  9040                  9045
```

-continued

```
Lys Ala Lys Ala Ile Gln Tyr Val Gln Ser Leu Ser Tyr Ile Asn
9050            9055            9060

Asp Ala Gln Arg His Ile Ala Glu Asn Asn Ile His Asn Ser Asp
9065            9070            9075

Asp Leu Ser Ser Leu Ala Asn Thr Leu Ser Lys Ala Ser Asp Leu
9080            9085            9090

Asp Asn Ala Met Lys Asp Leu Arg Asp Thr Ile Glu Ser Asn Ser
9095            9100            9105

Thr Ser Val Pro Asn Ser Val Asn Tyr Ile Asn Ala Asp Lys Asn
9110            9115            9120

Leu Gln Ile Glu Phe Asp Glu Ala Leu Gln Gln Ala Ser Ala Thr
9125            9130            9135

Ser Ser Lys Thr Ser Glu Asn Pro Ala Thr Ile Glu Glu Val Leu
9140            9145            9150

Gly Leu Ser Gln Ala Ile Tyr Asp Thr Lys Asn Ala Leu Asn Gly
9155            9160            9165

Glu Gln Arg Leu Ala Thr Glu Lys Ser Lys Asp Leu Lys Leu Ile
9170            9175            9180

Lys Gly Leu Lys Asp Leu Asn Lys Ala Gln Leu Glu Asp Val Thr
9185            9190            9195

Asn Lys Val Asn Ser Ala Asn Thr Leu Thr Glu Leu Ser Gln Leu
9200            9205            9210

Thr Gln Ser Thr Leu Glu Leu Asn Asp Lys Met Lys Leu Leu Arg
9215            9220            9225

Asp Lys Leu Lys Thr Leu Val Asn Pro Val Lys Ala Ser Leu Asn
9230            9235            9240

Tyr Arg Asn Ala Asp Tyr Asn Leu Lys Arg Gln Phe Asn Lys Ala
9245            9250            9255

Leu Lys Glu Ala Lys Gly Val Leu Asn Lys Asn Ser Gly Thr Asn
9260            9265            9270

Val Asn Ile Asn Asp Ile Gln His Leu Leu Thr Gln Ile Asp Asn
9275            9280            9285

Ala Lys Asp Gln Leu Asn Gly Glu Arg Arg Leu Lys Glu His Gln
9290            9295            9300

Gln Lys Ser Glu Val Phe Ile Ile Lys Glu Leu Asp Ile Leu Asn
9305            9310            9315

Asn Ala Gln Lys Ala Ala Ile Ile Asn Gln Ile Arg Ala Ser Lys
9320            9325            9330

Asp Ile Lys Ile Ile Asn Gln Ile Val Asp Asn Ala Ile Glu Leu
9335            9340            9345

Asn Asp Ala Met Gln Gly Leu Lys Glu His Val Ala Gln Leu Thr
9350            9355            9360

Ala Thr Thr Lys Asp Asn Ile Glu Tyr Leu Asn Ala Asp Glu Asp
9365            9370            9375

His Lys Leu Gln Tyr Asp Tyr Ala Ile Asn Leu Ala Asn Asn Val
9380            9385            9390

Leu Asp Lys Glu Asn Gly Thr Asn Lys Asp Ala Asn Ile Ile Ile
9395            9400            9405

Gly Met Ile Gln Asn Met Asp Asp Ala Arg Ala Leu Leu Asn Gly
9410            9415            9420

Ile Glu Arg Leu Lys Asp Ala Gln Thr Lys Ala His Asn Asp Ile
9425            9430            9435
```

```
Lys Asp Thr Leu Lys Arg Gln Leu Asp Glu Ile Glu His Ala Asn
9440                9445                9450

Ala Thr Ser Asn Ser Lys Ala Gln Ala Lys Gln Met Val Asn Glu
9455                9460                9465

Glu Ala Arg Lys Ala Leu Ser Asn Ile Asn Asp Ala Thr Ser Asn
9470                9475                9480

Asp Leu Val Asn Gln Ala Lys Asp Glu Gly Gln Ser Ala Ile Glu
9485                9490                9495

His Ile His Ala Asp Glu Leu Pro Lys Ala Lys Leu Asp Ala Asn
9500                9505                9510

Gln Met Ile Asp Gln Lys Val Glu Asp Ile Asn His Leu Ile Ser
9515                9520                9525

Gln Asn Pro Asn Leu Ser Asn Glu Glu Lys Asn Lys Leu Ile Ser
9530                9535                9540

Gln Ile Asn Lys Leu Val Asn Gly Ile Lys Asn Glu Ile Gln Gln
9545                9550                9555

Ala Ile Asn Lys Gln Gln Ile Glu Asn Ala Thr Thr Lys Leu Asp
9560                9565                9570

Glu Val Ile Glu Thr Thr Lys Lys Leu Ile Ile Ala Lys Ala Glu
9575                9580                9585

Ala Lys Gln Met Ile Lys Glu Leu Ser Gln Lys Lys Arg Asp Ala
9590                9595                9600

Ile Asn Asn Asn Thr Asp Leu Thr Pro Ser Gln Lys Ala His Ala
9605                9610                9615

Leu Ala Asp Ile Asp Lys Thr Glu Lys Asp Ala Leu Gln His Ile
9620                9625                9630

Glu Asn Ser Asn Ser Ile Asp Asp Ile Asn Asn Asn Lys Glu His
9635                9640                9645

Ala Phe Asn Thr Leu Ala His Ile Ile Ile Trp Asp Thr Asp Gln
9650                9655                9660

Gln Pro Leu Val Phe Glu Leu Pro Glu Leu Ser Leu Gln Asn Ala
9665                9670                9675

Leu Val Thr Ser Glu Val Val Val His Arg Asp Glu Thr Ile Ser
9680                9685                9690

Leu Glu Ser Ile Ile Gly Ala Met Thr Leu Thr Asp Glu Leu Lys
9695                9700                9705

Val Asn Ile Val Ser Leu Pro Asn Thr Asp Lys Val Ala Asp His
9710                9715                9720

Leu Thr Ala Lys Val Lys Val Ile Leu Ala Asp Gly Ser Tyr Val
9725                9730                9735

Thr Val Asn Val Pro Val Lys Val Val Glu Lys Glu Leu Gln Ile
9740                9745                9750

Ala Lys Lys Asp Ala Ile Lys Thr Ile Asp Val Leu Val Lys Gln
9755                9760                9765

Lys Ile Lys Asp Ile Asp Ser Asn Asn Glu Leu Thr Ser Thr Gln
9770                9775                9780

Arg Glu Asp Ala Lys Ala Glu Ile Glu Arg Leu Lys Lys Gln Ala
9785                9790                9795

Ile Asp Lys Val Asn His Ser Lys Ser Ile Lys Asp Ile Glu Thr
9800                9805                9810

Val Lys Arg Thr Asp Phe Glu Glu Ile Asp Gln Phe Asp Pro Lys
9815                9820                9825

Arg Phe Thr Leu Asn Lys Ala Lys Lys Asp Ile Ile Thr Asp Val
```

```
                       9830              9835                9840
Asn  Thr  Gln  Ile  Gln  Asn  Gly  Phe  Lys  Glu  Ile  Glu  Thr  Ile  Lys
                       9845              9850                9855

Gly  Leu  Thr  Ser  Asn  Glu  Lys  Thr  Gln  Phe  Asp  Lys  Gln  Leu  Thr
                       9860              9865                9870

Ala  Leu  Gln  Lys  Glu  Phe  Leu  Glu  Lys  Val  Glu  His  Ala  His  Asn
                       9875              9880                9885

Leu  Val  Glu  Leu  Asn  Gln  Leu  Gln  Gln  Glu  Phe  Asn  Asn  Arg  Tyr
                       9890              9895                9900

Lys  His  Ile  Leu  Asn  Gln  Ala  His  Leu  Leu  Gly  Glu  Lys  His  Ile
                       9905              9910                9915

Ala  Glu  His  Lys  Leu  Gly  Tyr  Val  Val  Val  Asn  Lys  Thr  Gln  Gln
                       9920              9925                9930

Ile  Leu  Asn  Asn  Gln  Ser  Ala  Ser  Tyr  Phe  Ile  Lys  Gln  Trp  Ala
                       9935              9940                9945

Leu  Asp  Arg  Ile  Lys  Gln  Ile  Gln  Leu  Glu  Thr  Met  Asn  Ser  Ile
                       9950              9955                9960

Arg  Gly  Ala  His  Thr  Val  Gln  Asp  Val  His  Lys  Ala  Leu  Leu  Gln
                       9965              9970                9975

Gly  Ile  Glu  Gln  Ile  Leu  Lys  Val  Asn  Val  Ser  Ile  Ile  Asn  Gln
                       9980              9985                9990

Ser  Phe  Asn  Asp  Ser  Leu  His  Asn  Phe  Asn  Tyr  Leu  His  Ser  Lys
                       9995             10000               10005

Phe  Asp  Ala  Arg  Leu  Arg  Glu  Lys  Asp  Val  Ala  Asn  His  Ile  Val
                      10010             10015               10020

Gln  Thr  Glu  Thr  Phe  Lys  Glu  Val  Leu  Lys  Gly  Thr  Gly  Val  Glu
                      10025             10030               10035

Pro  Gly  Lys  Ile  Asn  Lys  Glu  Thr  Gln  Gln  Pro  Lys  Leu  His  Lys
                      10040             10045               10050

Asn  Asp  Asn  Asp  Ser  Leu  Phe  Lys  His  Leu  Val  Asp  Asn  Phe  Gly
                      10055             10060               10065

Lys  Thr  Val  Gly  Val  Ile  Thr  Leu  Thr  Gly  Leu  Leu  Ser  Ser  Phe
                      10070             10075               10080

Trp  Leu  Val  Leu  Ala  Lys  Arg  Arg  Lys  Lys  Glu  Glu  Glu  Glu  Lys
                      10085             10090               10095

Gln  Ser  Ile  Lys  Asn  His  His  Lys  Asp  Ile  Arg  Leu  Ser  Asp  Thr
                      10100             10105               10110

Asp  Lys  Ile  Asp  Pro  Ile  Val  Ile  Thr  Lys  Arg  Lys  Ile  Asp  Lys
                      10115             10120               10125

Glu  Glu  Gln  Ile  Gln  Asn  Asp  Asp  Lys  His  Ser  Ile  Pro  Val  Ala
                      10130             10135               10140

Lys  His  Lys  Lys  Ser  Lys  Glu  Lys  Gln  Leu  Ser  Glu  Glu  Asp  Ile
                      10145             10150               10155

His  Ser  Ile  Pro  Val  Val  Lys  Arg  Lys  Gln  Asn  Ser  Asp  Asn  Lys
                      10160             10165               10170

Asp  Thr  Lys  Gln  Lys  Lys  Val  Thr  Ser  Lys  Lys  Lys  Lys  Thr  Pro
                      10175             10180               10185

Gln  Ser  Thr  Lys  Lys  Val  Val  Lys  Thr  Lys  Lys  Arg  Ser  Lys  Lys
                      10190             10195               10200

<210> SEQ ID NO 24
<211> LENGTH: 1973
<212> TYPE: PRT
<213> ORGANISM: Staphylococcus epidermidis
```

<400> SEQUENCE: 24

```
Met Lys Glu Asn Lys Arg Lys Asn Asn Leu Asp Lys Asn Asn Thr Arg
1               5                   10                  15
Phe Ser Ile Arg Lys Tyr Gln Gly Tyr Gly Ala Thr Ser Val Ala Ile
            20                  25                  30
Ile Gly Phe Ile Ile Ile Ser Cys Phe Ser Glu Ala Lys Ala Asp Ser
        35                  40                  45
Asp Lys His Glu Ile Lys Ser His Gln Gln Ser Met Thr Asn His Leu
    50                  55                  60
Thr Thr Leu Pro Ser Asp Asn Gln Glu Asn Thr Ser Asn Asn Glu Phe
65                  70                  75                  80
Asn Asn Arg Asn His Asp Ile Ser His Leu Ser Leu Asn Lys Ser Ile
                85                  90                  95
Gln Met Asp Glu Leu Lys Lys Leu Ile Lys Gln Tyr Lys Ala Ile Asn
            100                 105                 110
Leu Asn Asp Lys Thr Glu Glu Ser Ile Lys Leu Phe Gln Ser Asp Leu
        115                 120                 125
Val Gln Ala Glu Ser Leu Ile Asn Asn Pro Gln Ser Gln Gln His Val
    130                 135                 140
Asp Ala Phe Tyr His Lys Phe Leu Asn Ser Ala Gly Lys Leu Arg Lys
145                 150                 155                 160
Lys Glu Thr Val Ser Ile Lys His Glu Arg Ser Glu Ser Asn Thr Tyr
                165                 170                 175
Arg Leu Gly Asp Glu Val Arg Ser Gln Thr Phe Ser His Ile Arg His
            180                 185                 190
Lys Arg Asn Ala Val Ser Phe Arg Asn Ala Asp Gln Ser Asn Leu Ser
        195                 200                 205
Thr Asp Pro Leu Lys Ala Asn Glu Ile Asn Pro Glu Ile Gln Asn Gly
    210                 215                 220
Asn Phe Ser Gln Val Ser Gly Gly Pro Leu Pro Thr Ser Ser Lys Arg
225                 230                 235                 240
Leu Thr Val Val Thr Asn Val Asp Asn Trp His Ser Tyr Ser Thr Asp
                245                 250                 255
Pro Asn Pro Glu Tyr Pro Met Phe Tyr Thr Thr Thr Ala Val Asn Tyr
            260                 265                 270
Pro Asn Phe Met Ser Asn Gly Asn Ala Pro Tyr Gly Val Ile Leu Gly
        275                 280                 285
Arg Thr Thr Asp Gly Trp Asn Arg Asn Val Ile Asp Ser Lys Val Ala
    290                 295                 300
Gly Ile Tyr Gln Asp Ile Asp Val Val Pro Gly Ser Glu Leu Asn Val
305                 310                 315                 320
Asn Phe Ile Ser Thr Ser Pro Val Phe Ser Asp Gly Ala Ala Gly Ala
                325                 330                 335
Lys Leu Lys Ile Ser Asn Val Glu Gln Asn Arg Val Leu Phe Asp Ser
            340                 345                 350
Arg Leu Asn Gly Met Gly Pro Tyr Pro Thr Gly Lys Leu Ser Ala Met
        355                 360                 365
Val Asn Ile Pro Asn Asp Ile Asn Arg Val Arg Ile Ser Phe Leu Pro
    370                 375                 380
Val Ser Ser Thr Gly Arg Val Ser Val Gln Arg Ser Arg Glu His
385                 390                 395                 400
Gly Phe Gly Asp Asn Ser Ser Tyr Tyr His Gly Gly Ser Val Ser Asp
```

-continued

```
                405                 410                 415
Val Arg Ile Asn Ser Gly Ser Tyr Val Ser Lys Val Thr Gln Arg
                420                 425                 430

Glu Tyr Thr Thr Arg Pro Asn Ser Ser Asn Asp Thr Phe Ala Arg Ala
                435                 440                 445

Thr Ile Asn Leu Ser Val Glu Asn Lys Gly His Asn Gln Ser Lys Asp
                450                 455                 460

Thr Tyr Tyr Glu Val Ile Leu Pro Gln Asn Ser Arg Leu Ile Ser Thr
465                 470                 475                 480

Arg Gly Gly Ser Gly Asn Tyr Asn Asn Ala Thr Asn Lys Leu Ser Ile
                485                 490                 495

Arg Leu Asp Asn Leu Asn Pro Gly Asp Arg Arg Asp Ile Ser Tyr Thr
                500                 505                 510

Val Asp Phe Glu Ser Ser Pro Lys Leu Ile Asn Leu Asn Ala His
                515                 520                 525

Leu Leu Tyr Lys Thr Asn Ala Thr Phe Arg Gly Asn Asp Gly Gln Arg
                530                 535                 540

Thr Gly Asp Asn Ile Val Asp Leu Gln Ser Ile Ala Leu Leu Met Asn
545                 550                 555                 560

Lys Asp Val Leu Glu Thr Glu Leu Asn Glu Ile Asp Lys Phe Ile Arg
                565                 570                 575

Asp Leu Asn Glu Ala Asp Phe Thr Ile Asp Ser Trp Ser Ala Leu Gln
                580                 585                 590

Glu Lys Met Thr Glu Gly Gly Asn Ile Leu Asn Glu Gln Asn Gln
                595                 600                 605

Val Ala Leu Glu Asn Gln Ala Ser Gln Glu Thr Ile Asn Asn Val Thr
                610                 615                 620

Gln Ser Leu Glu Ile Leu Lys Asn Asn Leu Lys Tyr Lys Thr Pro Ser
625                 630                 635                 640

Gln Pro Ile Ile Lys Ser Asn Asn Gln Ile Pro Asn Ile Thr Ile Ser
                645                 650                 655

Pro Ala Asp Lys Ala Asp Lys Leu Thr Ile Thr Tyr Gln Asn Thr Asp
                660                 665                 670

Asn Glu Ser Ala Ser Ile Ile Gly Asn Lys Leu Asn Asn Gln Trp Ser
                675                 680                 685

Leu Asn Asn Asn Ile Pro Gly Ile Glu Ile Asp Met Gln Thr Gly Leu
                690                 695                 700

Val Thr Ile Asp Tyr Lys Ala Val Tyr Pro Glu Ser Val Val Gly Ala
705                 710                 715                 720

Asn Asp Lys Thr Gly Asn Ser Asp Ala Ser Ala Glu Ser Arg Ile Thr
                725                 730                 735

Met Pro Arg Lys Glu Ala Thr Pro Leu Ser Pro Ile Val Glu Ala Asn
                740                 745                 750

Glu Glu Arg Val Asn Val Val Ile Ala Pro Asn Gly Glu Ala Thr Gln
                755                 760                 765

Ile Ala Ile Lys Tyr Arg Thr Pro Asp Gly Gln Glu Ala Thr Leu Val
                770                 775                 780

Ala Ser Lys Asn Gly Ser Ser Trp Thr Leu Asn Lys Gln Ile Asp Tyr
785                 790                 795                 800

Val Asn Ile Glu Glu Asn Ser Gly Lys Val Thr Ile Gly Tyr Gln Ala
                805                 810                 815

Val Gln Pro Glu Ser Glu Val Ile Ala Thr Glu Thr Lys Gly Asn Ser
                820                 825                 830
```

-continued

Asp Glu Ser Ala Glu Ser Arg Val Thr Met Pro Arg Lys Glu Ala Thr
    835                 840                 845

Pro His Ser Pro Ile Val Glu Ala Asn Glu Glu His Val Asn Val Thr
850                 855                 860

Ile Ala Pro Asn Gly Glu Ala Thr Gln Ile Ala Ile Lys Tyr Arg Thr
865                 870                 875                 880

Pro Asp Gly Gln Glu Thr Thr Leu Ile Ala Ser Lys Asn Gly Ser Ser
                885                 890                 895

Trp Thr Leu Asn Lys Gln Ile Asp Tyr Val Asn Ile Glu Glu Asn Ser
            900                 905                 910

Gly Lys Val Thr Ile Gly Tyr Gln Ala Val Gln Leu Glu Ser Glu Val
        915                 920                 925

Ile Ala Thr Glu Thr Lys Gly Asn Ser Asp Ala Ser Ala Glu Ser Arg
    930                 935                 940

Ile Thr Met Leu Arg Lys Glu Ala Thr Pro His Ser Pro Ile Val Glu
945                 950                 955                 960

Ala Asn Glu Glu His Val Asn Val Thr Ile Ala Pro Asn Gly Glu Ala
                965                 970                 975

Thr Gln Ile Ala Ile Lys Tyr Arg Thr Pro Asp Gly Gln Glu Ala Thr
            980                 985                 990

Leu Val Ala Ser Lys Asn Glu Ser Ser Trp Thr Leu Asn Lys Gln Ile
        995                 1000                1005

Asp His Val Asn Ile Asp Glu Asn Ser Gly Lys Val Thr Ile Gly
    1010                1015                1020

Tyr Gln Ala Val Gln Pro Glu Ser Glu Ile Ile Ala Thr Glu Thr
    1025                1030                1035

Lys Gly Asn Ser Asp Ala Ser Ala Glu Ser Arg Ile Thr Met Pro
    1040                1045                1050

Arg Lys Glu Ala Thr Pro Ile Pro Pro Thr Leu Glu Ala Ser Val
    1055                1060                1065

Gln Glu Ala Ser Val Thr Val Thr Pro Asn Glu Asn Ala Thr Lys
    1070                1075                1080

Val Phe Ile Lys Tyr Leu Asp Ile Asn Asp Glu Ile Ser Thr Ile
    1085                1090                1095

Ile Ala Ser Lys Ile Asn Gln Gln Trp Thr Leu Asn Lys Asp Asn
    1100                1105                1110

Phe Gly Ile Lys Ile Asn Pro Leu Thr Gly Lys Val Ile Ile Ser
    1115                1120                1125

Tyr Val Ala Val Gln Pro Glu Ser Asp Val Ile Ala Ile Glu Ser
    1130                1135                1140

Gln Gly Asn Ser Asp Leu Ser Glu Glu Ser Arg Ile Ile Met Pro
    1145                1150                1155

Thr Lys Glu Glu Pro Pro Glu Pro Pro Ile Leu Glu Ser Asp Ser
    1160                1165                1170

Ile Glu Ala Lys Val Asn Ile Phe Pro Asn Asp Glu Ala Thr Arg
    1175                1180                1185

Ile Val Ile Met Tyr Thr Ser Leu Glu Gly Gln Glu Ala Thr Leu
    1190                1195                1200

Val Ala Ser Lys Asn Glu Ser Ser Trp Thr Leu Asn Lys Gln Ile
    1205                1210                1215

Asp His Val Asn Ile Asp Glu Asn Ser Gly Lys Val Thr Ile Gly
    1220                1225                1230

-continued

```
Tyr Gln Ala Val Gln Pro Glu Ser Glu Val Ile Ala Thr Glu Thr
    1235                1240                1245

Lys Gly Asn Ser Asp Ala Ser Ala Glu Ser Arg Val Thr Met Pro
    1250                1255                1260

Arg Lys Glu Ala Thr Pro His Ser Pro Ile Val Glu Thr Asn Glu
    1265                1270                1275

Glu Arg Val Asn Val Val Ile Ala Pro Asn Gly Glu Ala Thr Gln
    1280                1285                1290

Ile Ala Ile Lys Tyr Arg Thr Pro Asp Gly Gln Glu Thr Thr Leu
    1295                1300                1305

Ile Ala Ser Lys Asn Gly Ser Ser Trp Thr Leu Asn Lys Gln Ile
    1310                1315                1320

Asp His Val Asn Ile Asp Glu Asn Ser Gly Lys Val Thr Ile Gly
    1325                1330                1335

Tyr Gln Ala Val Gln Pro Glu Ser Glu Ile Ile Ala Thr Glu Thr
    1340                1345                1350

Lys Gly Asn Ser Asp Ala Ser Ala Glu Ser Arg Ile Thr Met Pro
    1355                1360                1365

Arg Lys Glu Ala Ile Pro His Ser Pro Ile Val Glu Ala Asn Glu
    1370                1375                1380

Glu His Val Asn Val Thr Ile Ala Pro Asn Gly Glu Thr Thr Gln
    1385                1390                1395

Ile Ala Val Lys Tyr Arg Thr Pro Asp Gly Gln Glu Ala Thr Leu
    1400                1405                1410

Ile Ala Ser Lys Asn Glu Ser Ser Trp Thr Leu Asn Lys Gln Ile
    1415                1420                1425

Asp His Val Asn Ile Asp Glu Asn Ser Gly Lys Val Thr Ile Gly
    1430                1435                1440

Tyr Gln Ala Val Gln Pro Glu Ser Glu Val Ile Ala Thr Glu Thr
    1445                1450                1455

Lys Gly Asn Ser Asp Ala Ser Ala Glu Ser Arg Ile Thr Met Pro
    1460                1465                1470

Val Lys Glu Lys Thr Pro Ala Pro Pro Ile Ser Ile Ile Asn Glu
    1475                1480                1485

Ser Asn Ala Ser Val Glu Ile Ile Pro Gln Val Asn Val Thr Gln
    1490                1495                1500

Leu Ser Leu Gln Tyr Ile Asp Ala Lys Gly Gln Gln Gln Asn Leu
    1505                1510                1515

Ile Ala Thr Leu Asn Gln Asn Gln Trp Thr Leu Asn Lys Asn Val
    1520                1525                1530

Ser His Ile Thr Val Asp Lys Asn Thr Gly Lys Val Leu Ile Asn
    1535                1540                1545

Tyr Gln Ala Val Tyr Pro Glu Ser Glu Val Ile Ala Arg Glu Ser
    1550                1555                1560

Lys Gly Asn Ser Asp Ser Ser Asn Val Ser Met Val Ile Met Pro
    1565                1570                1575

Arg Lys Thr Ala Thr Pro Lys Pro Pro Ile Ile Lys Val Asp Glu
    1580                1585                1590

Met Asn Ala Ser Leu Ala Ile Ile Pro Tyr Lys Asn Asn Thr Ala
    1595                1600                1605

Ile Asn Ile His Tyr Ile Asp Lys Lys Gly Ile Lys Ser Met Val
    1610                1615                1620

Thr Ala Ile Lys Asn Asn Asp Gln Trp Gln Leu Asp Glu Lys Ile
```

-continued

```
            1625                1630                1635

Lys Tyr Val Lys Ile Asp Ala Lys Thr Gly Thr Val Ile Ile Asn
    1640                1645                1650

Tyr Gln Ile Val Gln Glu Asn Ser Glu Ile Ile Ala Thr Ala Ile
    1655                1660                1665

Asn Gly Asn Ser Asp Lys Ser Glu Glu Val Lys Val Leu Met Pro
    1670                1675                1680

Ile Lys Glu Phe Thr Pro Leu Ala Pro Leu Leu Glu Thr Asn Tyr
    1685                1690                1695

Lys Lys Ala Thr Val Ser Ile Leu Pro Gln Ser Asn Ala Thr Lys
    1700                1705                1710

Leu Asp Phe Lys Tyr Arg Asp Lys Lys Gly Asp Ser Lys Ile Ile
    1715                1720                1725

Ile Val Lys Arg Phe Lys Asn Ile Trp Lys Ala Asn Glu Gln Ile
    1730                1735                1740

Ser Gly Val Thr Ile Asn Pro Glu Phe Gly Gln Val Val Ile Asn
    1745                1750                1755

Tyr Gln Ala Val Tyr Pro Glu Ser Asp Ile Leu Ala Ala Gln Tyr
    1760                1765                1770

Val Gly Asn Ser Asp Ala Ser Glu Trp Ala Lys Val Lys Met Pro
    1775                1780                1785

Lys Lys Glu Leu Ala Pro His Ser Pro Ser Leu Ile Tyr Asp Asn
    1790                1795                1800

Arg Asn Asn Lys Ile Leu Ile Ala Pro Asn Ser Asn Ala Thr Glu
    1805                1810                1815

Met Glu Leu Ser Tyr Val Asp Lys Asn Asn Gln Ser Leu Lys Val
    1820                1825                1830

Lys Ala Leu Lys Ile Asn Asn Arg Trp Lys Phe Asp Ser Ser Val
    1835                1840                1845

Ser Asn Ile Ser Ile Asn Pro Asn Thr Gly Lys Ile Val Leu Gln
    1850                1855                1860

Pro Gln Phe Leu Leu Thr Asn Ser Lys Ile Ile Val Phe Ala Lys
    1865                1870                1875

Lys Gly Asn Ser Asp Ala Ser Ile Ser Val Ser Leu Arg Val Pro
    1880                1885                1890

Ala Val Lys Lys Ile Glu Leu Glu Pro Met Phe Asn Val Pro Val
    1895                1900                1905

Leu Val Ser Leu Asn Lys Lys Arg Ile Gln Phe Asp Asp Cys Ser
    1910                1915                1920

Gly Val Lys Asn Cys Leu Asn Lys Gln Ile Ser Lys Thr Gln Leu
    1925                1930                1935

Pro Asp Thr Gly Tyr Ser Asp Lys Ala Ser Lys Ser Asn Ile Leu
    1940                1945                1950

Ser Val Leu Leu Leu Gly Phe Gly Phe Leu Ser Tyr Ser Arg Lys
    1955                1960                1965

Arg Lys Glu Lys Gln
    1970
```

BIOINFORMATIC METHOD FOR IDENTIFYING SURFACE-ANCHORED PROTEINS FROM GRAM-POSITIVE BACTERIA AND PROTEINS OBTAINED THEREBY

CROSS-REFERENCE TO RELATED APPLICATIONS

The present application claims the benefit of U.S. provisional application Ser. No. 60/410,303, filed Sep. 13, 2002.

STATEMENT REGARDING FEDERALLY SPONSORED RESEARCH OR DEVELOPMENT

This Invention was made with Government support under Contracts 7R01-AR44415-04 and 2R01-A120624-17 awarded by NIH. The government has certain rights in this invention.

FIELD OF THE INVENTION

The present invention relates to the fields of microbiology, molecular biology, and immunology and more particularly relates to surface-anchored proteins known as MSCRAMM®s, and to a bioinformatic method of identifying putative MSCRAMM® proteins, i.e., proteins that can bind to extracellular matrix molecules, from Gram positive bacteria having a recognizable cell wall sorting signal and the genes encoding those proteins through detecting structural features from potential proteins including immunoglobulin (Ig)—like fold regions. In addition, the invention relates to antibodies which recognize such proteins, including polyclonal and monoclonal antibodies as well as host cells transformed with nucleic acids encoding monoclonal antibodies, and the use of such antibodies in the diagnosis, treatment or prevention of Gram positive bacterial infections in humans and animals.

BACKGROUND OF THE INVENTION

There are numerous Gram positive bacteria which have been of interest in the fields of medicine and epidemiology because of their potential to cause a myriad of infectious diseases in humans and animals. One such Gram positive bacterium, *Enterococcus faecalis*, belongs to the commensal flora in mammalian intestines. It has also long been known as a major causative agent of bacterial endocarditis (Murray, 1990). During the last decades, *E. faecalis* has increasingly emerged as an opportunistic nosocomial pathogen, typically causing infections in hospitalized patients receiving antibiotic therapy. Clinical strains of this bacterium frequently harbor a multitude of acquired and intrinsically evolved resistance mechanisms toward the most commonly used antibiotics, which has complicated the treatment of enterococcal infections (Murray, 1990, 1999) (Tailor, 1993) (Huycke, 1998). Many of the antibiotic resistance genes are located in mobile genetic elements, e.g., small plasmids and transposons (Paulsen, 2003) This has raised fears for genetic transfer of resistance determinants from this organism to other bacterial species, e.g., the recently documented transfer of vancomycin resistance to *Staphylococcus aureus* (CDC, 2002). Still other Gram positive bacteria are known which commonly cause infections which are hard to control, including other bacteria from the *Enterococcus genus*, including *Enterococcus faecium*, as well as bacteria from species *Streptococcus*, such as *Streptococcus mutans* and *pneumoniae*, *Staphylococcus*, such as *Staphylococcus aureus* and *epidermidis*, and *Bacillus*, such as *Bacillus anthracis*.

The ability to adhere to mammalian tissue is a critical step in the colonization and onset of microbial infections. However, in light of the many unknown factors regarding microbial adherence, it remains a challenge to study and utilize information obtained regarding relatively little known adhesion mechanisms of Gram positive bacteria so as to provide a means for developing alternative antibacterial therapies. One such inroad into developing such therapies is the presence of the human extracellular matrix underneath epithelial and endothelial cells which is a complex, dynamic and multifunctional structure consisting mainly of collagens and other glycoproteins. As one of the outermost layers to external environment, it is a major adhesion target and entry point for pathogenic bacteria (Foster and Hook, 1998) (Westerlund and Korhonen, 1993). Numerous bacterial adhesins that specifically bind to ECM components have been characterized at the molecular level. A group of related cell surface proteins from Gram-positive bacteria, collectively designated MSCRAMM® proteins (microbial surface components recognizing adhesive matrix molecules) bind to major components of the ECM, such as collagens, fibronectin, laminin, fibrinogen, keratin, vitronectin and bone sialoprotein (Patti, 1994) (Foster and Hook, 1998) (Tung, 2000) (O'Brien, 2002). MSCRAMM® proteins are mosaic proteins that typically consist of an N-terminal signal sequence for Sec-dependent transport across the cytoplasmic membrane, followed by an N-terminal A domain which exhibits the binding activity in most cases and repetitive B domains that confer fibronectin binding in a group of fibronectin binding MSCRAMM® protein (Joh et al., 1994). Covalent attachment to the bacterial cell wall is mediated through a C-terminally located LPxTG motif preceded by a cell wall spanning domain and followed by a hydrophobic trans-membrane region and, finally, a cytosolic tail composed of a short sequence of positively charged amino acid residues (Schneewind et al., 1995) (Mazmanian et al., 2001).

In any event, it remains a distinct problem in the field of infectious diseases to develop new means of countering a wide range of bacterial infections in an efficient and effective manner without the potential of increasing the development of antibiotic-resistant bacterial strains. Moreover, in light of the potential problems that are caused by bacterial strains in general and antibiotic-resistant strains in general, particularly in hospitalized patients, it is increasingly important to develop methods to counteract such infections without utilizing antibiotics and without increasing the likelihood that antibiotic-resistant strains will develop. It is thus highly desirable to develop new means for identifying, treating and preventing infectious diseases caused by Gram positive bacteria, and to develop means for identifying and isolating new MSCRAMM® proteins from such bacteria which will allow the generation of antibodies thereto which will lead to new methods for treating and preventing the spread of infections from Gram-positive bacteria.

SUMMARY OF THE INVENTION

Accordingly, it is an object of the present invention to provide a bioinformatic method of identifying and isolating MSCRAMM® proteins from Gram-positive bacteria which can be utilized in methods of treating or preventing infectious diseases arising from Gram-positive bacteria.

It is another object of the present invention to identify and isolate proteins obtained using the bioinformatic method of the present invention, and to identify therein effective antigenic domains such as the A domain, and to utilize these antigenic domains in methods of treating or preventing infectious diseases arising from Gram-positive bacteria.

It is further an object of the present invention to utilize the proteins and antigenic domains isolated and identified using the bioinformatic method of the present invention to generate antibodies which can recognize these proteins and antigenic regions which can thus be useful in diagnosing, treating or preventing diseases and infections caused by Gram positive bacteria It is still further an object of the present invention to provide vaccines, kits and other therapeutic methods which utilize the proteins and antigenic domains identified and isolated using the bioinformatic method of the present invention which can be used as an alternative to conventional antibiotic therapy and can thus provide safe and effective modes of treating or preventing infections caused by Gram-positive bacteria.

These and other objects are provided by virtue of the present invention which utilizes a bioinformatic approach to identify proteins with MSCRAMM®—like characteristics among Gram positive bacteria, such as bacteria from *Enterococcus, Staphylococcus, Streptococcus* and *Bacillus,* among many others, which can then be utilized in methods to prevent and treat infections caused by Gram-positive bacteria. In particular, the method involves looking for proteins with a putative C-terminal LPXTG (SEQ ID NO:1) cell wall sorting signal and structural similarities to MSCRAMM® proteins having the LPXTG-anchored cell wall proteins. In particular, the present invention provides a method for identifying and isolating MSCRAMM® proteins, i.e., proteins that can bind to extracellular matrix molecules, such as by locating regions that adopt an immunoglobulin—like fold, and includes the recombinant production of these proteins from nucleic acids identified in the present process which code for those proteins. These Ig fold-containing regions consist of several consecutive and overlapping matches to solved crystal structures (~150-500 aa) of the immunoglobulin superfamily (IgSF), which consist of one to four domains of equal size and Ig-type fold. The homologous Ig-fold regions are indicative of a "beads-in-a-string" arrangement of consecutive modules such like the ones found in fibronectin and other IgSF proteins (Leahy, 1996)(Sharma, 1999)(Hamburger, 1999)(Luo, 2000). For example, a tandem repeat of Ig folded subdomains (N2 and N3) is found in the crystal structure of the fibrinogen-binding domain of ClfA. The full-length A domains of ClfA and the similarly structured ClfB consist of an additional N-terminal subdomain, N1 (Deivanayagam, 2002)(Perkins, 2001). Based on sequence and secondary structure similarities, an analogous subdomain organization is also expected in other MSCRAMM® proteins including FnbpA, FnbpB, Ace and the Sdr proteins. The solved crystal structure of CNA minimum collagen-binding domain is made of a single Ig-type subdomain (N2) (Symersky, 1997) and the C-terminal repeat domains B1 and B2 each consist of a tandem repeat of Ig-folded subdomains (Deivanayagam, 2000). A similar modular structure is expected in the B3 and B4 repeats.

In accordance with the invention, novel MSCRAMM®—like protein surface-anchored proteins which can bind to major extracellular matrix proteins are obtained from Gram-positive bacteria such as those from the genera *Enterococcus, Streptococcus, Staphylococcus* and *Bacillus,* and such proteins are characterized in that they are (i) structurally homologous to the solved Ig-folded crystal structures of ClfA and CNA as well as to the predicted tertiary structures of other MSCRAMM® proteins, (ii) share a similar β-sheet rich secondary structure as is found in Ig-folded proteins and (iii) have a similar organization with a secretion signal, a non-repeated domain followed by repeats as well as a C-terminal cell wall anchor domain. Moreover, the binding of proteins identified by the present method has confirmed that they target and bind to various extracellular matrix (ECM) molecules including proteins and other components. For example, three of the isolated proteins bind to major ECM proteins; two to fibrinogen and at least one to collagen and laminin. The proteins of the present invention have also been shown to be present in most isolates and are expressed in vivo during infection.

Thus, in accordance with the present invention, a method is provided for identifying and isolating a module structure of multiple Ig-folded units which appears to be a general characteristic in the MSCRAMM® protein family. The length of the N-subdomains of MSCRAMM® proteins is typically ~150 aa, and the proteins identified by the present invention including those set forth below may accommodate more than three Ig-folded subdomains in their A domains.

These embodiments and other alternatives and modifications within the spirit and scope of the disclosed invention will become readily apparent to those skilled in the art from reading the present specification and/or the references cited herein, all of which are incorporated by reference.

BRIEF DESCRIPTION OF THE DRAWING FIGURES

Figure 2:
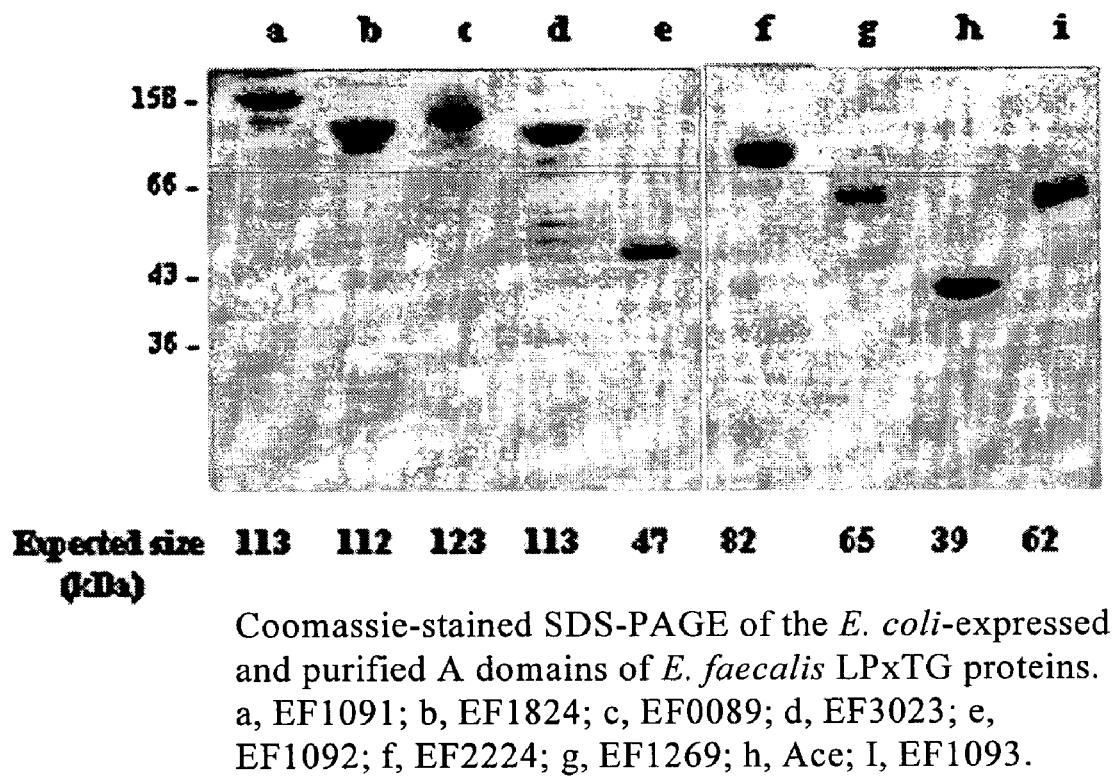

FIG. 1 is a schematic representation of MSCRAMM® proteins identified in accordance with the present invention illustrating the different regions of the proteins and their immunoglobulin—like fold regions FIG. 2 illustrates a Coomassie stained SDS-PAGE of the *E coli*-expressed and purified A domains of the LPXTG-containing proteins of the present invention.

DETAILED DESCRIPTION OF THE PREFERRED EMBODIMENTS

In accordance with the present invention, there is provided a bioinformatic method for identifying and isolating proteins from Gram-positive bacteria, for example bacteria from genera such as *Enterococcus, Staphylococcus, Streptococcus* and *Bacillus,* in particular proteins which have MSCRAMM®—like characteristics, and utilizing the identified and isolated proteins to generate antibodies and diagnose, treat or prevent infections caused by Gram-positive bacteria. In general, the method involves looking for proteins with a putative C-terminal LPXTG (SEQ ID NO:1) cell wall sorting signal and/or other structural similarities to MSCRAMM® proteins (Microbial Surface Components Recognizing Adhesive Matrix Molecules) having LPXTG-containing cell wall-anchored proteins. In the preferred embodiment, the present invention provides a method for identifying and isolating MSCRAMM® proteins, i.e., surface proteins that bind to extracellular matrix molecules, such as proteins, carbohydrates and other components, of host cells, wherein those located proteins contain regions that adopt an immunoglobulin—like fold. These Ig fold-containing regions consist of several consecutive and overlapping matches to solved crystal structures (~150-500 aa) of the immunoglobulin superfamily (IgSF), which consist of one to four domains of equal size and Ig-type fold. The homologous Ig-fold regions are indicative of a "beads-in-a-string" arrangement of consecutive modules such like the ones found in fibronectin and other IgSF proteins (Leahy, 1996)(Sharma, 1 999)(Hamburger, 1999)(Luo, 2000). For example, a tandem repeat of Ig folded subdomains (N2 and N3) is found in the crystal structure of the fibrinogen-binding domain of ClfA. The full-length A domains of ClfA and the similarly structured ClfB consist of an additional N-terminal subdomain, N1 (Deivanayagam, 2002)(Perkins, 2001). Based on sequence and secondary structure similarities, an analogous subdomain organization is also expected in other MSCRAMM® proteins including FnbpA, FnbpB, Ace and the Sdr proteins. The solved crystal structure of CNA minimum collagen-binding domain is made of a single Ig-type subdomain (N2) (Symersky, 1997) and the C-terminal repeat domains B1 and B2 each consist of a tandem repeat of Ig-folded subdomains (Deivanayagam, 2000). A similar modular structure is expected in the B3 and B4 repeats.

In accordance with the invention novel MSCRAMM®—like protein surface-anchored proteins are obtained from Gram-positive bacteria such as those from the genera *Enterococcus, Streptococcus, Staphylococcus* and *Bacillus,* and such proteins are characterized in that they are (i) structurally homologous to the solved Ig-folded crystal structures of ClfA and CNA as well as to the predicted tertiary structures of other MSCRAMM® proteins, (ii) share a similar β-sheet rich secondary structure as is found in Ig-folded proteins and (iii) have a similar organization with a secretion signal, a non-repeated domain followed by repeats as well as a C-terminal cell wall anchor domain. Moreover, the binding of proteins identified by the present method has confirmed that they target and bind to various extracellular matrix molecules. For example, three of the isolated proteins bind to major ECM proteins; two to fibrinogen and at least one to collagen and laminin. The proteins of the present invention have also been shown to be present in most isolates and are expressed in vivo during infection.

In accordance with the present invention, a method is provided for identifying and isolating a module structure of multiple Ig-folded units which have the general characteristics of the MSCRAMM® protein family. The length of the N-subdomains of MSCRAMM® proteins is typically ~150 aa, and the proteins identified by the present invention including those set forth below may accommodate more than three Ig-folded subdomains in their A domains. The isolation and use of the MSCRAMM® proteins of the present invention or their A domains in the generation of antibodies that can bind thereto or in methods of diagnosing, treating or preventing disease will be similar to that as described with other MSCRAMM® proteins such as in U.S. Pat. Nos. 6,288,214; 6,177,084; 6,008,241; 6,086,895; 5,980,908; 5,866,541; 5,851,794; 5,840,846; 5,789,549; 5,770,702; 5,652,217; 5,648,240; 5,571,514; 5,440,014; 5,416,021 and 5,320,951; and WO 00/68242; all of said references incorporated herein by reference.

In accordance with the present invention, a series of steps is undertaken in order to identify and isolate the characteristic module structure of one or more surface-anchored MSCRAMM® protein family of Gram positive bacteria, including the step of locating immunoglobulin—like (or Ig—like) folds in the putative LPXTG-containing proteins. This method can be used with any presently known database containing sequence information from Gram positive bacterial species, e.g., amino acid and/or nucleic acid sequences, and involves the steps of locating proteins with the LPXTG (SEQ ID NO:1) motif, and then reviewing and analyzing the sequence information so as to screen for proteins having particular structural similarities to MSCRAMM® as set forth below.

In the general process of the invention, the first part of the process is to search a database containing sequence information on one or more Gram positive bacteria so as to locate those proteins which contain the LPXTG (SEQ ID NO:1) motif contained in cell wall anchored proteins in annotated genomes of Gram-positive bacteria. This is done by initially obtaining the entire genome of amino acids sequences from one or more Gram positive bacteria of interest, such as from any of a number of web sites of sequencing centers, e.g., TIGR, NCBI, etc. In the preferred method, these sequences can be downloaded and stored in electronic memory before carrying out the identifying steps, such as in a local Silicon Graphics machine (SGI) or other suitable computer system. In the preferred method, this stored information is used to prepare a local searchable database, such as by using the program form "atdb" obtained from NCBI, and such a searchable database is installed locally on the SGI.

The LPXTG-motif is identified from the stored sequence information by any of a number of suitable programs. For example, these LPXTG-motif containing proteins can be identified using PHI-blast, which is obtained from NCBI and once again can be installed and stored locally on the SGI or other suitable computer system. The PHI-blast search uses a degenerate LPXTG pattern L-P-X-[TSA]-[GANS](SEQ ID NO:25), X being any amino acid. The exact templates for PHI-blast can vary depending on the particular organism, but in any case, the present system includes methods of identifying the LPXTG motif. For each organism, it is preferred to use at least two known cell wall anchored proteins of *S. aureus* with no sequence homology as well as known cell wall anchored proteins from the target organism if available.

Once LPXTG-containing proteins are identified obtained using a suitable system such as PHI-blast, these proteins are further analyzed so as to select for those that contain typical features of LPXTG-motif containing cell wall anchored proteins which have the properties of MSCRAMM®S. In the preferred process, these features will generally include a signal peptide at the N-terminus, the LPXTG-motif being close to the C-terminus, followed by a hydrophobic transmembrane segment, and several positively charged residues at the C-terminus. These are done as described below:

The signal peptides may be identified using any suitable identification method such as that method described in "Identification of prokaryotic and eukaryotic signal peptides and prediction of their cleavage sites". Henrik Nielsen, Jacob Engelbrecht, Søren Brunak and Gunnar von Heijne, *Protein Engineering* 10, 1-6 (1997), incorporated herein by reference. In the present process, a preferred system is to use the SignalP prediction server at cbs.dtu.dk/services/SipnalP, but other similar methods for identifying the signal peptide may also be used. Location of LPXTG-motif and the determination of positively charged amino acids residues at the C terminus are accomplished using visual examination of the sequence, although databases may also be used to determine the presence of these features.

In the preferred embodiment, the hydrophobic transmembrane segment after the LPXTG-motif may also be located using a conventional program which can predict the presence of such regions. An example of one such system is the TMHMM server available on the Internet at cbs.dtu.dk/services/TMHMM-2.0/ which can be used for the prediction of transmembrane segments. However, a number of other suitable prediction servers are available either on the Internet or in stored computer programs, including the TMpred available at ch.embnet.org/software/TMPRED form.html the DAS system available at www.sbc.su.se/~miklos/DAS/, and the HMMTOP at www.enzim.hu/hmmtop.

By following the procedures set forth above, putative LPXTG-containing sequences that contain the above features can be selected as highly likely to be MSCRAMM® proteins, i.e., to have the ability to bind extracellular matrix components. Following these initial steps, it is contemplated that the LPXTG-containing proteins identified in this matter will turn out be MSCRAMM® proteins at least about 90% of the time, as confirmed by expressing the putative protein or its A domain and determining if that protein or it's a domain binds to extracellular matrix components. This can be done by simple binding assays which are routine in the art and which would be well within the abilities of one skilled in the art.

Additionally, the LPXTG-containing sequences as initially located, or as further selected using the signal peptide/C terminal/transmembrane identifying characteristics as described above, can be further analyzed as indicated below to confirm the presence of immunoglobulin—like folds characteristic of MSCRAMM® proteins from Gram positive bacteria.

Similarly, in such a method, LPXTG-containing cell wall proteins may also be located using an annotated genomic nucleotide database such as the one located at the TIGR website (comprehensive microbial resource) at tigr.org/tigr-scripts/CMR2/CMRHomePage.spl http://www.tigr.org/tigr-scripts/CMR2/CMRHomePage.spl. With these databases, the term "LPXTG" or "cell wall" may be used to search for such proteins that are annotated as cell wall anchored proteins in the genome of interest.

Finally, LPXTG-motif containing cell wall anchored proteins may also be identified in un-annotated nucleotide genomes of Gram-positive bacteria. In this case, genome sequences are obtained from the web sites of sequencing centers, and the sequences may be stored as appropriate in computer memory such as a local Silicon Graphics machine (SGI). Gene prediction may be carried out using the program such as Glimmer 2.0 from TIGR, and this can be facilitated by UNIX C shell scripts which may be modified as desired to suit particular organisms or features. In the preferred process, the predicted genes are translated into amino acid sequences using a suitable translation program, preferably one that is capable of translating large batches of sequences. Finally, the translated amino acid sequences are formatted into a searchable database locally as described above, and subject to further analysis as described below.

In the preferred process of the present invention, steps are carried out by which the Immunoglobulin—like (Ig—like) fold in putative LPXTG-motif containing cell wall anchored proteins can be predicted and identified. In accordance with the invention, the amino acid sequences of putative LPXTG-motif containing cell wall anchored proteins are then analyzed to determine the presence of Ig—like folds which are characteristic of MSCRAMM® proteins. This can be done in a number of ways, such as by processing the putative MSCRAMM® using fold-recognition software, such as available using the web server 3D-PSSM available at sbg.bio-.ic.ac.uk/~3dpssm/ Additional methods of fold prediction are discussed in Kelley LA, MacCallum RM & Steinberg MJE. Enhanced Genome Annotation using Structural Profiles in the Program 3D-PSSM. J Mol Biol. 2000 June 2;299(2):499-520, incorporated herein by reference. Using this method, the output of 3D-PSSM gives a probability E value indicating the likelihood of the submitted sequence adopting a similar 3D structure as the known and published MSCRAMM®s. In accordance with the invention, proteins that have an E value <0.25 to a published Ig—like fold structure, are considered to contain the predicted Ig—like folds, and such proteins are identified as useful MSCRAMM® proteins in accordance with the invention, i.e., proteins that recognize adhesin molecules on the extracellular matrix of host cells.

The present invention has thus been carried out so as to identify and produce proteins and A domains therefrom which have MSCRAMM®—like characteristics from such Gram positive bacteria, such as *Enterococcus, Streptococcus, Staphylococcus* and *Bacillus*. In the preferred process, proteins identified as set forth above or their antigenic A domains may be expressed, purified and characterized as set forth herein.

Accordingly, in accordance with the present invention, a bioinformatic approach was used to identify proteins with MSCRAMM®—like characteristics among Gram positive bacteria, and those predicted proteins have been shown to have MSCRAMM—like characteristics. In one such case using *Enterococcus faecalis*, forty-two proteins with a putative C-terminal LPxTG cell wall sorting signal were identified in the *E. faecalis* genome. In accordance with the present method, these proteins were analyzed to determine the presence of Ig—like folds in the manner set forth above. Based on the present method, nine proteins were found to contain regions that adopt an immunoglobulin—like fold. The Ig fold-containing regions for these nine proteins are shown in FIG. 1 and consist of several consecutive and overlapping matches to solved crystal structures (~150-500 aa) of the immunoglobulin superfamily (IgSF), which consist of one to four domains of equal size and Ig-type fold. The homologous Ig-fold regions cover most of the enterococcal proteins and may indicate a similar "beads-in-a-string" arrangement of consecutive modules that are found in fibronectin and other IgSF proteins.

Further expression, purification and analysis of the A domains of these proteins was carried out. As shown in FIG. 2, the A regions of eight proteins expressed as N-terminal $His_6$-tag fusion proteins migrated as expected in SDS-PAGE gels, while EF1091 showed a band approx. 160 kDa in size; a larger-size molecule than the expected 113 kDa. Some degradation was observed in proteins EF1091, EF1824, EF0089 and EF3023, possibly due to their relatively large sizes. They were nevertheless estimated to be >95% pure. The putative glucosyl hydrolase domain of EF1824 (amino acids 42-819), which was cloned and expressed separately from the rest of the protein, (FIG. 1) was found in the insoluble fraction of *E. coli* cytoplasm. Hence, purification by metal affinity chromatography under native, non-denaturing conditions employed for the other expressed proteins was not feasible. The purified proteins were further characterized with Maldi-TOF mass spectrometry. All nine proteins, including EF1091 with aberrant migration in SDS-PAGE, gave peaks that were in good agreement with the molecular weights calculated from amino acid sequences (Table 1), and thus indicated that full-size proteins had been produced with no post-translational processing.

Secondary structure predictions and CD-measurements (Table 2) support finding of Ig-folded module-structures in the enterococcal proteins. Both methods show a similar high proportion of β-sheet (~50%) and coil and a minor quantity of α-helix, an identical situation as seen in MSCRAMM® proteins and in IgSF in general. The higher amount of α-helix in EF1824 and EF3023 probably reflects their relatively short predicted regions with Ig-folds and suggests the remainder of the proteins is structurally more distant to MSCRAMM® proteins.

TABLE 1

Molecular size analysis

| Protein | Molecular mass (Da) | |
|---|---|---|
| | Sequence prediction | Mass spectrometry |
| EF1091 | 113,021 | 113,025 |
| EF1824 | 111,893 | 111,901 |
| EF0089 | 122,853 | 122,857 |
| EF3023 | 113,338 | 113,323 |
| EF1092 | 47,291 | 47,295 |
| EF2224 | 82,194 | 82,199 |
| EF1269 | 64,776 | 64,776 |
| EF1099 | 39,281 | 39,293 |
| EF1093 | 62,363 | 62,366 |

TABLE 2

Summary of secondary structure components

| Protein | α-Helix | β-Sheet | Other |
|---|---|---|---|
| Sequence prediction | | | |
| EF1091 | 0.10 ± 0.05 | 0.33 ± 0.08 | 0.53 ± 0.06 |
| EF1824 | 0.45 ± 0.04 | 0.16 ± 0.04 | 0.39 ± 0.08 |
| EF0089 | 0.07 ± 0.07 | 0.44 ± 0.14 | 0.49 ± 0.08 |
| EF3023 | 0.24 ± 0.09 | 0.29 ± 0.10 | 0.47 ± 0.12 |
| EF1092 | 0.15 ± 0.05 | 0.36 ± 0.06 | 0.49 ± 0.10 |
| EF2224 | 0.15 ± 0.10 | 0.32 ± 0.05 | 0.54 ± 0.10 |
| EF1269 | 0.09 ± 0.10 | 0.42 ± 0.12 | 0.49 ± 0.10 |
| EF1099 | 0.04 ± 0.07 | 0.47 ± 0.07 | 0.49 ± 0.07 |
| EF1093 | 0.09 ± 0.06 | 0.41 ± 0.11 | 0.51 ± 0.11 |
| CD measurement | | | |
| EF1091 | 0.14 ± 0.05 | 0.41 ± 0.11 | 0.45 ± 0.10 |
| EF1824 | 0.29 ± 0.04 | 0.29 ± 0.17 | 0.44 ± 0.17 |
| EF0089 | 0.08 ± 0.04 | 0.49 ± 0.13 | 0.43 ± 0.12 |
| EF3023 | 0.33 ± 0.05 | 0.16 ± 0.05 | 0.51 ± 0.03 |
| EF1092 | 0.05 ± 0.04 | 0.50 ± 0.12 | 0.45 ± 0.14 |
| EF2224 | 0.16 ± 0.03 | 0.36 ± 0.10 | 0.48 ± 0.09 |
| EF1269 | 0.03 ± 0.04 | 0.55 ± 0.14 | 0.42 ± 0.12 |
| EF1099 | 0.07 ± 0.03 | 0.49 ± 0.13 | 0.44 ± 0.14 |
| EF1093 | 0.06 ± 0.05 | 0.57 ± 0.18 | 0.37 ± 0.17 |

In addition to EF1099 (Ace), the primary sequence of EF1269 is clearly related to the MSCRAMM® protein family. Similarly to Ace, it has homologous N2 and N3 subdomains including the conserved TYTDYVD-motif and a connecting tyrosine residue between the two subdomains. The absence of N1 further resembles Ace. However, the rest of their sequences share little homology. Although the A domain of EF1269 is made of similar N2 and N3 subdomains as the fibrinogen-binding ClfA, ClfB, SdrG, and to a lesser extent, FnbpA and FnbpB, it failed to bind fibrinogen. In this respect, EF1269 resembles SdrD and SdrE, which contain N2 and N3 subdomains, but for which the ligand is yet to be found. This is strengthened by our finding that the highest similarity of the EF1269 N2 and N3 domains is to the corresponding region in SdrE (identity 26%). Further, two putative repeats (95 and 109 aa) with lower conservation (identity 20%), which make up the rest of the C-terminal EF1269 sequence, show relatedness to the B repeats of SdrE (25% identity over 375 to 531 aa of EF1269). Proteins EF1091, EF0089, EF1092, EF2224 and EF1093 are not simply orthologs of previously described MSCRAMM® proteins, since they lack high sequence identity to streptococcal and staphylococcal adhesins. Yet, they share similar structural organization and an abundance of β-sheet rich secondary structures with similar predicted folding as MSCRAMM® proteins. The two remaining proteins, EF1824 and EF3023, have large regions related to known enzymes, glucosyl hydrolases and hyaluronan lyases, respectively, which sets these regions apart from MSCRAMM® proteins. Hyaluronidase activity could be significant for bacterial entry and spreading in hyaluronan-containing tissues during infection and/or potentially contribute to bacterial nutrition during commensal life in the human intestine. The large putative catalytic domains of EF1824 and EF3023 agree well with the above-discussed structural unrelatedness in these regions to MSCRAMM® proteins.

When screening binding to major ECM proteins, we found ligands for five of the MSCRAMM® proteins EF0089, EF1091, EF1092, EF1093, and EF2224. The presence of more than one fibrinogen-binding MSCRAMM® proteins in *E. faecalis* is consistent to findings in the related *S. aureus* in which four fibrinogen-binding MSCRAMM® proteins, ClfA, ClfB, FnbpA and FnbpB, have been described (McDevitt et al., 1994) (Ni Eidhin et al., 1998) (Wann et al., 2000) (Davis et al., 2001; Hartford et al., 2001). EF0089 and EF2224 have strong structural resemblance to MSCRAMM® proteins throughout their lengths: similar primary organization and homologous β-sheet rich secondary structure expected to form modular Ig-folded subdomains. Relatively low sequence identity to known fibrinogen binding adhesins may mean novel adaptations for ligand binding. Our initial results suggest EF2224 binds to the α- and β-chains of fibrinogen and thus resembles ClfB (Ni Eidhin et al., 1998). Mammalian tissue surfaces express a multitude of possible ligands for bacterial adherence. Here, we assessed binding to type I, III and IV collagens, laminin, fibronectin, fibrinogen and vitronectin.

In accordance with the invention, a PCR process may be used to amplify A domains from proteins identified and isolated using the present invention. Using PCR oligonucleotides such as those in Table 3, below, the A domains from EF0089, EF1091, EF1092, EF1093, EF1099, EF1269, EF1824, EF2224, and EF3023 were amplified from *E. faecalis* V583 or *E. faecalis* EF1 (EF1099) genomic DNA and subcloned into the *E. coli* expression vector PQE-30 (Qiagen). One liter culture of *E. coli* M15(pREP4) cultures harboring appropriate pQE-30 based constructs were grown to $OD_{600}$=0.6 with an initial 2% inoculation from overnight cultures. After 2-3 h induction with 0.4 mM isopropyl-beta-d-thiogalactoside (IPTG), cells were collected with centrifugation, resuspended in 10 mM Tris-Cl, 100 mM NaCl, pH 7.9 and stored at −80 C.

To lyse the cells and release the expressed protein, cells were passed twice through French Press with a gauge pressure setting at 1200 PSI to give an estimated internal cell pressure of 20,000 PSI. The lysate was centrifuged at $RCF_{max}$ of 165,000×g and the supernatant was filtered through a 0.45 □m filter. The volume was adjusted to 15 ml with 10 mM Tris-Cl, 100 mM NaCl, pH 7.9 and 0.2 M imidazole in the same buffer was added to increase the imidazole concentration to 6.5 mM in order to minimize non-specific binding. The sample was loaded to a nickel affinity chromatography column (HiTrap chelating, Pharmacia) connected to an FPLC system (Pharmacia) and previously equilibrated with 10 mM Tris-Cl, 100 mM NaCl, pH 7.9. Bound protein was eluted with a linear gradient of 0-100 mM imidazole in 10 mM Tris-Cl, 100 mM NaCl, pH 7.9 over 100-200 ml. Protein-containing fractions were analyzed in SDS-PAGE (FIG. 2) and dialyzed against 25 mM Tris-Cl, 1 mM EDTA, pH 6.5-9 (depending on pI of protein purified) before applying the samples to an ion-exchange column (HiTrap Q, Pharmacia) for further purification. Bound protein was eluted with a linear gradient of 0-0.5 M NaCl in 25 mM Tris-Cl, 1 mM EDTA, pH 6.5-9 over 100 ml. Finally, protein samples were dialyzed extensively against PBS and stored at +4° C.

Alternatively EF1091, EF1092, and EF1093 were expressed in shake flasks or in bioreactors, the cells were harvested by centrifugation and the cell paste frozen at −80° C. Cells were lysed in 1×PBS (10 mL of buffer/1 g of cell paste) using 2 passes through a microfluidizer at 10,000 psi.

titers are organized as a putative operon in the *E. faecalis* genome. The operon is preceded by two promoter consensus regions and a ribosome binding site and thus, these proteins are likely co-transcribed. The next gene downstream, EF1094, codes for a putative LPxTG transpeptidase sortase and EF1099 (Ace) is closely linked. It remains to be seen what role this cluster of MCSRAMM®—like proteins and a putative sortase may have in the infection process.

TABLE 3

Synthetic oligonucleotides used in this study (SEQ ID NO: 26-43)

| Oligonucleotide | | Location (aa) | Cloning site | Oligonucleotide |
|---|---|---|---|---|
| EF1091A | Fw | 102 | *Sph*I | 5'-CCGCATGCCAAGAGCAAACAGCAAAAGAAG-3' |
| | Rev | 1107 | *Sal*I | 5'-CCGTCGACTTAAGTACCAGAAGTGGTGGTTTTC-3' |
| EF1824AI | Fw | 42 | *Sph*I | 5'-CCGCATGCCAAGAGCAAACAGCAAAAGAAG-3' |
| | Rev | 819 | *Sal*I | 5'-GGGTCGACTTATTGTTTCAAGGTTACTTCTGTC |
| EF1824AII | Fw | 819 | *Bam*HI | 5'-CCGGATCCGCAGCTAATAAAGAAGAATTTTTAG |
| | Rev | 1829 | *Sal*I | 5'-CCGTCGACTTAAGTACCAGAAGTGGTGGTTTTC-3' |
| EF0089A | Fw | 35 | *Sac*I | 5'-CCGAGCTCGAAGAGGTTAACAGCGATGG-3' |
| | Rev | 1143 | *Pst*I | 5'-CCCTGCAGTTACCCACCAAATGTGATAACCC-3' |
| EF3023A | Fw | 25 | *Bam*HI | 5'-CCGGATCCGAAGAAATAACTGATTTATTTTTAC-3' |
| | Rev | 1024 | *Sac*I | 5'-CCGAGCTCTTATTGTTCCTGAATTAATTTTTCTAAC-3' |
| EF1092A | Fw | 27 | *Sph*I | 5'-CCGCATGCTCGCAAGCAAGCGTTCAAG-3' |
| | Rev | 438 | *Pst*I | 5'-CCCTGCAGTTAGAAGCCTGACTCTTTTACTTTT-3' |
| EF2224A | Fw | 30 | *Bam*HI | 5'-CCGGATCCCAAGAAGTAACAAGTGATGCTG-3' |
| | Rev | 771 | *Sac*I | 5'-CCGAGCTCTTAAGTTACTTGTTCGTCCGCAAT-3' |
| EF1269A | Fw | 26 | *Bam*HI | 5'-CCGGATCCGAAACAGGATATGCGCAAAC-3' |
| | Rev | 596 | *Sac*I | 5'-CCGAGCTCTTATTCCTTATTTACGAATCGCCTG-3' |
| EF1093A | Fw | 32 | *Bam*HI | 5'-GCGGGATCCGAAGAAAATGGGGAGAGCGC-3' |
| | Rev | 590 | *Sac*I | 5'-GCGGAGCTCTTAGGTACCTTTGTGTTTGTTTGG-3' |

5' overhang cloning site in each oligonucleotide sequence is marked in bold,
stop codon in italic
Fw, oligonucleotide primer in forward direction;
Rev, in reverse direction Lysed cells were spun down at 17,000 rpm for 30 minutes to remove cell debris. Supernatant was passed over a 5-mL HiTrap Chelating (Pharmacia) column charged with 0.1M NiCl$_2$. After loading, the column was washed with 5 column volumes of 10 mM Tris, pH 8.0, 100 mM NaCl (Buffer A). Protein was eluted using a 0-100% gradient of 10 mM Tris, pH 8.0, 100 mM NaCl, 500 mM imidazole (Buffer B). Protein containing fractions were dialyzed in 1×PBS.

The nine enterococcal genes encoding the MSCRAMM® are ubiquitous among *E. faecalis* strains as summarized in Table 3. Seven of the nine genes were 100% preserved in all strains. The two genes, EF1824 and EF3023, with predicted encoded protein catalytic domains and relatively low proportion of MSCRAMM®—like protein characteristics, were present in 16/30 and 23/30 strains, respectively. Nine enterococcal proteins encoded by their respective gene showed elevated titers in infected individuals suggesting expression in vivo during an *E. faecalis* infection. Although these proteins have a high distribution in strains, there were clear differences in induced antigenic responses; proteins EF1091, EF1092, EF1093 and EF2224 exhibited the highest titers. This may be due to different expression levels in physiological conditions or to highly immunogenic surface epitopes and, hence, a strong immune response. Interestingly, the three proteins (EF1091, EF1092 and EF1093) with the highest The presence of several MSCRAMM®—like proteins in *E. faecalis* including two that bind fibrinogen and the previously described collagen and laminin binding Ace, suggests that *E. faecalis* resembles *S. aureus* and other Gram-positive cocci by having an armory of ECM-binding adhesins. Since the introduction of antibiotic therapy, *E. faecalis* has shown an increasing tendency to emerge as an opportunistic pathogen capable of crossing the thin line from a harmless commensal to being able to invade host tissues and cause infections. A repertoire of adhesins may enhance its adaptability for colonizing and spreading in various human tissue types of susceptible human hosts.

Accordingly, the present invention allows for the identification and ultimate production of novel MSCRAMM®—like protein surface-anchored proteins from Gram positive bacteria which (i) are structurally homologous to the solved Ig-folded crystal structures of ClfA and CNA as well as to the predicted tertiary structures of other MSCRAMM® proteins, (ii) can share a similar β-sheet rich secondary structure as is found in Ig-folded proteins and (iii) have a similar organization with a secretion signal, a non-repeated domain followed by repeats as well as a C-terminal cell wall anchor domain. Further, these proteins may bind to major ECM proteins such as fibrinogen, collagen and laminin, and due to the similarities in proteins from different Gram positive bacterial species, these proteins may provide antibodies which are cross-reactive and can bind to similar proteins found in different Gram positive bacterial species. Such antibodies, as described further below, may thus be useful in diagnosing or fighting a variety of different infections at the same time.

In addition to proteins identified and isolated using the present method, particular, the present invention contemplates the generation of antibodies from the MSCRAMM®—like proteins obtained using the present method, or from antigenic regions such as the A domains from these proteins. By "antibody" is meant any intact antibody molecule or fragments thereof that recognize antigen (e.g. Fab or F(ab')2 fragments) and can be of polyclonal or monoclonal type, and the antibodies in accordance with the invention will be capable of recognizing the MSCRAMM® proteins of the invention and/or the specific antigenic epitopes from said proteins including their A domains. These antibodies will thus be effective in methods of diagnosing, monitoring, treating or preventing infection from Gram positive bacteria. By "epitope" is meant any antigenic determinant responsible for immunochemical binding with an antibody molecule. Epitopes usually reside within chemically active surface groupings of protein molecules (including amino acids and often also sugar side-chains) and have specific three-dimensional structural characteristics and specific charge characteristics. With reference to the proteins of the invention, or epitopes and peptides as described herein, it is understood that such terms also include those proteins and peptides which differ from a naturally occurring or recombinant protein by the substitution, deletion and/or addition of one or more amino acids but which retains the ability to be recognized by an antibody raised against the entire protein. An example is a carrier/antigen fusion polypeptide of the whole antigen or an immunoreactive fragment thereof, where the antigen or fragment can be embedded within the carrier polypeptide or linked to the carrier polypeptide at either end.

Accordingly, in accordance with the present invention, isolated and/or purified antibodies can be generated from the Gram-positive MSCRAMM® proteins of the present invention, or from particular epitopes such as those epitopic peptide sequences from the A domains from those proteins as described herein. These antibodies may be monoclonal or polyclonal and may be generated using any suitable method to raise such antibodies such as would be well known in this art. The antibodies in accordance with the invention will be particularly useful in inhibiting the binding of Gram positive bacteria to extracellular matrix components of the host cells and in diagnosing, treating or preventing infections of Gram positive bacteria.

For example, with regard to polyclonal antibodies, these may be generated using a number of suitable methods generally involving the injection of the isolated and/or purified or recombinantly produced proteins (or their immunogenic active peptides or epitopes) into a suitable host in order to generate the polyclonal antibodies which can then be recovered from the host. For example, in accordance with the invention, an isolated and purified MSCRAMM® protein or its A domain may be injected into rabbits in order to generate polyclonal antisera recognizing this protein.

In addition, monoclonal antibodies in accordance with the invention may be generated using a suitable hybridoma as would be readily understood by those of ordinary skill in the art. In the preferred process, a protein in accordance with the invention is first identified and isolated using the bioinformatic method as described above. Next, the protein is isolated and/or purified in any of a number of suitable ways commonly known in the art, or after the protein is sequenced, the protein used in the monoclonal process may be produced by recombinant means as would be commonly used in the art and then purified for use. In one suitable purification process, the cell wall proteins of the invention are isolated and examined using polyacrylamide gel electrophoresis (PAGE) and Western-blot techniques, and other conventional techniques including those discussed herein. In one suitable process, monoclonal antibodies were generated from proteins isolated and purified as described above by mixing the protein with an adjuvant, and injecting the mixture into BALB/c mice.

Immunization protocols consisted of a first injection (using complete Freund's adjuvant), two subsequent booster injections (with incomplete Freund's adjuvant) at three-week intervals, and one final booster injection without adjuvant three days prior to fusion (all injections were subcutaneous). For hybridoma production, mice were sacrificed and their spleen removed aseptically. Antibody secreting cells isolated and mixed with myeloma cells (NS1) using drop-wise addition of polyethylene glycol. After the fusion, cells were diluted in selective medium (vitamin-supplemented DMEM/HAT) and plated at low densities in multiwell tissue culture dishes. Tissue supernatants from the resulting fusion were screened by both ELISA (using the total 2-ME extract to coat the wells of a microtiter plate) and immunoblot techniques. Cells from these positive wells were grown and single cell cloned by limiting dilution, and supernatants subjected to one more round of screening by both ELISA and immunoblot. Positive clones were identified, and monoclonal antibodies collected as hybridoma supernatants.

In accordance with the invention, antibodies are thus produced which are capable of recognizing and binding proteins obtained using the bioinformatic method of the present invention and/or its epitopes and active regions such as the A domain, and such antibodies can be utilized in many diagnostic and therapeutic applications such as the ones described in more detail below.

Vaccines, Humanized Antibodies and Adjuvants

The isolated antibodies of the present invention, or the isolated proteins or epitopes as described above, may also be utilized in the development of vaccines for active and passive immunization against bacterial infections, as described further below. In the case of active vaccines, said vaccines are prepared by providing an immunogenic amount of the proteins of the invention or their active regions or epitopes as set forth above, and the active vaccine in accordance with the invention will thus comprise an immunogenic amount of the protein or peptide and will be administered to a human or animal in need of such a vaccine. The vaccine may also comprise a suitable, pharmaceutically acceptable vehicle, excipient or carrier which will be those known and commonly used in the vaccine arts. As referred to above, an "immunogenic amount" of the antigen to be used in accordance with the invention is intended to mean a nontoxic but sufficient amount of the agent, such that an immunogenic response will be elicited in the host so that the desired prophylactic or therapeutic effect is produced. Accordingly, the exact amount of the antigen that is required will vary from subject to subject, depending on the species, age, and general condition of the subject, the severity of the condition being treated, the particular carrier or adjuvant being used and its mode of administration, and the like. Similarly, the "immunogenic amount" of any such antigenic vaccine composition will vary based on the particular circumstances, and an appropriate immunogenic amount may be determined in each case of application by one of ordinary skill in the art using only routine experimentation. The dose should be adjusted to suit the individual to whom the composition is administered and will vary with age, weight and metabolism of the individual.

Further, when administered as pharmaceutical composition to a patient or used to coat medical devices or polymeric biomaterials in vitro and in vivo, the antibodies of the present invention may also be useful because these antibodies may be able to interfere with the ability of Gram positive bacteria to adhere to host cells and limit the extent and spread of the infection.

In addition, the antibody may be modified as necessary so that, in certain instances, it is less immunogenic in the patient to whom it is administered. For example, if the patient is a human, the antibody may be "humanized" by transplanting the complimentarity determining regions of the hybridoma-derived antibody into a human monoclonal antibody as described, e.g., by Jones et al., *Nature* 321:522-525 (1986) or Tempest et al. *Biotechnology* 9:266-273 (1991) or "veneered" by changing the surface exposed murine framework residues in the immunoglobulin variable regions to mimic a homologous human framework counterpart as described, e.g., by Padlan, Molecular Imm. 28:489-498 (1991), these references incorporated herein by reference. Even further, under certain circumstances, it may be desirable to combine the monoclonal antibodies of the present invention with a suitable antibiotic when administered so as to further enhance the ability of the present compositions to fight or prevent infections.

In a preferred embodiment, the antibodies may also be used as a passive vaccine which will be useful in providing suitable antibodies to treat or prevent a Gram-positive bacterial infection. As would be recognized by one skilled in this art, a vaccine may be packaged for administration in a number of suitable ways, such as by parenteral (i.e., intramuscular, intradermal or subcutaneous) administration or nasopharyngeal (i.e., intranasal) administration. One such mode is where the vaccine is injected intramuscularly, e.g., into the deltoid muscle, however, the particular mode of administration will depend on the nature of the bacterial infection to be dealt with and the condition of the patient. The vaccine is preferably combined with a pharmaceutically acceptable vehicle, carrier or excipient to facilitate administration, and the carrier is usually water or a buffered saline, with or without a preservative. The vaccine may be lyophilized for resuspension at the time of administration or in solution.

The preferred dose for administration of an antibody composition in accordance with the present invention is that amount will be effective in preventing of treating a bacterial infection, and one would readily recognize that this amount will vary greatly depending on the nature of the infection and the condition of a patient. An "effective amount" of antibody or pharmaceutical agent to be used in accordance with the invention is intended to mean a nontoxic but sufficient amount of the agent, such that the desired prophylactic or therapeutic effect is produced. Accordingly, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual. The compositions may additionally contain stabilizers or pharmaceutically acceptable preservatives, such as thimerosal (ethyl(2-mercaptobenzoate-S)mercury sodium salt) (Sigma Chemical Company, St. Louis, Mo.).

In addition, the antibody compositions of the present invention and the vaccines as described above may also be administered with a suitable adjuvant in an amount effective to enhance the immunogenic response against the conjugate. For example, suitable adjuvants may include alum (aluminum phosphate or aluminum hydroxide), which is used widely in humans, and other adjuvants such as saponin and its purified component Quil A, Freund's complete adjuvant, and other adjuvants used in research and veterinary applications. Still other chemically defined preparations such as muramyl dipeptide, monophosphoryl lipid A, phospholipid conjugates such as those described by Goodman-Snitkoff et al. *J. Immunol.* 147:410-415 (1991) and incorporated by reference herein, encapsulation of the conjugate within a proteoliposome as described by Miller et al., *J. Exp. Med.* 176:1739-1744 (1992) and incorporated by reference herein, and encapsulation of the protein in lipid vesicles such as Novasome™ lipid vesicles (Micro Vescular Systems, Inc., Nashua, N.H.) may also be useful.

Pharmaceutical Compositions

As would be recognized by one skilled in the art, the identified and isolated proteins or the invention, and the antibodies thereto capable of recognizing and binding to said proteins may also be formed into suitable pharmaceutical compositions for administration to a human or animal patient in order to treat or prevent a Gram-positive bacterial infection, such as those caused by *Enterococcus, Streptococcus, Staphylococcus,* etc. Pharmaceutical compositions containing the proteins or antibodies of the present invention as defined and described above may be formulated in combination with any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition may be formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

Additional forms of compositions, and other information concerning compositions, methods and applications with regard to other microbial surface proteins and peptides of the present invention and antibodies thereto, will be found in other patent references relating to MSCRAMM®s, including, for example, in U.S. Pat. No. 6,288,214 (Hook et al.), incorporated herein by reference.

The compositions which are generated in accordance with the present invention may also be administered with a suitable adjuvant in an amount effective to enhance the immunogenic response in a patient. For example, suitable adjuvants may include alum (aluminum phosphate or aluminum hydroxide), which is used widely in humans, and other adjuvants such as saponin and its purified component Quil A, Freund's complete adjuvant, RIBI adjuvant, and other adjuvants used in research and veterinary applications. Still other chemically defined preparations such as muramyl dipeptide, monophosphoryl lipid A, phospholipid conjugates such as those described by Goodman-Snitkoff et al. *J. Immunol.* 147:410-415 (1991) and incorporated by reference herein, encapsulation of the conjugate within a proteoliposome as described by Miller et al., *J. Exp. Med.* 176:1739-1744 (1992) and incorporated by reference herein, and encapsulation of the protein in lipid vesicles such as Novasome™ lipid vesicles (Micro Vescular Systems, Inc., Nashua, N.H.) may also be useful.

In any event, the compositions of the present invention will thus be useful for interfering with, modulating, or inhibiting binding interactions by Gram positive bacteria. Accordingly, the present invention will have particular applicability in developing compositions and methods of preventing or treating Gram positive bacterial infections, and in inhibiting binding and spreading of bacteria to host cells.

Methods:

Detecting and Diagnosing Infections

In accordance with the present invention, methods are provided for identifying and diagnosing infection from Gram positive bacteria through the use of the proteins, epitopes and peptides obtained by the bioinformatic method of the invention as described above and antibodies that recognize such proteins, epitopes and/or peptides. In accordance with the present invention, the antibodies of the invention as set forth above may be used in kits to diagnose such infections, and such kits may be of the type generally known in the art and commonly used to detect an antigen or microorganism of interest which will bind to the antibodies of the invention. These diagnostic kits will generally include the antibodies of the invention along with suitable means for detecting binding by that antibody such as would be readily understood by one skilled in this art. For example, the means for detecting binding of the antibody may comprise a detectable label that is linked to said antibody. These kits can then be used in diagnostic methods to detect the presence of a Gram positive bacterial infection wherein one obtains a sample suspected of being infected by one or more Gram positive bacteria, such as a sample taken from an individual, for example, from one's blood, saliva, urine, cerebrospinal fluid, genitourinary tract, tissues, bone, muscle, cartilage, or skin, and introduces to the sample one or more of the antibodies as set forth herein. After introduction of the antibodies, it is then determined through conventional means whether there has been binding by the antigens or microorganisms in the sample, such as through suitable labeling, or assays wherein the antibodies are bound to solid supports, and this binding is reflective of the presence of the target antigens or microorganisms in the sample.

Methods for Monitoring Levels of Antibodies or Antigens

In accordance with the present invention, it is also contemplated that another use of the invention may be in monitoring the level of Gram positive bacterial antigens, or antibodies recognizing said antigens in a human or animal patients suspected of containing said antigens or antibodies. In the preferred process, this may be carried out by first obtaining a biological sample from the human or animal patient, and this would include any suitable sample routinely monitored for infection, such as for example, from one's blood, serum, saliva, tissues, bone, muscle, cartilage, or skin. Next, one would introduce into the sample either (1) when monitoring levels of one's antibodies to Gram positive bacteria, a determinable level of a protein or its A domain to which such antibodies will bind; or (2), when monitoring levels of bacterial infestation is desired, introducing into said sample a measurable level of an antibody to a protein as set forth above. The next step in the process is, after allowing sufficient time and conditions so that the antigens and antibodies in the sample can achieve binding, then determining the level of antigen-antibody binding which will be reflective of the amount or level of the Gram positive bacteria, or antibodies thereto, which are located in the sample. In the desired process, levels may be monitored at regular time periods (e.g., hourly, daily, etc.) so as to track the progression/remission of a Gram positive bacterial infection such as during the period of hospitalization or treatment.

Assays for Detecting and Diagnosing Infections

In accordance with the present invention, the detection of Gram positive bacteria present in a biological fluid (e.g. blood, serum, plasma, saliva, urine, cerebrospinal fluid, genitourinary tract) or other biological material (e.g., tissues, bone, muscle, cartilage, or skin) can constitute a method for the diagnosis of acute or chronic infections caused by Gram positive bacteria. Because the antibodies as set forth above can recognize the epitopes found in several Gram positive bacteria, these antibodies can be used in assays to allow the diagnosis of a wide variety of Gram positive bacteria and disease conditions. Either monoclonal antibodies or polyclonal antibodies could be used in the assay, and in the case of the monoclonals such as those referred to above. The detected antigens identified by use of the present assays can be detected by a number of conventional means, including Western immunoblot and other similar tests.

With regard to the assays of the present invention, these assays may use the antibodies of the invention in labeled form, and all well-known methods of labeling antibodies are contemplated, including without limitation enzymatic conjugates, direct labeling with dye, radioisotopes, fluorescence, or particulate labels, such as liposome, latex, polystyrene, and colloid metals or nonmetals. Multiple antibody assay systems, such as antigen capture sandwich assays, are also within the scope of this invention. Further, competitive immunoassays involving labeled protein or assays using the labeled protein to detect serum antibodies are also contemplated forms of the diagnostic assays of the present invention. Beyond diagnostic assays which occur in solution, assays which involve immobilized antibody or protein are also considered within the scope of the invention. (See, for example, Miles et al., Lancet 2:492, 1968; Berry et al., J. Virol. Met. 34:91-100, 1991; Engvall et al., G. Immunochemistry, 8:871, 1971, Tom, Liposomes and Immunology, Elsevier/North Holland, New York, N.Y., 1980; Gribnau et al., J. of Chromatogr. 376:175-89, 1986 and all references cited therein). Examples of the types of labels which can be used in the present invention include, but are not limited to, enzymes, radioisotopes, fluorescent compounds, chemiluminescent compounds, bioluminescent compounds, particulates, and metal chelates. Those of ordinary skill in the art will know of other suitable labels for binding to the monoclonal or polyclonal antibody (or to an antigen) or will be able to ascertain the same by the use of routine experimentation. Furthermore, the binding of these labels to the monoclonal or polyclonal antibody (or antigen) can be accomplished using standard techniques commonly known to those of ordinary skill in the art.

One of the ways in which an assay reagent (generally, a monoclonal antibody, polyclonal antibody or antigen) of the present invention can be detectably labeled is by linking the monoclonal antibody, polyclonal antibody, or antigen to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label the reagents of the present invention include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The presence of the detectably labeled reagent of the present invention can also be detected by labeling the reagent with a radioactive isotope which can then be determined by such means as the use of a gamma counter or a scintillation counter. Isotopes which are particularly useful for the purpose of the present invention are $^3$H, $^{125}$I, $^{32}$P, $^{35}$S, $^{14}$C, $^{51}$Cr, $^{36}$Cl, $^{57}$Co, $^{58}$Co, $^{59}$Fe and $^{75}$Se. It is also possible to detect the binding of the detectably labeled reagent of the present invention by labeling the monoclonal or polyclonal antibody with a fluorescent compound. When the fluorescently labeled reagent is exposed to light of the proper wave length, its presence can then be detected due to the fluorescence of the dye. Among the most commonly used fluorescent labeling compounds are fluorescein isothiocyanate, rhodamine, phycoerythrin, phycocyanin, allophycocyanin, o-phthaldehyde and fluorescamine. The reagents of the present invention also can be detectably labeled by coupling it to a chemiluminescent compound. The presence of the chemiluminescent-tagged reagent is then determined by detecting the presence of luminescence that arises during the course of the chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the reagent of the present invention. Bioluminescence is a type of chemiluminescence found in biological systems in which a catalytic protein increases the efficiency of the chemiluminescent reaction. The presence of a bioluminescent reagent is determined by detecting the presence of luminescence. Important bioluminescent compounds for purposes of labeling are luciferin, luciferase and aequorin.

Another technique which may also result in greater sensitivity when used in conjunction with the present invention consists of coupling the monoclonal or polyclonal antibody of the present invention to low molecular weight haptens. The haptens can then be specifically detected by means of a second reaction. For example, it is common to use such haptens as biotin (reacting with avidin) or dinitrophenol, pyridoxal and fluorescamine (reacting with specific antihapten antibodies) in this manner. Any biological sample containing the detectable yet unknown amount of a Gram positive antigen can be used in the assay. Normally, the sample is preferably a liquid, such as, for example, urine, saliva, cerebrospinal fluid, blood, serum and the like, or a solid or semi-solid, such as, for example, tissue, feces and the like.

The diagnostic assay of the present invention includes kit forms of such an assay. This kit would include antibodies as described above (raised against whole proteins or active immunoreactive fragments such as the A domain or immunogenic analogs thereof) which can be optionally immobilized, as well as any necessary reagents and equipment to prepare the biological sample for and to conduct analysis, e.g. preservatives, reaction media such as nontoxic buffers, microtiter plates, micropipettes, etc. The reagent (Abs and/or antigens) can be lyophilized or cryopreserved. As described above, depending on the assay format, the antibodies can be labeled, or the kit can further comprise labeled proteins, fragments or analogs thereof containing the relevant epitopes so as to enable the detection of antibodies to Gram positive bacteria in biological fluids and tissues. By analog is meant a protein or peptide which may differs from its naturally occurring or recombinant counterpart by the substitution, deletion and/or addition of one or more amino acids but which retains the ability to be recognized by an antibody raised against the entire protein. An example is a carrier/antigen fusion polypeptide of the whole antigen or an immunoreactive fragment thereof, where the antigen or fragment can be embedded within the carrier polypeptide or linked to the carrier polypeptide at either end. Accordingly, antibodies in accordance with the invention may also recognize such analogs. The types of immunoassays which can be incorporated in kit form are many. Typical examples of some of the immunoassays which can utilize the antibodies of the invention are radioimmunoassays (RIA) and immunometric, or sandwich, immunoassays.

By "immunometric assay" or "sandwich immunoassay", in meant to include simultaneous sandwich, forward sandwich and reverse sandwich immunoassays. These terms are well understood by those skilled in the art. Those of skill will also appreciate that the monoclonal antibodies, polyclonal antibodies and/or antigens of the present invention will be useful in other variations and forms of immunoassays which are presently known or which may be developed in the future. These are intended to be included within the scope of the present invention. In a forward sandwich immunoassay, a sample is first incubated with a solid phase immunoadsorbent containing monoclonal or polyclonal antibody(ies) against the antigen. Incubation is continued for a period of time sufficient to allow the antigen in the sample to bind to the immobilized antibody in the solid phase. After the first incubation, the solid phase immunoadsorbent is separated from the incubation mixture and washed to remove excess antigen and other interfering substances, such as non-specific binding proteins, which also may be present in the sample. Solid phase immunoadsorbent containing antigen bound to the immobilized antibody is subsequently incubated for a second time with soluble labeled antibody or antibodies. After the second incubation, another wash is performed to remove unbound labeled antibody(ies) from the solid phase immunoadsorbent and removing non-specifically bound labeled antibody(ies). Labeled antibody(ies) bound to the solid phase immunoadsorbent is then detected and the amount of labeled antibody detected serves as a direct measure of the amount of antigen present in the original sample.

Alternatively, labeled antibody which is not associated with the immunoadsorbent complex can also be detected, in which case the measure is in inverse proportion to the amount of antigen present in the sample. Forward sandwich assays are described, for example, in U.S. Pat. Nos. 3,867,517; 4,012,294 and 4,376,110, incorporated herein by reference. In carrying out forward immunometric assays, the process may comprise, in more detail: (a) first forming a mixture of the sample with the solid phase bound antibody(ies) and incubating the mixture for a time and under conditions sufficient to allow antigen in the sample to bind to the solid phase bound antibody(ies), (b) adding to the mixture after said incubation of step (a) the detectably labeled antibody or antibodies and incubating the new resulting mixture for a time and under conditions sufficient to allow the labeled antibody to bind to the antigen-antibody complex on the solid phase immunoadsorbent; (c) separating the solid phase immunoadsorbent from the mixture after the incubation in step (b); and (d) detecting either the labeled antibody or antibodies bound to the antigen-antibody complex on the solid phase immunoadsorbent or detecting the antibody not associated therewith.

In a reverse sandwich assay, the sample is initially incubated with labeled antibody(ies), after which the solid phase immunoadsorbent containing multiple immobilized antibodies is added thereto, and a second incubation is carried out. The initial washing step of a forward sandwich assay is not required, although a wash is performed after the second incubation. Reverse sandwich assays have been described, for example, in U.S. Pat. Nos. 4,098,876 and 4,376,110. In carrying out reverse immunometric assays, the process may comprise, in more detail; (a) first forming a mixture of the sample with the soluble detectably labeled antibody for a time and under conditions sufficient to allow antigen in the sample to bind to the labeled antibody; (b) adding to the mixture after the incubation of step (a) the solid phase bound antibodies and incubating the new resulting mixture for a time and under conditions sufficient to allow antigen bound to the labeled antibody to bind to the solid phase antibodies; (c) separating the solid phase immunoadsorbent from the incubating mixture after the incubation in step (b); and (d) detecting either the labeled antibody bound to the solid phase immunoadsorbent or detecting the labeled antibody not associated therewith.

In a simultaneous sandwich assay, the sample, the immunoadsorbent having multiple immobilized antibodies thereon and labeled soluble antibody or antibodies are incubated simultaneously in one incubation step. The simultaneous assay requires only a single incubation and does not include washing steps. The use of a simultaneous assay is by far the preferred one. This type of assay brings about ease of handling, homogeneity, reproducibility, and linearity of the assays and high precision. The sample containing antigen, solid phase immunoadsorbent with immobilized antibodies and labeled soluble antibody or antibodies is incubated under conditions and for a period of time sufficient to allow antigen to bind to the immobilized antibodies and to the soluble antibody(ies). In general, it is desirable to provide incubation conditions sufficient to bind as much antigen as possible, since this maximizes the binding of labeled antibody to the solid phase, thereby increasing the signal. Typical conditions of time and temperature are two hours at 45 degrees C., or twelve hours at 37 degrees C. Antigen typically binds to labeled antibody more rapidly than to immobilized antibody, since the former is in solution whereas the latter is bound to the solid phase support. Because of this, labeled antibody may be employed in a lower concentration than immobilized antibody, and it is also preferable to employ a high specific activity for labeled antibody. For example, labeled antibody might be employed at a concentration of about 1-50 ng per assay, whereas immobilized antibody might have a concentration of 10-500 ng per assay per antibody. The labeled antibody might have a specific activity with, for instance, one radioiodine per molecule, or as high as two or more radioiodines per molecule of antibody.

Of course, the specific concentrations of labeled and immobilized antibodies, the temperature and time of incubation as well as other assay conditions can be varied, depending on various factors including the concentration of antigen in the sample, the nature of the sample and the like. Those skilled in the art will be able to determine operative and optimal assay conditions for each determination by employing routine experimentation.

In carrying out the simultaneous immunometric assay on a sample containing a multivalent antigen, the process may comprise, in more detail: (a) simultaneously forming a mixture comprising the sample, together with the solid phase bound antibody and the soluble labeled antibody or antibodies; (b) incubating the mixture formed in step (a) for a time and under conditions sufficient to allow antigen in the sample to bind to both immobilized and labeled antibodies;(c) separating the solid phase immunoadsorbent from the incubation mixture after the incubation; and(d) detecting either labeled antibody bound to the solid phase immunoadsorbent or detecting labeled antibody not associated therewith. Other such steps as washing, stirring, shaking filtering and the like may of course be added to the assays, as is the custom or necessity for any particular situation.

There are many solid phase immunoadsorbents which have been employed and which can be used in the present invention. Well-known immunoadsorbents include nitrocellulose, glass, polystyrene, polypropylene, dextran, nylon and other materials; tubes, beads, and microtiter plates formed from or coated with such materials, and the like. The immobilized antibodies can be either covalently or physically bound to the solid phase immunoadsorbent, by techniques such as covalent bonding via an amide or ester linkage, or by absorption. Those skilled in the art will know many other suitable solid phase immunoadsorbents and methods for immobilizing antibodies thereon, or will be able to ascertain such, using no more than routine experimentation.

Kits

As indicated above, in accordance with the present invention, the antibodies of the invention as set forth above may be used in kits to diagnose a Gram positive infection. Such diagnostic kits are well known in the art and will generally be prepared so as to be suitable for determining the presence of epitopes or proteins that will bind to the antibodies of the invention. These diagnostic kits will generally include the antibodies of the invention along with suitable means for detecting binding by that antibody such as would be readily understood by one skilled in this art. For example, the means for detecting binding of the antibody may comprise a detectable label that is linked to said antibody. These kits can then be used in diagnostic methods to detect the presence of a bacterial infection wherein one obtains a biological sample suspected of having such an infection, such as a sample taken from an individual, for example, from one's blood, saliva, urine, cerebrospinal fluid, genitourinary tract, tissues, bone, muscle, cartilage, or skin, introduces to the sample one or more of the antibodies as set forth herein, and then determines if the antibodies bind to the sample which would indicated the presence of such microorganisms in the sample.

In addition, as set forth above, these kits can also be useful in methods of monitoring the level of antibodies or bacterial antigens in the serum of a human or animal patient. If monitoring the level of antigen is desired, the kit will include an antibody in accordance with the present invention as described above along with a means of determining the level of binding to that antibody. When it is desired to measure the level of antibodies to Gram positive bacteria in a sample, the kit will preferably include an isolated protein or epitope (e.g., the A domain) such as described above, along with means for detecting binding of those antigens to antibodies present in the sample.

Treating or Protecting Against Infections

In accordance with the present invention, methods are provided for preventing or treating an infection caused by Gram positive bacteria which comprise administering an effective amount of the antibodies as described above to a human or animal patient in need of such treatment in amounts effective to treat or prevent the infection. Accordingly, in accordance with the invention, administration of an effective amount of the antibodies of the present invention in any of the conventional ways described above (e.g., topical, parenteral, intramuscular, etc.), and will thus provide an extremely useful method of treating or preventing bacterial infections in human or animal patients. As indicated above, by effective amount is meant that level of use, such as of an antibody titer, that will be sufficient to either prevent adherence of the bacteria, or to inhibit binding and colonization of such organisms to host cells and thus be useful in the treatment or prevention such infections. In addition, these antibodies also exhibit protective effects by a number of other mechanisms, including direct killing of the infectious microorganisms, increased opsonization, inhibition of morphological transition, etc., and thus an effective amount of antibodies will also include that amount by which any of the means to achieve a protective effect is obtained. As would be recognized by one of ordinary skill in this art, the level of antibody titer needed to be effective in treating or preventing infections will vary depending on the nature and condition of the patient, and/or the severity of the pre-existing infection.

Eliciting an Immune Response

In accordance with the present invention, a method is provided for eliciting an immunogenic reaction in a human or animal comprising administering to the human or animal an immunologically effective amount of a protein isolated using the bioinformatic method as described above, or a recombinantly produced version of such a protein, or an immunogenic fragment, region or epitope as described above so as to elicit an immunogenic response. As indicated above, an "immunogenic amount" of the antigen to be used in accordance with the invention to obtain an immunogenic reaction is intended to mean a nontoxic but sufficient amount of the agent, such that an immunogenic response will be elicited in the host so that the desired prophylactic or therapeutic effect is produced. Accordingly, the exact amount of the isolated protein that is required to elicit such a response will vary from subject to subject, depending on the species, age, and general condition of the subject, the severity of the condition being treated, the particular carrier or adjuvant being used and its mode of administration, and the like. The invention also contemplates methods of generating antibodies which recognize the proteins and epitopes as described above, and suitable methods of generating monoclonal and polyclonal antibodies are described in more detail above.

Coating Devices

In accordance with the invention, the antibodies and compositions as described above may also be utilized to treat or protect against outbreaks of bacterial infections on certain medical devices and other implanted materials such as prosthetic devices. Medical devices or polymeric biomaterials that may be advantageously coated with the antibodies and/or compositions described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the antibody or composition as defined above to a surface of the device, preferably an outer surface that would be exposed to an infection such as those caused by Gram positive bacteria. The surface of the device need not be entirely covered by the protein, antibody or active fragment.

As indicated above, the antibodies of the present invention, or active portions or fragments thereof, may also be useful for interfering with the physical interaction between bacteria responsible for infection and a mammalian host, and may also be useful in interfering with the ability of the bacteria to adhere to extracellular matrix proteins such as fibrinogen, collagen, laminin, etc. Accordingly, the antibodies of the invention may be useful both in treating patients and in preventing or reducing bacterial infections, or for reducing or eliminating infection and infestation of such organisms in-dwelling medical devices and prosthetics to make them safer for use.

In short, the antibodies of the present invention as described above can be extremely useful in detecting, treating or preventing infections by Gram positive bacteria in human and animal patients, or in preventing or reducing infection of medical devices and prosthesis that can be caused by such organisms. In particular, the present invention will be of importance in the treatment or prevention of such infections in highly susceptible groups such as premature newborns, AIDS and debilitated cancer patients, and are particularly frequent and severe after bone marrow transplantation.

EXAMPLES

The following examples are provided which exemplify aspects of the preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Method to Identify MSCRAMM® Proteins from Gram Positive Bacteria and Expression and Purification of Their A Domains A. Searching for LPXTG-motif containing cell wall anchored proteins in annotated genomes of Gram-positive bacteria.
1. Obtain the amino acid sequences of the entire genome of interest from web sites of sequencing centers. These sequences are stored in a local Silicon Graphics machine (SGI).
2. A local searchable database is established using the program format db obtained from NCBI and installed locally on the SGI.
3. LPXTG-motif containing proteins are identified using PHI-blast, which is obtained from NCBI and installed locally on the SGI. The PHI-blast search uses a degenerate LPXTG pattern L-P-X-[TSA]-[GANS], X being any amino acid. The templates for PHI-blast vary depend on the particular organism. For each organism, two known cell wall anchored proteins of *S. aureus* with no sequence homology were used as well as known cell wall anchored proteins from that particular organism if available.
4. The LPXTG-containing proteins obtained from PHI-blast were analyzed to select for those that contain typical features of LPXTG-motif containing cell wall anchored proteins: a signal peptide at the N-terminus, the LPXTG-motif being close to the C-terminus followed by a hydrophobic transmembrane segment, and several positively charged residues at the C-terminus. These are done as described below:

Signal peptide: we use the SignalP prediction server. The method has been described in "Identification of prokaryotic and eukaryotic signal peptides and prediction of their cleavage sites". Henrik Nielsen, Jacob Engelbrecht, Søren Brunak and Gunnar von Heijne, *Protein Engineering* 10, 1-6 (1997).

Location of LPXTG-motif: visual examination of the sequence.

A hydrophobic transmembrane segment after the LPXTG-motif: we use the TMHMM server for the prediction of transmembrane segments. Several other prediction web servers can also be used, among which are TMpred, DAS, and HMMTOP.

Positively charged residues at C-terminus: visual examination.
5. Sequences that contain the above features are putative LPXTG-motif containing cell wall anchored proteins.
6. The term "LPXTG" or "cell wall" are used to search for proteins that are annotated as cell wall anchored proteins in the genome of interest at TIGR website (comprehensive microbial resource, http://www.tigr.org/tigrscripts/CMR2/CMRHomePage.spl).

B. Searching for LPXTG-motif containing cell wall anchored proteins in unannotated genomes of Gram-positive bacteria.
1. Obtain genome sequences from the web sites of sequencing centers. These sequences are stored in a local Silicon Graphics machine (SGI).
2. Gene prediction using the program Glimmer 2.0 from TIGR. This is facilitated by UNIX C shell scripts written in house.
3. The predicted genes are translated into amino acid sequences using a translation program written in house. This program is capable of translating large batch of sequences.
4. The translated amino acid sequences are formatted into a searchable database locally as in Section A.2. Subsequent analysis is as described in Section A.3-5.

C. Prediction of Immunoglobulin—like (Ig—like) fold in putative LPXTG-motif containing cell wall anchored proteins.

The amino acid sequences of putative LPXTG-motif containing cell wall anchored proteins are submitted to a Fold recognition web server 3D-PSSM. The method of prediction is described in Kelley LA, MacCallum RM & Steinberg MJE. Enhanced Genome Annotation using Structural Profiles in the Program 3D-PSSM. J Mol Biol. 2000 June 2;299(2):499-520

The output of 3D-PSSM gives a probability E value indicating the likelihood of the submitted sequence adopting a similar 3D structure as a published structure.

Proteins that have E value <0.25 to a published Ig—like fold structure, are considered containing predicted Ig—like folds. These should be considered MSCRAMM® proteins.

Accordingly, in accordance with the present invention, a bioinformatic approach was used to identify proteins with MSCRAMM®—like characteristics among Gram positive bacteria, particularly *Enterococcus faecalis*. Forty-two proteins with a putative C-terminal LPxTG cell wall sorting signal were identified in the *E. faecalis* genome. We then looked for structural similarities to MSCRAMM® proteins among LPxTG-anchored enterococcal proteins. Nine proteins were predicted to contain regions that adopt an immunoglobulin—like fold. The Ig fold-containing regions in FIG. 1 consist of several consecutive and overlapping matches to solved crystal structures (~150-500 aa) of the immunoglobulin superfamily (IgSF), which consist of one to four domains of equal size and Ig-type fold. The homologous Ig-fold regions cover most of the enterococcal proteins and may indicate a similar "beads-in-a-string" arrangement of consecutive modules that are found in fibronectin and other IgSF proteins (Leahy, 1996)(Sharma, 1999)(Hamburger, 1999)(Luo, 2000). A tandem repeat of Ig folded subdomains (N2 and N3) is found in the crystal structure of the fibrinogen-binding domain of ClfA. The full-length A domains of ClfA and the similarly structured ClfB consist of an additional N-terminal subdomain, N1 (Deivanayagam, 2002)(Perkins, 2001). Based on sequence and secondary structure similarities, an analogous subdomain organization is also expected in other MSCRAMM® proteins including FnbpA, FnbpB, Ace and the Sdr proteins. The solved crystal structure of CNA minimum collagen-binding domain is made of a single Ig-type subdomain (N2) (Symersky, 1997) and the C-terminal repeat domains B1 and B2 each consist of a tandem repeat of Ig-folded subdomains (Deivanayagam, 2000). A similar modular structure is expected in the B3 and B4 repeats. Thus, a module structure of multiple Ig-folded units seems a general characteristic in the MSCRAMM® protein family. The length of the N-subdomains of MSCRAMM® proteins is typically ~150 aa suggesting that the large size of the A domains of EF1091 and EF0089 could accommodate more than three Ig-folded subdomains in their A domains.

Example 3

Expression and Purification of Recombinant Enterococcal MSCRAMM® Protein Fragments To further characterize the utility of this invention, the A-domains of EF1091, EF1092 and EF1093 proteins from *E.* *faecalis* as well as Efae 2926, Efae 2925 and Efae 2924 proteins from *E. faecium* were cloned, expressed and purified. In addition, EF1824 was cloned in two segments, EF1824AI (aa 43-819) and EF1824AII (aa 820-1829) because of the large size of the protein. EF1824AI was insoluble in *E. coli* cytoplasm and excluded from the assays. Bolded and underlined sequence represents the putative A-domains that were cloned.

```
EF1824A1: amino acid residues 43-819                                (SEQ ID NO: 2)
QEQTAKEDVADSATSVGAIVSIEKAEKNFVITYASGKKAQISILNDHLFRYHLDP
TGKFEEYPTPNDPKHVAKITAKTMADYGTQAFEQTNVTDSGNQFILENNGLKI
MFEKESALMKVLDKKKNQVILEETAPLSFKNDKATQTLKQSSQENYFGGGTQ
NGRFTHKGTAIQIVNTNNWVDGGVASPNPFYWSTAGYGVVRNTWKPGNYDF
GSHDPQKTTTTHEGTDFDAFYFFNDSSAGILKDYYELTGKPALMPEYGFYEAH
LNAYNRDYWVKVAEGTAGAVKFEDGNFYKEYQPGDLGNLNGTLESLNGEKE
NYQFSARAVIDRYKKNDMPLGWFLPNDGYGAGYGQTDSLDGDVQNLKEFTEY
AQANGVEVGLWTQSNLHPADPKNPKKGERDIAKEVSVAGVKALKTDVAWVG
YGYSFGLNGVEDAANVFVKETDGAVRPMIVSLDGWAGTQRHAGIWTGDQTG
GQWEYIRFHIPTYIGTSLSGQPNVGSDMDGIFGGKNKEINIRDFQWKTFTPVQL
NMDGWGSNPKTPFAFDQEATDLNRAYLKLKSMMMPYNYSIAKESVDGLPMV
RAMALEFPNEGTAYTKDSQYQYMWGPNLLVAPIYNGNQDEAGNSIRDGIYLPD
EKQVWVDLFTGEKYQGGRVLNGVKTPLWKVPVFVKDGSIIPMTNPNNNPKEI
QRDQRSFLIYPNGTTSFNMYEDDGISTSYEAGQSATTKINSQGPKSNEKGDLT
VTIEPTKGSYKDFVDERSTTLDLLASEAPESVTAMVGGTEVTLKQ EF1824A1: amino acid residues 820-1829                              (SEQ ID NO: 3)
AANKEEFLAGTNLYYFDKEFQVNQYLSEASGEKLNQSALSVKLAKQSVTAKDVQITVK
GFINKGTVDGGNTTVDDQLTIPANVAINEEKTTPSSLTLQWDQVTEATSYEVERDGTVF
GNIQTNTATFDGFSFLSEHTFRVRAVGKNGVSEWSEPIKGKTQDDPYKETINQVKATS
NLPEQPGAELKKLTDKDLSTGWHTNWSTGIANPSDGNFLSLKFDLGAEYQMDKIEYL
PRDNAGNGNILQLQYRTSKDGANWTEFSEPINWKQDALTKTIETKDQAYRFVEMKVL
KSVGNFGSGREMLFYKQPGTEGILHGDITNDGTIDENDAMSYRNYTGLESVDSDFNGY
VEKGDLNKNGVIDAYDISYVLRQLDGGIEIPDVEEIAGGLSLAVVNENGKDTYLPGDTLT
FILKGQDLKNINALSTKMSFDSSKFELVGQPATTNNTQQMENYSKYRKHSNDVENLYL
VLSNQGNKQLLNGSMDLVTFKVKVKETTRVKRATTVEQPLQFDMSQGLLVGQGFQQ
ATLSDFSVTVKPTELVDKELLQALITLNQARVEKEYTPETWAIFKPILDEAVAVLANEQA
TQTDVSAAAENLEKAASQLEKMPDVANKADLEKAIQEGLAKKPSDGQEFTEETKKVL
EESLAAAQKVFAQEKVTQEEIDQATKTLREAIAQLKEQPVAVDKETLKEQIAQARGRK
PEEGYQFTKETEKQLQEAIQAAEAIVAKETATKEEVSEALNALETAMAQLKEVPLVNK
DQLQEWKRAQQVTPSEGHQFTASSLQELQKALLAAKNTLKNPAANQKMIDEAVAEL
TSAIDGLQEEVLVTDKKALEAMIAKAKAIKPSAGKEFTSESKARLTEAIDQAEGILADKN
ARQEQIDIAEKNVKTALDSLEEQVLQTDKTKLKELLQKAETLKPKAGKQFTKASQEAL
AEAIKQAKALVEDPNATQEAVDKCLSILSQAIEAMAEEPISSNSTGNNGNHSTVSGTGG
VTSQGKGTATGGTTTKTTTSGT EF0089A: amino acid residues 36-1143                                (SEQ ID NO: 4)
EEVNSDGQLTLGEVKQTSQQEMTLALQGKAQPVTQEVVVHYSANVSIKAAHWAAPN
NTRKIQVDDQKKQIQIELNQQALADTLVLTLNPTATEDVTFSYGQQQRALTLKTGTDPT
ESTAITSSPAASANEGSTEEASTNSSVPRSSEETVASTTKAIESKTTESTTVKPRVAGPT
DISDYFTGDETTIIDNFEDPIYLNPDGTPATPPYKEDVTIHWNFNWSIPEDVREQMKAGD
YFEFQLPGNLKPNKPGSGDLVDAEGNVYGTYTISEDGTVRFTFNERITSESDIHGDFSL
DTHLNDSDGRGPGDWVIDIPTQEDLPPVVIPIVPDTEQQIDKQGHFDRTPNPSAITWTV
DINQAMKDQTNPVTETWPTGNTFKSVKVYELVMNLDGTIKEVGRELSPDEYTVDKNG
NVTIKGDTNKAYRLEYQTTIDEAVIPDGGGDVPFKNHATLTSDNNPNGLDAEATVTATY
GKMLDKRNIDYDEANQEFTWEINYNYGEQTIPKDQAVITDTMGDNLTFEPDSLHLYSVT
FDDKGNEVVGAELVEGKDYKVVINGDGSFAIDFLHDVTGAVKIDYKTKVDGIVEGDVAV
NNRVDVGTGQHSEDDGTASQQNIIKNTGAVDYQNSTIGWTLAVNQNNYLMENAVITDT
YEPVPGLTMVPNSLVVKDTTTGAQLTLGKDFMVEITRNADGETGFKVSFIGAYAKTSD
AFHITYTTFFDVTELDANNPALDHYRNTAAIDWTDEAGNNHHSEDSKPFKPLPAFDLNA
QKSGVYNAVTKEITWTIAVNLSNNRLVDAFLTDPILTNQTYLAGSLKVYEGNTKPDGSV
EKVKPTQPLTDITMEEPSEKNQNTWRVDFPNDSRTYVIEFKTSVDEKVIEGSASYDNTA
SYTNQGSSRDVTGKVSIQHGGESVKKGGEYHKDDPDHVYWHVMINGAQSVLDDVVIT
DTPSPNQVLDPESLVIYGTNVTEDGTITPDKSVILEEGKDYTLEVTTDNETGQQKIVVKM
AHIEAPYYMEYRSLVTSSAAGSTDTVSNQVSITGNGSEVVHGDDNGDVVVDIDHSGGH
ATGTKGKIQLKKTAMDETTILAGAHFQIWDQAKTQVLREGTVDATGVITFGG EF3023A: amino acid residues 26-1024                                (SEQ ID NO: 5)
EEITDLFLQKEVTYSGVEGGKIGENWKYPQFVGEKAVDGDETTRWSADKQDEQWLIV
DLGEVKNIGELVLQLHAESPVYEILVSTDGESYQSIFKEENGKGGQPTKKYIDGNNVQA
RFVKYQQMKMWQHTNKQFYSSSIISFEAYEKKRLPEAIKLLTENLTISEKRKQQLAFEV
SPAGVDITEDQIEWSSSDPTIVTVDQTGNLTAVKSGEAKVTVKIKGTEISDTIPVTVVAEN
KQYAEMRAKWKMRLLGTTQYDNDADVQQYRAQIATESLALWQTLNQAADREYLWER
KPSDTVSADYTTQFTNIKKLALGYYEPSSELFEKPEVYDAIVKGIEFMIDTKKYNGTYYT
GNWWDWQIGSAQPLTDTLILLHDDLLNTDAEKLNKFTAPLMLYAKDPNIQWPIYRATG
ANLTDISITVLGTGLLLEDNQRLVQVQEAVPSVLKSVSSGDGLYPDGSLIQHGYFPYNG
```

-continued

SYGNELLKGFGRIQTILQGSDWEMNDPNISNLFNVVDKGYLQLMVNGKMPSMVSGRS
ISRAPETNPFTTEFESGKETIANLTLIAKFAPENLRNDIYTSIQTWLQQSGSYYHFFKKP
RDFEALIDLKNVVNSASPAQATPMQSLNVYGSMDRVLQKNNEYAVGISMYSQRVGNY
EFGNTENKKGWHTADGMLYLYNQDFAQFDEGYWATIDPYRLPGTTVDTRELANGAYT
GKRSPQSWVGGSNNGQVASIGMFLDKSNEGMNLVAKKSWFLLDGQIINLGSGITGTT
DASIETILDNRMIHPQEVKLNQGSDKDNSWISLSAANPLNNIGYVFPNSMNTLDVQIEE
RSGRYGDINEYFVNDKTYTNTFAKISKNYGKTVENGTYEYLTVVGKTNEEIAALSKNKG
YTVLENTANLQAIEAGNYVMMNTWNNDQEIAGLYAYDPMSVISEKIDNGVYRLTLANPL
QNNASVSIEFDKGILEVVAADPEISVDQNIITLNSAGLNGSSRSIIVKTTPEVTKEALEKLI
QEQ

EF2224A: amino acid residues 31-771
QEVTSDAEKTVEKDGLKVIGKIEDTSSQEDIKTVTYEVTNTRDVPIKDLILKQKNTNDSPI (SEQ ID NO: 6)
KFVLDTLSEERGPTSLEEQAKVETNEKDQTTDIKLLNLQPNSTRKITINGQITTKASNKL
LVSVLIEDNEKGTLVIDLPSKDILADKESVSKEKQETSETKVENQANETASSTNEMTATT
SNETKPEAGKAIESIQETALTQATESPEQPPLKAQPTGPLVPPTPGRGFNTPIYQSVHK
GELFSTGNTNLKIANENTAAAQTFLNTRGASSGYAINNFPLEFADVDNDPNTYNSSRAY
IDLNGAKEIAWAGLFWSASRYKGPAYGTNLSDEEISAPVQFTTPNGTVQRVSPQRYHR
IDQDATNPGQRFGYNNTGFSNYADVTSILQGDKSATGSYTLADIPMTSSLNGQYQYYN
FSGWSLFVVTKDQASKSRAFSIYYGARGNAAGTNNEFTMSNFLTAKQGNLDPIVTWFT
VQGDKYWTGDNAQIKNSAGTWVNISNTLNPVNNAMNATVTDNDEHMVDKYPGKFAP
DHPNFLDIDIDRMAIPEGVLNAGQNQINFRTTSSGDDYSTNAIGFAVNAETPEFEIKKEIV
EPKETYKVGETITYRVSLKNTKADSEAINSVSKDALDGRLNYLPGSLKIISGPNSGEKTD
ASGDDQAEYDETNKQIIVRVGNGATATQGGSYKADTAETIYEFKARINERAKANELVPN
SATVEAVDILTSAKVNETSNIVEAKIADEQVT EF1269A: amino acid residues 27-596
ETGYAQTEPTSTSETNQISATPNVVPRKQVGNIVTAIQLTDKEGNPLGTINQYTDIYLRIE (SEQ ID NO: 7)
FNLPDNTVNSGDTSVITLPEELRLEKNMTFNVVDDTGTVVAIAQTDVANKTVTLTYTDY
VENHANISGSLYFTSLIDFENVENESKIPIYVTVEGEKIFAGDLDYQGEGDDVNEKFSKY
SWFIEDDPTEIYNVLRINPTGQTYTDLEVEDVLKTESLSYMKDTMKIERGQWTLDGNAI
WQFTPEEDITDQLAVQYGPDDRNFSVHFGNIGTNEYRITYKTKIDHLPEKGETFTNYAK
LTENQTVVEEVEVSRVSQTGGGEANGEQYVVEIHKEDEAGQRLAGAEFELIRNSTNQT
VAKITTDQNGTAIVKGLLKDNYTLVETKAPTGYQLSQNKIPITPEDFGKNLVALKTVVNH
KISYQPVAASFLAGKVLLGKPLKDAEFQFELLDEKGTVLETVSNDTLGKIQFSPLTFET
PGNYQYTIREVNTQQTGVSYDTHNLQVQVTVEALLGNLVATTQYDGGQVFTNHYTPE
KPIESTTPPTSGTTDTTTNSTTETTSITIEKQAIRNKE EF1091: Nucleotide Sequence
===0===ATGATAACAG=ATGAGAATGA=TAAAACGAAT=ATTAATATCG=AGTTAAATCT (SEQ ID NO: 8)
==50===TCTCAACCAA=ACAGAGCAGC=CATTACAACG=AGAAATTCAA=TTGAAAAATG
=100===CACAGTTCAT=GGATACTGCT=GTAATTGAAA=AAGACGGATA=TTCTTACCAA
=150===GTGACTAATG=GTACGCTTTA=TCTGACTTTG=GACGCACAAG=TAAAAAAGCC
=200===GGTACAGCTT=TCGTTAGCTG=TTGAGCAAAG=TTCGCTTCAA=ACAGCTCAGC
=250===CACCTAAGTT=ATTGTATGAA=AACAACGAAT=ATGATGTTTC=AGTTACTTCT
=300===GAAAAAATAA=CAGTAGAGGA=TTCTGCTAAA=GAATCAACTG=AACCAGAAAA
=350===AATAACTGTA=CCAGAAAATA=CGAAAGAAAC=TAACAAAAAT=GATTCGGCTC
=400===CAGAAAAAAC=AGAACAGCCG=ACCGCAACAG=AAGAGGTAAC=CAATCCATTT
=450===GCAGAAGCAA=GAATGGCGCC=AGCTACTTTG=AGAGCGAATC=TGGCACTGCC
=500===TTTAATTGCA=CCACAATACA=CGACGGATAA=TTCTGGGACT=TATCCGACAG
=550===CTAATTGGCA=GCCCACAGGC=AATCAAAATG=TGTTAAACCA=TCAAGGGAAT
=600===AAAGACGGTA=GTGCACAATG=GGACGGCCAA=ACGAGTTGGA=ATGGGGACCC
=650===TACTAATCGC=ACAAATTCTT=ATATTGAGTA=TGGCGGTACA=GGAGACCAAG
=700===CCGATTATGC=CATCCGAAAA=TATGCTAGAG=AAACAACAAC=ACCAGGGCTT
=750===TTTGATGTAT=ATCTTAATGT=GCGTGGGAAT=GTTCAGAAAG=AAATCGCCTC
=800===ATTGGATTTG=GTCTTAGTCG=TTGACTGGTC=CGGTAGTATG=AATGAAAACA
=850===ATCGGATTGG=TGAAGTTCAA=AAAGGAGTGA=ACCGTTTTGT=TGATACATTG
=900===GCAGATAGCG=GTATTACCAA=TAACATCAAC=ATGGGCTATG=TTGGCTACTC
=950===AAGTGACGGT=TATAATAACA=ACGCCATTCA=AATGGGGCCG=TTTGATACAG
1000===TCAAAAATCC=AATTAAAAAT=ATTACGCCAA=GTAGCACTAG=AGGAGGAACT
1050===TTCACTCAAA=AAGCATTAAG=AGATGCTGGT=GATATGTTAG=CAACGCCAAA
1100===TGGACATAAG=AAAGTCATTG=TACTTTTAAC=GGATGGCGTC=CCAACCTTCT
1150===CTTATAAAGT=GAGTCGAGTT=CAAACAGAGG=CAGATGTCG=CTTTTACGGG
1200===ACACAATTTA=CGAATCGACA=AGATCAACCA=GGTAGCACTT=CTTATATCTC
1250===TGGTAGCTAT=AATGCGCCAG=ATCAAAACAA=TATCAATAAA=CGGATTAACA
1300===GTACGTTTAT=CGCCACGATA=GGTGAGGCAA=TGGTCTTAAA=ACAACGTGGG
1350===ATTGAAATAC=ATGGATTGGG=CATTCAATTG=CAAAGCGATC=CACGAGCTAA
1400===TTTATCTAAA=CAACAAGTTG=AAGATAAAAT=GCGTGAGATG=GTGTCAGCCG
1450===ATGAAAATGG=AGACTTTAT=TATGAATCCG=CGGATTATGC=ACCAGACATT
1500===TCTGATTATT=TAGCGAAAAA=AGCCGTTCAG=ATTTCAGGAA=CGGTTGTAAA
1550===CGGAAAAGTA=GTTGATCCAA=TTGCTGAACC=TTTTAAATAC=GAGCCAAATA
1600===CATTATCAAT=GAAAAGTGTG=GGTCCTGTTC=AGGTTCAAAC=ATTACCAGAA
1650===GTGTCGCTAA=CAGGCGCTAC=AATTAATAGT=AATGAGATTT=ATTTGGGTAA
1700===AGGGCAAGAA=ATTCAAATTC=ATTATCAAGT=ACGTATTCAA=ACAGAGTCAG
1750===AAAACTTCAA=ACCTGATTTT=TGGATCAAAA=TGAATGGTCG=GACAACGTTT
1800===CAGCCATTAG=CCACGGCCCC=TGAAAAAGTT=GATTTTGGGG=TTCCTTCGGG
1850===AAAAGCACCT=GGCGTGAAGT=TAAACGTGAA=AAAAATCTGG=GAAGAGTATG
1900===ATCAAGACCC=GACAAGTCGG=CCAGATAATG=TGATTTATGA=AATTAGTAGA
1950===AAGCAAGTAA=CTGACACAGC=CAACTGGCAA=ACTGGGTATA=TTAAATTATC
2000===AAAACCAGAA=AATGATACCA=GCAATAGTTG=GGAGCGCAAA=AATGTAACCC -continued

```
2050===AACTTTCCAA=AACCGCGGAT=GAAAGCTATC=AAGAAGTTCT=TGGGCTTCCC
2100===CAATACAACA=ATCAAGGACA=AGCTTTCAAT=TATCAAACAA=CCCGTGAATT
2150===AGCAGTTCCT=GGTTACAGTC=AAGAAAAAAT=CGACGATACT=ACTTGGAAAA
2200===ACACGAAGCA=GTTCAAGCCA=TTAGATTTAA=AAGTAATCAA=AAATTCTTCC
2250===TCAGGTGAGA=AAAACTTAGT=GGGAGCCGTC=TTTGAATTGA=GTGGTAAAAA
2300===TGTTCAAACA=ACATTAGTGG=ACAATAAAGA=TGGTAGCTAT=TCCTTGCCAA
2350===AAGATGTGCG=CCTACAAAAA=GGGGAACGCT=ATACATTAAC=TGAAGTAAAA
2400===GCACCTGCAG=GACATGAGTT=AGGCAAGAAA=ACGACTTGGC=AAATTGAGGT
2450===GAGTGAGCAA=GGCAAAGTAA=GCATCGATGG=ACAAGAAGTG=ACCACCACAA
2500===ATCAAGTTAT=TCCATTGGAA=ATTGAAAATA=AATTTTCTTC=TTTGCCAATC
2550===AGAATTAGAA=AATACACCAT=GCAAAATGGC=AAACAAGTGA=ACTTAGCAGA
2600===GGCGACTTTT=GCGTTGCAAA=GAAAAAATGC=TCAAGGAAGT=TACCAAACTG
2650===TGGCAACTCA=AAAAACAGAT=ACTACAGGAT=TGAGCTATTT=TAAAATTAGT
2700===GAACCTGGTG=AGTATCGAAT=GGTGGAACAA=TCAGGACCAT=TAGGCTACGA
2750===CACTCTTGCT=GGAAATTATG=AATTTACTGT=TGATAAATAT=GGGAAAATTC
2800===ACTATGCAGG=CAAAAATATT=GAAGAAAATG=CGCCAGAATG=GACACTGACA
2850===CATCAAAATA=ATTTGAAACC=TTTTGACTTA=ACAGTTAATA=AAAAAGCCGA
2900===TAATCAGACG=CCACTTAAAG=GAGCGAAATT=CCGTTTAACA=GGACCAGATA
2950===CGGATATTGA=ATTACCAAAA=GATGGCAAAG=AAACGGATAC=TTTTGTTTTT
3000===GAAAACTTAA=AACCAGGGAA=ATATGTTCTA=ACAGAAACCT=TTACGCCAGA
3050===AGGATATCAG=GGGTTAAAAG=AACCAATCGA=ATTAATAATT=CGTGAAGATG
3100===GTTCAGTCAC=GATAGATGGG=GAAAAAGTAG=CAGATGTTTT=AATTTCTGGA
3150===GAGAAGAATA=ATCAAATTAC=TTTAGACGTT=ACGAACCAAG=CAAAGGTTCC
3200===TTTACCTGAA=ACTGGTGGCA=TAGGACGCTT=GTGGTTTTAC=TTGATAGCGA
3250===TTAGTACATT=CGTGATAGCG=GGTGTTTATC=TCTTTATTAG=ACGACCAGAA
3300===GGGAGTGTG

EF1091 amino acid residues 63-1067
===0===MITDENDKTN=INIELNLLNQ=TEQPLQREIQ=LKNAQFMDTA=VIEKDGYSYQ   (SEQ ID NO: 9)
==50===VTNGTLYLTL=DAQVKKPVQL=SLAVEQSSLQ=TAQPPKLLYE=NNEYDVSVTS
=100===EKITVEDSAK=ESTEPEKITV=PENTKETNKN=DSAPEKTEQP=TATEEVTNPF
=150===AEARMAPATL=RANLALPLIA=PQYTTDNSGT=YPTANWQPTG=NQNVLNHQGN
=200===KDGSAQWDGQ=TSWNGDPTNR=TNSYIEYGGT=GDDQADYAIRK=YARETTTPGL
=250===FDVYLNVRGN=VQKEITPLDL=VLVVDWSGSM=NENNRIGEVQ=KGVNRFVDTL
=300===ADSGITNNIN=MGYVGYSSDG=YNNNAIQMGP=FDTVKNPIKN=ITPSSTRGGT
=350===FTQKALRDAG=DMLATPNGHK=KVIVLLTDGV=PTFSYKVSRV=QTEADGRFYG
=400===TQFTNRQDQP=GSTSYISGSY=NAPDQNNINK=RINSTFIATI=GEAMVLKQRG
=450===IEIHGLGIQL=QSDPRANLSK=QQVEDKMREM=VSADENGDLY=YESADYAPDI
=500===SDYLAKKAVQ=ISGTVVNGKV=VDPIAEPFKY=EPNTLSMKSV=GPVQVQTLPE
=550===VSLTGATINS=NEIYLGKGQE=IQIHYQVRIQ=TESENFKPDF=WYQMNGRTTF
=600===QPLATAPEKV=DFGVPSGKAP=GVKLNVKKIW=EEYDQDPTSR=PDNVIYEISR
=650===KQVTDTANWQ=TGYIKLSKPE=NDTSNSWERK=NVTQLSKTAD=ESYQEVLGLP
=700===QYNNQGQAFN=YQTTRELAVP=GYSQEKIDDT=TWKNTKQFKP=LDLKVIKNSS
=750===SGEKNLVGAV=FELSGKNVQT=TLVDNKDGSY=SLPKDVRLQK=GERYTLTEVK
=800===APAGHELGKK=TTWQIEVSEQ=GKVSIDGQEV=TTTNQVIPLE=IENKFSSLPI
=850===RIRKYTMQNG=KQVNLAEATF=ALQRKNAQGS=YQTVATQKTD=TTGLSYFKIS
=900===EPGEYRMVEQ=SGPLGYDTLA=GNYEFTVDKY=GKIHYAGKNI=EENAPEWTLT
=950===HQNNLKPFDL=TVNKKADNQT=PLKGAKFRLT=GPDTDIELPK=DGKETDTFVF
1000===ENLKPGKYVL=TETFTPEGYQ=GLKEPIELII=REDGSVTIDG=EKVADVLISG
1050===EKNNQITLDV=TNQAKVPLPE=TGGIGRLWFY=LIAISTFVIA=GVYLFIRRPE
1100===GSV EF1092: Nucleotide Sequence
===0===ATGAAAAACG=CACGTTGGTT=AAGTATTTGC=GTCATGCTAC=TCGCTCTTTT   (SEQ ID NO: 10)
==50===CGGGTTTTCA=CAGCAAGCAT=TAGCAGAGGC=ATCGCAAGCA=AGCGTTCAAG
=100===TTACGTTGCA=CAAATTATTG=TTCCCTGATG=GTCAATTACC=AGAACAGCAG
=150===CAAAACACAG=GGGAAGAGGG=AACGCTGCTT=CAAAATTATC=GGGGCTTAAA
=200===TGACGTCACT=TATCAAGTCT=ATGATGTGAC=GGATCCGTTT=TATCAGCTTC
=250===GTTCTGAAGG=AAAAACGGTC=CAAGAGGCAC=AGCGTCAAGA=CAGAAACC
=300===GGTGCAACAA=ATAGAAAACC=GATCGCAGAA=GATAAAACAC=AGACAATAAA
=350===TGGAGAAGAT=GGAGTGGTTT=CTTTTTCATT=AGCTAGCAAA=GATTCGCAGC
=400===AACGAGATAA=AGCCTATTTA=TTTGTTGAAG=CGGAAGCACC=AGAAGTGGTA
=450===AAGGAAAAAG=CTAGCAACCT=AGTAGTGATT=TTGCCTGTTC=AGATCCACA
=500===AGGGCAATCG=TTAACGCATA=TTCATTTATA=TCCAAAAAAT=GAAGAAAATG
=550===CCTATGACTT=ACCACCACTT=GAAAAACGG=TACTCGATAA=GCAACAAGGC
=600===TTTAATCAAG=GAGAGCACAT=TAACTATCAG=TTAACGACTC=AGATTCCAGC
=650===GAATATTTTA=GGATATCAGG=AATTCCGTTT=GTCAGATAGA=GCGGATACAA
=700===CGTTGACACT=TTTACCAGAA=TCAATTGAGG=TAAAAGTGGC=TGGAAAAACA
=750===GTTACTACAG=GTTACACACT=GACGACGCAA=AAGCATGGAT=TTACGCTTGA
=800===TTTTTCAATT=AAAGACTTAC=AAAACTTTGC=AAATCAAACA=ATGACTGTGT
=850===CGTATCAAAT=GCGTTTAGAA=AAGACCGCTG=AACCTGACAC=TGCGATTAAC
=900===AACGAAGGAC=AATTAGTCAC=GGACAAACAT=ACCTTGACTA=AAAGAGCCAC
=950===AGTTCGTACA=GGCGGCAAGT=CTTTTGTCAA=AGTTGATAGT=GAAAATGCGA
1000===AAATCACCTT=GCCAGAGGCT=GTTTTTATCG=TCAAAAATCA=AGCGGGGGAA
1050===TACCTCAATG=AAACAGCAAA=CGGGTATCGT=TGGCAAAAAG=AAAAAGCATT
1100===AGCTAAAAAA=TTCACGTCTA=ATCAAGCCGG=TGAATTTTCA=GTTAAAGGCT
1150===TAAAAGATGG=CCAGTACTTC=TTGGAAGAAA=TCTCTGCACC=AAAAGGTTAT
1200===CTTCTGAATC=AAACAGAAAT=TCCTTTTACG=GTGGGAAAAA=ATTCTTATGC
1250===AACGAACGGA=CAACGAACAG=CACCGTTACA=TGTAATCAAT=AAAAAAGTAA
1300===AAGAGTCAGG=CTTCTTACCA=AAAACAAATG=AAGAACGTTC=TATTTGGTTG
```

-continued
1350    ACGATTGCAG GCCTGCTAAT CATTGGGATG GTAGTCATTT GGCTATTTTA
1400    TCAAAAACAA AAAAGAGGAG AGAGAAAA EF1092 amino acid residues 28-438
   0    MKNARWLSIC VMLLALFGFS QQALAEASQA SVQVTLHKLL FPDGQLPEQQ                (SEQ ID NO: 11)
  50    QNTGEEGTLL QNYRGLNDVT YQVYDVTDPF YQLRSEGKTV QEAQRQLAET
 100    GATNRKPIAE DKTQTINGED GVVSFSLASK DSQQRDKAYL FVEAEAPEVV
 150    KEKASNLVVI LPVQDPQGQS LTHIHLYPKN EENAYDLPPL EKTVLDKQQG
 200    FNQGEHINYQ LTTQIPANIL GYQEFRLSDK ADTTLTLLPE SIEVKVAGKT
 250    VTTGYTLTTQ KHGFTLDFSI KDLQNFANQT MTVSYQMRLE KTAEPDTAIN
 300    NEGQLVTDKH TLTKRATVRT GGKSFVKVDS ENAKITLPEA VFIVKNQAGE
 350    YLNETANGYR WQKEKALAKK FTSNQAGEFS VKGLKDGQYF LEEISAPKGY
 400    LLNQTEIPFT VGKNSYATNG QRTAPLHVIN KKVKESGFLP KTNEERSIWL
 450    TIAGLLIIGM VVIWLFYQKQ KRGERK EF1093 (V583): Nucleotide Sequence
   0    ATGAAGCAAT TAAAAAAAGT TTGGTACACC GTTAGTACCT TGTTACTAAT                    (SEQ ID NO: 12)
  50    TTVGCCACTT TTCACAAGTG TATTAGGGAC AACAACTGCA TTTGCAGAAG
 100    AAAATGGGGA GAGCGCACAG CTCGTGATTC ACAAAAAGAA AATGACGGAT
 150    TTACCAGATC CGCTTATTCA AAATAGCGGG AAAGAAATGA GCGAGTTTGA
 200    TAAATATCAA GGACTGGCAG ATGTGACGTT TAGTATTTAT AACGTGACGA
 250    ACGAATTTTA CGAGCAACGA GCGGCAGGCG CAAGCGTTGA TGCAGCTAAA
 300    CAAGCTGTCC AAAGTTTAAC TCCTGGGAAA CCTGTTGCTC AAGGAACCAC
 350    CGATGCAAAT GGGAATGTCA CTGTTCAGTT ACCTAAAAAA CAAAATGGTA
 400    AAGATGCAGT GTATACCATT AAAGAAGAAC CAAAGAGGGT TGTAGTTGCT
 450    GCTACGAATA TGGTGGTGGC GTTCCCAGTT TACGAAATGA TCAAGCAAAA
 500    AGATGGTTCC TATAAATATG GAACAGAAGA ATTAGCGGTT GTTCATATTT
 550    ATCCTAAAAA TGTGGTAGCC AATGATGGTA GTTTACATGT GAAAAAAGTA
 600    GGAACTGCTG AAAATGAAGG ATTAAATGGC GCAGAATTTG TTATTTCTAA
 650    AAGCGAAGGC TCACCAGGCA CAGTAAAATA TATCCAAGGA GTCAAAGATG
 700    GATTATATAC ATGGACAACG GATAAAGAAC AAGCAAAACG CTTTATTACT
 750    GGGAAAAGTT ATGAAATTGG CGAAAATGAT TTCACAGAAG CAGAGAATGG
 800    AACGGGAGAA TTAACAGTTA AAAATCTTGA GGTTGGTTCA TATATTTTAG
 850    AAGAAGTAAA AGCTCCAAAT AATGCAGAAT TAATTGAAAA TCAAACAAAA
 900    ACACCATTTA CAATTGAAGC AAACAATCAA ACACCTGTTG AAAAAACAGT
 950    CAAAAATGAT ACCTCTAAAG TTGATAAAAC AACACCAAGC TTAGATGGTA
1000    AAGATGTGGC AATTGGCGAA AAAATTAAAT ATCAAATTTC TGTAAATATT
1050    CCATTGGGGA TTGCAGACAA AGAAGGCGAC GCTAATAAAT ACGTCAAATT
1100    CAATTTAGTT GATAAACATG ATGCAGCCTT AACTTTTGAT AACGTGACTT
1150    CTGGAGAGTA TGCTTATGCG TTATATGATG GGGATACAGT GATTGCTCCT
1200    GAAAAATTATC AAGTGACTGA ACAAGCAAAT GGCTTCACTG TCGCCGTTAA
1250    TCCAGCGTAT ATTCCTACGC TAACACCAGG CGGCACACTA AAATTCGTTT
1300    ACTTTATGCA TTTAAATGAA AAAGCAGATC CTACGAAAGG CTTTAAAAAT
1350    GAGGCGAATG TTGATAACGG TCATACCGAC GACCAAACAC CACCAACTGT
1400    TGAAGTTGTG ACAGGTGGGA AACGTTTCAT TAAAGTCGAT GGCGATGTGA
1450    CAGCGACACA AGCCTTGGCG GGAGCTTCCT TTGTCGTCCG TGATCAAAAC
1500    AGCGACACAG CAAATTATTT GAAAATCGAT GAAACAACGA AAGCAGCAAC
1550    TTGGGTGAAA ACAAAAGCTG AAGCAACTAC TTTTACAACA ACGGCTGATG
1600    GATTAGTTGA TATCACAGGG CTTAAATACG GTACCTATTA TTTAGAAGAA
1650    ACTGTAGCTC CTGATGATTA TGTCTTGTTA ACAAATCGGA TTGAATTTGT
1700    GGTCAATGAA CAATCATATG GCAACAACAGA AAACCTAGTT TCACCAGAAA
1750    AAGTACCAAA CAAACACAAA GGTACCTTAC CTTCAACAGG TGGCAAAGGA
1800    ATCTACGTTT ACTTAGGAAG TGGCGCAGTC TTGCTACTTA TTGCAGGAGT
1850    CTACTTTGCT AGACGTAGAA AAGAAAATGC T EF1093 amino acid residues 33-592
   0    MKQLKKVWYT VSTLLLILPL FTSVLGTTTA FAEENGESAQ LVIHKKKMTD                 (SEQ ID NO: 13)
  50    LPDPLIQNSG KEMSEFDKYQ GLADVTFSIY NVTNEFYEQR AAGASVDAAK
 100    QAVQSLTPGK PVAQGTTDAN GNVTVQLPKK QNGKDAVYTI KEEPKEGVVA
 150    ATNMVVAFPV YEMIKQTDGS YKYGTEELAV VHIYPKNVVA NDGSLHVKKV
 200    GTAENEGLNG AEFVISKSEG SPGTVKYIQG VKDGLYTWTT DKEQAKRFIT
 250    GKSYEIGEND FTEAENGTEE LTVKNLEVGS YILEEVKAPN NAELIENQTK
 300    TPFTIEANNQ TPVEKTVKND TSKVDKTTPS LDGKDVAIGE KIKYQISVNI
 350    PLGIADKEGD ANKYVKFNLV DKHDAALTFD NVTSGEYAYA LYDGDTVIAP
 400    ENYQVTEQAN GFTVAVNPAY IPTLTPGGTL KFVYFMHLNE KADPTKGFKN
 450    EANVDNGHTD DQTPPTVEVV TGGKRFIKVD GDVTATQALA GASFVVRDQN
 500    SDTANYLKID ETTKAATWVK TKAEATTFTT TADGLVDITG LKYGTYYLEE
 550    TVAPDDYVLL TNRIEFVVNE QSYGTTENLV SPEKVPNKHK GTLPSTGGKG
 600    IYVYLGSGAV LLLIAGVYFA RRRKENA Efae2926: Nucleotide Sequence
   0    ATGACGACCA CAGGGAAGAA ACTGAAAGTT ATTTTCATGC TGATAATATT                    (SEQ ID NO: 14)
  50    GAGTTTATCA AACTTTGTGC CATTATCTGC AATAGCAGAC ACTACAGATG
 100    ATCCAACAGT TTTAGAAACA ATTTCAGCTG AAGTCATTTC GGATCAGTCT
 150    GGAAAAAAAG CACTGAACAT CAAGCTAAAT GCGAATAACA CCAGTGCTGA
 200    AAAGATAGAA AAAGAAATTG GTCTAGTCGA AAATTACTTA AGTGATGTGG
 250    AAAGAAAAGA AGGGAGATGG CTATGCTTAT CAGGTAAATAG CGGGAAAATT
 300    ACGTTGGAAA TCTCATCAAA CACTAAACAA ACTATCGATC TGAGTTTTCC
 350    AATCGATCCA GCACTTTACC ACAGCCAGGC AAACAAGCTG ATCGTCGATA
 400    ATAAAGAATA TGACATTATT GATGAGACAG AAAATAAGAA AGATACAGAT

-continued
```
 450    GTGTCAGTAC CAAAGCCAGA CGAAATAGAA GAAGAATCAT CAAAAGAAAA
 500    CGAAAATTCT GTCAGCCCAT TTACATTGCC TACATTATCC TTGCCAGCTG
 550    TGAGTGTGCC ATCTAATCAA ACGATTCCTA CAGAATATAC AACAGATGAT
 600    CAGGGCACTT ATCCTAAAGC CAGTTGGCAA CCTACAGGAA ATACAAATGT
 650    TCTTGATCAT CAAGGCAATA AAAACGGAAC AAATCAATGG GATGGTATAA
 700    ATTCTTGGAA TGGAGATCCT AATGATCGGA CCCATTCGTA TATCGAATAT
 750    GGAGGAACCG GTAATCAAGC AGACTATGCG ATACGAAAGT ATGCAAAGGA
 800    AACAAGTACA CCCGGATTGT TTGATGTTTA TTTGAATGCT CGTGGAAATG
 850    TACAAAAAGA TATCACGCCT CTTGATCTCG TATTGGTCGT AGACTGGTCA
 900    GGAAGTATGA ACGACAATAA TCGGATCGGT GAAGTAAAGA TTGGTGTCGA
 950    TCGTTTTGTC GATACTTTAG CAGATAGCGG TATCACAGAC AAAATCAATA
1000    TGGGATATGT CGGCTACTCA AGCGAAGGAT ATAGCTACAG TAACGGTGCA
1050    GTACAGATGG GTTCATTTGA TTCAGTGAAA AATCAAGTGA AATCCATTAC
1100    ACCTTCACGG ACAAATGGTG GTACTTTTAC ACAAAAAGCA CTAAGAGATG
1150    CAGGAAGCAT GCTATCCGTT CCAAATGGAC ATAAAAAAGT GATCGTTTTG
1200    CTGACGGATG GTGTACCAAC ATTTTCCTAT AAAGTACAGC GGGTACACGC
1250    ACAATCAAGC AGCAATTATT ACGGAACTCA GTTTTCTAAT CAGCAAGATC
1300    GGCCGGGAAA TACTTCTCTA ATCTCAAGAA TCTATGATGC ACCTGACCAA
1350    AACAATCTAT CCAGAAGAAT CGACAGTACG TTTATCGCAA CCATCGGAGA
1400    AGCGATGGCA CTCAAAGAAC GAGGAATCGA AATACATGGT CTTGGCATCC
1450    AACTTCAAAG CGATCCGGCA GCTGGTCTCT CAAAAGCAGA AGTAGAGTCT
1500    CGTATGCGAC AAATGGTTTC ATCAGATGAA AAAGGCGATC TTTACTATGA
1550    ATCAGCTGAT CATGCAACAG ATATCTCTGA ATACCTAGCC AAAAAAGCTG
1600    TACAGATCTC AGCAACTGTA AGCAATGGAC AAATAAATGA TCCAATCGCA
1650    GAACCATTCA TTTATCAGCC TGGTACACTT TCAGTCAAGA GTGTGGGGAC
1700    AAGTCCTACA ACGGTCACTC CATCTATTTC CATAGAAGGA AATACCATCA
1750    AGAGCAATCA GATCTATTTA GGAAAAGACC AAGAAATCCA AATCCATTAC
1800    CAAGTGAGAA TCCAAACAGA AAATGAGGAC TTCCATCCAA ATTTCTGGTA
1850    TCAAATGAAC GGCAGGACAA CTTTCCAGCC AAACATTGAT ACCAATGAAT
1900    TAGCTGAATT CGGTATACCA TCTGCTAAAG CTCCCGGAGT CAGTCTTCAC
1950    ATCAAAAAGT TATGGGAAGA ATTTGACAAC AATCTAGCTG ATCGTCCAGA
2000    TCAAGTTACT TTTGAGATTC AACGGGAACA TACGACAAAT GCTGCAGCTT
2050    GGAAAAACGG ATATATTCGA ATCATTAAAC CAGCTAAAGA TACAACAAAT
2100    ACGTGGGAAC GTGCAGACAT TGACAAATTA TCTGCAAATA GCGGAGAAAG
2150    TTATCAAGAG ATATTATCAC TACCTCAATA CAATAATCAA GGTCAAGCAT
2200    TC AGTTACCA AACAATCAAA GAATTACCTG TACCAGGATA CGATTCTCAA
2250    CAAATAGATG CAATGACATG GAAAAATACT AAACAATTCA CACCGTTAAA
2300    CTTGAAAATA ACGAAAAATT CCTCTACAGG TGAAAAGGAT CTTATTGGCG
2350    CTGTTTTCAA ATTAACAGGA GATTCTATTG ATACTTTACT AACAGATCAT
2400    GGCGACGAA  CCTATTCTCT TCCAGAAAAT GTCAAATTGC AAAAAGAAAT
2450    GACCTATACG CTGACAGAAA CAAAAGCTCC AGAAGGGCAT GGATTAAGCA
2500    AAAAGACTAC TTGGGAAATC AAGATCGCTT CTGATGGTAC GGTAACCATT
2550    GATGGAAAAA CAGTCACTAC TTCCGATGAT ACGATCCAGT TGACTATTGA
2600    AAATCCTTTT GTTGAAGTTC CTGTAGCAGT ACGTAAGTAT GCGATGCAAG
2650    GGACGGACAA AGAGATAAAT CTTAAAGGAG CAGCATTTTC CCTACAGAAA
2700    AAAGAAGCAA ATGGTACTTA TCAGCCAATT GACAGCCAAA CAACGAATGA
2750    AAAAGGTCTT GCCAGTTTTG ATTCACTCAC ACCTGGTAAA TATCGAGTCG
2800    TTGAAACAGC TGGTCCTGCC GGATATGATA CTTCGCCGGG AAATTATGAA
2850    TTCCAAATCG ATAAATATGG AAAAATCATT TACACGGGAA AAAATACCGA
2900    TGATGACAAAT AATGTATGGA CGCTCACTCA TCAAAATCGA CTAAAAGCGT
2950    TTGATCTAAC GGTACACAAA AAAGAAGACA ACGGACAGAC ATTAAAAGGA
3000    GCAAAATTCA GACTGCAGGG ACCAGAAATG GACTTAGAAT CGCCAAAAGA
3050    TGGACAAGAA ACAGATACCT TTCTATTCGA AAATTTAAAA CCTGGAACTT
3100    ATACGCTGAC CGAAACTTTT ACACCAGAAG GATACCAAGG TCTAAAAGAG
3T50    CCAGTTACTA TAGTTATACA CGAAGATGGG TCAATTCAAG TGGATGGACA
3200    AGATCATGAA TCTGTTCTGT CACCAGGAGC CAAAAACAAC CAGATTTCTT
3250    TAGACATGAC GAATCAGGCA AAAGTACCAT TACCTGAAAC GGGAGGAATT
3300    GGCCGTTTAG GAATCTATCT AGTAGGGATG ATTGGTTGTG CGTTTTCTAT
3350    TTGGTATCTT TTTTTGAAAA AAGAAAGAGG GGGCAGC Efae2926: amino acid residues 53-734
   0    MTTTGKKLKV IFMLIILSLS NFVPLSAIAD TTDDPTVLET ISAEVISDQS    (SEQ ID NO: 15)
  50    GKKALNIKLN ANNTSAEKIE KEIGLVENYL SDVERKEGDG YAYQVNSGKI
 100    TLEISSNTKQ TIDLSFPIDP ALYHSQANKL IVDNKEYDII DETENKKDTD
 150    VSVPKPDEIE EESSKENENS VSPFTLPTLS LPAVSVPSNQ TIPTEYTTDD
 200    QGTYPKASWQ PTGNTNVLDH QGNKNGTNQW DGINSWNGDP NDRTHSYIEY
 250    GGTGNQADYA IRKYAKETST PGLFDVYLNA RGNVQKDITP LDLVLVVDWS
 300    GSMNDNNRIG EVKIGVDRFV DTLADSGITD KINMGYVGYS SEGYSYSNGA
 350    VQMGSFDSVK NQVKSITPSR TNGGTFTQKA LRDAGSMLSV PNGHKKVIVL
 400    LTDGVPTFSY KVQRVHAQSS SNYYGTQFSN TQDRPGNTSL ISRIYDAPDQ
 450    NNLSRRIDST FIATIGEAMA LKERGIEIHG LGIQLQSDPA AGLSKAEVES
 500    RMRQMVSSDE KGDLYYESAD HATDISEYLA KKAVQISATV SNGQINDPIA
 550    EPFIYQPGTL SVKSVGTSPT TVTPSISIEG NTIKSNQIYL GKDQEIQIHY
 600    QVRIQTENED FHPNFWYQMN GRTTFQPNID TNELAEFGIP SAKAPGVSLH
 650    IKKLWEEFDN NLADRPDQVT FEIQREHTTN AAAWKNGYIR IIKPAKDTTN
 700    TWERADIDKL SANSGESYQE ILSLPQYNNQ GQAFSYQTIK ELPVPGYDSQ
 750    QIDAMWIKNT KQFTPLNLKI TKNSSTGEKD LIGAVFKLTG DSIDTLLTDH
 800    GDGTYSLPEN VKLQKEMTYT LTETKAPEGH GLSKKTTWEI KIASDGTVTI
 850    DGKTVTTSDD TIQLTIENPF VEVPVAVRKY AMQGTDKEIN LKGAAFSLQK
 900    KEANGTYQPI DSQTTNEKGL ASFDSLTPGK YRVVETAGPA GYDTSPGNYE
```

-continued
```
= 950===FQIDKYGKII=YTGKNTEMTN=NVWTLTHQNR=LKAFDLTVHK=KEDNGQTLKG
=1000===AKFRLQGPEM=DLESPKDGQE=TDTFLFENLK=PGTYTLTETF=TPEGYQGLKE
=1050===PVTIVIHEDG=SIQVDGQDHE=SVLSPGAKNN=QISLDITNQA=KVPLPETGGI
=1100===GRLGIYLVGM=IGCAFSIWYL=FLKKERGGS
```

Efae2925: Nucleotide Sequence
```
===0===ATGAAAAAAC=TTGGTTGGCT=TAGTATGTGT=CTCTTCTTGT=TACTATTTAA    (SEQ ID NO: 16)
==50===ACCAGCTTTT=ACTCAGGTAG=CAACAGAAAC=AGAAACAGAA=ATGGTTCAGA
=100===TTACTTTACA=CAAATTGCTT=TTCCCAAACG=GGCAACTGCC=GAAAAATCAT
=150===CCAAATGACG=GACAAGAAAA=AGCTTTATTA=CAAACGTATC=GAGGATTAAA
=200===TGGTGTCACA=TTCCAAGTTT=ATGATGTCAC=AGATTCTTTT=TACCATCTAC
=250===GGGAAAAGGG=CAAAACGGTA=GAAGAAGCAC=AAGCAGAGAT=CGCAAAAAAC
=300===GGTGCGTCTT=CCGGTATGTT=TACCGCAGAA=GCAACAACTA=CAACTCTTAA
=350===CAACGAAGAT=GGTATCGCTT=CTTTTTCTCT=GGCCGCTAAA=GATCAAGAAA
=400===AAAGAGATAA=AGCGTATCTT=TTCATTGAAT=CCAAAGTACC=AGAAGTCGTC
=450===AAAGAAAAGG=CAGAGAATAT=GGTAGTTGTT=CTTCCTGTAC=ATGGACAAAA
=500===CAATCAAAAA=CTTTCAACTA=TCCATTTGTA=TCCTAAAAAT=GAAGAAAACG
=550===ACTACCCTGA=TCCACCTTTT=GAGAAGGTAT=TAGAAGAGCC=TAGAAATGAT
=600===TTTACGATTG=GTGAAAAAAT=CACTTATTCC=TTGCATACGA=CAATTCCTGT
=650===AAATATCCTT=GACTATCAAA=AGTTCGAATT=GTCAGATAGT=GCGGATGAAG
=700===CATTAACGTT=TTTACCTAAT=AGTTTAACGA=TTTCATCGAA=TGGAGAAAAG
=750===CTGACAGAAG=GCTTTGTCAT=ACACAAGAAA=CCTCACGGAT=TTGATGTTTT
=800===ATTTTCGATC=CCTTCGTTGG=AAAAATATGC=TGGAAAAAAA=CTGACCATTT
=850===CTTATCAGAT=GCAGCTAAGC=AGTACAGCAC=AGGCGAACAA=GGAAATCAAC
=900===AACAACGGAA=CACTGGATTT=TGGTTTTGGT=GTCAGTACAA=AGAAAGTCTC
=950===TGTATATACA=GGGAGTAAGC=AATTTGTCAA=AATCGAGACA=AATAAACCAG
=1000===ATAAACGATT=AGCTGGCGCA=GTATTCCTTA=TTAAAAACAA=AGCAGGAAAT
=1050===TACCTCCAGC=AAACAGCCAA=CGGATACAAG=TGGACAAAGA=ACGAATCAGA
=1100===TGCGCTTCAC=CTGATTTCCG=ATAAAAATGG=CGCTTTTTCA=ATTTCCGGGT
=1150===TGAAAACAGG=AAGTTATCGA=TTAAAAGAGA=TCGAAGCACC=TTCTGGTTAT
=1200===ATTTTAAGTG=AAACAGAAAT=TCCGTTTACC=ATTTCAACTT=TTCTTTCTGA
=1250===GGATAAAGAG=GCGGACAGTA=TATTGAAAGT=AGTCAATAAA=AAAGAAAATA
=1300===GCCGTCCATT=TCTTCCAAAA=ACAAACGAAA=CGAAAAATAC=ACTTTTAGGC
=1350===GTTGTTGGTA=TGGTATTCGC=AAGCTTTGCA=ATCTGGTTGT=TATCAAAAA
=1400===AAGAACAGGA=GTGAAAAAAT=GA
```

Efae 2925: amino acid residues 30-429
```
===0===MKKLGWLSMC=LFLLLFKPAF=TQVATETETE=MVQITLHKLL=FPNGQLPKNH    (SEQ ID NO: 17)
==50===PNDGQEKALL=QTYRGLNGVT=FQVYDVTDSF=YHLREKGKTV=EEAQAEIAKN
=100===GASSGMFTAE=ATTTTLNNED=GIASFSLAAK=DQEKRDKAYL=FIESKVPEVV
=150===KEKAENMVVV=LPVHGQNNQK=LSTIHLYPKN=EENDYPDPPF=EKVLEEPRND
=200===FTIGEKITYS=LHTTIPVNIL=DYQKFELSDS=ADEALTFLPN=SLTISSNGEK
=250===LTEGFVIHKK=PHGFDVLFSI=PSLEKYAGKK=LTISYQMQLS=STAQANKEIN
=300===NNGTLDFGFG=VSTKKVSVYT=GSKQFVKIET=NKPDKRLAGA=VFLIKNKAGN
=350===YLQQTANGYK=WTKNESDALH=LISDKNGAFS=ISGLKTGSYR=LKEIEAPSGY
=400===ILSETEIPFT=ISTFLSEDKE=ADSILKVVNK=KENSRPFLPK=TNETKNTLLG
=450===VVGMVFASFA=IWLFIKKRTG=VKK
```

Efae 2924: Nucleotide sequence
```
===0===ATGAAAAATC=ATAAAAAAAT=AAACGTTATG=TTAGGAGTCC=TTTTCCTTAT    (SEQ ID NO: 18)
==50===TTTACCATTA=CTCACAAACA=GCTTCGGCGC=AAAAAAAGTG=TTTGCAGAGG
=100===AGACAGCAGC=TCAAGTCATC=CTTCATAAAA=AGAAAATGAC=TGATTTACCC
=150===GATCCTTTAA=TCCAAAACAG=CGGGAAAGAA=ATGAGCGAAT=TCGATCAATA
=200===CCAAGGATTA=GCCGATATTT=CATTTTCAGT=TTATAACGTC=ACTCAAGAAT
=250===TTTATGCGCA=ACGAGATAAA=GGAGCGTCCG=TGGATGCAGC=AAAACAAGCA
=300===GTCCAGTCTT=TGACTCCTGG=TACACCAGTT=GCTTCAGGAA=CGACAGATGC
=350===TGATGGAAAT=GTCACTTTAT=CTTTACCTAA=AAAACAAAAT=GGGAAAGATG
=400===CAGTCTACAC=GATCAAAGAA=GAACCAAAAG=ACGGAGTGTC=AGCTGCCGCA
=450===AACATGGTTT=TAGCTTTCCC=TGTATATGAG=ATGATCAAAC=AAGCAGATGG
=500===CTCTTATAAA=TACGGGACAG=AAGAACTAGA=TACTATCCAT=CTCTACCCTA
=550===AAAATACAGT=CGGTAATGAT=GGAACGTTGA=AGTTACAAA=AATCGGTACT
=600===GCCGAAAACG=AAGCACTAAA=TGGAGCAGAA=TTTATTATTT=CTAAAGAAGA
=650===AGGAACACCA=AGCGTCAAAA=AATACATCCA=AAGTGTCACA=GATGGATTGT
=700===ACACTTGGAC=AACTGATCAA=ACCAAAGCCA=AACATTTCAT=TACTGGTCAT
=750===TCTTATGACA=TCGGCAACAA=TGACTTTGCC=GAGGCATCTA=TTGAAAAAGG
=800===CCAGTTGATC=GTTAATCATT=TAGAAGTTGG=AAAATATAAT=TTAGAAGAAG
=850===TAAAAGCTCC=TGATAATGCG=GAAATGATTG=AAAAGCAAAC=AATCACGCCT
=900===TTTGAGATCC=TGGCAAATGA=CCAAACACCA=GTAGAAAAGA=CCATCAAAAA
=950===TGATACGTCT=AAAGTTGATA=AAACAACACC=TCAATTGAAT=GGAAAAGATG
=1000===TCGCAATCGG=TGAAAAAATT=CAATATGAGA=TTTCTGTCAA=TATCCCATTA
=1050===GGTATCGCTG=ATAAAGAAGG=AACGCAAAAC=AAGTACACAA=CATTCAAACT
=1100===TATCGATACT=CATGACGCTG=CTTTAACATT=TGATAATGAT=TCTTCAGGAA
=1150===CGTATGCTTA=TGCCTTATAT=GATGGAAATA=AAGAAATCGA=CCCAGTAAAT
=1200===TATTCTGTCA=CTGAGCAAAC=AGACGGATTC=ACGGTTTCAG=TTGATCCGAA
=1250===TTATATTCCT=TCATTAACTC=CTGGCGGTAC=AATTGAAATTC=GTTTACTATA
=1300===TGCATTTGAA=CGAAAAAGCA=GATCCAACCA=AGGATTTTC=TAACCAAGCA
=1350===AATGTCGATA=ACGGGCATAC=AAATGATCAA=ACACCACCGT=CAGTCGATGT
=1400===CGTTACTGGG=GGCAAACGAT=TGTTAAAGT=AGATGGTGAC=GTTACATCAG
=1450===ACCAAACACT=TGCTGGAGCA=GAATTCGTCG=TTCGTGATCA=AGATAGTGAC
=1500===ACAGCGAAAT=ATTTATCGAT=CGACCCATCC=ACAAAAGCCG=TCAGCTGGGT
```

```
-continued
1550===ATCGGCGAAA=GAATCAGCAA=CGGTTTTTAC=AACCACAAGT=AACGGTTTAA
1600===TCGATGTGAC=AGGTCTAAAA=TATGGCACGT=ACTATCTGGA=AGAAACGAAA
1650===GCGCCAGAAA=AATATGTTCC=ATTAACAAAC=CGTGTAGCAT=TTACTATCGA
1700===TGAACAATCT=TATGTAACAG=CAGGACAGTT=GATTTCTCCT=GAAAAAATAC
1750===CAAATAAACA=CAAAGGTACA=CTTCCTTCAA=CAGGCGGTAA=GGGAATCTAT
1800===GTGTATATCG=GTGCAGGAGT=AGTCCTTCTA=CTGATTGCTG=GACTGTACTT
1850===TGCTAGACGC=AAGCACAGTC=AGATTTAG Efae 2924: amino acid residues 55-588
===0===MKNHKKINVM=LGVLFLILPL=LTNSFGAKKV=FAEETAAQVI=LHKKKMTDLP    (SEQ ID NO: 19)
==50===DPLIQNSGKE=MSEFDQYQGL=ADISFSVYNV=TQEFYAQRDK=GASVDAAKQA
=100===VQSLTPGTPV=ASGTTDADGN=VTLSLPKKQN=GKDAVYTIKE=EPKDGVSAAA
=150===NMVLAFPVYE=MIKQADGSYK=YGTEELDTIH=LYPKNTVGND=GTLKVTKIGT
=200===AENEALNGAE=FIISKEEGTP=SVKKYIQSVT=DGLYTWTTDQ=TKAKHFITGH
=250===SYDIGNNDFA=EASIEKGQLI=VNHLEVGKYN=LEEVKAPDNA=EMIEKQTITP
=300===FEILANSQTP=VEKTIKNDTS=KVDKTTPQLN=GKDVAIGEKI=QYEISVNIPL
=350===GIADKEGTQN=KYTTFKLIDT=HDAALTFDND=SSGTYAYALY=DGNKEIDPVN
=400===YSVTEQTDGF=TVSVDPNYIP=SLTPGGTLKF=VYYMHLNEKA=DPTKGFSNQA
=450===NVDNGHTNDQ=TPPSVDVVTG=GKRFVKVDGD=VTSDQTLAGA=EFVVRDQDSD
=500===TAKYLSIDPS=TKAVSWVSAK=ESATVFTTTS=NGLIDVTGLK=YGTYYLEETK
=550===APEKYVPLTN=RVAFTIDEQS=YVTAGQLISP=EKIPNKHKGT=LPSTGGKGIY
=600===VYIGAGVVLL=LIAGLYFARR=KHSQI
```

Protein Expression and Purification

Using PCR (the oligonucleotides used in the PCR reaction are shown in Table 3), the A domains from EF0089, EF1091, EF1092, EF1093, EF1099, EF1269, EF1824, EF2224, and EF3023 were amplified from *E. faecalis* V583 or *E. faecalis* EF1 (EF1099) genomic DNA and subcloned into the *E. coli* expression vector PQE-30 (Qiagen). One liter culture of *E. coli* M15(pREP4) cultures harboring appropriate pQE-30 based constructs were grown to $OD_{600}$=0.6 with an initial 2% inoculation from overnight cultures. After 2-3 h induction with 0.4 mM isopropyl-beta-d-thiogalactoside (IPTG), cells were collected with centrifugation, resuspended in 10 mM Tris-Cl, 100 mM NaCl, pH 7.9 and stored at −80 C.

To lyse the cells and release the expressed protein, cells were passed twice through French Press with a gauge pressure setting at 1200 PSI to give an estimated internal cell pressure of 20,000 PSI. The lysate was centrifuged at $RCF_{max}$ of 165,000×g and the supernatant was filtered through a 0.45 □m filter. The volume was adjusted to 15 ml with 10 mM Tris-Cl, 100 mM NaCl, pH 7.9 and 0.2 M imidazole in the same buffer was added to increase the imidazole concentration to 6.5 mM in order to minimize non-specific binding. The sample was loaded to a nickel affinity chromatography column (HiTrap chelating, Pharmacia) connected to an FPLC system (Pharmacia) and previously equilibrated with 10 mM Tris-Cl, 100 mM NaCl, pH 7.9. Bound protein was eluted with a linear gradient of 0-100 mM imidazole in 10 mM Tris-Cl, 100 mM NaCl, pH 7.9 over 100-200 ml. Protein-containing fractions were analyzed in SDS-PAGE (FIG. 2) and dialyzed against 25 mM Tris-Cl, 1 mM EDTA, pH 6.5-9 (depending on pI of protein purified) before applying the samples to an ion-exchange column (HiTrap Q, Pharmacia) for further purification. Bound protein was eluted with a linear gradient of 0-0.5 M NaCl in 25 mM Tris-Cl, 1 mM EDTA, pH 6.5-9 over 100 ml. Finally, protein samples were dialyzed extensively against PBS and stored at +4° C.

Alternatively EF1091, EF1092, and EF1093 were expressed in shake flasks or in bioreactors, the cells were harvested by centrifugation and the cell paste frozen at −80° C. Cells were lysed in 1×PBS (10 mL of buffer/1 g of cell paste) using 2 passes through a microfluidizer at 10,000 psi. Lysed cells were spun down at 17,000 rpm for 30 minutes to remove cell debris. Supernatant was passed over a 5-mL HiTrap Chelating (Pharmacia) column charged with 0.1M $NiCl_2$. After loading, the column was washed with 5 column volumes of 10 mM Tris, pH 8.0, 100 mM NaCl (Buffer A). Protein was eluted using a 0-100% gradient of 10 mM Tris, pH 8.0, 100 mM NaCl, 500 mM imidazole (Buffer B). Protein containing fractions were dialyzed in 1×PBS.

Example 3

MSCRAMM® Genes Common to *E. faecalis* and *E. faecium* PCR Analysis

Primers for flanking regions of sequences above were used to amplify 1µg genomic DNA from each *E. faecalis* strain. PCR products from 5 *E. faecalis* strains in Table 1 were sequenced and compared to the TIGR database sequence. Primers used to amplify the enterococcal MSCRAMM® A-domain gene products are shown below.

| Protein | 5'=Primer | 3'=Primer |
|---|---|---|
| ACE40 | GAATTGAGCAAAAGTTCAATCG (SEQ ID NO: 44) | GTCTGTCTTTTCACTTGTTTCTGTTG (SEQ ID NO: 51) |
| EF1091 | CAAGTAAAAAAGCCGGTACAGC (SEQ ID NO: 45) | AAAGGAACCTTTGCTTGGTTC (SEQ ID NO: 52) |
| EF1092 | TCGCAAGCAAGCGTTCAAG (SEQ ID NO: 46) | AAGCCTGACTCTTTTACTTTTTTATTG (sEQ ID NO: 53) |
| EF1093 | GAGAGCGCACAGCTCGTG (SEQ ID NO: 47) | GGTACCTTTGTGTTTGTTTGGTAC (SEQ ID NO: 54) |
| Efae2924 | CGGGATCCCAAAACAGCGGGAAAGAAATGAGCGA (SEQ ID NO: 48) | CCCAAGCTTTCATGTACCTTTGTGTTTATTTGG (SEQ ID NO: 55) |
| Efae2925 | CGGGATCCGAAATGGTTCAGATTACTTTACAC (SEQ ID NO: 49) | TCTGCAGTTCAATTGACTACTTTCAATATACTGTC (SEQ ID NO: 56) |
| Efae2926 | CGGGATCCAAAGCACTGAACATCAAGCTAAATGCG (SEQ ID NO: 50) | CCCAAGCTTTCAGAATGCTTGACCTTGATTATTGTA (SEQ ID NO: 57) |

Homology Among Enterococcal MSCRAMM® Proteins

A blastp search was performed using the AA sequence listed above with the NCBI search engine. The accession number is given for each putative homologue found. Both percent identity and similarity refer to the percentage of AA that match the query sequence exactly while similarity includes conservative AA changes in the matching calculation.

TABLE 4

Comparison of *E. faecium* homologues of *E. faecalis* MSCRAMM® protein

| E. faecalis Protein Similarity | E. faecium Protein Homologue Name | Accession Number | % Identity | % |
|---|---|---|---|---|
| EF1091 | Efae2926 | 00038011 | 60 | 75 |
| EF1092 | Efae2925 | 00038010 | 48 | 63 |
| EF1093 | Efae2924 | 00038009 | 74 | 83 |

The "A" domain amino acid sequence from each *E. faecalis* MSCRAMM® protein was used as a query in a blastp search. Results shown were scored by NCBI computers. Identity is calculated as exact matches between the subject and query sequences while similarity also includes conservative changes in sequence at the same position.

Example 4

Additional Gram Positive Amino Acid Sequences Predicted to Be MSCRAMM® Proteins

List of LPXTG-motif containing cell wall anchored proteins that contain predicted immunoglobulin—like fold. The sequencing center for each genome is indicated in the parenthesis. All the sequence except for those of CNA from *S. aureus* and *Staphylococcus epidermidis* can be obtained from TIGR website (www.tir.org), comprehensive microbial resource section. The *S. epidermidis* RP64A genome is not annotated. However, the nucleotide coordinates of the genes encoding the listed *S. epidermidis* proteins can be obtained through TIGR website.

*Streptococcus pneumoniae* TIGR4 (TIGR)
SP0368
SP0462
SP0463
SP0464

*Enterococcus faecalis* V583 (TIGR)
EF2224
EF1099
EF1092
EF3023
EF1269
EF0089
EF1824
EF1091
EF1093
EF1075
EF1074
EF1651

*Streptococcus mutans* UA159 (University of Oklahoma)
SMU.610
SMU.987
SMU.63c

*Staphylococcus aureus* N315 (Juntendo University, Japan)
SA2447
SA2290
SA2291
SA2423
SA0742
SA0519
SA0520
SA0521

*Bacillus anthracis* Ames (TIGR)
BA0871
BA5258

*Staphylococcus epidermidis* strain RP62A (TIGR)
(SEQ ID NO: 20)
>SERP_GSE_14_6.AA 2402 residues

```
mknkqgflpnllnkygirklsagtaslligatlvfgingqvkaaetdnivsqngdnktndsessdkelvkseddkts
ststdtnlesefdqnnnpssieestnrndedtlnqrtstetekdthvksadtqttnettnknddnattnhtesisdes
tyqsddskttqhdnsntnqdtqstlnptskessnkdeatsptpkestsiektnlsndanhqttdevnhsdsdnmt
nstpndteneldttqltshdespspqsdnftgftnlmatplnlrndnprinllaatedtkpktykkpnnseysyllndl
gydattvkensdlrhagisqsqdntgsviklnltkwlslqsdfvnggkvnlsfaqsdfytqiesitlndvkmdttnng
qnwsapingstvrsgligsvtnhdivitlknsqtlsslgysnnkpvylthtwttndgaiaeesiqvasitptldskapnt
iqksdftagrmtnkikydssqnsiksvhtfkpnenflqtdyravlyikeqvnkelipyidpnsvklyvsdpdgnpisq
dryvngsidndglfdsskineisiknnntsgqlsnartsldrnvffgtlgqsrsytisyklkdgytlesvaskvsaretfd
swmevdyldsydsgapnkrllgsyassyidmidrippvapkansittedtsikgtaevdtninltfndgrtlngkvd
sngnfsiaipsyyvltgketikitsidkgdnvspaitisvidktppavkaisnktqkvnteiepikieatdnsgqavtnk
veglpagmtfdeatntisgtpsevgsyditvtttdengnsetttftidvedttkptvesvadqtqevnteiepikieatd
nsgravtnkvdglpdgvtfdeatntisgtpsevgsyditvtttdesgnvtetiftidvedttkptvesiagqtqevntei
epikieakdnsgqtvtnkvdglpdgvtfdeatntisgtpsevgsydvtvtttdesgnsetttftievkdttkptvesva
dqtqevnteiepikieardnsgqavtnkvdglpdgvtfdeatntisgtpsevgsyditvtttdesgnvtettftievedt
tkptvenvadqtqevnteitpitiesednsgqtvtnkvdglpdgvtfdettntisgtpskvgsyditvtttdesgnatet
```

-continued tftievedttkptvenvagqtqeinteiepikieatdnsgqavtnkveglpagvtfdeatntisgtpsevgsytvtvtt mdesgnatettftidvedttkptvesvadqtqevnteitpitiesednsdqavtnkvdglpdgvtfdeatntisgtps evgsytvtvtttdesgnatettftidvedttkptvksvsdqtqevnteitpikieatdnsgqtvtnkvdglpdgitfdeat ntisgtpsevgsyditvtttdesgnatettftinvedttkptvediadqtqevnteiepikieatdnggqavtnkvdglp dgvtfdeatntisgtpsevgsydiivtttdengnsetttftidvedttkptvesvvdqtqevnteitpikieatdnsgqa vankvdglpngvtfdettntisgtpsevgsydiivtttdesgnvtetiftidvedttkptvesiagqtqevnteiepikie atdnsgqavtnkvdglpngvtfdeatntisgtpsevgiytvtvtttdesgnatettftidvedttkptvesvadqtqev nteitpitiesednsgqavtnkveglpagmtfdettntisgtpsevgsytvtvtttdesgnetettftidvedttkptves ianqtqevnteitpikieatdnsgqavtnkvdglpngvtfdettntisgtpsevgsydikvtttdesgnatettftinve dttkptvesvadqtqeinteiepikieardnsgqavtnkvdglpdgvtfdeatntisgtpsevgsyditvtttdesgn atettftidvedttkptveditdqtqeintemtpikieatdnsgqavtnkveglpdgvtfdeatntisgtpsevgkylitit tidkdgntatttltinvidtttpeqptinkvtenstevngrgepgtvvevtfpdgnkvegkvdsdgnyhiqipsettlkg gqpiqviaidkagnkseatttnvidttapeqptinkvtenstevsgrgepgtvvevtfpdgnkvegkvdsdgnyhi qipsderfkvgqqlivkvvdeegnvsepsitmvqkedknseklstvtgtvtknnskslkhkaseqqsyhnkseki knvnkptkivekdmstydysryskdisnknnksatfeqqnvsdinnnqysrnkvnqpvkksrkneinkdlpqtg eenfnkstlfgtlvaslgalllffkrrkkdendeke >SERP_GSE_2_50.AA 892 residues (SEQ ID NO: 21)

lfglghneakaeentvqdvkdsnmddelsdsndqssneekndvinnsqsintdddnqikkeetnsndaienr skditqsttnvdeneatflqktpqdntqlkeevvkepssvessnssmdtaqqpshttinseasiqtsdneensrv sdfanskiiesntesnkeentieqpnkvredsitsqpssyknidekisnqdellnlpineyenkvrplsttsaqpss krvtvnqlaaeqgsnvnhlikvtdqsitegyddsdgiikahdaenliydvtfevddkvksgdtmtvnidkntvpsdl tdsfaipkikdnsgeiiatgtydntnkqitytftdyvdkyenikahlkltsyidkskvpnnntkldveyktalssvnktitv eyqkpnenrtanlqsmftnidtknhtveqtiyinplrysaketnvnisgngdegstiiddstiikvykvgdnqnlpds nriydyseyedvtnddyaqlgnnndvninfgnidspyiikviskydpnkddyttiqqtvtmqttineytgefrtasyd ntiafstssgqgqgdlppektykigdyvwedvdkdgiqntndnekplsnvlvtltypdgtsksvrtdeegkyqfdgl kngltykitfetpegytptlkhsgtnpaldsegnsvwvtingqddmtidsgfyqtpkyslgnyvwydtnkdgiqgd dekgisgvkvtlkdengniistttdengkyqfdnlnsgnyivhfdkpsgmtqtttdsgdddeqdadgeevhvtit dhddfsidngyydddsdsdsdsdsddsdsdsdsdsdsdsdsdsdsdsdsdsdsdsdsdsd sdsgldnssdkntkdklpdtganedhdskgtllgalfaglgalllgkrrknrknkn >SERP_GSE_9_28.AA 1973 residues (SEQ ID NO: 22)

mkenkrknnldknntrfsirkyqgygatsvaiigfiiiscfseakadsdkheikshqqsmtnhlttlpsdnqentsn nefnnrnhdishlslnksiqmdelkklikqykainlndkteesiklfqsdlvqaeslinnpqsqqhvdafyhkflnsa gklrkketvsikhersesntyrlgdevrsqtfshirhkrnavsfrnadqsnlstdplkaneinpeiqngnfsqvsggp lptsskrltvvtnvdnwhsystdpnpeypmfytttavnypnfmsngnapygvilgrttdgwnrnvidskvagiyq didvvpgselnvnfistspvfsdgaagaklkisnveqnrvtfdsrlngmgpyptgklsamvnipndinrvrisflpvs stgrvsvqrssrehgfgdnssyyhggsvsdvrinsgsyvvskvtqreyttrpnssndtfaratinlsvenkghnqs kdtyyevilpqnsrlistrggsgnynnatnklsirldnlnpgdrrdisytvdfesspklinlnahllyktnatfrgndgqr tgdnivdlqsiallmnkdvletelneidkfirdlneadftidswsalqekmteggnilneqqnqvalenqasqetinn vtqsleilknnlkyktpsqpiiksnnqipnitispadkadkltityqntdnesasiignklnnqwslnnnipgieidmqt glvtidykavypesvvgandktgnsdasaesritmprkeatplspiveaneervnvviapngeatqiaikyrtpd -continued gqeatlvaskngsswtlnkqidyvnieensgkvtigyqavqpeseviatetkgnsdesaesrvtmprkeatphs piveaneehvnvtiapngeatqiaikyrtpdgqettliaskngsswtlnkqidyvnieensgkvtigyqavqiesev iatetkgnsdasaesritmlrkeatphspiveaneehvnvtiapngeatqiaikyrtpdgqeatlvasknesswtl nkqidhvnidensgkvtigyqavqpeseiiatetkgnsdasaesritmprkeatpipptleasvqeasvtvtpne natkvfikyldindeistiiaskinqqwtlnkdnfgikinpltgkviisyvavqpesdviaiesqgnsdlseesriimptk eeppeppilesdsieakvnifpndeatrivimytslegqeatlvasknesswtlnkqidhvnidensgkvtigyqa vqpeseviatetkgnsdasaesrvtmprkeatphspivetneervnvviapngeatqiaikyrtpdgqettliask ngsswtlnkqidhvnidensgkvtigyqavqpeseiiatetkgnsdasaesritmprkeaiphspiveaneehv nvtiapngettqiavkyrtpdgqeatliasknesswtlnkqidhvnidensgkvtigyqavqpeseviatetkgns dasaesritmpvkektpappisiinesnasveiipqvnvtqlslqyidakgqqqnhiatlnqnqwtlnknvshitvd kntgkvlinyqavypeseviareskgnsdssnvsmvimprktatpkppiikvdemnaslaiipyknntainihyi dkkgiksmvtaiknndqwqldekikyvkidaktgtviinyqivqenseiiataingnsdkseevkvlmpikeftpla plletnykkatvsilpqsnatkldfkyrdkkgdskiiivkrfkniwkaneqisgvtinpefgqvvinyqavypesdila aqyvgnsdasewakvkmpkkelaphspsliydnrrnkiliapnsnatemelsyvdknnqslkvkalkinnrwk fdssvsnisinpntgkivlqpqflltnskiivfakkgnsdasisvslrvpavkkielepmfnvpvlvslnkkriqfddcs gvknclnkqisktqlpdtgysdkasksnilsvlllgfgflsysrkrkekq >|cl|SEPN_5_124.AA 10203 residues (SEQ ID NO: 23)

MKSKPKLNGRNICSFLLSKCMSYSLSKLSTLKTYNFQITSNNKEKTSRIGVAIALN

NRDKLQKFSIRKYAIGTFSTVIAT

LVFMGINTNHASADELNQNQKLIKQLNQTDDDDSNTHSQEIENNKQNSSGKTE

SLRSSTSQNQANARLSDQFKDTNETSQ

QLPTNVSDDSINQSHSEANMNNEPLKVDNSTMQAHSKIVSDSDGNASENKHHK

LTENVLAESRASKNDKEKENLQEKDKS

QQVHPPLDKNALQAFFDASYHNYRMIDRDRADATEYQKVKSTFDYVNDLLGNN

QNIPSEQLVSAYQQLEKALELARTLPQ

QSTTEKRGRRSTRSVVENRSSRSDYLDARTEYYVSKDDDDSGFPPGTFFHAS

NRRWPYNLPRSRNILRASDVQGNAYITT

KRLKDGYQWDILFNSNHKGHEYMYYWFGLPSDQTPTGPVTFTIINRDGSSTST

GGVGFGSGAPLPQFWRSAGAINSSVAN

DFKHGSATNYAFYDGVNNFSDFARGGELYFDREGATQTNKYYGDENFALLNSE

KPDQIRGLDTIYSFKGSGDVSYRISFK

TQGAPTARLYYAAGARSGEYKQATNYNQLYVEPYKNYRNRVQSNVQVKNRTL

HLKRTIRQFDPTLQRTTDVPILDSDGSG

SIDSVYDPLSYVKNVTGTVLGIYPSYLPYNQERWQGANAMNAYQIEELFSQENL

QNAARSGRPIQFLVGFDVEDSHHNPE

TLLPVNLYVKPELKHTIELYHDNEKQNRKEFSVSKRAGHGVFQIMSGTLHNTVG

SGILPYQQEIRIKLTSNEPIKDSEWS

ITGYPNTLTLQNAVGRTNNATEKNLALVGHIDPGNYFITVKFGDKVEQFEIRSKP

TPPRIITTANELRGNSNHKPEIRVT

DIPNDTTAKIKLVMGGTDGDHDPEINPYTVPENYTVVAEAYHDNDPSKNGVLTF

-continued

RSSDYLKDLPLSGELKAIVYYNQYVQ

SNFSNSVPFSSDTTPPTINEPAGLVHKYYRGDHVEITLPVTDNTGGSGLRDVNV

NLPQGWTKTFTINPNNNTEGTLKLIG

NIPSNEAYNTTYHFNITATDNSGNTTNPAKTFILNVGKLADDLNPVGLSRDQLQL

VTDPSSLSNSEREEVKRKISEANAN

IRSYLLQNNPILAGVNGDVTFYYRDGSVDVIDAENVITYEPERKSIFSENGNTNK

KEAVITIARGQNYTIGPNLRKYFSL

SNGSDLPNRDFTSISAIGSLPSSSEISRLNVGNYNYRVNAKNAYHKTQQELNLKL

KIVEVNAPTGNNRVYRVSTYNLTND

EINKIKQAFKAANSGLNLNDNDITVSNNFDHRNVSSVTVTIRKGDLIKEFSSNLNN

MNFLRWVNIRDDYTISWTSSKIQG

RNTDGGLEWSPDHKSLIYKYDATLGRQINTNDVLTLLQATAKNSNLRSNINSNE

KQLAERGSNGYSKSIIRDDGEKSYLL

NSNPIQVLDLVEPDNGYGGRQVSHSNVIYNEKNSSIVNGQVPEANGASAFNIDK

VVKANAANNGIMGVIYKAQLYLAPYS

PKGYIEKLGQNLSNTNNVINVYFVPSDKVNPSITVGNYDHHTVYSGETFKNTINV

NDNYGLNTVASTSDSAITMTRNNNE

LVGQAPNVTNSTNKIVKVKATDKSGNESIVSFTVNIKPLNEKYRITTSSSNQTPV

RISNIQNNANLSIEDQNRVKSSLSM

TKILGTRNYVNESNNDVRSQWSKVNRSGNNATVNVTTTFSDGTTNTITVPVKH

VLLEVVPTTRTTVRGQQFPTGKGTSP

NDFFSLRTGGPVDARIVWVNNQGPDINSNQIGRDLTLHAEIFFDGETTPIRKDTT

YKLSQSIPKQIYETTINGRFNSSGD

AYPGNFVQAVNQYWPEHMDFRWAQGSGTPSSRNAGSFTKTVTVVYQNGQTE

NVNVLFKVKPNKPVIDSNSVISKGQLNGQ

QILVRNVPQNAQVTLYQSNGTVIPNTNTTIDSNGIATVTIQGTLPTGNITAKTSMT

NNVTYTKQNSSGIASNTTEDISVF

SENSDQVNVTAGMQAKNDGIKIIKGTNYNFNDFNSFISNIPAHSTLTWNEEPNS

WKNNIGTTTKTVTVTLPNHQGTRTVD

IPITIYPTVTAKNPVRDQKGRNLTNGTDVYNYIIFENNNRLGGTASWKDNRQPDK

NIAGVQNLIALVNYPGISTPLEVPV

KVWVYNFDFTQPIYKIQVGDTFPKGTWAGYYKHLENGEGLPIDGWKFYWNQQ

STGTTSDQWQSLAYTRTPFVKTGTYDVV

NPSNWGVWQTSQSAKFIVTNAKPNQPTITQSKTGDVTVTPGAVRNILISGTNDY

IQASADKIVINKNGNKLTTFVKNNDG

RWTVETGSPDINGIGPTNNGTAISLSRLAVRPGDSIEAIATEGSGETISTSATSEI

YIVKAPQPEQVATHTYDNGTFDIL

PDNSRNSLNPTERVEINYTEKLNGNETQKSFTITKNNNGKWTINNKPNYVEFNQ

DNGKVVFSANTIKPNSQITITPKAGQ

GNTENTNPTVIQAPAQHTLTINEIVKEQGQNVTNDDINNAVQVPNKNRVAIKQG

-continued

NALPTNLAGGSTSHIPVVIYYSDGSS

EEATETVRTKVNKTELINARRRLDEEISKENKTPSSIRNFDQAMNRAQSQINTAK

SDADQVIGTEFATPQQVNSALSKVQ

AAQNKINEAKALLQNKADNSQLVRAKEQLQQSIQPAASTDGMTQDSTRNYKNK

RQAAEQAIQHANSVINNGDATSQQIND

AKNTVEQAQRDYVEAKSNLRADKSQLQSAYDTLNRDVLTNDKKPASVRRYNEA

ISNIRKELDTAKADASSTLRNTNPSVE

QVRDALNKINTVQPKVNQAIALLQPKENNSELVQAKKRLQDAVNDIPQTQGMTQ

QTINNYNDKQREAERALTSAQRVIDN

GDATTQEITSEKSKVEQAMQALTNAKSNLRADKNELQTAYNKLIENVSTNGKKP

ASIRQYETAKARIQNQINDAKNEAER

ILGNDNPQVSQVTQALNKIKAIQPKLTEAINMLQNKENNTELVNAKNRLENAVND

TDPTHGMTQETINNYNAKKREAQNE

IQKANMIINNGDATAQDISSEKSKVEQVLQALQNAKNDLRADKRELQTAYNKLIQ

NVNTNGKKPSSIQNYKSARRNIENQ

YNTAKNEAHNVLENTNPTVNAVEDALRKINAIQPEVTKAINILQDKEDNSELVRA

KEKLDQAINSQPSLNGMTQESINNY

TTKRREAQNIASSADTIINNGDASIEQITENKIRVEEATNALNEAKQHLTADTTSL

KTEVRKLSRRGDTNNKKPSSVSAY

NNTIHSLQSEITQTENRANTIINKPIRSVEEVNNALHEVNQLNQRLTDTINLLQPL

ANKESLKEARNRLESKINETVQTD

GMTQQSVENYKQAKIKAQNESSIAQTLINNGDASDQEVSTEIEKLNQKLSELTN

SINHLTVNKEPLETAKNQLQANIDQK

PSTDGMTQQSVQSYERKLQEAKDKINSINNVLANNPDVNAIRTNKVETEQINNE

LTQAKQGLTVDKQPLINAKTALQQSL

DNQPSTTGMTEATIQNYNAKRQKAEQVIQNANKIIENAQPSVQQVSDEKSKVEQ

ALSELNNAKSALRADKQELQQAYNQL

IQPTDLNNKKPASITAYNQRYQQFSNELNSTKTNTDRILKEQNPSVADVNNALN

KVREVQQKLNEARALLQNKEDNSALV

RAKEQLQQAVDQVPSTEGMTQQTKDDYNSKQQAAQQEISKAQQVIDNGDATT

QQISNAKTNVERALEALNNAKTGLRADK

EELQNAYNQLTQNIDTSGKTPASIRKYNEAKSRIQTQIDSAKNEANSILTNDNPQ

VSQVTAALNKIKAVQPELDKAIAML

KNKENNNALVQAKQQLQQIVNEVDPTQGMTTDTANNYKSKKREAEDEIQKAQQ

IINNGDATEQQITNETNRVNQAINAIN

KAKNDLRADKSQLENAYNQLIQNVDTNGKKPASIQQYQAARQAIETQYNNAKS

EAHQILENSNPSVNEVAQALQKVEAVQ

LKVNDAIHILQNKENNSALVTAKNQLQQSVNDQPLTTGMTQDSINNYEAKRNEA

QSAIRNAEAVINNGDATAKQISDEKS

KVEQALAHLNDAKQQLTADTTELQTAVQQLNRRGDTNNKKPRSINAYNKAIQSL

-continued

ETQITSAKDNANAVIQKPIRTVQEVN

NALQQVNQLNQQLTEAINQLQPLSNNDALKAARLNLENKINQTVQTDGMTQQSI

EAYQNAKRVAQNESNTALALINNGDA

DEQQITTETDRVNQQTTNLTQAINGLTVNKEPLETAKTALQNNIDQVPSTDGMT

QQSVANYNQKLQIAKNEINTINNVLA

NNPDVNAIKTNKAEAERISNDLTQAKNNLQVDTQPLEKIKRQLQDEIDQGTNTD

GMTQDSVDNYNDSLSAAIIEKGKVNK

LLKRNPTVEQVKESVANAQQVIQDLQNARTSLVPDKTQLQEAKNRLENSINQQT

DTDGMTQDSLNNYNDKLAKARQNLEK

ISKVLGGQPTVAEIRQNTDEANAHKQALDTARSQLTLNREPYINHINNESHLNNA

QKDNFKAQVNSAPNHNTLETIKNKA

DTLNQSMTALSESIADYENQKQQENYLDASNNKRQDYDNAVNAAKGILNQTQS

PTMSADVIDQKAEDVKRTKTALDGNQR

LEVAKQQALNHLNTLNDLNDAQRQTLTDTINHSPNINSVNQAKEKANTVNTAMT

QLKQTIANYDDELHDGNYINADKDKK

DAYNNAVNNAKQLINQSDANQAQLDPAEINKVTQRVNTTKNDLNGNDKLAEAK

RDANTTIDGLTYLNEAQRNKAKENVGK

ASTKTNITSQLQDYNQLNIAMQALRNSVNDVNNVKANSNYINEDNGPKEAYNQA

VTHAQTLINAQSNPEMSRDWNQKTQ

AVNTAHQNLHGQQKLEQAQSSANTEIGNLPNLTNTQKAKEKELVNSKQTRTEV

QEQLNQAKSLDSSMGTLKSLVAKQPTV

QKTSVYINEDQPEQSAYNDSITMGQTIINKTADPVLDKTLVDNAISNISTKENALH

GEQKLTTAKTEAINALNTLADLNT

PQKEAIKTAINTAHTRTDVTAEQSKANQINSAMHTLRQNISDNESVTNESNYINA

EPEKQHAFTEALNNAKEIVNEQQAT

LQANSINQKAQAILTTKNALDGEEQLRRAKENADQEINTLNQLTDAQRNSEKGL

VNSSQTRTEVASQLAKAKELNKVMEQ

LNHLINGKNQMINSSKFINEDANQQQAYSNAIASAEALKNKSQNPELDKVTIEQA

INNINSAINNLNGEAKLTKAKEDAV

ASINNLSGLTNEQKPKENQAVNGAQTRDQVANKLRDAEALDQSMQTLRDLVNN

QNAIHSTSNYFNEDSTQKNTYDNAIDN

GSTYITGQHNPELNKSTIDQTISRINTAKNDLHGVEKLQRDKGTANQEIGQLGYL

NDPQKSGEESLVNGSNTRSEVEEHL

NEAKSLNNAMKQLRDKVAEKTNVKQSSDYINDSTEHQRGYDQALQEAENIINEI

GNPTLNKSEIEQKLQQLTDAQNALQG

SHLLEEAKNNAITGINKLTALNDAQRQKAIENVQAQQTIPAVNQQLTLDREINTA

MQALRDKVGQQNNVHQQSNYFNEDE

QPKHNYDNSVQAGQTIIDKLQDPIMNKNEIEQAINQINTTQTALSGENKLHTDQE

STNRQIEGLSSLNTAQINAEKDLVN

QAKTRTDVAQKLAAAKEINSAMSNLRDGIQNKEDIKRSSAYINADPTKVTAYDQ

-continued

```
ALQNAENIINATPNVELNKATIEQAL

SRVQQAQQDLDGVQQLANAKQQATQTVNGLNSLNDGQKRELNLLINSANTRT

KVQEELNKATELNHAMEALRNSVQNVDQ

VKQSSNYVNEDQPEQHNYDNAVNEAQATINNNAQPVLDKLAIERLTQTVNTTK

DALHGAQKLTQDQQAAETGIRGLTSLN

EPQKNAEVAKVTAATTRDEVRNIRQEATTLDTAMLGLRKSIKDKNDTKNSSKYI

NEDHDQQQAYDNAVNNAQQVIDETQA

TLSSDTINQLANAVTQAKSNLHGDTKLQHDKDSAKQTIAQLQNLNSAQKHMED

SLIDNESTRTQVQHDLTEAQALDGLMG

ALKESIKDYTNIVSNGNYINAEPSKKQAYDAAVQNAQNIINGTNQPTINKGNVTT

ATQTVKNTKDALDGDHRLEEAKNNA

NQTIRNLSNLNNAQKDAEKNLVNSASTLEQVQQNLQTAQQLDNAMGELRQSIA

KKDQVKADSKYLNEDPQIKQNYDDAVQ

RVETIINETQNPELLKANIDQATQSVQNAEQALHGAEKLNQDKQTSSTELDGLT

DLTDAQREKLREQINTSNSRDDIKQK

IEQAKALNDAMKKLKEQVAQKDGVHANSDYTNEDSAQKDAYNNALKQAEDIIN

NSSNPNLNAQDITNALNNIKQAQDNLH

GAQKLQQDKNTTNQAIGNLNHLNQPQKDALIQAINGATSRDQVAEKLKEAEALD

EAMKQLEDQVNQDDQISNSSPFINED

SDKQKTYNDKIQAAKEIINQTSNPTLDKQKIADTLQNIKDAVNNLHGDQKLAQSK

QDANNQLNHLDDLTEEQKNHFKPLI

NNADTRDEVNKQLEIAKQLNGDMSTLHKVINDKDQIQHLSNYINADNDKKQNYD

NAIKEAEDLIHNHPDTLDHKALQDLL

NKIDQAHNELNGESRFKQALDNALNDIDSLNSLNVPQRQTVKDNINHVTTLESL

AQELQKAKELNDAMKAMRDSIMNQEQ

IRKNSNYTNEDLAQQNAYNHAVDKINNIIGEDNATMDPQIIKQATQDINTAINGLN

GDQKLQDAKTDAKQQITNFTGLTE

PQKQALENIINQQTSRANVAKQLSHAKFLNGKMEELKVAVAKASLVRQNSNYIN

EDVSEKEAYEQAIAKGQEIINSENNP

TISSTDINRTIQEINDAEQNLHGDNKLRQAQEIAKNEIQNLDGLNSAQITKLIQDIG

RTTTKPAVTQKLEEAKAINQAMQ

QLKQSIADKDATLNSSNYLNEDSEKKLAYDNAVSQAEQLINQLNDPTMDISNIQA

ITQKVIQAKDSLHGANKLAQNQADS

NLIINQSTNLNDKQKQALNDLINHAQTKQQVAEIIAQANKLNNEMGTLKTLVEEQ

SNVHQQSKYINEDPQVQNIYNDSIQ

KGREILNGTTDDVLNNNKIADAIQNIHLTKNDLHGDQKLQKAQQDATNELNYLTN

LNNSQRQSEHDEINSAPSRTEVSND

LNHAKALNEAMRQLENEVALENSVKKLSDFINEDEAAQNEYSNALQKAKDIING

VPSSTLDKATIEDALLELQNARESLH

GEQKLQEAKNQAVAEIDNLQALNPGQVLAEKTLVNQASTKPEVQEALQKAKEL
```

-continued

NEAMKALKTEINKKEQIKADSRYVNAD
SGLQANYNSALNYGSQIIATTQPPELNKDVINRATQTIKTAENNLNGQSKLAEAK
SDGNQSIEHLQGLTQSQKDKQHDLI
NQAQTKQQVDDIVNNSKQLDNSMNQLQQIVNNDNTVKQNSDFINEDSSQQDA
YNHAIQAAKDLITAHPTIMDKNQIDQAI
ENIKQALNDLHGSNKLSEDKKEASEQLQNLNSLTNGQKDTILNHIFSAPTRSQV
GEKIASAKQLNNTMKALRDSIADNNE
ILQSSKYFNEDSEQQNAYNQAVNKAKNIINDQPTPVMANDEIQSVLNEVKQTKD
NLHGDQKLANDKTDAQATLNALNYLN
QAQRGNLETKVQNSNSRPEVQKWQLANQLNDAMKKLDDALTGNDAIKQTSN
YINEDTSQQVNFDEYTDRGKNIVAEQTN
PNMSPTNINTIADKITEAKNDLHGVQKLKQAQQQSINTINQMTGLNQAQKEQLN
QEIQQTQTRSEVHQVINKAQALNDSM
NTLRQSITDEHEVKQTSNYINETVGNQTAYNNAVDRVKQIINQTSNPTMNPLEV
ERATSNVKISKDALHGERELNDNKNS
KTFAVNHLDNLNQAQKEALTHEIEQATIVSQVNNIYNKAKALNNDMKKLKDIVAQ
QDNVRQSNNYINEDSTPQNMYNDTI
NHAQSIIDQVANPTMSHDEIENAINNIKHAINALDGEHKLQQAKENANLLINSLND
LNAPQRDAINRLVNEAQTREKVAE
QLQSAQALNDAMKHLRNSIQNQSSVRQESKYINASDAKKEQYNHAVREVENIIN

EQHPTLDKEIIKQLTDGVNQANNDLN

GVELLDADKQNAHQSIPTLMHLNQAQQNALNEKINNAVTRTEVAAIIGQAKLLDH

AMENLEESIKDKEQVKQSSNYINED

SDVQETYDNAVDHVTEILNQTVNPTLSIEDIEHAINEVNQAKKQLRGKQKLYQTI

DLADKELSKLDDLTSQQSSSISNQI

YTAKTRTEVAQAIEKAKSLNHAMKALNKVYKNADKVLDSSRFINEDQPEKKAYQ

QAINHVDSIIHRQTNPEMDPTVINSI

THELETAQNNLHGDQKLAHAQQDAANVINGLIHLNVAQREVMINTNTNATTREK

VAKNLDNAQALDKAMETLQQWAHKN

NILNDSKYLNEDSKYQQQYDRVIADAEQLLNQTTNPTLEPYKVDIVKDNVLANEK

ILFGAEKLSYDKSNANDEIKHMNYL

NNAQKQSIKDMISHAALRTEVKQLLQQAKILDEAMKSLEDKTQWITDTTLPNYT

EASEDKKEKVDQTVSHAQAIIDKIN

GSNVSLDQVRQALEQLTQASENLDGDQRVEEAKVHANQTIDQLTHLNSLQQQT

AKESVKNATKLEEIATVSNNAQALNKV

MGKLEQFINHADSVENSDNYRQADDDKIIAYDEALEHGQDIQKTNATQNETKQA

LQQLIYAETSLNGFERLNHARPRALE

YIKSLEKINNAQKSALEDKVTQSHDLLELEHIVNEGTNLNDIMGELANAIVNNYAP

TKASINYINADNLRKDNFTQAINN

ARDALNKTQGQNLDFNAIDTFKDDIFKTKDALNGIERLTAAKSKAEKLIDSLKFIN

-continued

```
KAQFTHANDEIINTNSIAQLSRIV
NQAFDLNDAMKSLRDELNNQAFPVQASSNYINSDEDLKQQFDHALSNARKVLA
KENGKNLDEKQIQGLKQVIEDTKDALN
GIQRLSKAKAKAIQYVQSLSYINDAQRHIAENNIHNSDDLSSLANTLSKASDLDN
AMKDLRDTIESNSTSVPNSVNYINA
DKNLQIEFDEALQQASATSSKTSENPATIEEVLGLSQAIYDTKNALNGEQRLATE
KSKDLKLIKGLKDLNKAQLEDVTNK
VNSANTLTELSQLTQSTLELNDKMKLLRDKLKTLVNPVKASLNYRNADYNLKRQ
FNKALKEAKGVLNKNSGTNVNINDIQ
HLLTQIDNAKDQLNGERRLKEHQQKSEVFIIKELDILNNAQKAAIINQIRASKDIKII
NQIVDNAIELNDAMQGLKEHVA
QLTATTKDNIEYLNADEDHKLQYDYAINLANNVLDKENGTNKDANIIGMIQNMD
DARALLNGIERLKDAQTKAHNDIKD
TLKRQLDEIEHANATSNSKAQAKQMVNEEARKALSNINDATSNDLVNQAKDEG
QSAIEHIHADELPKAKLDANQMIDQKV
EDINHLISQNPNLSNEEKNKLISQINKLVNGIKNEIQQAINKQQIENATTKLDEVIET
TKKLIIAKAEAKQMIKELSQKK
ROAINNNTDLTPSQKAHALADIDKTEKDALQHIENSNSIDDINNNKEHAFNTLAHII
IWDTDQQPLVFELPELSLQNALV
TSEVVVHRDETISLESIIGAMTLTDELKVNIVSLPNTDKVADHLTAKVKVILADGS
YVTVNVPVKWEKELQIAKKDAIK
TIDVLVKQKIKDIDSNNELTSTQREDAKAEIERLKKQAIDKVNHSKSIKDIETVKRT
DFEEIDQFDPKRFTLNKAKKDII
TDVNTQIQNGFKEIETIKGLTSNEKTQFDKQLTALQKEFLEKVEHAHNLVELNQL
QQEFNNRYKHILNQAHLLGEKHIAE
HKLGYVVVNKTQQILNNQSASYFIKQWALDRIKQIQLETMNSIRGAHTVQDVHK
ALLQGIEQILKVNVSIINQSFNDSLH
NFNYLHSKFDARLREKDVANHIVQTETFKEVLKGTGVEPGKINKETQQPKLHKN
DNDSLFKHLVDNFGKTVGVITLTGLL
SSFWLVLAKRRKKEEEEKQSIKNHHKDIRLSDTDKIDPIVITKRKIDKEEQIQNDD
KHSIPVAKHKKSKEKQLSEEDIHS
IPWKRKQNSDNKDTKQKKVTSKKKKTPQSTKKWKTKKRSKK
>|cl|SEPN_8_63.AA 1973 residues                          (SEQ ID NO: 24)
MKENKRKNNLDKNNTRFSIRKYQGYGATSVAIIGFIIISCFSEAKADSDKHEIKSH
QQSMTNHLTTLPSDNQENTSNNEF
NNRNHDISHLSLNKSIQMDELKKLIKQYKAINLNDKTEESIKLFQSDLVQAESLIN
NPQSQQHVDAFYHKFLNSAGKLRK
KETVSIKHERSESNTYRLGDEVRSQTFSHIRHKRNAVSFRNADQSNLSTDPLKA
NEINPEIQNGNFSQVSGGPLPTSSKR
LTVVTNVDNWHSYSTDPNPEYPMFYTTTAVNYPNFMSNGNAPYGVILGRTTDG
```

-continued

```
WNRNVIDSKVAGIYQDIDWPGSELNV
NFISTSPVFSDGAAGAKLKISNVEQNRVLFDSRLNGMGPYPTGKLSAMVNIPNDI
NRVRISFLPVSSTGRVSVQRSSREH
GFGDNSSYYHGGSVSDVRINSGSYWSKVTQREYTTRPNSSNDTFARATINLS
VENKGHNQSKDTYYEVILPQNSRLIST
RGGSGNYNNATNKLSIRLDNLNPGDRRDISYTVDFESSSPKLINLNA
HLLYKTNATFRGNDGQRTGDNIVDLQSIALLMN
KDVLETELNEIDKFIRDLNEADFTIDSWSALQEKMTEGGNILNEQ
QNQVALENQASQETINNVTQSLEILKNNLKYKTPS
QPIIKSNNQIPNITISPADKADKLTITYQNTDNESASIIGNKLNNQWSLNNNIPGIEI
DMQTGLVTIDYKAVYPESWGA
NDKTGNSDASAESRITMPRKEATPLSPIVEANEERVNWIAPNGEATQIAIKYRT
PDGQEATLVASKNGSSWTLNKQIDY
VNIEENSGKVTIGYQAVQPESEVIATETKGNSDESAESRVTMPRKEATPHSPIVE
ANEEHVNVTIAPNGEATQIAIKYRT
PDGQETTLIASKNGSSWTLNKQIDYVNIEENSGKVTIGYQAVQLESEVIATETKG
NSDASAESRITMLRKEATPHSPIVE
ANEEHVNVTIAPNGEATQIAIKYRTPDGQEATLVASKNESSWTLNKQIDHVNIDE
NSGKVTIGYQAVQPESEIIATETKG
NSDASAESRITMPRKEATPIPPTLEASVQEASVTVTPNENATKVFIKYLDINDEIS
TIIASKINQQWTLNKDNFGIKINP
LTGKVIISYVAVQPESDVIAIESQGNSDLSEESRIIMPTKEEPPEPPILESDSIEAK
VNIFPNDEATRIVIMYTSLEGQE
ATLVASKNESSWTLNKQIDHVNIDENSGKVTIGYQAVQPESEVIATETKGNSDA
SAESRVTMPRKEATPHSPIVETNEER
VNWIAPNGEATQIAIKYRTPDGQETTLIASKNGSSWTLNKQIDHVNIDENSGKV
TIGYQAVQPESEIIATETKGNSDAS
AESRITMPRKEAIPHSPIVEANEEHVNVTIAPNGETTQIAVKYRTPDGQEATLIAS
KNESSWTLNKQIDHVNIDENSGKV
TIGYQAVQPESEVIATETKGNSDASAESRITMPVKEKTPAPPISIINESNASVEIIP
QVNVTQLSLQYIDAKGQQQNLIA
TLNQNQWTLNKNVSHITVDKNTGKVLINYQAVYPESEVIARESKGNSDSSNVSM
VIMPRKTATPKPPIIKVDEMNASLAI
IPYKNNTAINIHYIDKKGIKSMVTAIKNNDQWQLDEKIKYVKIDAKTGTVIINYQIVQ
ENSEIIATAINGNSDKSEEVKV
LMPIKEFTPLAPLLETNYKKATVSILPQSNATKLDFKYRDKKGDSKIIIVKRFKNIW
KANEQISGVTINPEFGQWINYQ
AVYPESDILAAQYVGNSDASEWAKVKMPKKELAPHSPSLIYDNRNNKILIAPNSN
ATEMELSYVDKNNQSLKVKALKINN
RWKFDSSVSNISINPNTGKIVLQPQFLLTNSKIIVFAKKGNSDASISVSLRVPAVK
```

```
KIELEPMFNVPVLVSLNKKRIQFD

DCSGVKNCLNKQISKTQLPDTGYSDKASKSNILSVLLLGFGFLSYSRKRKEKQ
```

Example 5

Immunization Strategies for Antibody Production Using Three Representative Enterococcal MSCRAMM® Proteins Purified EF1091, EF1092, and EF1093 proteins were used to generate a panel of murine antibodies. Briefly, a group of Balb/C mice received a series of subcutaneous immunizations of 1-10 mg of protein in solution or mixed with adjuvant as described below in Table 5:

TABLE 5

| Conventional Injection | Day | Amount (µg) | Route | Adjuvant |
|---|---|---|---|---|
| Primary | 0 | 5 | Subcutaneous | FCA |
| Boost #1 | 14 | 1 | Intraperitoneal | RIBI |
| Boost #2 | 28 | 1 | Intraperitoneal | RIBI |
| Boost #3 | 42 | 1 | Intraperitoneal | RIBI |

At the time of sacrifice serum was collected and titered in ELISA assays against MSCRAMM® proteins ACE, EF1091, EF1092 and EF1093 (Table 6).

Serum ELISA

Immulon 2-HB high protein binding 96 well plates were coated with 100 ng/well of the purified A-domains of EF1091, EF1092 or EF1093 and incubated overnight at 2-8° C. Plates were washed four times (350 µl/well) with PBS/ 0.5% Tween 20 using the Skatron Skanwasher plate washer and then blocked with 1% bovine serum albumin (BSA) solution, 200 µl/well for 1-2 hour at room temperature. Following incubation, the plates were washed as before and 100 µl of 1×PBS, 0.05% Tween 20, 0.1% BSA buffer was added to each well of rows B-H of the 96-well plate. The negative control serum (preimmune Balb/C serum) and hyperimmune samples were then diluted 1:100 in 1×PBS, 0.05% Tween 20, 0.1% BSA buffer. 200 µl of negative control serum was added in duplicate to wells A1 and A2 of the 96-well plate and 200 µl of each diluted hyperimmune test serum were added in duplicate to wells A3 toA12. Two-fold serial dilutions were performed down the plate ending with Row H with the remaining 100 µl being discarded. The plates were incubated for 1 hour at room temperature. The plates were again washed as before followed by the addition of 1:5000 dilution of a secondary antibody solution, Goat anti-mouse IgG (whole molecule)-AP conjugate (Sigma Cat. A-5153), to each well (100 µl/well) and incubated for 1 hour at room temperature. Following incubation, the plates were washed 4 times (350 µl/well) with PBS/0.5% Tween 20. The developing solution, 1 mg/ml 4-nitrophenyl phosphate (pNPP) in 1M Diethanolamine, pH9.8, 0.5mM $MgCl_2$, was added to each well (100 µl/well) and the plates incubated at 37° C. for 30 minutes. After incubation, the absorbance ($A405_{nm}$) of each well was measured using the Spectra MAX 190 plate reader (Molecular Devices Corp., Sunnyvale, Calif.). The data was analyzed using SOFTmax Pro v.3.1.2. software (Molecular Devices Corp.) The dilution of the hyperimmune sera where the absorbance was 2-fold above the negative control serum absorbance was used as the titre for that hyperimmune serum sample.

TABLE 6

Antibody Titer at Sacrifice

| Antigen | Polyclonal Antibody Titre |
|---|---|
| EF1091 | >12,800 |
| EF1092 | >12,800 |
| EF1093 | >12,800 |

Example 6

Antibody Reactivity Against E. faecalis MSCRAMM® Proteins

Antisera derived from Balb/c mice (as described in Example 3) was used to identify EF1091, EF1092 or EF1093 natively expressed on the surface of E. faecalis strains.

Flow Cytometry Analysis—Whole Cell Staining

Bacterial samples (Table 7) were collected, washed and incubated with polyclonal antisera or pre-immune sera (control) at a dilution of 1:2000 after blocking with rabbit IgG (50 mg/ml). Following incubation with sera, bacterial cells were incubated with Goat-$F_{(ab')2}$-Anti-Mouse-$F_{(ab')2}$-FITC which served as the detection antibody. After antibody labeling, bacterial cells were aspirated through the FACScaliber flow cytometer to analyze fluorescence emission (excitation: 488, emission: 570). For each bacterial strain, 10,000 events were collected and measured.

TABLE 7

Whole Cell Staining of E. faecalis and E. faecium

| | EF1091 | EF1092 | EF1093 |
|---|---|---|---|
| E. faecalis | | | |
| ATCC700802 | — | — | Not done (NA) |
| 687097 | — | — | ND |
| V583 | — | — | ND |
| OG110 | — | — | ND |
| OG1RF | + | + | + |
| TX2708 | — | — | ND |
| TX0020 | ND | ND | ND |
| TX0045 | — | — | ND |
| TX0002 | — | — | ND |
| TX0039 | — | — | ND |
| TX0052 | ND | ND | ND |
| TX0012 | — | — | ND |
| TX0017 | ND | ND | ND |
| TX0008 | ND | ND | ND |
| TX0024 | ND | ND | ND |
| E. faecium | | | |
| 935/01 | — | — | ND |
| TX0016 | ND | ND | ND |
| TX0054 | +/− | +/− | ND |
| TX0074 | + | + | ND |
| TX0078 | — | — | ND |

TABLE 7-continued

Whole Cell Staining of E. faecalis and E. faecium

|  | EF1091 | EF1092 | EF1093 |
|---|---|---|---|
| TX0080 | +/− | +/− | ND |
| TX0081 | +/− | +/− | ND |
| TX2535 | ND | ND | ND |
| TX2555 | +/− | + | + |
| TX0110 | — | — | — |
| TX0111 | ND | ND | ND |

Polyclonal antisera raised in mice against EF1091, EF1092 and EF1093 were shown to recognize the native protein expressed on the surface of E. faecalis strains as well as E. faecium strains in flow cytometry studies (Table 7).

Example 7

Immunization Strategies for Monoclonal Antibody Production

With the goal of generating and characterizing monoclonal antibodies (mAbs), strategies were formulated to generate mAbs against EF1091, EF 1092 and EF 1093 that were of high affinity, able to interrupt or restrict the binding of extracellular matrix proteins (ECM) and demonstrate therapeutic efficacy in vivo. E. coli expressed and purified EF1091, EF1092, and EF1093 proteins were used to generate a panel of murine monoclonal antibodies. Briefly, a group of Balb/C or SJL mice received a series of subcutaneous immunizations of 1-10 □g of protein in solution or mixed with adjuvant as described below in Table 8:

TABLE 8

Immunization Schemes

|  | Day | Amount (µg) | Route | Adjuvant |
|---|---|---|---|---|
| RIMMS Injection |  |  |  |  |
| #1 | 0 | 5 | Subcutaneous | FCA/RIBI |
| #2 | 2 | 1 | Subcutaneous | FCA/RIBI |
| #3 | 4 | 1 | Subcutaneous | FCA/RIBI |
| #4 | 7 | 1 | Subcutaneous | FCA/RIBI |
| #5 | 9 | 1 | Subcutaneous | FCA/RIBI |
| Conventional Injection |  |  |  |  |
| Primary | 0 | 5 | Subcutaneous | FCA |
| Boost #1 | 14 | 1 | Intraperitoneal | RIBI |
| Boost #2 | 28 | 1 | Intraperitoneal | RIBI |
| Boost #3 | 42 | 1 | Intraperitoneal | RIBI |

At the time of sacrifice (RIMMS) or seven days after a boost (conventional) serum was collected and titered in ELISA assays against in immunizing MSCRAMM or on whole cells (E. faecalis and/or E. faecium). Three days after the final boost, the spleens or lymph nodes were removed, teased into a single cell suspension and the lymphocytes harvested. The lymphocytes were then fused to a P3X63Ag8.653 myeloma cell line (ATCC #CRL-1580). Cell fusion, subsequent plating and feeding were performed according to the Production of Monoclonal Antibodies protocol from Current Protocols in Immunology (Chapter 2, Unit 2.).

Example 8

Screening and Selection of Anti-EF1091 Monoclonal Antibodies

Any clones that were generated from the EF1091 fusion were then screened for specific anti-EF1091 antibody production using a standard ELISA assay. Positive clones were expanded and tested further for activity in a whole bacterial cell binding assay by flow cytometry and EF1091 binding by Biacore analysis (Table 9).

ELISA Analysis

Immulon 2-HB high-binding 96-well microtiter plates (Dynex) were coated with 1 pg/well of rEF1091 in 1×PBS, pH 7.4 and incubated for 2 hours at room temperature. All washing steps in ELISAs were performed three times with 1×PBS, 0.05% Tween-20 wash buffer. Plates were washed and blocked with a 1% BSA solution at room temperature for 1 hour before hybridoma supernatant samples were added to wells. Plates were incubated with samples and relevant controls such as media alone for one hour at room temperature, washed, and goat anti-mouse IgG-AP (Sigma) diluted 1:5000 in 1×PBS, 0.05% Tween-20, 0.1% BSA was used as a secondary reagent. Plates were developed by addition of 1 mg/ml solution of 4-nitrophenyl phosphate (pNPP) (Sigma), followed by incubation at 37° C. for 30 minutes. Absorbance was read at 405 nm using a SpectraMax 190 Plate Reader (Molecular Devices Corp.). Antibody supernatants that had an $OD_{405} \geq 3$ times above background (media alone, ~0.1 OD) were considered positive.

Biacore Analysis

Throughout the analysis, the flow rate remained constant at 10 ml/min. Prior to the EF1091 injection, test antibody was adsorbed to the chip via RAM-Fc binding. At time 0, EF1091 at a concentration of 30 mg/ml was injected over the chip for 3 min followed by 2 minutes of dissociation. This phase of the analysis measured the relative association and disassociation kinetics of the mAb/EF1091 interaction.

Flow Cytometric Analysis

Bacterial samples were collected, washed and incubated with mAb or PBS alone (control) at a concentration of 2 mg/ml after blocking with rabbit IgG (50 mg/ml). Following incubation with antibody, bacterial cells were incubated with Goat-$F_{(ab')2}$-Anti-Mouse-$F_{(ab')2}$-FITC which served as the detection antibody. After antibody labeling, bacterial cells were aspirated through the FACScaliber flow 10 cytometer to analyze fluorescence emission (excitation: 488, emission: 570). For each bacterial strain, 10,000 events were collected and measured.

TABLE 9

Representative Examples of Hybridoma Supernatants

| Fusion-Clone | Immunization Antigen | ELISA Data (EF1091) | Biacore Analysis | Flow Cytometric E. faecalis Staining |
|---|---|---|---|---|
| 85-8 | EF 1091 | 0.70 | + | + |
| 85-25 | EF 1091 | 0.75 | + | + |
| 85-58 | EF 1091 | 0.76 | + | — |

TABLE 9-continued

Representative Examples of Hybridoma Supernatants

| Fusion-Clone | Immunization Antigen | ELISA Data (EF1091) | Biacore Analysis | Flow Cytometric E. faecalis Staining |
|---|---|---|---|---|
| 85-78 | EF 1091 | 0.83 | + | + |
| 85-81 | EF 1091 | 0.84 | + | + |
| 85-162 | EF 1091 | 0.78 | + | + |
| 85-310 | EF 1091 | 0.30 | — | — |
| 85-341 | EF 1091 | 0.31 | — | — |
| 85-359 | EF 1091 | 0.48 | — | — |
| 85-374 | EF 1091 | 0.39 | — | — |
| 85-380 | EF 1091 | 0.32 | — | — |
| 85-399 | EF 1091 | 0.98 | + | — |
| 85-473 | EF 1091 | 0.55 | + | — |
| 85-511 | EF 1091 | 0.85 | + | — |
| 85-581 | EF 1091 | 0.88 | + | + |
| 85-586 | EF 1091 | 0.88 | + | + |
| 85-641 | EF 1091 | 0.45 | + | + |
| 85-661 | EF 1091 | 0.32 | — | — |
| 85-712 | EF 1091 | 0.30 | — | — |

Example 9

Binding of Enterococcal MSCRAMM Proteins to Extracellular Matrix (ECM) Proteins

Understanding the potential extracellular matrix proteins that these MSCRAMMs expressed from *Enterococcus* bind to is of great biological importance with therapeutic implications.

ELISA Based Extracellular Matrix Ligand Screening

To determine the binding activity of the recombinant proteins EF1091, EF1092 and EF1093 (Table 10) with extracellular matrix molecules, duplicate wells of a 96-well Costar microtiter plate (Corning) were coated overnight at 4° C. with 2 µg of either human collagen type I, III, IV, V or VI (Rockland Immunochemicals), fibrinogen, fibronectin, plasminogen, vitronectin (Sigma) or elastin (CalBiochem) in 100 µL of 1×PBS, pH 7.4 (Gibco). Wells were washed 4 times with 1×PBS, pH 7.4 containing 0.05% Tween 20 (1×PBST). Wells were then blocked with a 1% (w/v) solution of BSA in 1×PBS, pH 7.4 for 1 hour followed by 4 washes with 1×PBST. Next, 5 µg of recombinant protein in 100µL of 1×PBST containing 0.1%BSA (1×PBST-BSA) was added to each well. After incubation with the protein for 1 hour at room temperature, wells were washed 4 times with 1×PBST and 100 µL of mouse polyclonal antisera raised against the respective recombinant protein was added to each well at a dilution of 1:2000 in 1×PBST-BSA. Following the 1 hour incubation at room temperature with antisera, the wells were washed 4 times with 1×PBST. Finally, goat anti-mouse IgG-alkaline phsophatase conjugate (Sigma) was diluted 1:2000 with 1×PBST-BSA and 100 µL was added to each well. This incubation proceeded for 1 hour at room temperature and the wells were then washed 4 times with 1×PBST. The alkaline phosphatase was developed by adding 100 µL of a 1 mg/mL pNP solution (Sigma 104 tablets) to each well and incubating for 30 minutes at room temperature. Development was stopped by addition of 50 µL of 2M NaOH to each well. The absorbance at 405 nm ($A_{405}$) was measured using a Spectra-Max 190 (Molecular Devices). Reactivity was noted as positive if the signal was 2.5× greater than background.

Alternatively, EF0089 and EF2224 binding to components of the ECM (Table 10) was tested by immobilizing 1 µg of each ECM protein (human laminin, fibronectin, fibrinogen, type I, III and IV collagens) in 100 µl PBS, or 3% acetic acid in the case of collagens, on microplate wells (96-well, 4HBX, Thermo Labsystems, Franklin, Mass.) overnight at 4°C. Plates were washed once with PBS and blocked with 1% BSA in PBS for 1 h. Fifty µl of 5 and 10 µM concentrations of purified His-tag proteins in the blocking buffer were added and incubated at ambient temperature for 2 h. Plates were washed three times with 0.05% Tween20 in PBS and incubated 2 h with 1:3000 dilution of $His_6$-tag monoclonal antibody (Amersham Biosciences Corp., Piscataway, N.J.) in blocking buffer. After three washes, 1:3000 dilution of alkaline phosphatase-conjugated anti-mouse antibody in blocking buffer was added to the wells and incubated 2 h. Finally, signal was detected with nitrobluetetrazolium (NBT) and 5-bromo-4-chloro-3-indolyl-phosphate (BCIP) in 0.1 M $NaHCO_3$, 1 mM $MgCl_2$, pH 9.8. Absorbance at 405 nm was measured with an ELISA reader

TABLE 10

MSCRAMM ® Protein Recognition of ECM Proteins

| ECM Proteins | EF0089 | EF2224 | EF 1091 | EF 1092 | EF 1093 |
|---|---|---|---|---|---|
| Fibrinogen | + | + | — | — | + |
| Fibronectin | — | — | — | — | — |
| Collagen I | — | — | — | — | — |
| Collagen III | — | — | — | — | — |
| Collagen IV | — | — | — | — | — |
| Collagen V | Not determined (ND) | ND | — | — | — |
| Collagen VI | — | — | — | + | — |
| Vitronectin | — | — | — | — | — |
| Elastin | ND | ND— | — | — | — |
| Plasminogen | ND | ND | + | + | + |

Example 10

Serum From Patients Infected With *E. faecalis* Contain Elevated Levels of Antibodies Against MSCRAMM® Proteins The presence of antibodies against enterococcal proteins in human sera collected from hospitalized patients with and without a previous *E. faecalis* infection was tested by an ELISA assay described in (Arduino et al., 1994) (Nallapareddy et al., 2000b) with some modifications (Table 11). Briefly, 20 ng of each purified enterococcal protein in 100 µl PBS was coated on microplates (96 well, 4HBX, Thermo Labsystems, Franklin, Mass.) overnight at 4 °C. The plates were blocked with 1% BSA, 0.01% Tween20 in PBS at ambient temperature for 1 h and 100 µl of the sera in blocking buffer were added. Each serum was tested in triplicate with serial dilutions from 1:100 to 1:6400. Plates were incubated for 2 h at ambient temperature and washed three times with 0.01% Tween20 in PBS. 100 µl of 1:3000 dilution of horseradish peroxidase-conjugated anti human IgG was added and incubated 2 h. After three washes, signal was detected with 3,3',5,5'-tetramethylbenzidine (TMB) in the presence of $H_2O_2$ in 0.1 M citrate-acetate buffer, pH 6.0 at ambient temperature for 15 min. The reaction was stopped with 2 M $H_2SO_4$ and absorbance at 450 nm was recorded. Titers were determined after subtracting $A_{450nm}$ values from appropriate controls. To determine a cut-off level for serum titers, four additional control sera from healthy individuals without a prior *E. faecalis* infection were assayed. The sum of average $A_{450nm}$ values and two times the standard deviations for each dilution of the control sera were set as cut-off levels for positive titers.

TABLE 11

Infection

| | EF1091 | EF1824 | EF0089 | EF3023 | EF1092 | EF2224 | EF1269 | EF1093 |
|---|---|---|---|---|---|---|---|---|
| ≥1:6400 | •••••• | • | •• | • | •• | •• | | •••••• |
| 1:3200 | • | | • | | | | • | |
| 1:1600 | | | | | | | | |
| 1:800 | | | | | | | | |
| 1:400 | | | | | | | | • |
| 1:200 | | • | •• | • | • | • | • | |
| ≥1:100 | •••••• | ••• | •••••• | ••••• | ••••• | ••••• | •••••• | • |

No infection

| | EF1091 | EF1824 | EF0089 | EF3023 | EF1092 | EF2224 | EF1269 | EF1093 |
|---|---|---|---|---|---|---|---|---|
| ≥1:6400 | | | | | | | | • |
| 1:3200 | | | | | | | | |
| 1:1600 | | | | | | | | |
| 1:800 | | | | | | | | |
| 1:400 | | | | | | | | |
| 1:200 | • | • | • | • | • | | | |
| ≥1:100 | ••••••••• | ••••••••• | ••••••••• | ••••••••• | ••••••••• | ••••••••• | ••••••••• | •••••••• |

The following references referred to in the above description are incorporated as is set forth in their entirety herein:

CDC. 2002. Vancomycin-resistant *Staphylococcus aureus*—Pennsylvania, 2002. *Morb. Mortal. Wkly.* 51:902.

Deivanayagam, C. C., R. L. Rich, M. Carson, R. T. Owens, S. Danthuluri, T. Bice, M. Hook, and S. V. Narayana. 2000. Novel fold and assembly of the repetitive B region of the *Staphylococcus aureus* collagen-binding surface protein. *Structure Fold Des* 8:67-78.

Deivanayagam, C. C., E. R. Wann, W. Chen, M. Carson, K. R. Rajashankar, M. Hook, and S. V. Narayana. 2002. A novel variant of the immunoglobulin fold in surface adhesins of *Staphylococcus aureus*: crystal structure of the fibrinogen-binding MSCRAMM, clumping factor A. *Embo J* 21:6660-72.

Hamburger, Z. A., M. S. Brown, R. R. Isberg, and P. J. Bjorkman. 1999. Crystal structure of invasin: a bacterial integrin-binding protein. *Science* 286:291-5.

Huycke, M. M., D. F. Sahm, and M. S. Gilmore. 1998. Multiple-drug resistant enterococci: the nature of the problem and an agenda for the future. *Emerg Infect Dis* 4:239-49.

Leahy, D. J., I. Aukhil, and H. P. Erickson. 1996. 2.0 A crystal structure of a four-domain segment of human fibronectin encompassing the RGD loop and synergy region. *Cell* 84:155-64.

Luo, Y., E. A. Frey, R. A. Pfuetzner, A. L. Creagh, D. G. Knoechel, C. A. Haynes, B. B. Finlay, and N. C. Strynadka. 2000. Crystal structure of enteropathogenic *Escherichia coli* intimin-receptor complex. *Nature* 405:1073-7.

O'Brien, L. M., E. J. Walsh, R. C. Massey, S. J. Peacock, and T. J. Foster. 2002. *Staphylococcus aureus* clumping factor B (ClfB) promotes adherence to human type I cytokeratin 10: implications for nasal colonization. *Cell Microbiol* 4:759-70.

Patti, J. M., and M. Hook. 1994. Microbial adhesins recognizing extracellular matrix macromolecules. *Curr. Biol.* 6:752-758.

Paulsen, I. T., L. Banerjei, G. S. Myers, K. E. Nelson, R. Seshadri, T. D. Read, D. E. Fouts, J. A. Eisen, S. R. Gill, J. F. Heidelberg, H. Tettelin, R. J. Dodson, L. Umayam, L. Brinkac, M. Beanan, S. Daugherty, R. T. DeBoy, S. Durkin, J. Kolonay, R. Madupu, W. Nelson, J. Vamathevan, B. Tran, J. Upton, T. Hansen, J. Shetty, H. Khouri, T. Utterback, D. Radune, K. A. Ketchum, B. A. Dougherty, and C. M. Fraser. 2003. Role of mobile DNA in the evolution of vancomycin-resistant *Enterococcus faecalis*. *Science* 299: 20714.

Perkins, S., E. J. Walsh, C. C. Deivanayagam, S. V. Narayana, T. J. Foster, and M. Hook. 2001. Structural organization of the fibrinogen-binding region of the clumping factor B MSCRAMM of *Staphylococcus aureus*. *J Biol Chem* 276: 44721-8.

Sharma, A., J. A. Askari, M. J. Humphries, E. Y. Jones, and D. I. Stuart. 1999. Crystal structure of a heparin- and integrin-binding segment of human fibronectin. *Embo J* 18:1468-79.

Symersky, J., J. M. Patti, M. Carson, K. House-Pompeo, M. Teale, D. Moore, L. Jin, A. Schneider, L. J. DeLucas, M. Hook, and S. V. Narayana. 1997. Structure of the collagen-binding domain from a *Staphylococcus aureus* adhesin. *Nat Struct Biol* 4:833-8.

Tailor, S. A., E. M. Bailey, and M. J. Rybak. 1993. *Enterococcus*, an emerging pathogen. *Ann Pharmacother* 27:1231-42.

Tung, H., B. Guss, U. Hellman, L. Persson, K. Rubin, and C. Ryden. 2000. A bone sialoprotein-binding protein from *Staphylococcus aureus:* a member of the staphylococcal Sdr family. Biochem J 345 Pt 3:611-9.

Arduino, R. C., Murray, B. E., and Rakita, R. M. (1994) Roles of antibodies and complement in phagocytic killing of enterococci. *Infection and Immunity* 62: 987-993.

Davis, S. L., Gurusiddappa, S., McCrea, K. W., Perkins, S., and Hook, M. (2001) SdrG, a fibrinogen-binding bacterial adhesin of the microbial surface components recognizing adhesive matrix molecules subfamily from *Staphylococcus epidermidis*, targets the thrombin cleavage site in the Bbeta chain. *J Biol Chem* 276: 27799-27805.

Deivanayagam, C. C., Perkins, S., Danthuluri, S., Owens, R. T., Bice, T., Nanavathy, T., Foster, T. J., Hook, M., and Narayana, S. V. (1999) Crystallization of ClfA and ClfB fragments: the fibrinogen-binding surface proteins of *Staphylococcus aureus*. *Acta Crystallogr D Biol Crystallogr* 55 ( Pt 2): 554-556.

Deivanayagam, C. C., Wann, E. R., Chen, W., Carson, M., Rajashankar, K. R., Hook, M., and Narayana, S. V. (2002) A novel variant of the immunoglobulin fold in surface adhesins of *Staphylococcus aureus:* crystal structure of the fibrinogen-binding MSCRAMM, clumping factor A. *Embo J* 21: 6660-6672.

Foster, T. J., and Hook, M. (1998) Surface protein adhesins of *Staphylococcus aureus*. *Trends Microbiol.* 6: 484488.

Hartford, O., O'Brien, L., Schofield, K., Wells, J., and Foster, T. J. (2001) The Fbe (SdrG) protein of *Staphylococcus epidermidis* HB promotes bacterial adherence to fibrinogen. *Microbiology* 147: 2545-2552.

Joh, H. J., House-Pompeo, K., Patti, J. M., Gurusiddappa, S., and Hook, M. (1994) Fibronectin receptors from Gram-positive bacteria: comparison of active sites. *Biochemistry* 33: 6086-6092.

Lee, J. O., Rieu, P., Arnaout, M. A., and Liddington, R. (1995) Crystal structure of the A-domain from the a subunit of integrin CR3 (CDllb/CD18). *Cell* 80: 631-638.

Mazmanian, S. K., Ton-That, H., and Schneewind, O. (2001) Sortase-catalyzed anchoring of surface proteins to the cell wall of *Staphylococcus aureus*. *Molecular Microbiology* 40: 1049-1057.

McDevitt, D., Francois, P., Vaudaux, P., and Foster, T. J. (1994) Molecular characterization of the clumping factor (fibrinogen receptor) of *Staphylococcus aureus*. *Mol Microbiol* 11: 237-248.

Murray, B. E. (1990) The life and times of the *enterococcus*. *Clin. Microbiol. Rev* 3: 46-65.

Murray, B. E., and Weinstock, G. M. (1999) Enterococci: new aspects of an old organism. *Proc. Assoc. Am. Physicians* 111: 328-334.

Nallapareddy, S. R., Qin, X., Weinstock, G. M., Hook, M., and Murray, B. E. (2000a) *Enterococcus faecalis* adhesin, ace, mediates attachment to extracellular matrix proteins collagen type IV and laminin as well as collagen type I. *Infect Immun* 68: 5218-5224.

Nallapareddy, S. R., Singh, K. V., Duh, R. W., Weinstock, G. M., and Murray, B. E. (2000b) Diversity of ace, a gene encoding a microbial surface component recognizing adhesive matrix molecules, from different strains of *Enterococcus faecalis* and evidence for production of ace during human infections. *Infect Immun* 68: 5210-5217.

Ni Eidhin, D., Perkins, S., Francois, P., Vaudaux, P., Hook, M., and Foster, T. J. (1998) Clumping factor B (ClfB), a new surface-located fibrinogen-binding adhesin of *Staphylococcus aureus*. *Mol Microbiol* 30: 245-257.

Pace, C. N., Vajdos, F., Fee, L., Grimsley, G., and Gray, T. (1995) How to measure and predict the molar absorption coefficient of a protein. *Protein Science* 4: 2411-2423.

Perkins, S., Walsh, E. J., Deivanayagam, C. C., Narayana, S. V., Foster, T. J., and Hook, M. (2001) Structural organization of the fibrinogen-binding region of the clumping factor B MSCRAMM of *Staphylococcus aureus*. *J Biol Chem* 276: 44721-44728.

Ponnuraj, K., Xu, Y., Moore, D., Deivanayagam, C. C., Boque, L., Hook, M., and Narayana, S. V. (2002) Crystallization and preliminary X-ray crystallographic analysis of Ace: a collagen-binding MSCRAMM from *Enterococcus faecalis*. *Biochim Biophys Acta* 1596: 173-176.

Rich, R. L., Kreikemeyer, B., Owens, R. T., LaBrenz, S., Narayana, S. V., Weinstock, G. M., Murray, B. E., and Hook, M. (1999) Ace is a collagen-binding MSCRAMM from *Enterococcus faecalis*. *J Biol Chem* 274: 26939-26945.

Sahm, D. F., Kissinger, J., Gilmore, M. S., Murray, P. R., Mulder, R., Solliday, J., and Clarke, B. (1989) In vitro susceptibility studies of vancomycin-resistant *Enterococcus faecalis*. *Antimicrob. Agents Chemother.* 33: 1588-1591.

Schneewind, O., Fowler, A., and Faull, K. F. (1995) Structure of the cell wall anchor of surface proteins in *Staphylococcus aureus*. *Science* 268: 103-106.

Symersky, J., Patti, J. M., Carson, M., House-Pompeo, K., Teale, M., Moore, D., Jin, L., Schneider, A., DeLucas, L. J., Hook, M., and Narayana, S. V. (1997) Structure of the collagen-binding domain from a *Staphylococcus aureus* adhesin. *Nature Structural Biology* 4: 833-838.

Wann, E. R., Gurusiddappa, S., and Hook, M. (2000) The fibronectin-binding MSCRAMM FnbpA of *Staphylococcus aureus* is a bifunctional protein that also binds to fibrinogen. *J Biol Chem* 275: 13863-13871.

Westerlund, B., and Korhonen, T. K. (1993) Bacterial proteins binding to the mammalian extracellular matrix. *Mol. Microbiol.* 9: 687-694.

What is claimed is:

1. An isolated antibody capable of binding to an amino acid sequence consisting of amino acids 33-592 of SEQ ID NO: 13.

2. The antibody according to claim 1 wherein the antibody is a monoclonal antibody.

3. The antibody according to claim 1 selected from the group consisting of single chain, chimeric, murine, humanized and human monoclonal antibodies.

4. The antibody according to claim 1, wherein said antibody treats an *E. faecalis* bacterial infection in a human or animal.

5. The antibody according to claim 1, wherein said antibody is suitable for parenteral, oral, intranasal, subcutaneous, aerosolized or intravenous administration in a human or animal.

6. Isolated antisera containing an antibody according to claim 1.

7. A diagnostic kit comprising an antibody according to claim 1 and means for detecting binding by that antibody.

8. A diagnostic kit according to claim 7 wherein said means for detecting binding comprises a detectable label that is linked to said antibody.

9. A pharmaceutical composition comprising an effective amount of the antibody of claim 1 and a pharmaceutically acceptable vehicle, carrier or excipient.

10. The antibody according to claim 1, wherein the antibody is a polyclonal antibody.

* * * * *

UNITED STATES PATENT AND TRADEMARK OFFICE
CERTIFICATE OF CORRECTION

| | | |
|---|---|---|
| PATENT NO. | : 7,615,616 B2 | Page 1 of 1 |
| APPLICATION NO. | : 10/661809 | |
| DATED | : November 10, 2009 | |
| INVENTOR(S) | : Hook et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 590 days.

Signed and Sealed this

Nineteenth Day of October, 2010

David J. Kappos
*Director of the United States Patent and Trademark Office*